United States Patent
Crosignani et al.

(10) Patent No.: US 9,216,991 B2
(45) Date of Patent: Dec. 22, 2015

(54) PYRIMIDINE PYRAZOLYL DERIVATIVES

(71) Applicant: Ares Trading S.A., Aubonne (CH)

(72) Inventors: Stefano Crosignani, Nivelles (BE); Catherine Jorand-Lebrun, Arlington, MA (US); Patrick Gerber, Etoy (CH); Mathilde Muzerelle, Gaillard (FR)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 14/406,389

(22) PCT Filed: Jul. 3, 2013

(86) PCT No.: PCT/EP2013/001950
§ 371 (c)(1),
(2) Date: Dec. 8, 2014

(87) PCT Pub. No.: WO2014/008992
PCT Pub. Date: Jan. 16, 2014

(65) Prior Publication Data
US 2015/0141396 A1 May 21, 2015

Related U.S. Application Data

(60) Provisional application No. 61/669,843, filed on Jul. 10, 2012.

(30) Foreign Application Priority Data

Jul. 10, 2012 (EP) .................... 12175660

(51) Int. Cl.
| | | |
|---|---|---|
| A61K 31/506 | (2006.01) |
| C07D 493/10 | (2006.01) |
| C07D 401/14 | (2006.01) |
| C07D 413/14 | (2006.01) |
| C07D 491/08 | (2006.01) |
| C07D 403/04 | (2006.01) |
| C07D 403/14 | (2006.01) |
| C07D 407/14 | (2006.01) |
| C07D 417/14 | (2006.01) |
| C07D 487/08 | (2006.01) |
| C07D 491/10 | (2006.01) |
| A61K 31/5377 | (2006.01) |
| A61K 31/5386 | (2006.01) |
| A61K 31/553 | (2006.01) |
| A61K 45/06 | (2006.01) |
| C07D 405/14 | (2006.01) |
| C07D 491/107 | (2006.01) |
| C07D 498/08 | (2006.01) |

(52) U.S. Cl.
CPC ............ *C07D 493/10* (2013.01); *A61K 31/506* (2013.01); *A61K 31/5377* (2013.01); *A61K 31/5386* (2013.01); *A61K 31/553* (2013.01); *A61K 45/06* (2013.01); *C07D 401/14* (2013.01); *C07D 403/04* (2013.01); *C07D 403/14* (2013.01); *C07D 405/14* (2013.01); *C07D 407/14* (2013.01); *C07D 413/14* (2013.01); *C07D 417/14* (2013.01); *C07D 487/08* (2013.01); *C07D 491/08* (2013.01); *C07D 491/10* (2013.01); *C07D 491/107* (2013.01); *C07D 498/08* (2013.01)

(58) Field of Classification Search
CPC .. C07D 493/10; C07D 401/14; C07D 403/04; C07D 403/14; C07D 405/14; C07D 407/14; C07D 413/14; C07D 417/14; C07D 487/08; C07D 491/08; C07D 491/10; C07D 491/107; C07D 498/08; A61K 31/506; A61K 31/5377; A61K 31/5389; A61K 31/553; A61K 45/06
See application file for complete search history.

(56) References Cited

U.S. PATENT DOCUMENTS

2011/0071153 A1* 3/2011 Dorsch et al. .............. 514/236.5

FOREIGN PATENT DOCUMENTS

| WO | 2010100144 A1 | 9/2010 |
| WO | 2010112210 A1 | 10/2010 |
| WO | 2012007375 A1 | 1/2012 |

OTHER PUBLICATIONS

C. Wietek et al., 2 Molecular Interventions, 212-215 (2002).*
K.W. Song et al., 46 Molecular Immunology, 1458-1466 (2009).*
I. Isnardi et al., 29 Immunity, 746-757 (2008).*
E Sanchez et al., 21 Lupus, 1166-1171 (2012).*
Braghiroli, "Asymmetric synthesis of (R)- and (S)-2-pyrrolidinemethanesulfonic acid", Tetrahedron: Asymmetry, 1997, 8(13): 2209-2213.

(Continued)

*Primary Examiner* — Alexander R Pagano
(74) *Attorney, Agent, or Firm* — Dwight D. Kim; EMD Serono Research and Development Institute

(57) ABSTRACT

The present invention provides compounds of Formula (I) for the treatment of cancer, rheumatoid arthritis and other diseases.

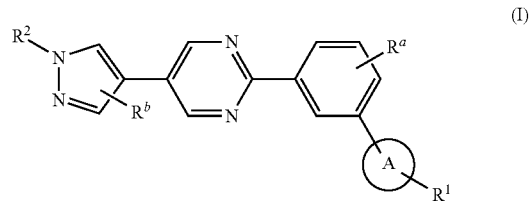

15 Claims, No Drawings

(56) References Cited

OTHER PUBLICATIONS

Buckley, "IRAK-4 inhibitors, Part II: A structure-based assessment of imidazo [1,2-a] pyridine binding", Bioorg. Med Chem Lett., 2008, 18(11): 3291-3295.

Buckley, "IRAK-4 inhibitors. Part III: A series of imidazo[1,2-a]pyridines", Bioorg. Med Chem Lett., 2008, 18(12): 3656-3660.

Cao, "IRAK: A Kinase Associated with the Interleukin-1 Receptor", Science, 1996, 271(5252): 1128-31.

Cohen, "Targeting protein kinases for the development of anti-inflammatory drugs", Current Opinion in Cell Biology, 2009, 21(2): 317-324.

Gokhale and Kumar, "Amino/guanidino-functionalized N-(pyrrolidin-2-ethyl)glycine-based pet-PNA: Design, synthesis and binding with DNA/RNA", Org. Biomol. Chem., 2010, 8(16): 3742-3750.

Green, "Effect of Tarenflurbil on Cognitive Decline and Activities of DailyLiving in Patients With Mild Alzheimer Disease: A Randomized Controlled Trial", JAMA, 2009, 302(23): 2557-2564.

Greene and Wuts, "Protective Groups in Organic Synthesis", Wiley Interscience, 3rd Edition, 1999.

Higuchi and Stella, "Pro-drugs as Novel Delivery Systems", vol. 14 of the A.C.S. Symposium Series, American Chemical Society (1975).

Hughes, D. L. Organic Reactions (New York), John Wiley & Sons, Inc., 1992, 42: 335-656.

Kocienski Philip J., "Protecting Groups", Georg Thieme Verlag Stuttgart, New York, 1994.

Li, "IRAK-4: A novel member of the IRAK family with the properties of an IRAK-kinase", Proc. Natl. Acad. Sci. USA, 2002, 99(8): 5567-5572.

Miyaura, "Palladium-Catalyzed Cross-Coupling Reactions of Organoboron Compounds", Chem. Rev. 1995, 95: 2457-2483.

Muzio, "IRAK (Pelle) Family Member IRAK-2 and MyD88 as Proximal Mediators of IL-1 Signaling", Science, 1997, 278(5343): 1612-1615.

Reynolds, "Recent Advances in the Mitsunobu Reaction: Modifications and Applications to Biologically Active Molecules", Current Organic Chemistry, 2009, 13(16); 1610-1632.

Ringwood and Li, "The involvement of the interleukin-1 Receptor-Associated Kinases (IRAKs) in cellular signaling networks controlling inflammation", Cytokine, 2008, 42(1): 1-7.

Roche, "Bioreversible Carriers in Drug Design: Theory and Application", Pergamon Press (New York), (1987), pp. 14-21.

Takahiro and Toshiaki, "Direct synthesis of hetero-biaryl compounds containing an unprotected NH2 group via Suzuki-Miyaura reaction", Tetrahedron Letters, 2005, 46: 3573-3577.

Tyle, "Iontophoretic Devices for Drug Delivery", Pharmaceutical Resarch, 1986, 3(6): 318-319.

Wesche, "IRAK-M Is a Novel Member of the Pelle/Interleukin-1 Receptor-associated Kinase (IRAK) Family", J. Biol. Chem., 1999, 274(27): 19403-10.

Yoshida, "Study of biodegradable copoly (L-lactic acid/glycolic acid) formulations with controlled release of Z-100 for application in radiation therapy", Int. J. Pharm., 1995, 115: 61-67.

* cited by examiner

PYRIMIDINE PYRAZOLYL DERIVATIVES

RELATED APPLICATIONS

The present application is a U.S. national stage application of PCT International Application PCT/EP2013/001950, filed on Jul. 3, 2013, which claims the benefit of U.S. Provisional Application USSN 61/669,843, filed on Jul. 10, 2012, and European application EP 12175660.5, filed on Jul. 10, 2012. The entire contents of the aforementioned applications are incorporated herein by reference.

The present invention provides Pyrimidine pyrazolyl derivatives of Formula (I) as IRAK inhibitors and their use in the treatment of cancer, and other diseases related to IRAK overexpression, like rheumatoid arthritis, systemic lupus erythematosus or lupus nephritis.

BACKGROUND

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAKI (Muzio et al., 1997. Science 278(5343): 1612-5). IRAK3 (also called IRAKM) was identified using a murine EST sequence encoding a polypeptide with significant homology to IRAK1 to screen a human phytohemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem Lett. 18(12):3656-60). IRAK1 is essential for the TLR7-mediated and TLR9-mediated activation of IRF7 and the production of interferon-alpha (IFN-α) suggesting that IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

According to one aspect of the invention, are provided compounds of Formula (I).

According to another aspect of the invention, are provided compounds of Formula (I) which are suitable for the treatment and/or prevention of disorders related to IRAK.

According to another aspect of the invention, are provided compounds, which are able to modulate, especially inhibit the activity or function of IRAK in disease states in mammals, especially in humans.

According to another aspect of the invention, are provided methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect, the present invention provides compounds of Formula (I) which are selective of IRAK-4 and/or IRAK-1 over the other isoforms.

According to another aspect of the invention is provided a kit or a set comprising at least one compound of Formula (I), preferably in combination with immunomodulating agents.

Preferably, the kit consists of separate packs of:
(a) an effective amount of a compound of the formula (I) and/or pharmaceutically usable derivatives, solvates, salts, hydrates and stereoisomers thereof, including mixtures thereof in all ratios, and
(b) an effective amount of a further medicament active ingredient.

According to another aspect of the invention, is provided a process for the synthesis of compounds of Formulae (I) and related Formulae.

DETAILED DESCRIPTION OF THE INVENTION

In one embodiment, the present invention provides a compound of Formula (I)

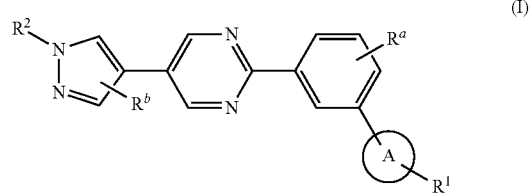

wherein
$R^1$ denotes absent or denotes A or Q-Het,
Z denotes a group:

wherein
X denotes O, S or N,
Y denotes C or N,
T denotes C or N, or
Z denotes a pyridine or a pyridazine group,
$R^a$ is absent or denotes $OR^3$, $CF_3$, Hal, $NO_2$,
$R^b$ is absent or denotes one of the groups selected from A and COHet,
$R^2$ denotes H, Het, Q-Het, Cyc, A or OA,
Het denotes a 4-9 membered monocyclic ring or a fused, spiro or bridged bicyclic ring, which is saturated, unsaturated, or aromatic, which contains 1 to 3 heteroatoms independently selected from N, O, S and a group CO, SO or $SO_2$, and wherein 1 or 2 H atoms may be replaced by A, OA, COA, CN, Hal, $NO_2$, $OR^3$, SOA and/or $SO_2A$,
Cyc denotes a 4-8 saturated carbocyclic ring optionally containing a group SO, $SO_2$, CO, and optionally substituted once or twice by a group selected from $CO(NR^3)_2$, and COHet, $OR^3$, $Het^1$, A, $CH_2Het^1$, $NH_2$, NHCOA, $OCH_2Cyc^1$, $SO_2A$ and/or —SA(=NH)(=O),
Q denotes a linear or branched alkylene, having 1 to 6 carbon atoms wherein 1-5 H atoms may be replaced by a group independently selected from $OR^3$, Hal, $N(R^3)_2$, and wherein 1 or 2 $CH_2$ groups may be replaced by a group independently selected from CO, SO, $SO_2$ and $NR^3$, or Q denotes a 4-8-membered bivalent heterocyclic ring, which is saturated, unsaturated or aromatic and which contains 1 to 3 heteroatoms independently selected from N, O and S,
A denotes a linear or branched alkyl having 1 to 10 carbon atoms wherein 1 to 7 H atoms may be replaced by a group independently selected from —$OR^3$, Hal, $NHSO_2A$, $SO_2A$, SOA, $N(R^3)_2$, and wherein 1, 2 or 3 non-adjacent —$CH_2$— groups may be replaced by a group independently selected from —CO—, $NR^3$ and/or —O—,
Hal denotes F, Cl, Br or I,
$R^3$ denotes H or $C_1$-$C_6$ alkyl wherein 1 H atom may be replaced by a group selected from OH, O—$C_1$-$C_6$-alkyl, and Hal,
$Het^1$ denotes a five- or six membered saturated monocyclic heterocycle, which contains 1-3 N- and/or O-atoms, which optionally is monosubstituted by A,
$Cyc^1$ denotes cycloalkyl with 3-7 atoms,
and pharmaceutically acceptable derivatives, solvates, tautomers, salts, hydrates and stereoisomers thereof, including mixtures thereof in all ratios.

In the definitions above and below, when a group is mentioned several times, like $R^3$ in $CO(NR^3)_2$, It independently takes any values given in the corresponding definition.

In the compounds of Formula (I) and related formulae, Z may denote a group

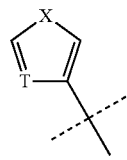

wherein X is O, S or N and T is C or N.

Alternatively, Z is selected from the following specific groups:

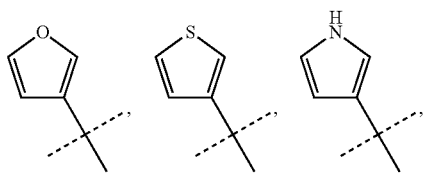

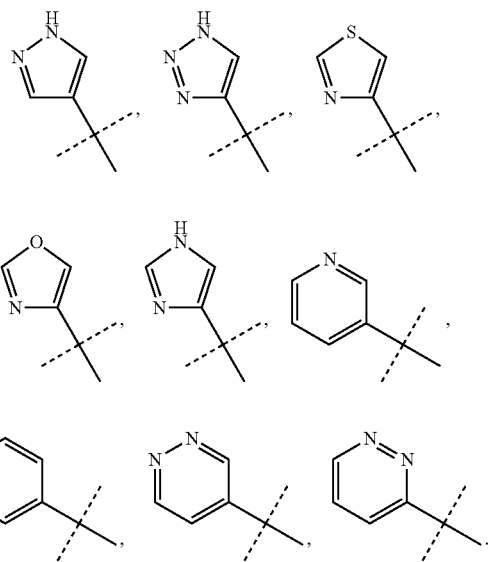

Z, in Formula (I) and related Formulae preferably denotes a group selected from a pyridazine, a pyrazole, and a 4-pyridine.

$R^1$ in Formula (I) and related Formulae preferably denotes a linear or branched $C_1$-$C_6$-alkyl group.

Alternatively, the group Z—$R^1$ in Formula (I) and related Formulae is selected from the following groups:

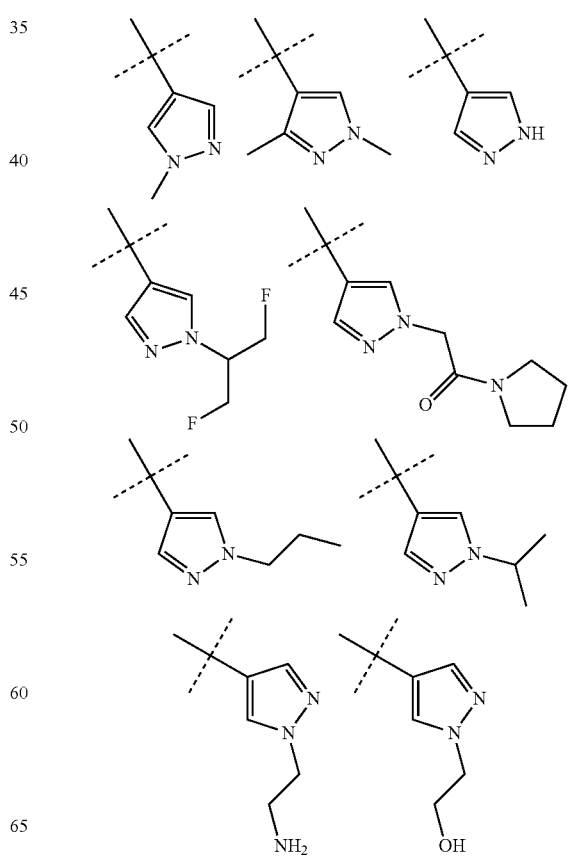

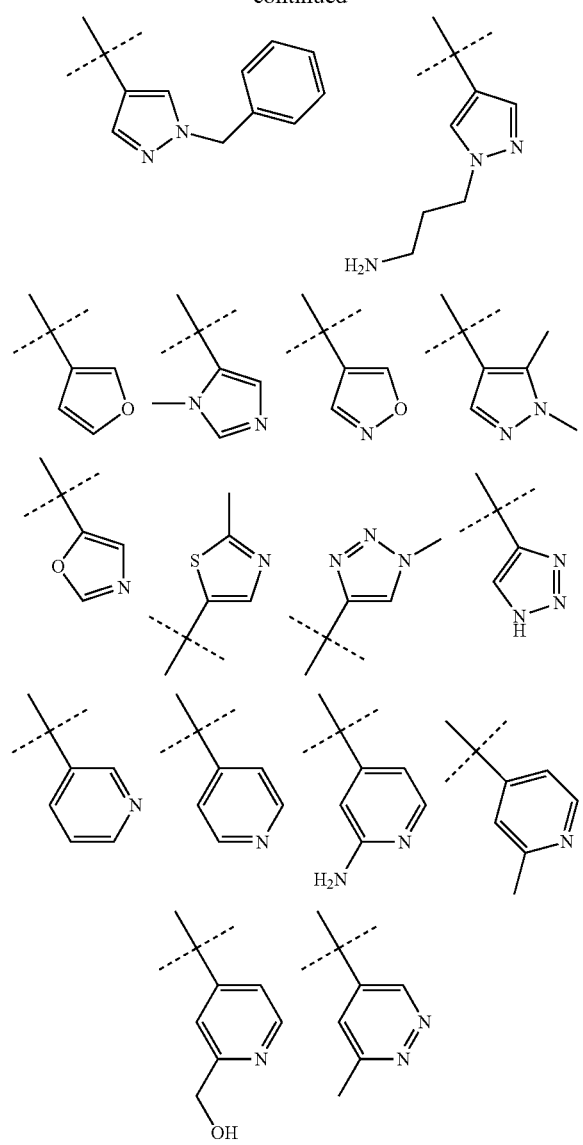
In a specific embodiment, the group $R^2$ in Formula (I) and related Formulae denotes a piperidine or the group Cyc defined above.
Alternatively, the group $R^2$ in Formula (I) and related Formulae is preferably selected from the following groups:
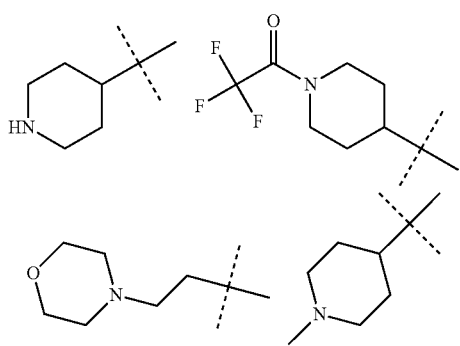
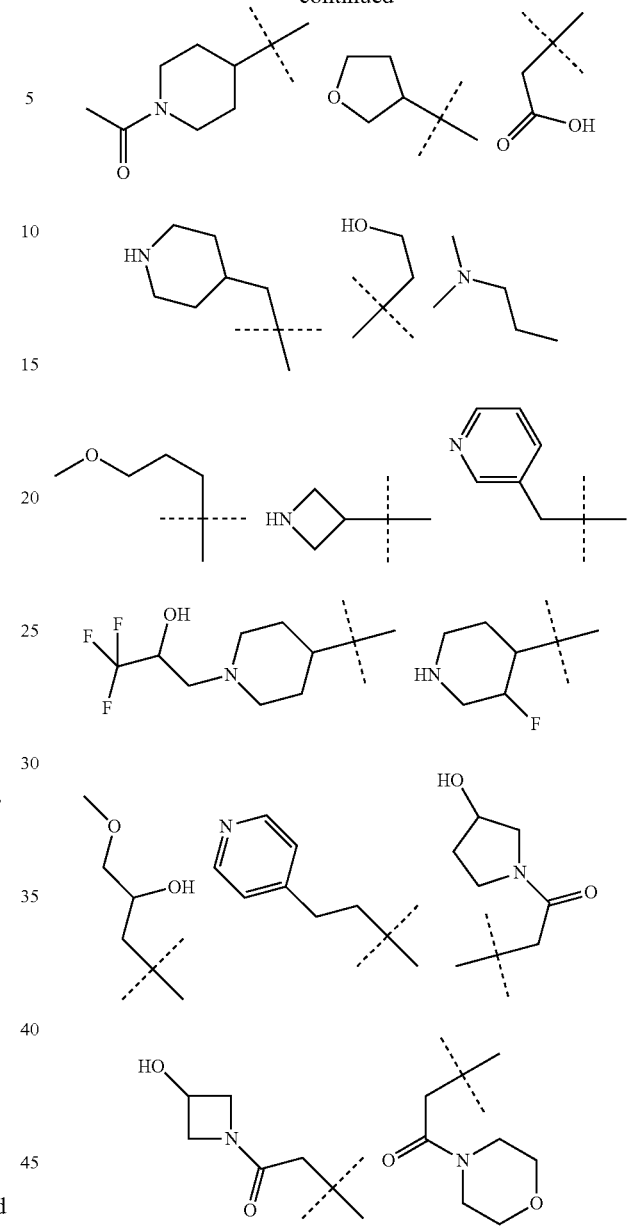
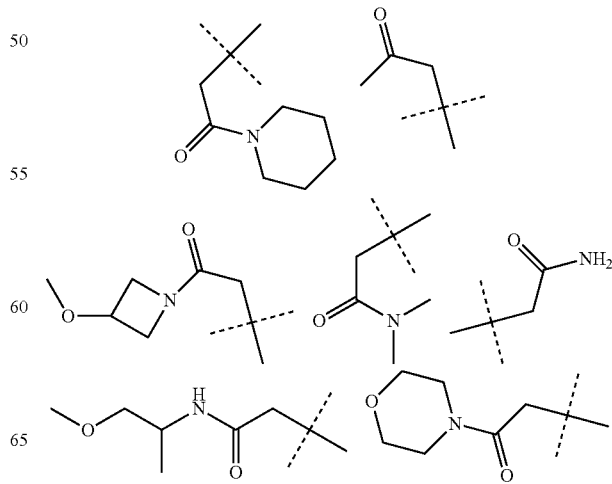

-continued
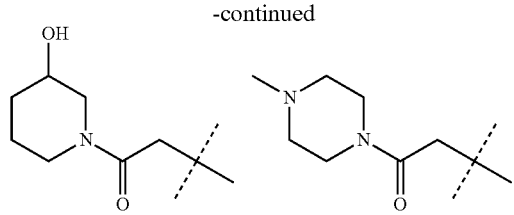
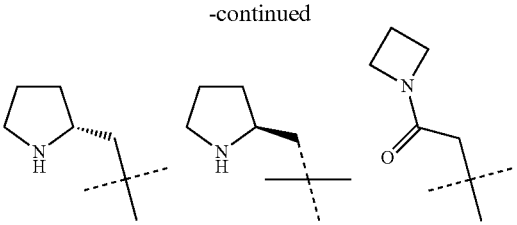
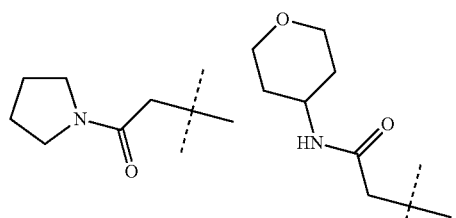
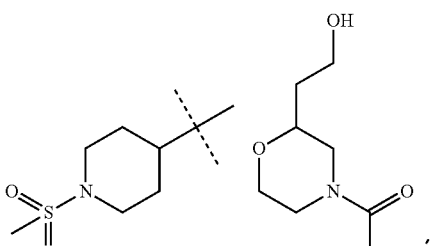
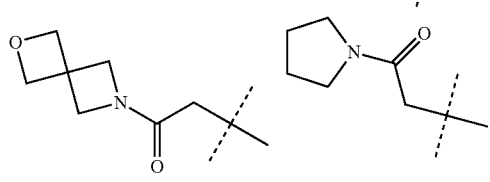
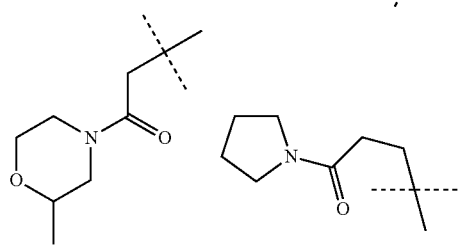
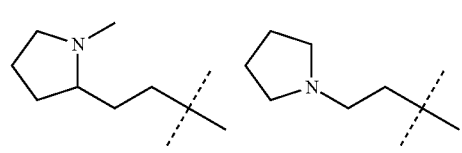
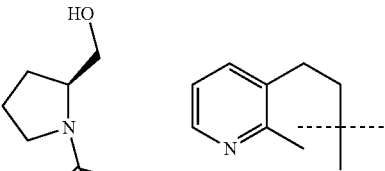
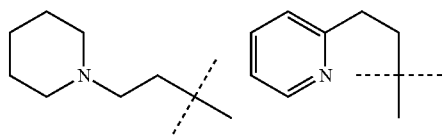
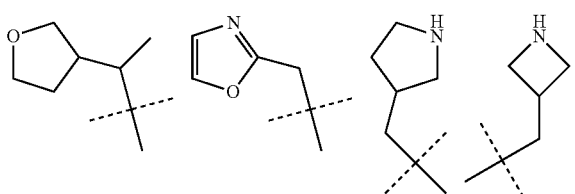
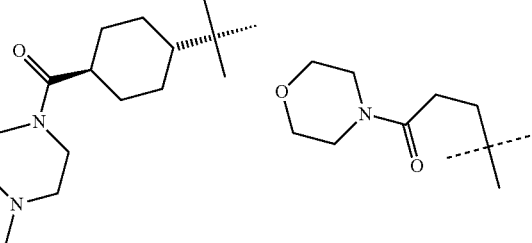
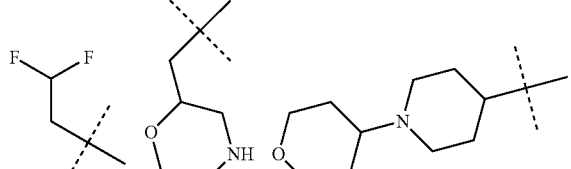
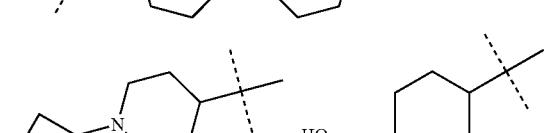
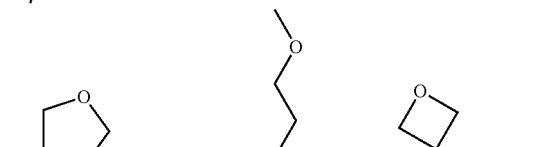
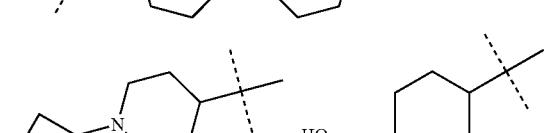

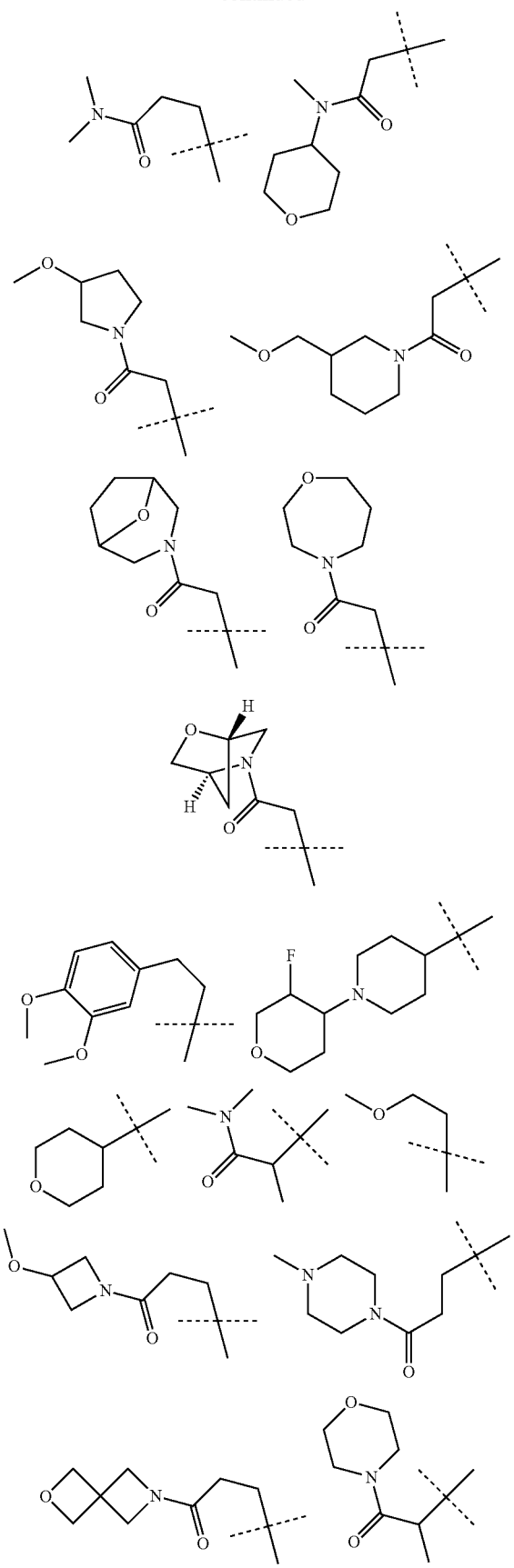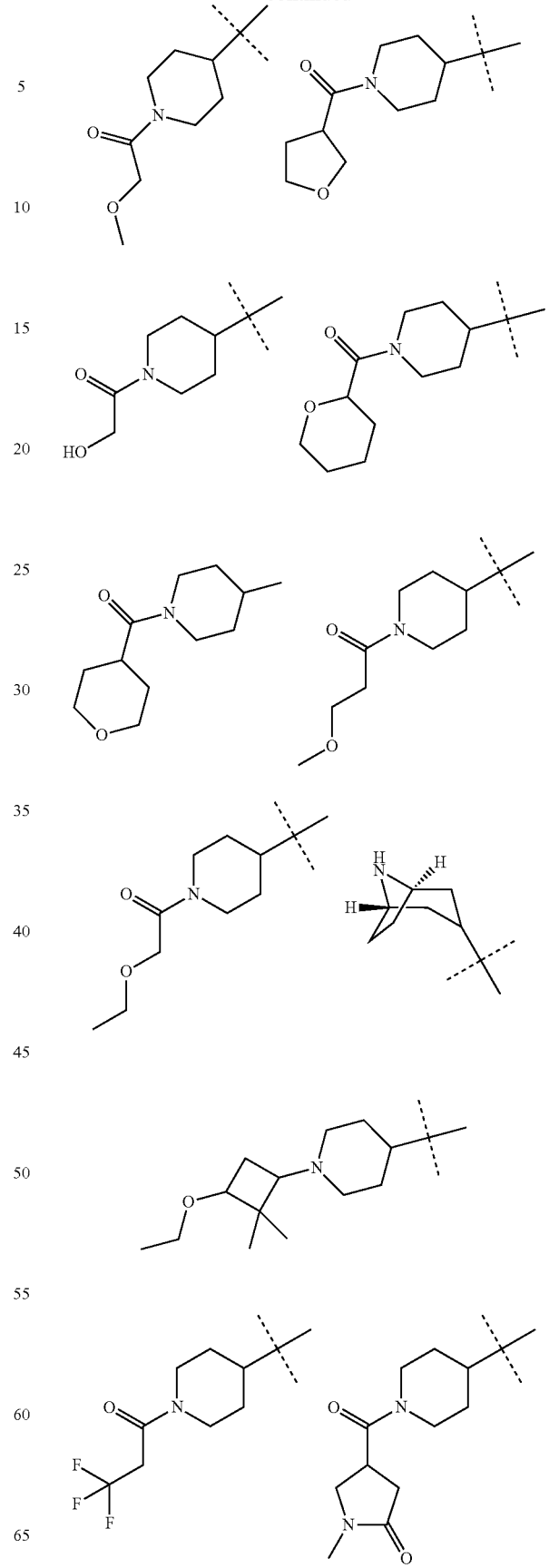

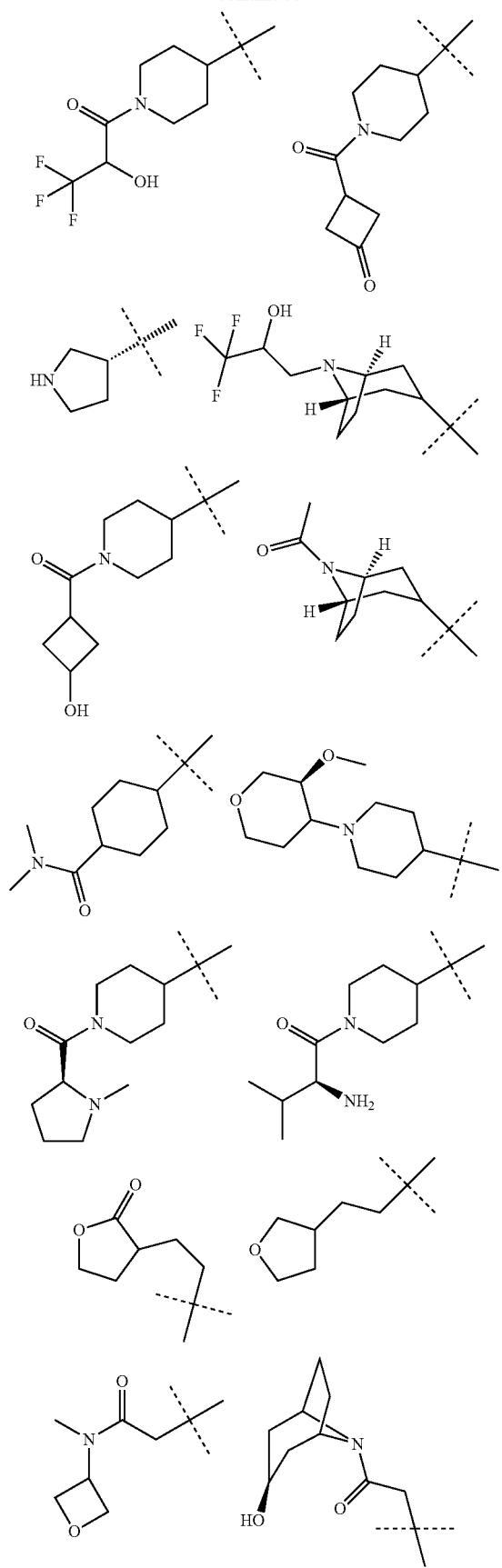
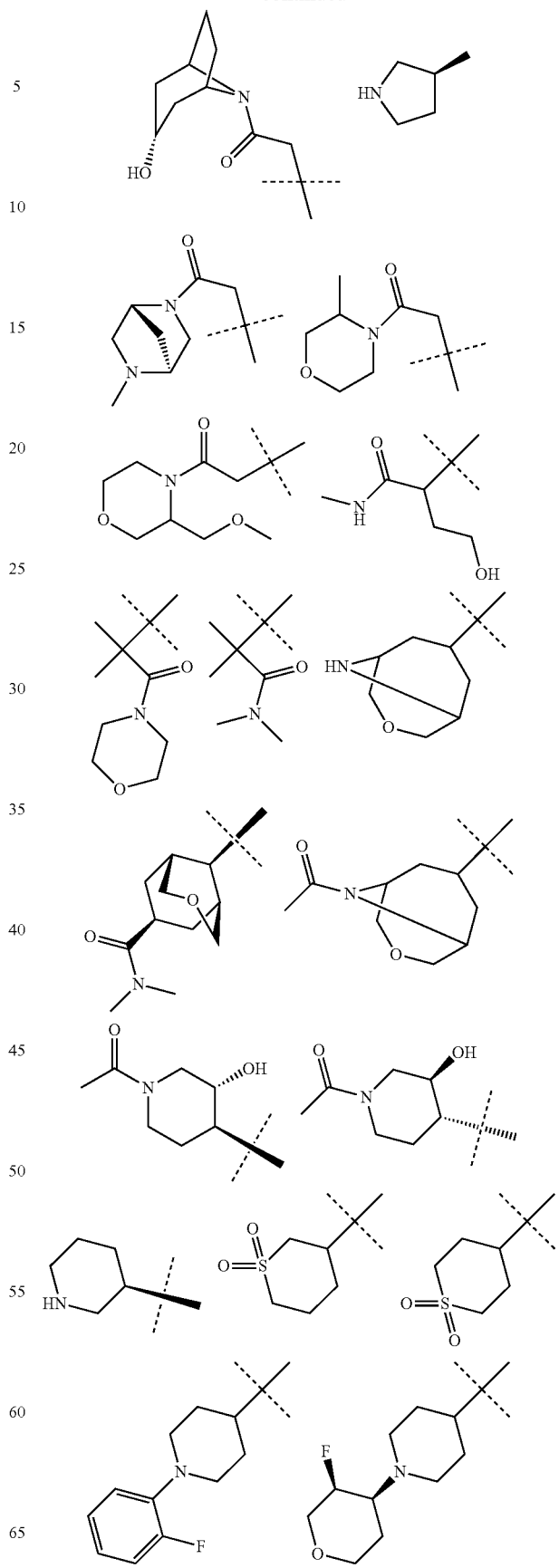

-continued
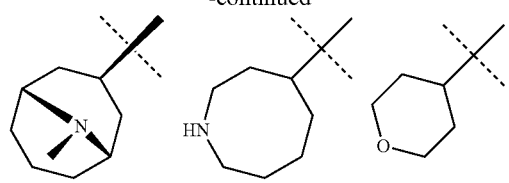
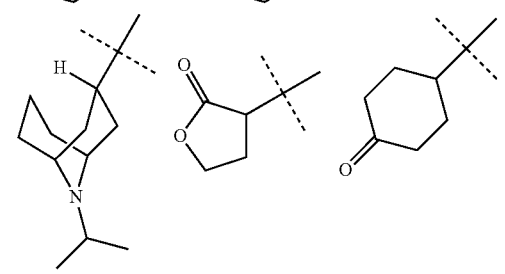
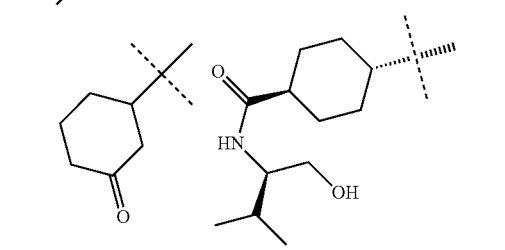
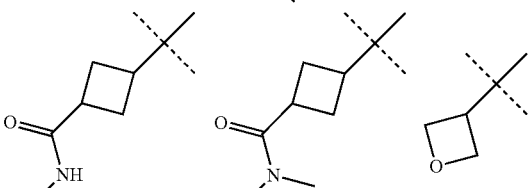
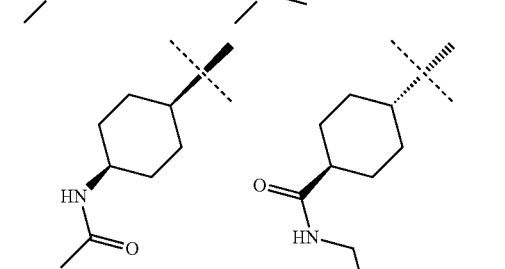
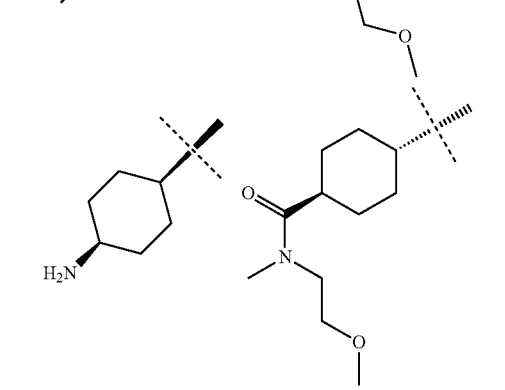
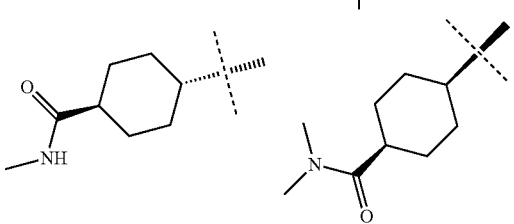
-continued
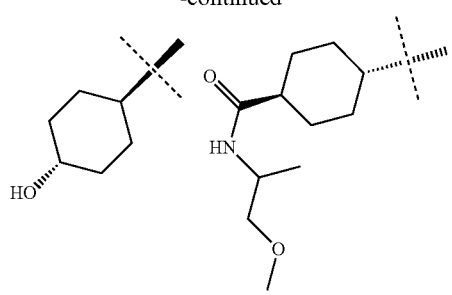
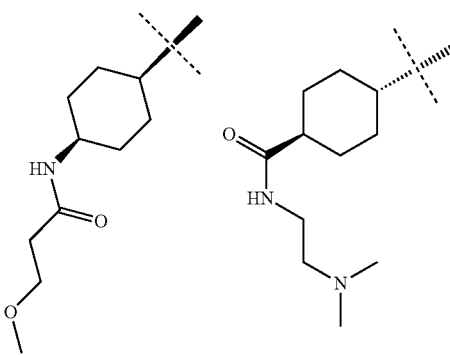
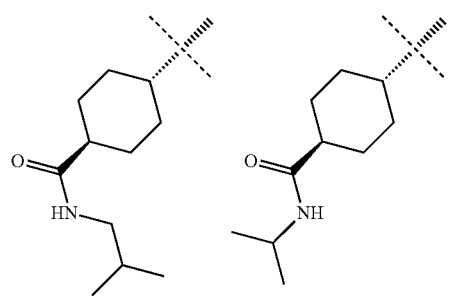
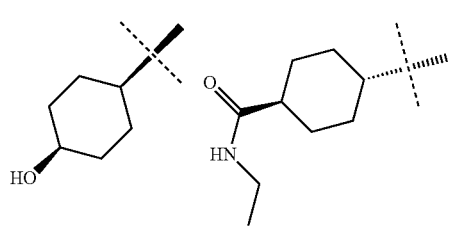
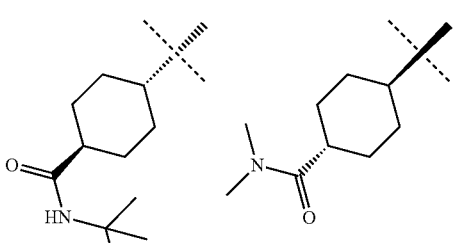
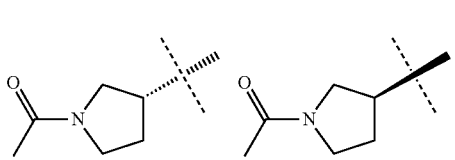

-continued

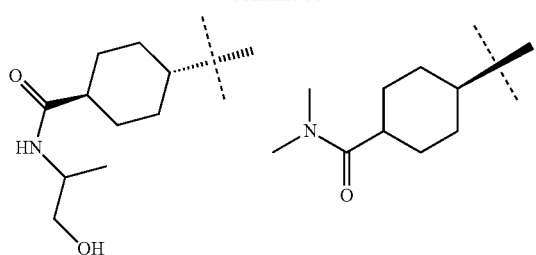
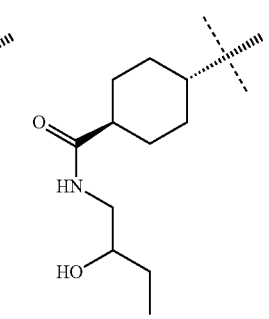
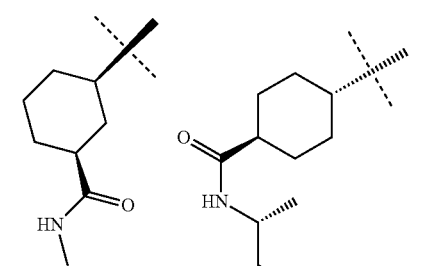
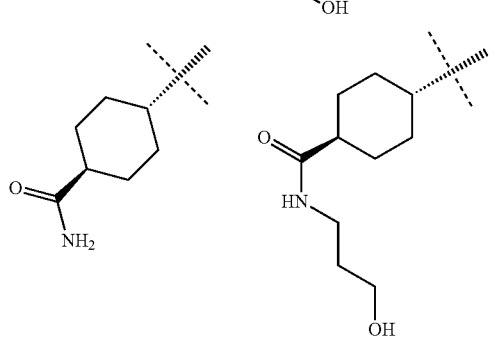
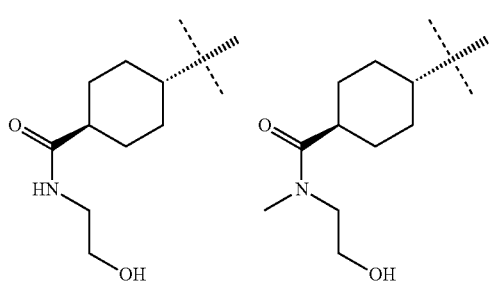
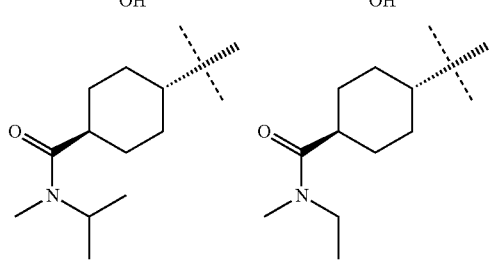

-continued

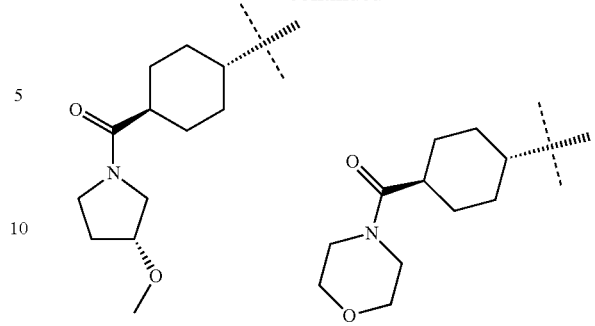
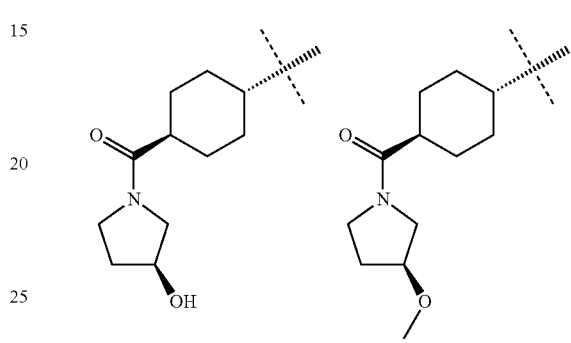
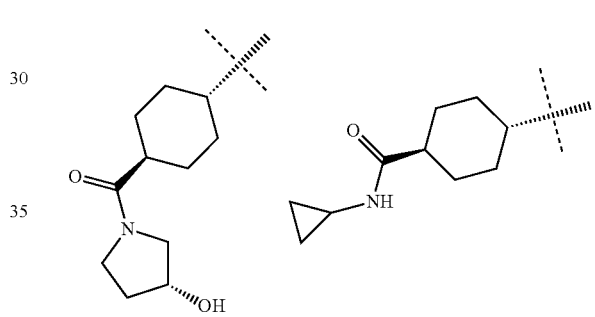
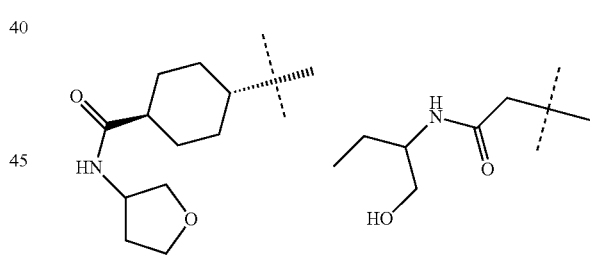
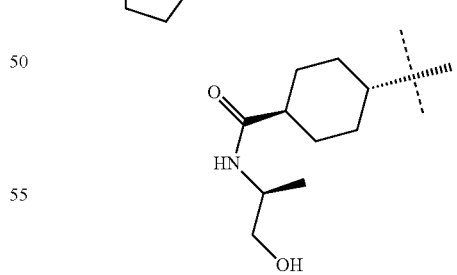

The group $R^b$ in Formula (I) and related Formulae preferably denotes H.

Alternatively, $R^b$ may denote a group selected from COHet or a linear or branched $C_1$-$C_6$-alkyl group wherein 1 H atoms may be replaced by a group selected from $NR^3$ or $OR^3$, and wherein 1 $CH_2$ group may be replaced by a group CO.

More specifically, $R^b$ in Formula (I) and related Formulae may be selected from the following groups:

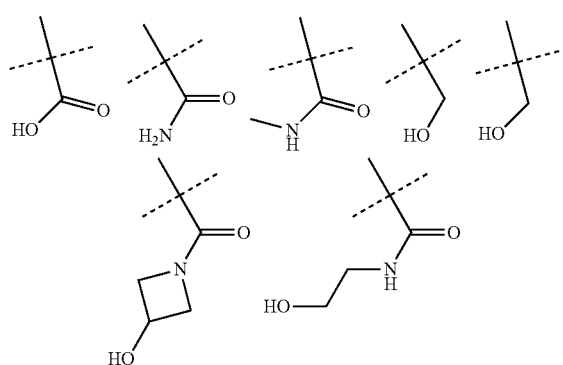

Het, in Formula (I) and related Formulae preferably denotes a saturated 4-6-membered single ring containing 1 heteroatom selected from nitrogen, wherein 1 H atom may be replaced by a group selected from $COC_1$-$C_6$-alkyl, and an oxacyclohexane.

Alternatively, Het in Formula (I) and related Formulae denotes a 4-9-membered spiro- or bridged bicyclic ring, containing 1 to 2 heteroatoms selected from Nitrogen and oxygen, and optionally monosubstituted by a group A.

More preferably, Het denotes a piperidine group wherein 1 or 2 H atom may be independently replaced by a group selected from A, OA, COA, CN, Hal, $NO_2$, $OR^3$, SOA and $SO_2A$.

$Cyc^1$ is cyclopropyl, cyclobytyl, cyclopentyl, cyclohexyl or cycloheptyl.

The compounds of the present invention also include compounds of Formula (Ia)

(Ia)

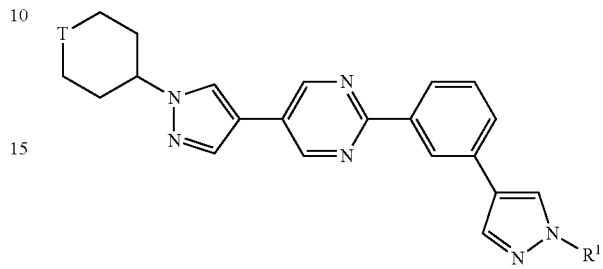

Wherein T denotes a group NCOA, whereby A is as defined above or T denotes a carbon atom which may be substituted by $CON(R^3)_2$ whereby $R^3$ is as defined above, and wherein $R^1$ in Formula (Ia) is as defined above.

The following compounds are the most preferred:

| Ex | |
|---|---|
| 1 | 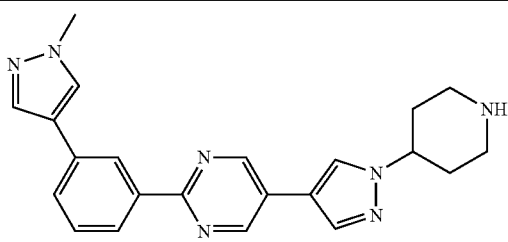 |
| 2 | 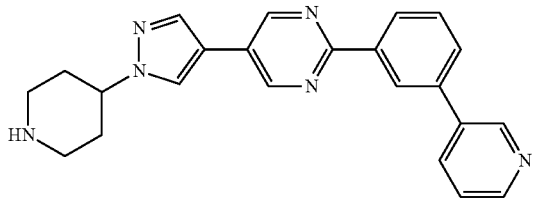 [SMILES: c1cncc(-c2cccc(-c3ncc(-c4cnn(C5CCNCC5)c4)cn3)c2)c1] |
| 3 | 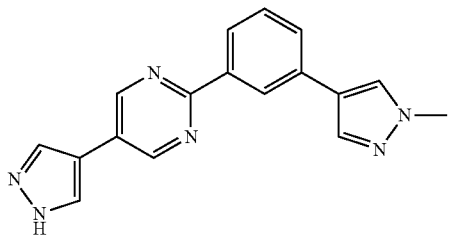 [SMILES: Cn1cc(-c2cccc(-c3ncc(-c4cn[nH]c4)cn3)c2)cn1] |
| 4 | 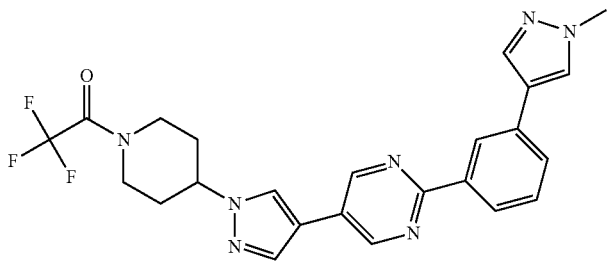 [SMILES: Cn1cc(-c2cccc(-c3ncc(-c4cnn(C5CCN(C(=O)C(F)(F)F)CC5)c4)cn3)c2)cn1] |

-continued
| Ex | |
|---|---|
| 5 | 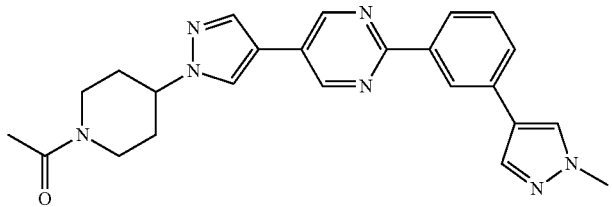 [SMILES: CC(=O)N1CCC(n2cc(-c3cnc(-c4cccc(-c5cnn(C)c5)c4)nc3)cn2)CC1] |
| 6 | 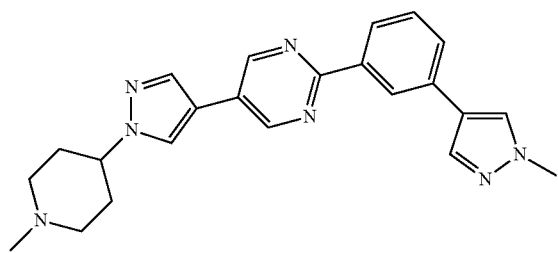 |
| 7 | 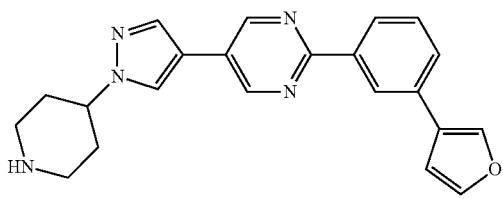 [SMILES: c1cc(-c2ccoc2)cc(-c2ncc(-c3cnn(C4CCNCC4)c3)cn2)c1] |
| 8 | 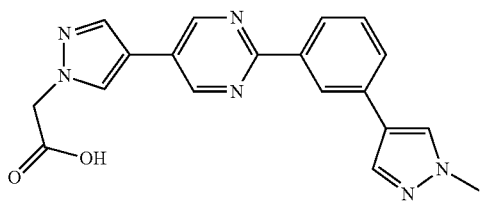 [SMILES: Cn1cc(-c2cccc(-c3ncc(-c4cnn(CC(=O)O)c4)cn3)c2)cn1] |
| 9 | 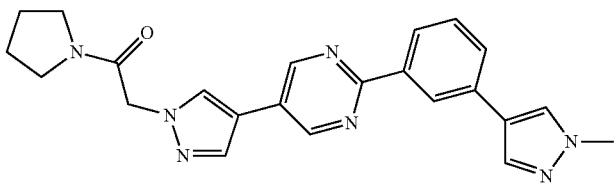 [SMILES: Cn1cc(-c2cccc(-c3ncc(-c4cnn(CC(=O)N5CCCC5)c4)cn3)c2)cn1] |
| 10 | 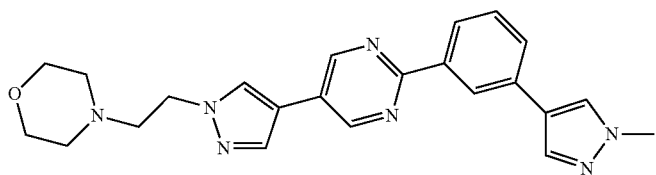 [SMILES: Cn1cc(-c2cccc(-c3ncc(-c4cnn(CCN5CCOCC5)c4)cn3)c2)cn1] |
| 11 | 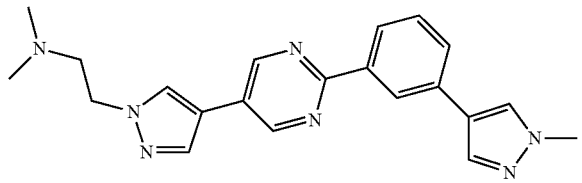 |

-continued
| Ex | |
|---|---|
| 12 | 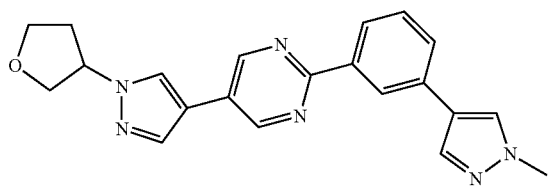 [SMILES: Cn1cc(-c2cccc(-c3ncc(-c4cnn(C5CCOC5)c4)cn3)c2)cn1] |
| 13 | 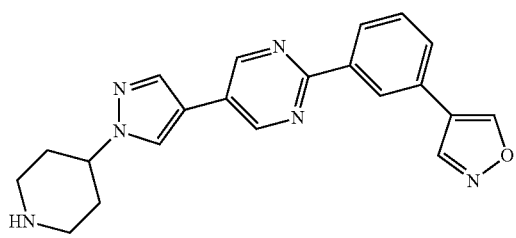 [SMILES: c1cc(-c2cnoc2)cc(-c2ncc(-c3cnn(C4CCNCC4)c3)cn2)c1] |
| 14 | 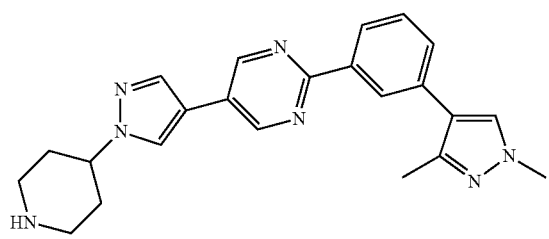 [SMILES: Cc1nn(C)cc1-c1cccc(-c2ncc(-c3cnn(C4CCNCC4)c3)cn2)c1] |
| 15 | 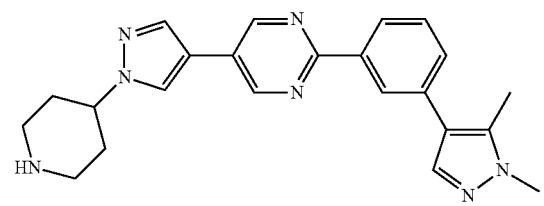 [SMILES: Cc1c(-c2cccc(-c3ncc(-c4cnn(C5CCNCC5)c4)cn3)c2)cnn1C] |
| 16 | 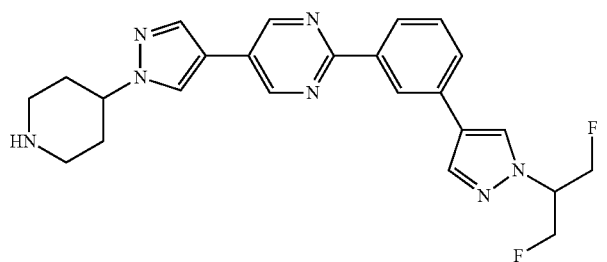 [SMILES: FCC(CF)n1cc(-c2cccc(-c3ncc(-c4cnn(C5CCNCC5)c4)cn3)c2)cn1] |
| 17 | 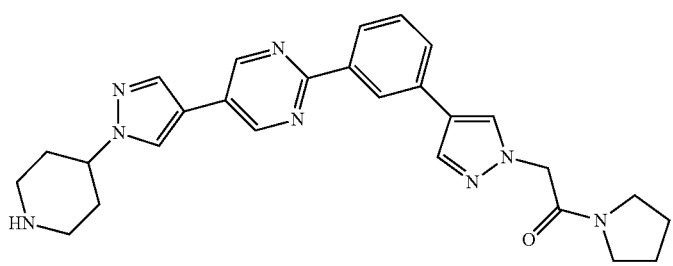 [SMILES: O=C(Cn1cc(-c2cccc(-c3ncc(-c4cnn(C5CCNCC5)c4)cn3)c2)cn1)N1CCCC1] |

-continued
| Ex | |
|---|---|
| 18 | 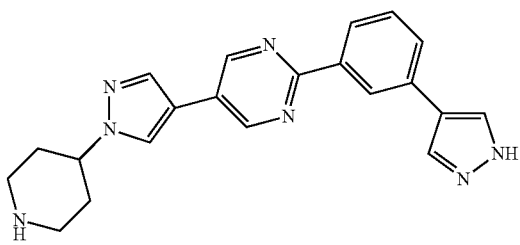 [SMILES: c1cc(-c2cn[nH]c2)cc(-c2ncc(-c3cnn(C4CCNCC4)c3)cn2)c1] |
| 19 | 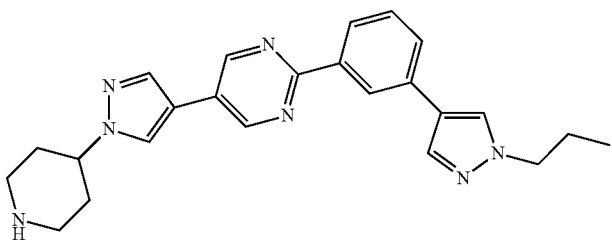 [SMILES: CCCn1cc(-c2cccc(-c3ncc(-c4cnn(C5CCNCC5)c4)cn3)c2)cn1] |
| 20 | 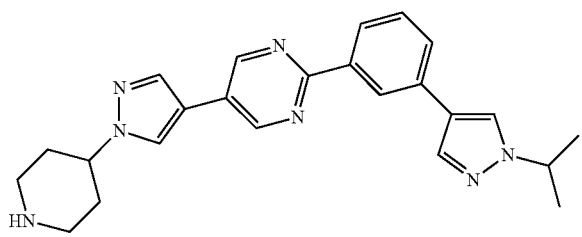 [SMILES: CC(C)n1cc(-c2cccc(-c3ncc(-c4cnn(C5CCNCC5)c4)cn3)c2)cn1] |
| 21 | 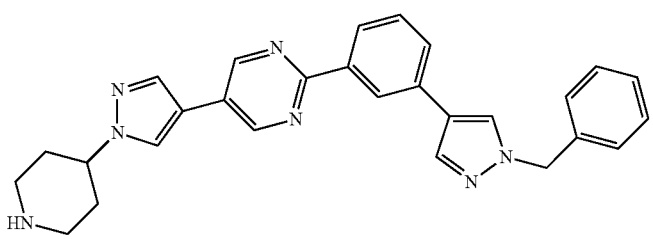 [SMILES: c1ccc(Cn2cc(-c3cccc(-c4ncc(-c5cnn(C6CCNCC6)c5)cn4)c3)cn2)cc1] |
| 22 | 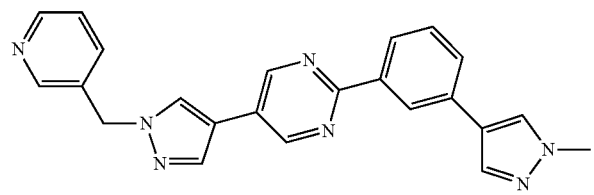 [SMILES: Cn1cc(-c2cccc(-c3ncc(-c4cnn(Cc5cccnc5)c4)cn3)c2)cn1] |
| 23 | 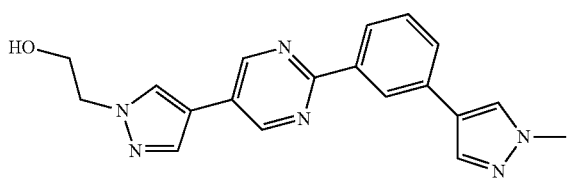 [SMILES: Cn1cc(-c2cccc(-c3ncc(-c4cnn(CCO)c4)cn3)c2)cn1] |

-continued
| Ex | |
|---|---|
| 24 | 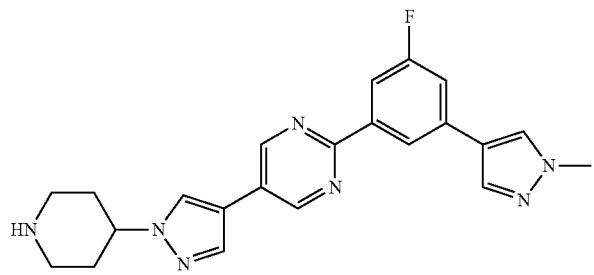 [SMILES: Cn1cc(-c2cc(F)cc(-c3ncc(-c4cnn(C5CCNCC5)c4)cn3)c2)cn1] |
| 25 | 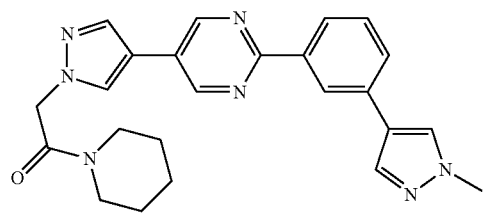 [SMILES: Cn1cc(-c2cccc(-c3ncc(-c4cnn(CC(=O)N5CCCCC5)c4)cn3)c2)cn1] |
| 26 | 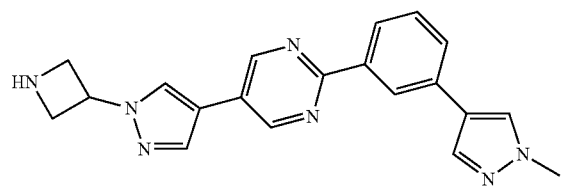 [SMILES: Cn1cc(-c2cccc(-c3ncc(-c4cnn(C5CNC5)c4)cn3)c2)cn1] |
| 27 | 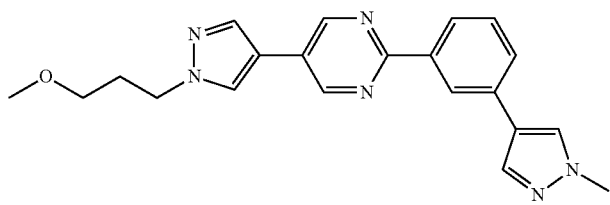 |
| 28 | 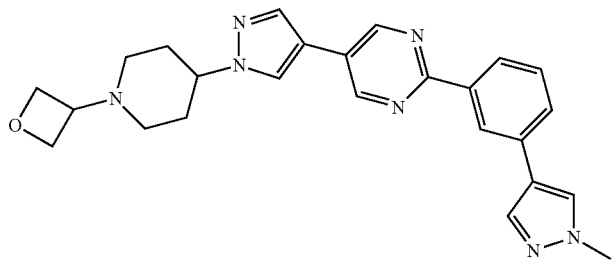 [SMILES: Cn1cc(-c2cccc(-c3ncc(-c4cnn(C5CCN(C6COC6)CC5)c4)cn3)c2)cn1] |
| 29 | 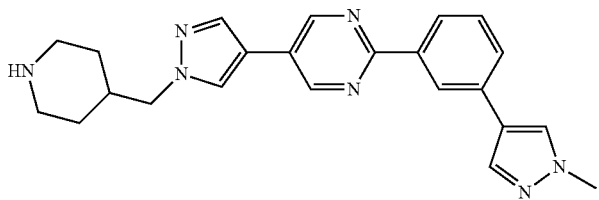 [SMILES: Cn1cc(-c2cccc(-c3ncc(-c4cnn(CC5CCNCC5)c4)cn3)c2)cn1] |

-continued
| Ex | |
|---|---|
| 30 | 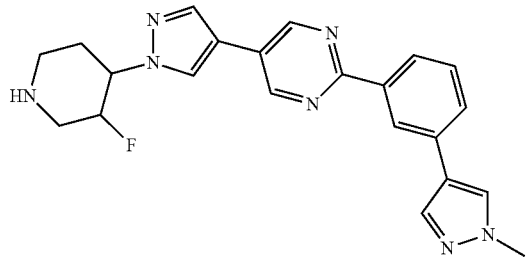 [SMILES: Cn1cc(-c2cccc(-c3ncc(-c4cnn(C5CCNCC5F)c4)cn3)c2)cn1] |
| 31 | 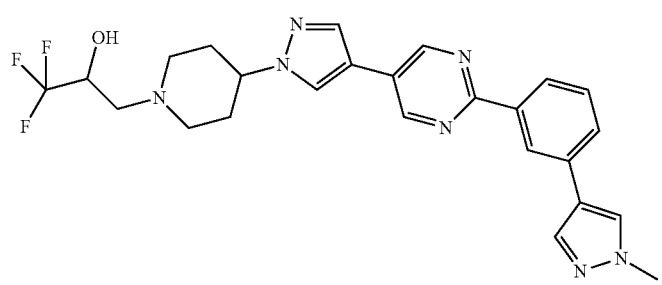 [SMILES: Cn1cc(-c2cccc(-c3ncc(-c4cnn(C5CCN(CC(O)C(F)(F)F)CC5)c4)cn3)c2)cn1] |
| 32 | 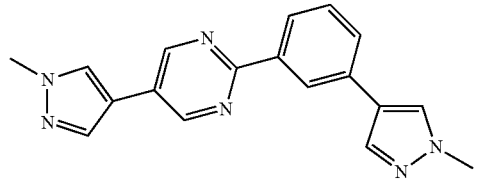 |
| 33 | 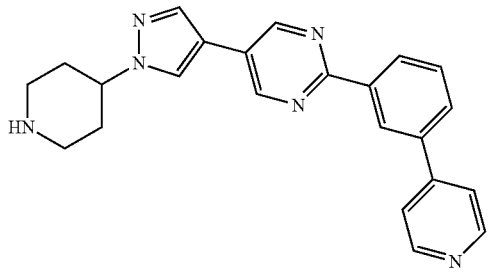 [SMILES: c1cc(-c2ccncc2)cc(-c2ncc(-c3cnn(C4CCNCC4)c3)cn2)c1] |
| 34 | 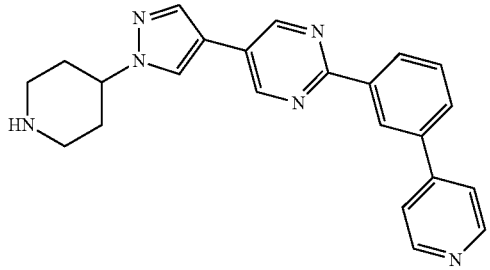 [SMILES: c1cc(-c2ccncc2)cc(-c2ncc(-c3cnn(C4CCNCC4)c3)cn2)c1] |
| 35 | 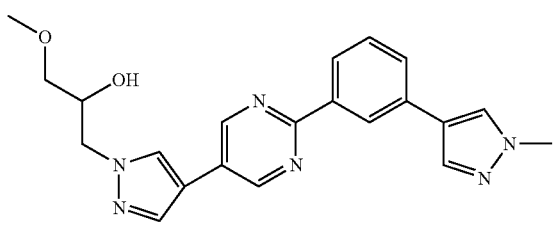 |

| Ex | |
|---|---|
| 36 | 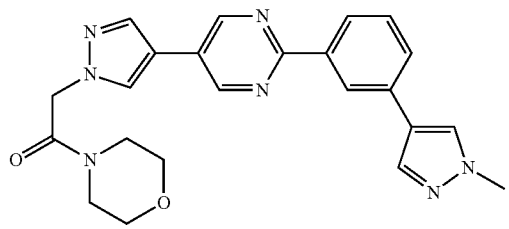 [SMILES: Cn1cc(-c2cccc(-c3ncc(-c4cnn(CC(=O)N5CCOCC5)c4)cn3)c2)cn1] |
| 37 | 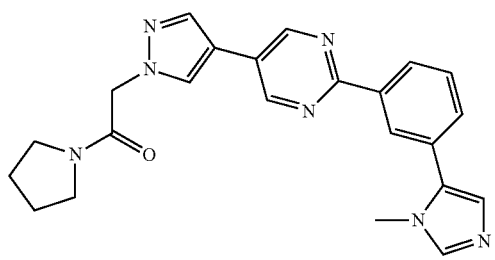 [SMILES: Cn1cncc1-c1cccc(-c2ncc(-c3cnn(CC(=O)N4CCCC4)c3)cn2)c1] |
| 38 | 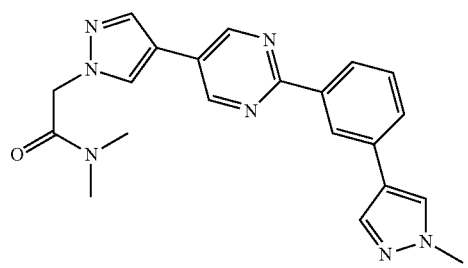 [SMILES: CN(C)C(=O)Cn1cc(-c2cnc(-c3cccc(-c4cnn(C)c4)c3)nc2)cn1] |
| 39 | 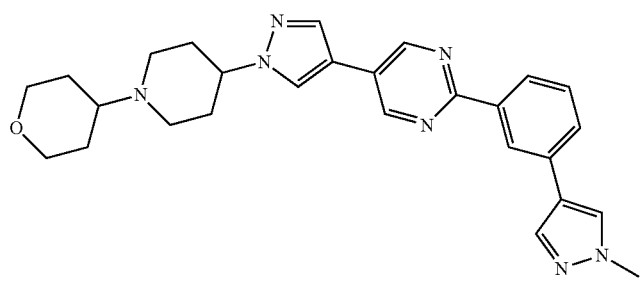 [SMILES: Cn1cc(-c2cccc(-c3ncc(-c4cnn(C5CCN(C6CCOCC6)CC5)c4)cn3)c2)cn1] |
| 40 | 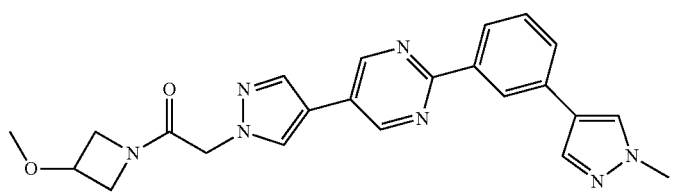 |
| 41 | 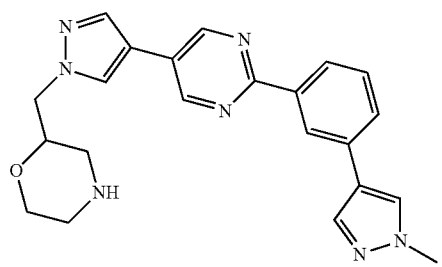 [SMILES: Cn1cc(-c2cccc(-c3ncc(-c4cnn(CC5CNCCO5)c4)cn3)c2)cn1] |

| Ex |
|---|
| 42 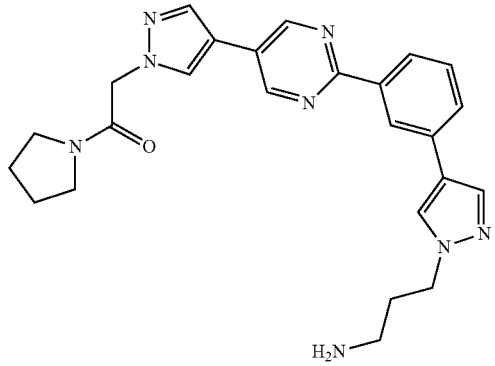 [SMILES: NCCCn1cc(-c2cccc(-c3ncc(-c4cnn(CC(=O)N5CCCC5)c4)cn3)c2)cn1] |
| 43 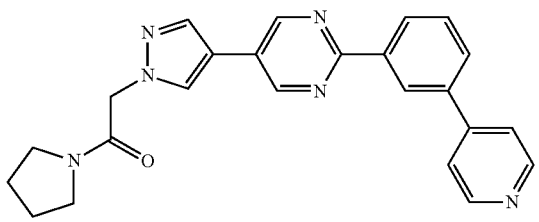 [SMILES: O=C(Cn1cc(-c2cnc(-c3cccc(-c4ccncc4)c3)nc2)cn1)N1CCCC1] |
| 44 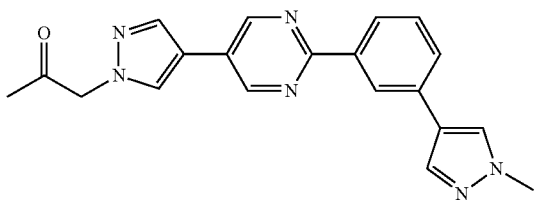 [SMILES: CC(=O)Cn1cc(-c2cnc(-c3cccc(-c4cnn(C)c4)c3)nc2)cn1] |
| 45 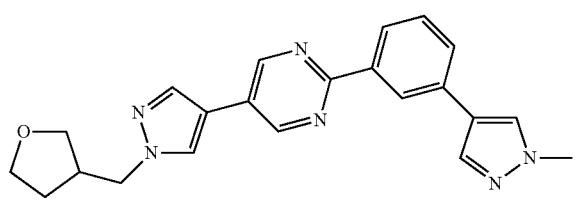 [SMILES: Cn1cc(-c2cccc(-c3ncc(-c4cnn(CC5CCOC5)c4)cn3)c2)cn1] |
| 46 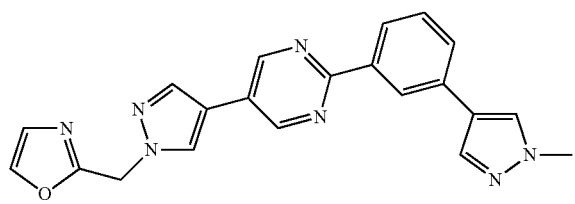 [SMILES: Cn1cc(-c2cccc(-c3ncc(-c4cnn(Cc5ncco5)c4)cn3)c2)cn1] |
| 47 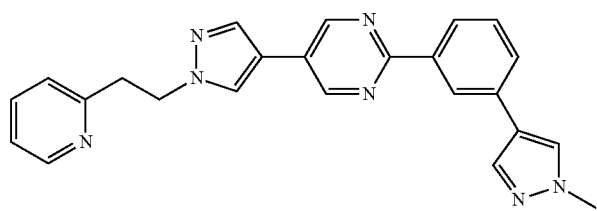 [SMILES: Cn1cc(-c2cccc(-c3ncc(-c4cnn(CCc5ccccn5)c4)cn3)c2)cn1] |

-continued
| Ex | |
|---|---|
| 48 | 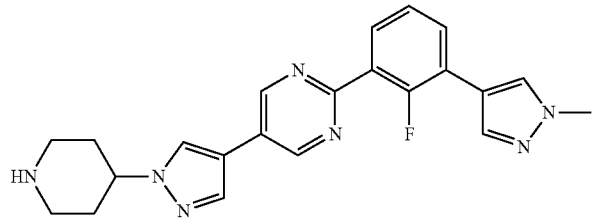 [SMILES: Cn1cc(-c2cccc(-c3ncc(-c4cnn(C5CCNCC5)c4)cn3)c2F)cn1] |
| 49 | 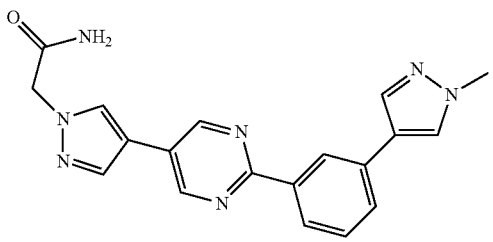 [SMILES: Cn1cc(-c2cccc(-c3ncc(-c4cnn(CC(N)=O)c4)cn3)c2)cn1] |
| 50 | 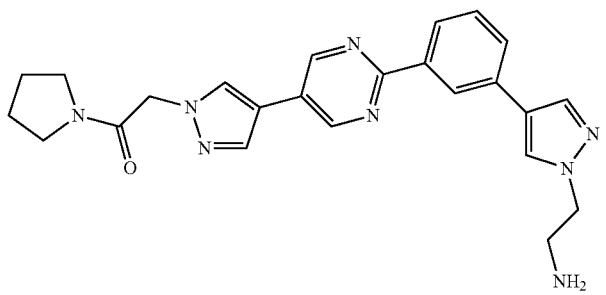 [SMILES: NCCn1cc(-c2cccc(-c3ncc(-c4cnn(CC(=O)N5CCCC5)c4)cn3)c2)cn1] |
| 51 | 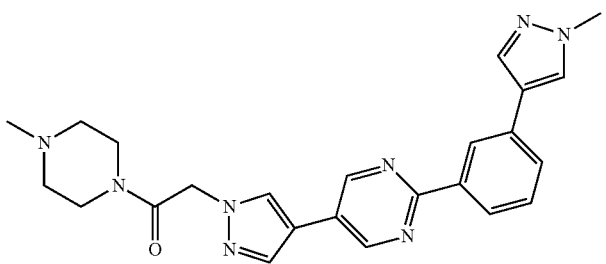 |
| 52 | 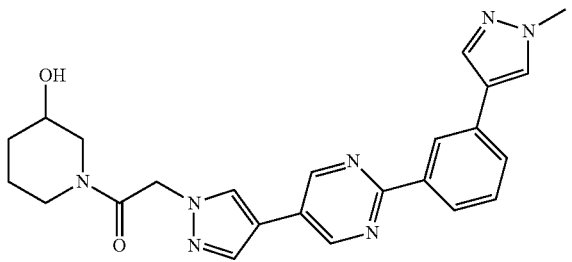 [SMILES: Cn1cc(-c2cccc(-c3ncc(-c4cnn(CC(=O)N5CCCC(O)C5)c4)cn3)c2)cn1] |
| 53 | 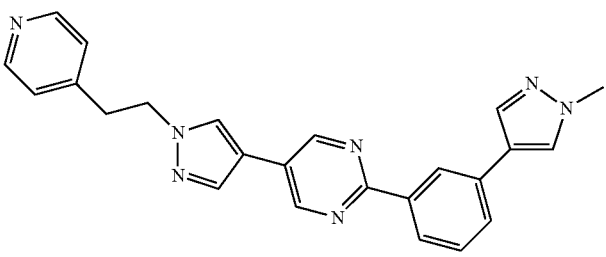 [SMILES: Cn1cc(-c2cccc(-c3ncc(-c4cnn(CCc5ccncc5)c4)cn3)c2)cn1] |

| Ex |
|---|
| 54 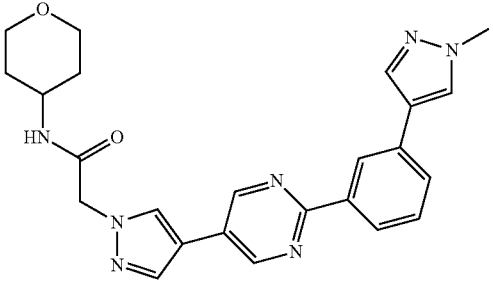 [SMILES: Cn1cc(-c2cccc(-c3ncc(-c4cnn(CC(=O)NC5CCOCC5)c4)cn3)c2)cn1] |
| 55 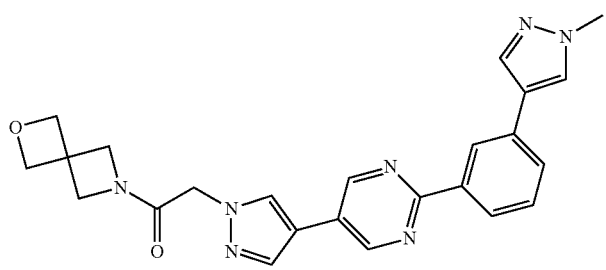 [SMILES: Cn1cc(-c2cccc(-c3ncc(-c4cnn(CC(=O)N5CC6(COC6)C5)c4)cn3)c2)cn1] |
| 56 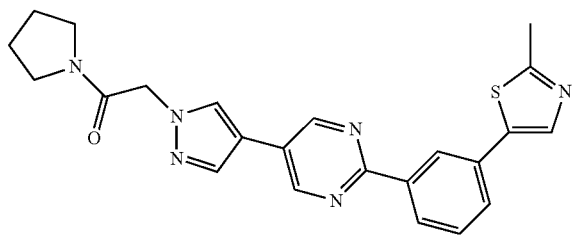 [SMILES: Cc1ncc(-c2cccc(-c3ncc(-c4cnn(CC(=O)N5CCCC5)c4)cn3)c2)s1] |
| 57 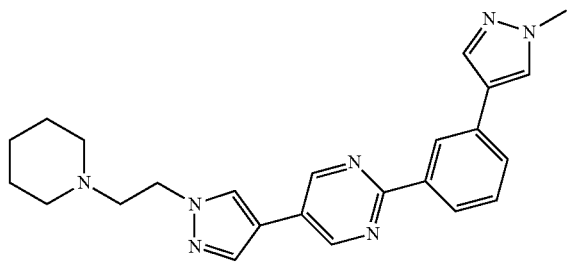 [SMILES: Cn1cc(-c2cccc(-c3ncc(-c4cnn(CCN5CCCCC5)c4)cn3)c2)cn1] |
| 58 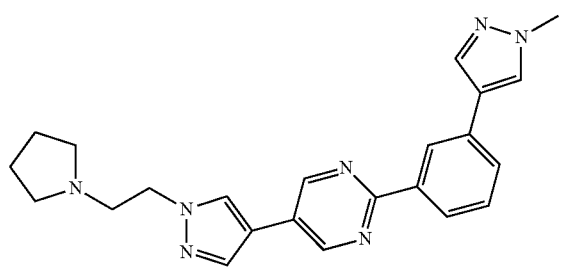 [SMILES: Cn1cc(-c2cccc(-c3ncc(-c4cnn(CCN5CCCC5)c4)cn3)c2)cn1] |

| Ex | |
|---|---|
| 59 | 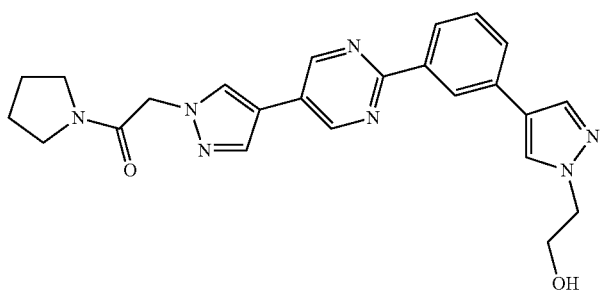 [SMILES: O=C(Cn1cc(-c2cnc(-c3cccc(-c4cnn(CCO)c4)c3)nc2)cn1)N1CCCC1] |
| 60 | 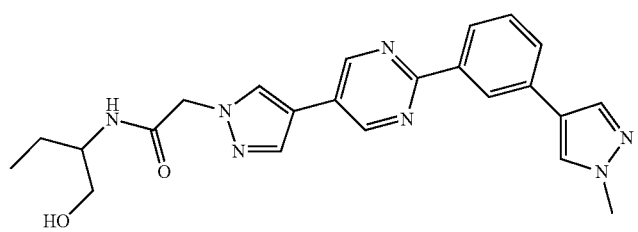 [SMILES: CCC(CO)NC(=O)Cn1cc(-c2cnc(-c3cccc(-c4cnn(C)c4)c3)nc2)cn1] |
| 61 | 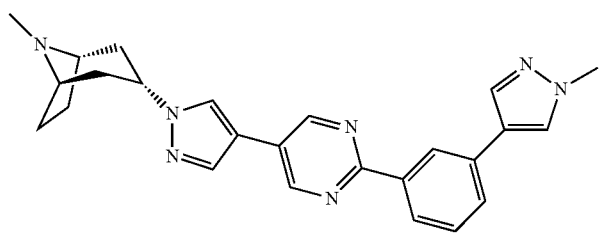 |
| 62 | 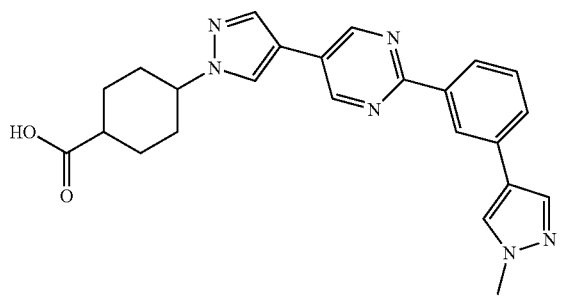 [SMILES: Cn1cc(-c2cccc(-c3ncc(-c4cnn(C5CCC(C(=O)O)CC5)c4)cn3)c2)cn1] |
| 63 | 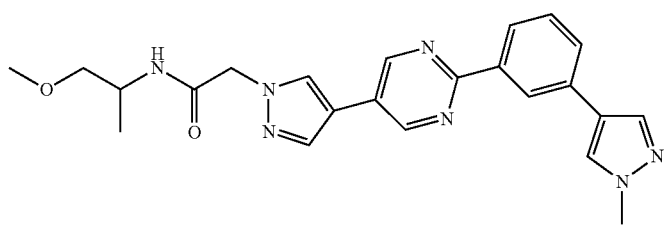 [SMILES: COCC(C)NC(=O)Cn1cc(-c2cnc(-c3cccc(-c4cnn(C)c4)c3)nc2)cn1] |
| 64 | 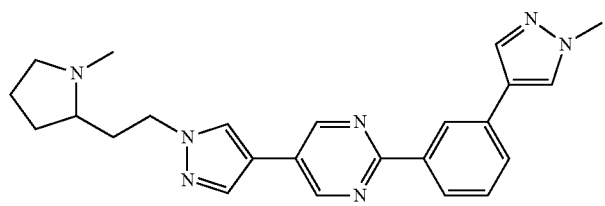 [SMILES: CN1CCCC1CCn1cc(-c2cnc(-c3cccc(-c4cnn(C)c4)c3)nc2)cn1] |

-continued
| Ex | |
|---|---|
| 65 | 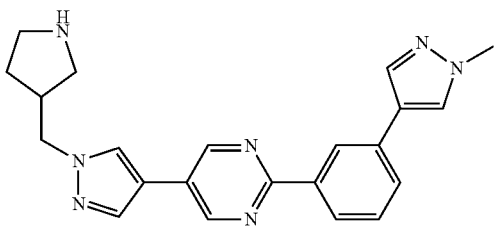 [SMILES: Cn1cc(-c2cccc(-c3ncc(-c4cnn(CC5CCNC5)c4)cn3)c2)cn1] |
| 66 | 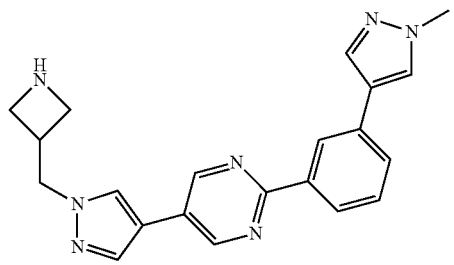 [SMILES: Cn1cc(-c2cccc(-c3ncc(-c4cnn(CC5CNC5)c4)cn3)c2)cn1] |
| 67 | 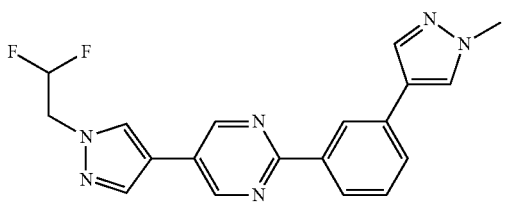 [SMILES: Cn1cc(-c2cccc(-c3ncc(-c4cnn(CC(F)F)c4)cn3)c2)cn1] |
| 68 | 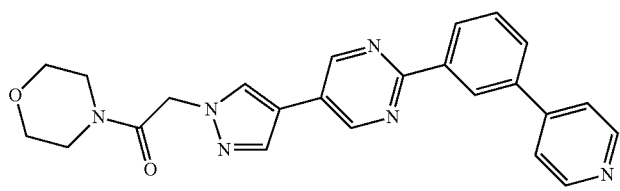 [SMILES: O=C(Cn1cc(-c2cnc(-c3cccc(-c4ccncc4)c3)nc2)cn1)N1CCOCC1] |
| 69 | 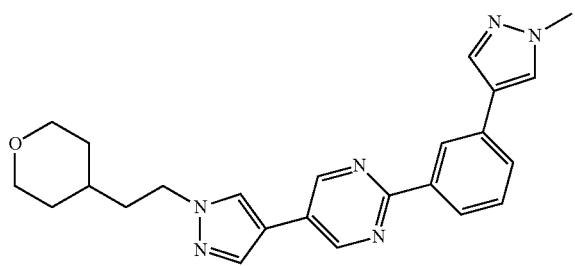 [SMILES: Cn1cc(-c2cccc(-c3ncc(-c4cnn(CCC5CCOCC5)c4)cn3)c2)cn1] |
| 70 | 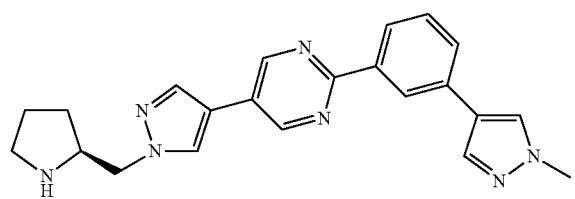 [SMILES: Cn1cc(-c2cccc(-c3ncc(-c4cnn(C[C@@H]5CCCN5)c4)cn3)c2)cn1] |
| 71 | 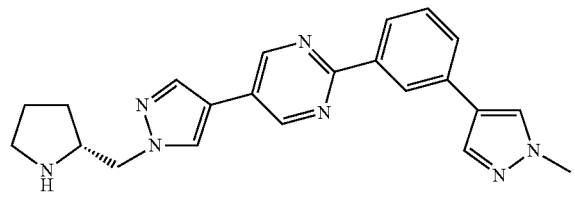 [SMILES: Cn1cc(-c2cccc(-c3ncc(-c4cnn(C[C@H]5CCCN5)c4)cn3)c2)cn1] |

| Ex | |
|---|---|
| 72 | 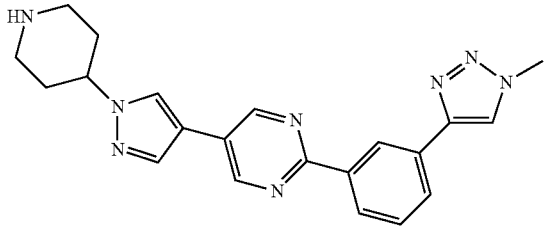 [SMILES: Cn1cc(-c2cccc(-c3ncc(-c4cnn(C5CCNCC5)c4)cn3)c2)nn1] |
| 73 | 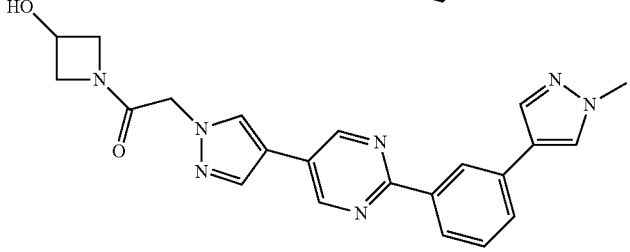 [SMILES: Cn1cc(-c2cccc(-c3ncc(-c4cnn(CC(=O)N5CC(O)C5)c4)cn3)c2)cn1] |
| 74 | 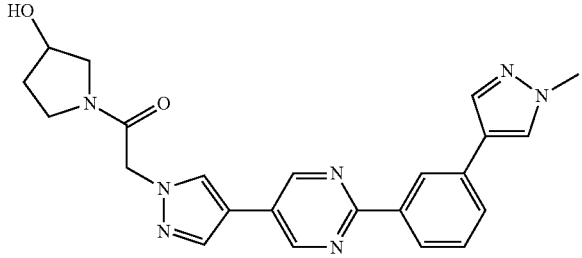 [SMILES: Cn1cc(-c2cccc(-c3ncc(-c4cnn(CC(=O)N5CCC(O)C5)c4)cn3)c2)cn1] |
| 75 | 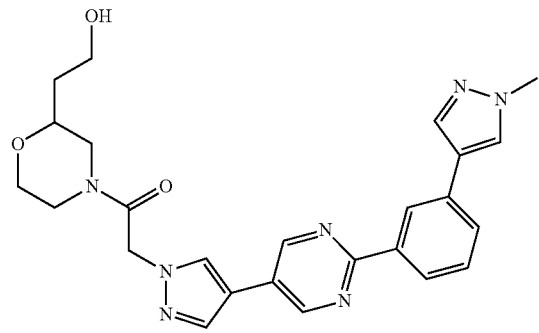 [SMILES: Cn1cc(-c2cccc(-c3ncc(-c4cnn(CC(=O)N5CCOC(CCO)C5)c4)cn3)c2)cn1] |
| 76 | 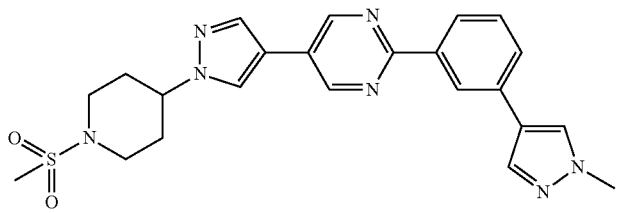<br>HPLC: (max plot) 96%; (254 nm) 96%; Rt (min) 3.38; MS: (ESI+): 464.4 |
| 77 | 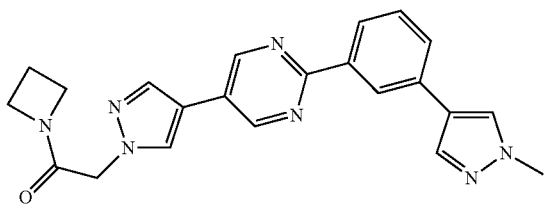 [SMILES: Cn1cc(-c2cccc(-c3ncc(-c4cnn(CC(=O)N5CCC5)c4)cn3)c2)cn1]<br>HPLC: (max plot) 99%; (254 nm) 99%; Rt (min) 2.64; MS: (ESI+) 400.2. |

| Ex | |
|---|---|
| 78 | 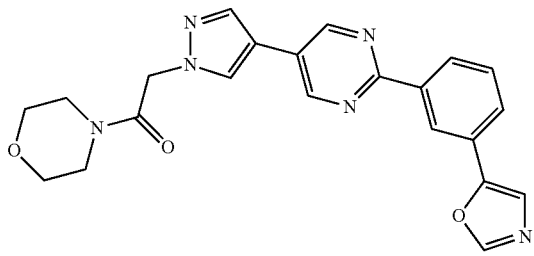 [SMILES: O=C(Cn1cc(-c2cnc(-c3cccc(-c4cnco4)c3)nc2)cn1)N1CCOCC1]
HPLC: (max plot) 99%; (254 nm) 99%; Rt (min) 2.72; MS: (ESI+): 417.4. |
| 79 | 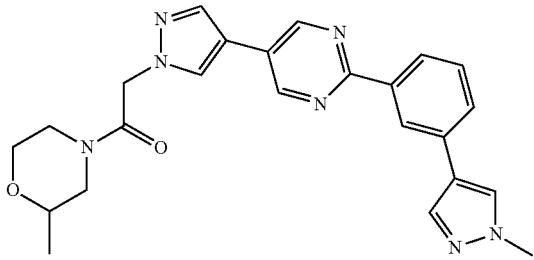 [SMILES: CC1CN(C(=O)Cn2cc(-c3cnc(-c4cccc(-c5cnn(C)c5)c4)nc3)cn2)CCO1]
HPLC (max plot) 98%; (254 nm) 99%; Rt (min) 2.27; MS: (ESI+): 417.4 |
| 80 | 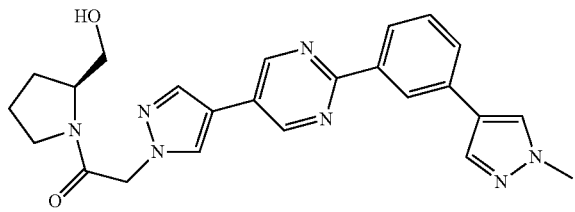 [SMILES: Cn1cc(-c2cccc(-c3ncc(-c4cnn(CC(=O)N5CCC[C@H]5CO)c4)cn3)c2)cn1]
HPLC (max plot) 95%; (254 nm) 95%; Rt 2.81; MS: (ESI+) 444.2 |
| 81 | 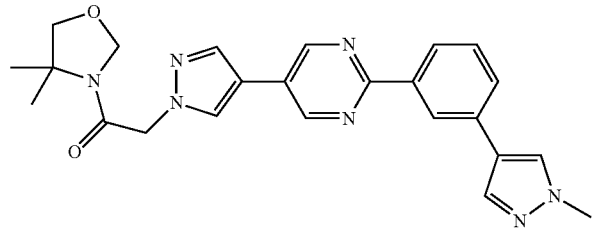
HPLC (max plot) 100%; (254 nm) 100%; Rt 2.59; MS: (ESI+) 444.2 |
| 82 | 
HPLC (max plot) 94%; (254 nm) 93%; Rt (min) 2.69; MS: (ESI+) 432.2. |

| Ex |
| --- |
| 82a |
| 83 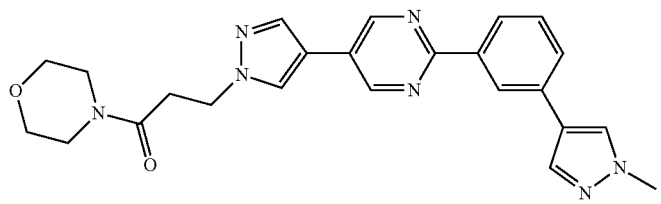 [SMILES: Cn1cc(-c2cccc(-c3ncc(-c4cnn(CCC(=O)N5CCOCC5)c4)cn3)c2)cn1]
HPLC (max plot) 100%; (254 nm) 100%; Rt (min) 2.73; MS: (ESI+) 444.2 |
| 84 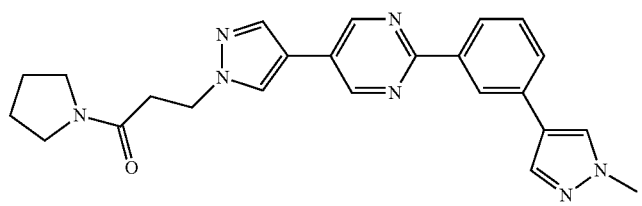 [SMILES: Cn1cc(-c2cccc(-c3ncc(-c4cnn(CCC(=O)N5CCCC5)c4)cn3)c2)cn1]
HPLC (max plot) 95%; (254 nm) 97%; Rt (min) 2.97; MS: (ESI+) 428.3 |
| 85 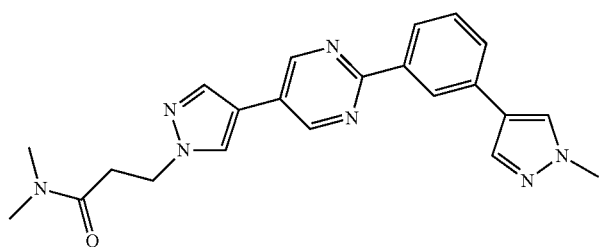
HPLC (max plot) 99%; (254 nm) 100%; Rt (min) 2.77; MS: (ESI+) 402.2 |
| 86 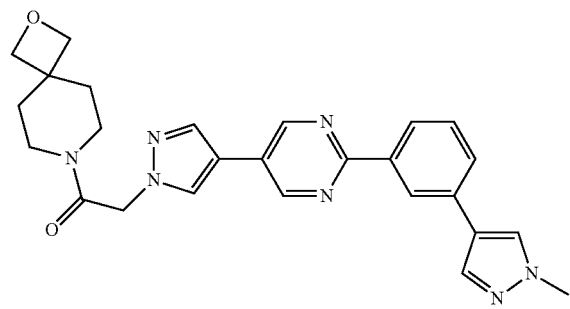 [SMILES: Cn1cc(-c2cccc(-c3ncc(-c4cnn(CC(=O)N5CCC6(CC5)COC6)c4)cn3)c2)cn1]
HPLC (max plot) 100%; (254 nm) 99%; Rt (min) 2.92; MS: (ESI+) 488.3 |
| 87 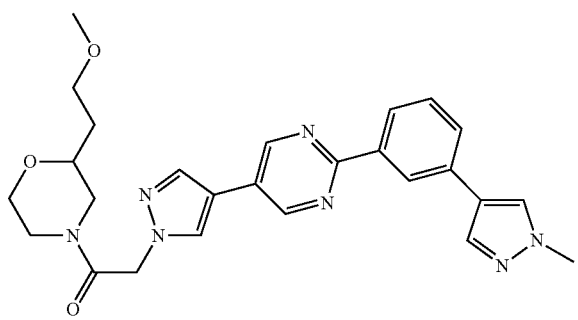 [SMILES: COCCC1CN(C(=O)Cn2cc(-c3cnc(-c4cccc(-c5cnn(C)c5)c4)nc3)cn2)CCO1]
HPLC (max plot) 100%; (254 nm) 99%; Rt (min) 2.92; MS: (ESI+) 488.3 |

| Ex | |
|---|---|
| 88 | 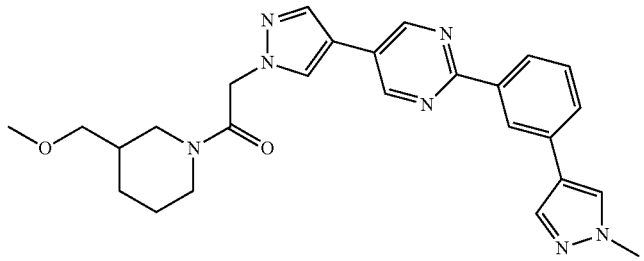<br>HPLC (max plot) 99%; (254 nm) 99%; Rt (min) 3.15; MS: (ESI+) 472.3 |
| 89 | 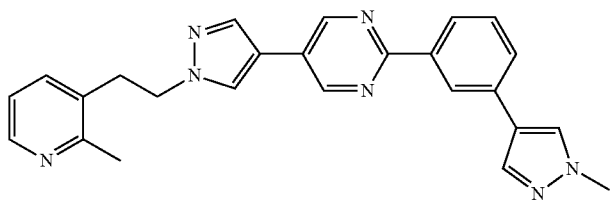 [SMILES: Cc1ncccc1CCn1cc(-c2cnc(-c3cccc(-c4cnn(C)c4)c3)nc2)cn1]<br>HPLC (max plot) 100%; (254 nm) 100%; Rt (min) 2.54; MS: (ESI+) 422.4 |
| 90 | 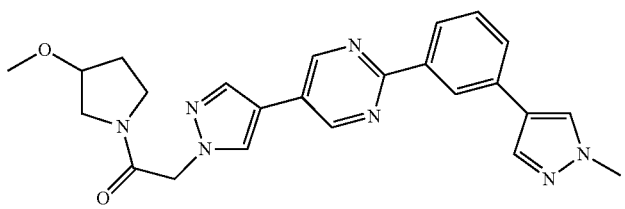<br>HPLC (max plot) 100%; (254 nm) 100%; Rt (min) 2.90; MS: (ESI+) 444.2 |
| 91 | 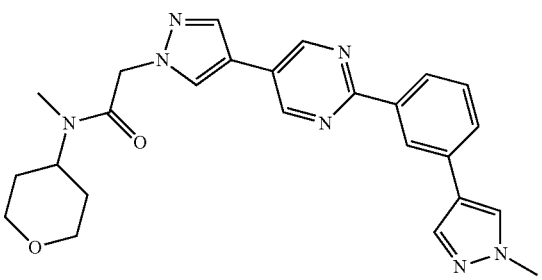 [SMILES: CN(C(=O)Cn1cc(-c2cnc(-c3cccc(-c4cnn(C)c4)c3)nc2)cn1)C1CCOCC1]<br>HPLC (max plot) 100%; (254 nm) 100%; Rt (min) 2.95; MS: (ESI+) 458.3 |
| 92 | 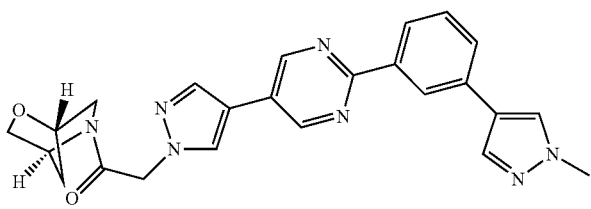 [SMILES: Cn1cc(-c2cccc(-c3ncc(-c4cnn(CC(=O)N5C[C@@H]6C[C@H]5CO6)c4)cn3)c2)cn1]<br>HPLC (max plot) 100%; (254 nm) 100%; Rt (min) 2.72; MS: (ESI+) 442.2 |

| Ex | |
|---|---|
| 93 | 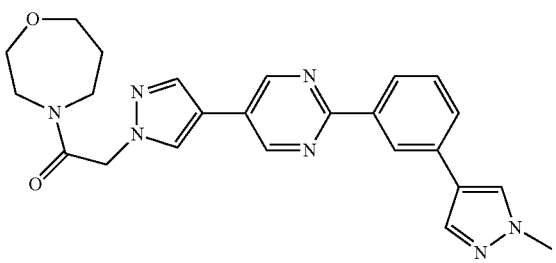 [SMILES: Cn1cc(-c2cccc(-c3ncc(-c4cnn(CC(=O)N5CCCOCC5)c4)cn3)c2)cn1]
HPLC (max plot) 100%; (254 nm) 100%; Rt (min) 2.84; MS: (ESI+) 444.2 |
| 94 | 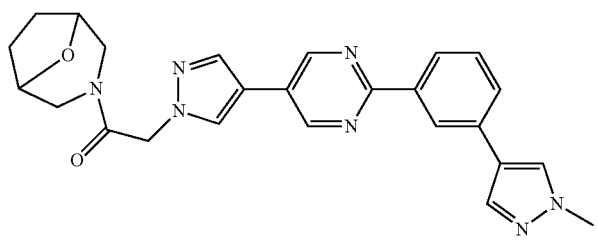 [SMILES: Cn1cc(-c2cccc(-c3ncc(-c4cnn(CC(=O)N5CC6CCC(C5)O6)c4)cn3)c2)cn1]
HPLC (max plot) 100%; (254 nm) 100%; Rt (min) 2.94; MS: (ESI+) 456.2 |
| 95 | 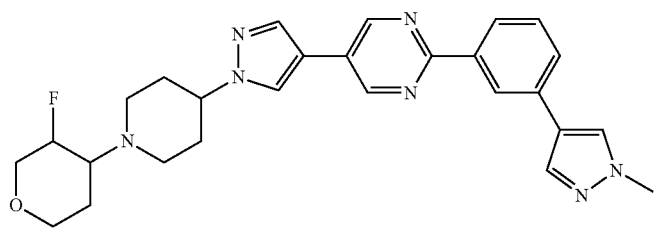 [SMILES: Cn1cc(-c2cccc(-c3ncc(-c4cnn(C5CCN(C6CCOCC6F)CC5)c4)cn3)c2)cn1] |
| 96 | 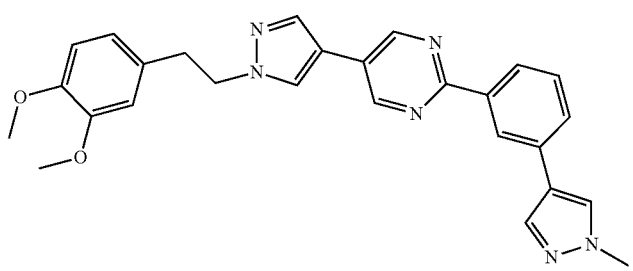
HPLC (max plot) 99%; (254 nm) 100%; Rt (min) 4.00; MS: (ESI+) 467.2 |
| 97 | 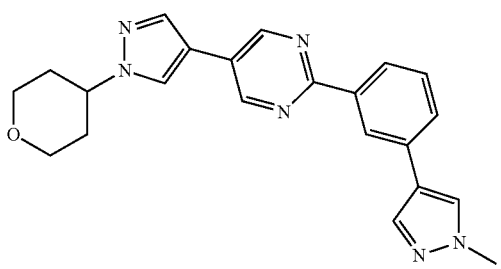 [SMILES: Cn1cc(-c2cccc(-c3ncc(-c4cnn(C5CCOCC5)c4)cn3)c2)cn1]
HPLC (max plot) 98%; (254 nm) 99%; Rt (min) 3.29; MS: (ESI+) 387.2 |

| Ex | |
|---|---|
| 98 | 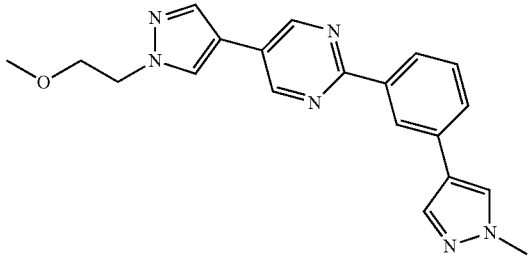<br>HPLC (max plot) 99%; (254 nm) 99%; Rt (min) 3.19; MS (ESI+) 361.2 |
| 99 | 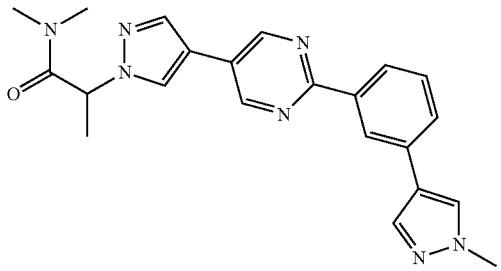 [SMILES: CC(C(=O)N(C)C)n1cc(-c2cnc(-c3cccc(-c4cnn(C)c4)c3)nc2)cn1]<br>HPLC (max plot) 99%; (254 nm) 99%; Rt (min) 2.86; MS: (ESI+) 402.2 |
| 100 | 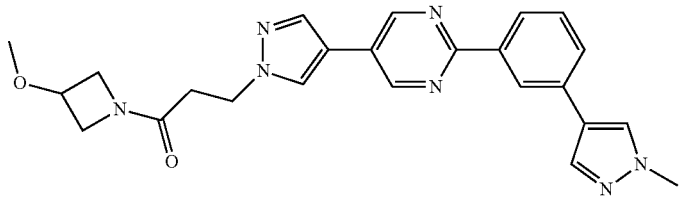<br>HPLC (max plot) 99%; (254 nm) 98%; Rt (min) 2.73; MS: (ESI+) 444.3 |
| 101 | 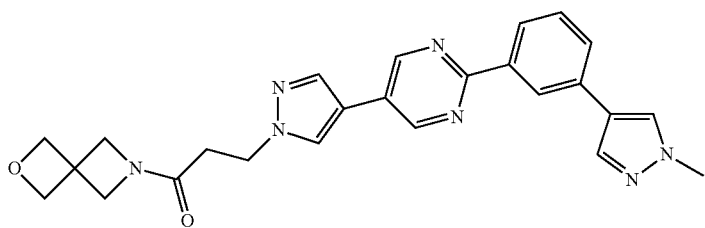 [SMILES: Cn1cc(-c2cccc(-c3ncc(-c4cnn(CCC(=O)N5CC6(COC6)C5)c4)cn3)c2)cn1]<br>HPLC (max plot) 100%; (254 nm) 100%; Rt (min) 2.55; MS: (ESI+) 456.2 |
| 102 | 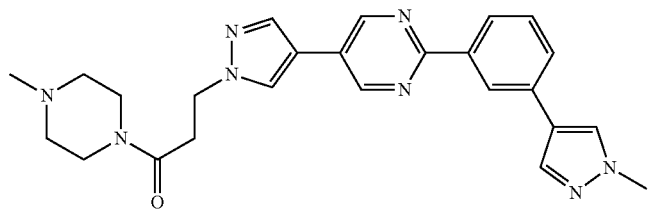<br>HPLC (max plot) 100%; (254 nm) 100%; Rt (min) 2.30; MS: (ESI+) 457.2 |

| Ex | |
|---|---|
| 103 | 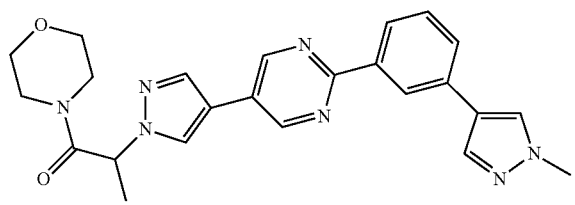 [SMILES: CC(C(=O)N1CCOCC1)n1cc(-c2cnc(-c3cccc(-c4cnn(C)c4)c3)nc2)cn1]
HPLC (max plot) 99%; (254 nm) 98%; Rt (min) 2.85; MS: (ESI+) 444.2 |
| 104 | 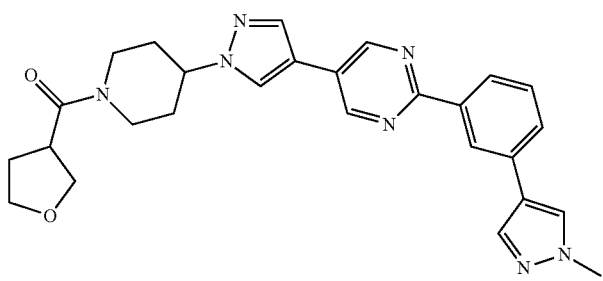 [SMILES: Cn1cc(-c2cccc(-c3ncc(-c4cnn(C5CCN(C(=O)C6CCOC6)CC5)c4)cn3)c2)cn1]
HPLC (max plot) 95%; (254 nm) 96%; Rt (min) 3.00; MS: (ESI+) 484.2 |
| 105 | 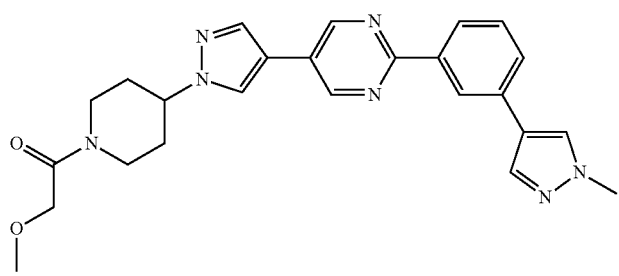 [SMILES: COCC(=O)N1CCC(n2cc(-c3cnc(-c4cccc(-c5cnn(C)c5)c4)nc3)cn2)CC1]
HPLC (max plot) 100%; (254 nm) 100%; Rt (min) 2.88; MS: (ESI+) 458.2 |
| 106 | 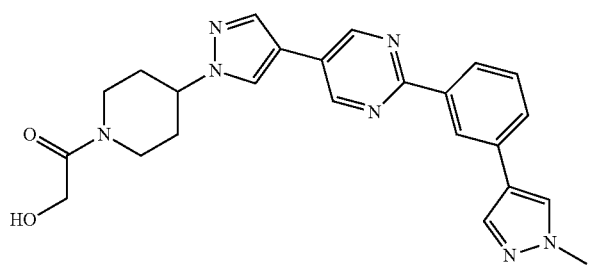 [SMILES: Cn1cc(-c2cccc(-c3ncc(-c4cnn(C5CCN(C(=O)CO)CC5)c4)cn3)c2)cn1]
HPLC (max plot) 100%; (254 nm) 97%; Rt (min) 2.74; MS: (ESI+) 444.4 |
| 107 | 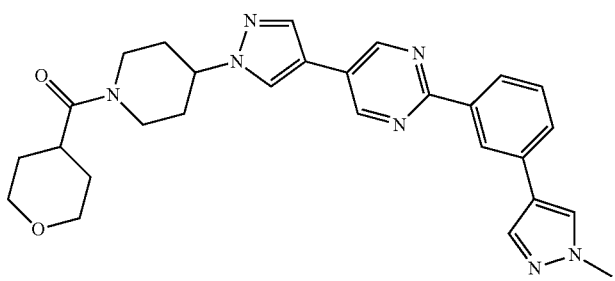 [SMILES: Cn1cc(-c2cccc(-c3ncc(-c4cnn(C5CCN(C(=O)C6CCOCC6)CC5)c4)cn3)c2)cn1]
HPLC (max plot) 99%; (254 nm) 99%; Rt (min) 3.21; MS: (ESI+) 498.5 |

| Ex | |
|---|---|
| 108 | 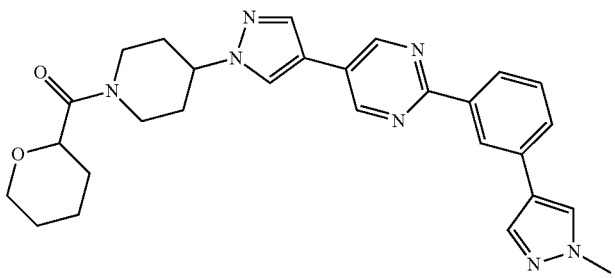 [SMILES: Cn1cc(-c2cccc(-c3ncc(-c4cnn(C5CCN(C(=O)C6CCCCO6)CC5)c4)cn3)c2)cn1]<br>HPLC (max plot) 100%; (254 nm) 100%; Rt (min) 3.49; MS: (ESI+) 498.4 |
| 109 | 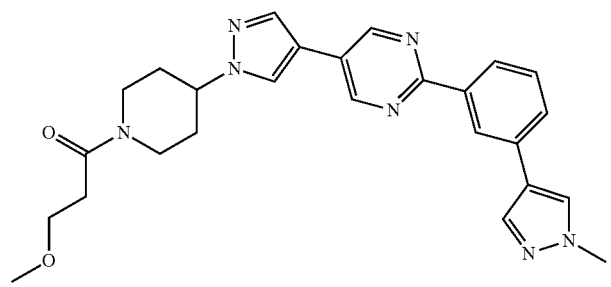<br>HPLC (max plot) 97%; (254 nm) 98%; Rt (min) 3.17; MS: (ESI+) 472.3 |
| 110 | 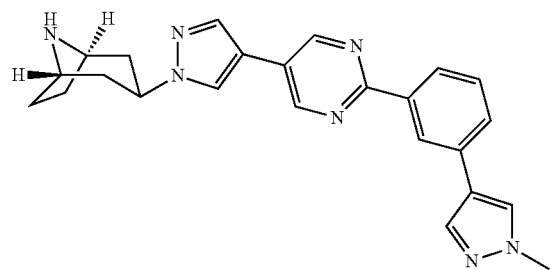 [SMILES: Cn1cc(-c2cccc(-c3ncc(-c4cnn(C5C[C@H]6CC[C@@H](C5)N6)c4)cn3)c2)cn1]<br>HPLC (max plot) 100%; (254 nm) 100%; Rt (min) 2.58; MS: (ESI+) 412.2 |
| 111 | 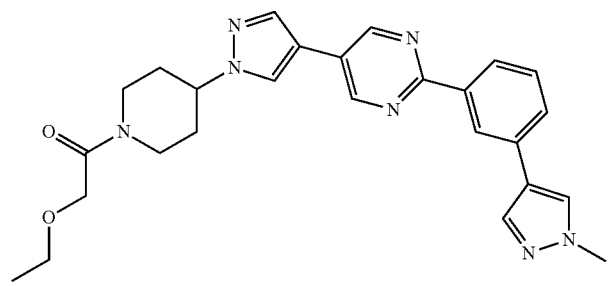 [SMILES: CCOCC(=O)N1CCC(n2cc(-c3cnc(-c4cccc(-c5cnn(C)c5)c4)nc3)cn2)CC1]<br>HPLC (max plot) 98%; (254 nm) 97%; Rt (min) 3.09; MS: (ESI+) 472.3 |
| 112 | 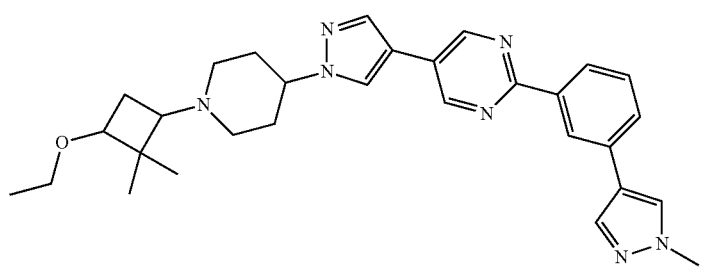 [SMILES: CCOC1CC(N2CCC(n3cc(-c4cnc(-c5cccc(-c6cnn(C)c6)c5)nc4)cn3)CC2)C1(C)C]<br>HPLC (max plot) 99%; (254 nm) 100%; Rt (min) 2.89; MS: (ESI+) 512.5 |

-continued
| Ex | |
|---|---|
| 113 | 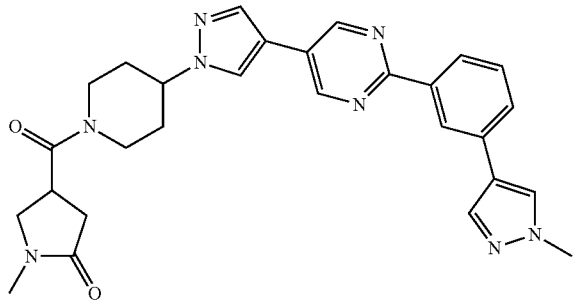 HPLC (max plot) 99%; (254 nm) 100%; Rt (min) 2.95; MS: (ESI+) 511.4 |
| 114 | 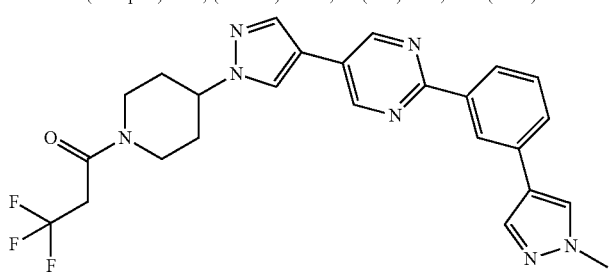 HPLC (max plot) 100%; (254 nm) 100%; Rt (min) 3.53; MS: (ESI+) 496.4 |
| 115 | 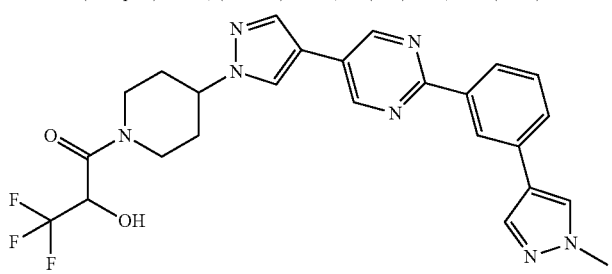 HPLC (max plot) 100%; (254 nm) 99%; Rt (min) 3.43; MS: (ESI+) 512.2 |
| 116 | 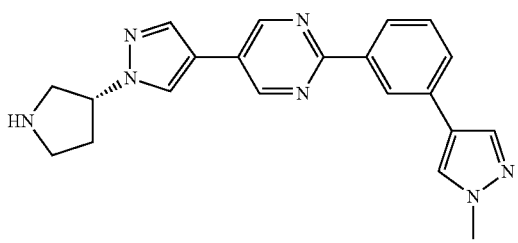 [SMILES: Cn1cc(-c2cccc(-c3ncc(-c4cnn([C@@H]5CCNC5)c4)cn3)c2)cn1] HPLC (max plot) 98%; (254 nm) 97%; Rt 2.31; MS: (ESI+) 372.4 |
| 117 | 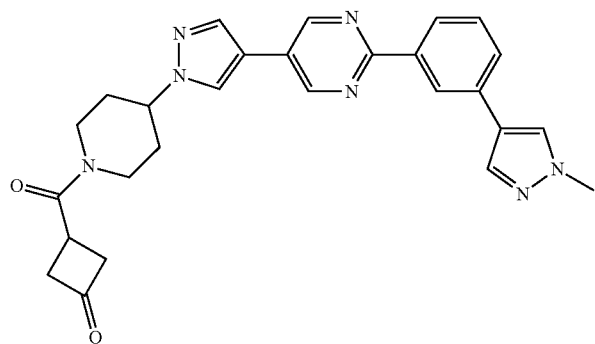 [SMILES: Cn1cc(-c2cccc(-c3ncc(-c4cnn(C5CCN(C(=O)C6CC(=O)C6)CC5)c4)cn3)c2)cn1] HPLC (max plot) 98%; (254 nm) 97%; Rt (min) 3.03; MS: (ESI+) 482.2 |

-continued
| Ex | |
|---|---|
| 118 | 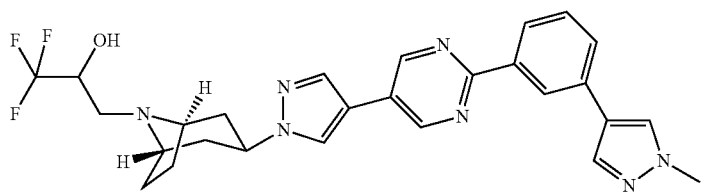 [SMILES: Cn1cc(-c2cccc(-c3ncc(-c4cnn(C5C[C@H]6CC[C@@H](C5)N6CC(O)C(F)(F)F)c4)cn3)c2)cn1]<br>HPLC (max plot) 98%; (254 nm) 98%; Rt (min) 2.88; MS: (ESI+) 524.4 |
| 119 | 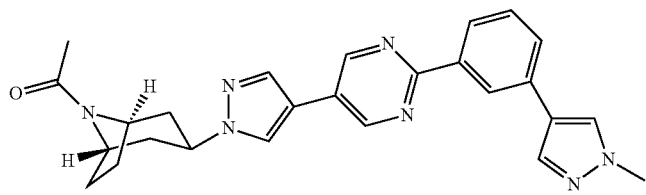 [SMILES: CC(=O)N1[C@@H]2CC[C@H]1CC(n1cc(-c3cnc(-c4cccc(-c5cnn(C)c5)c4)nc3)cn1)C2]<br>HPLC (max plot) 97%; (254 nm) 98%; Rt (min) 3.21; MS: (ESI+) 454.4 |
| 120 | 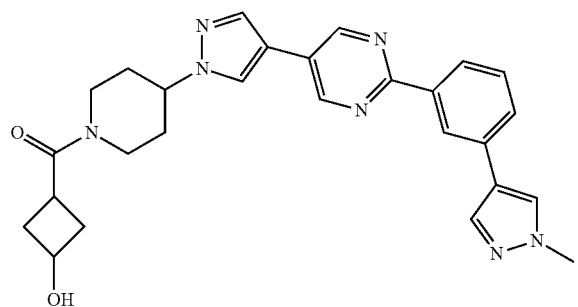 [SMILES: Cn1cc(-c2cccc(-c3ncc(-c4cnn(C5CCN(C(=O)C6CC(O)C6)CC5)c4)cn3)c2)cn1]<br>HPLC (max plot) 99%; (254 nm) 99%; Rt (min) 2.79; MS: (ESI+) 484.4 |
| 121 | 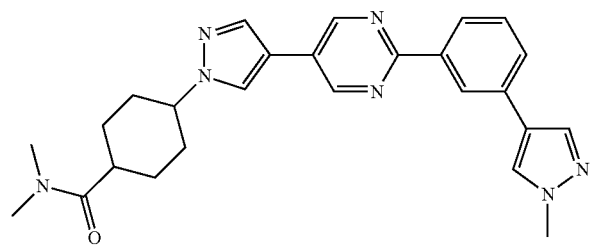<br>HPLC (max plot) 97.6%; (254 nm) 96.6%; Rt (min) 2.90; MS: (ESI+) 500.2. |
| 122 | 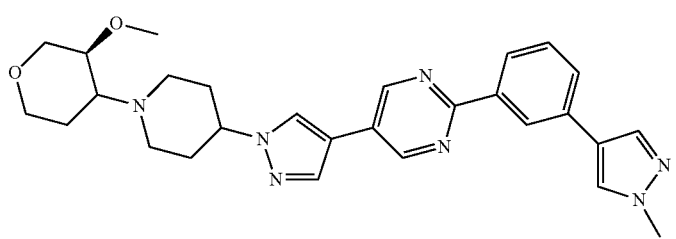 [SMILES: CO[C@@H]1COCCC1N1CCC(n2cc(-c3cnc(-c4cccc(-c5cnn(C)c5)c4)nc3)cn2)CC1]<br>HPLC (max plot) 97.6%; (254 nm) 96.6%; Rt (min) 2.90; MS: (ESI+) 500.2. |

-continued
| Ex | |
|---|---|
| 123 | 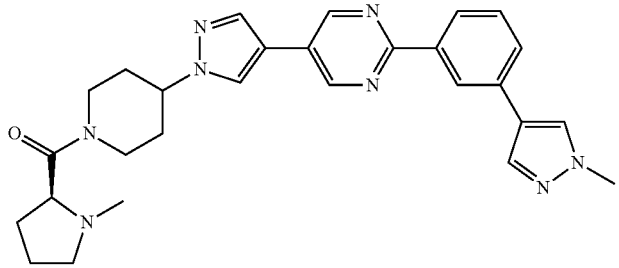 [SMILES: CN1CCC[C@H]1C(=O)N1CCC(n2cc(-c3cnc(-c4cccc(-c5cnn(C)c5)c4)nc3)cn2)CC1]
HPLC (max plot) 98%; (254 nm) 99%; Rt (min) 2.56 |
| 124 | 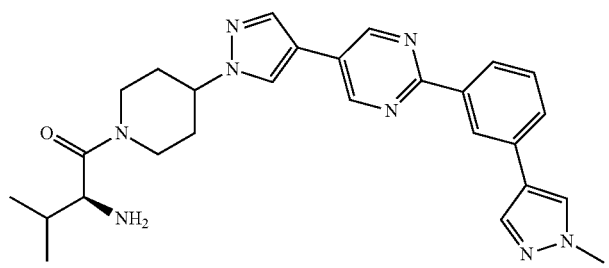 [SMILES: CC(C)[C@H](N)C(=O)N1CCC(n2cc(-c3cnc(-c4cccc(-c5cnn(C)c5)c4)nc3)cn2)CC1]
HPLC (max plot) 100%; (254 nm) 100%; Rt (min) 2.78; MS: (ESI+) 485.5 |
| 125 | 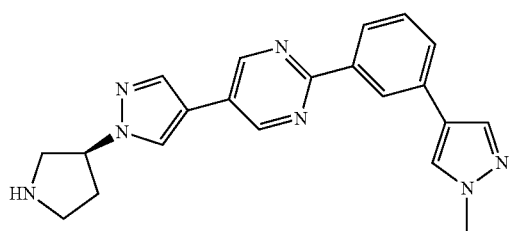 [SMILES: Cn1cc(-c2cccc(-c3ncc(-c4cnn([C@H]5CCNC5)c4)cn3)c2)cn1]
HPLC (max plot) 100%; (254 nm) 96%; Rt (min) 2.29 |
| 126 | 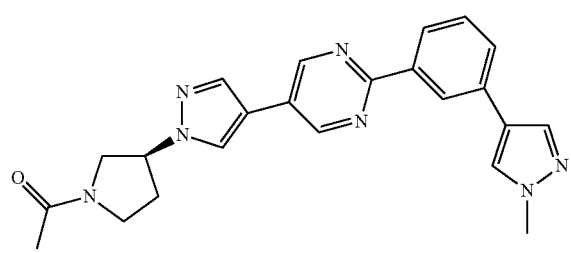 [SMILES: CC(=O)N1CC[C@H](n2cc(-c3cnc(-c4cccc(-c5cnn(C)c5)c4)nc3)cn2)C1]
HPLC (max plot) 98%; (254 nm) 96%; Rt (min) 2.76 ; MS: (ESI+) 414.2 |
| 127 | 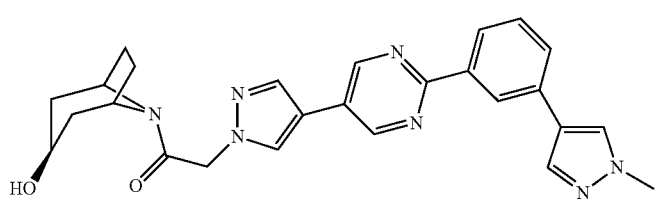
HPLC (max plot) 100%; (254 nm) 100%; Rt (min) 2.97; MS: (ESI+) 470.4 |

| Ex |
| --- |
| 128 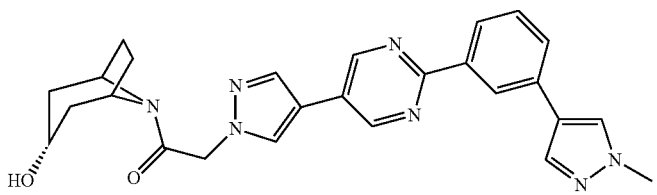
HPLC (max plot) 100%; (254 nm) 100%; Rt (min) 2.89; MS: (ESI+) 470.2 |
| 129 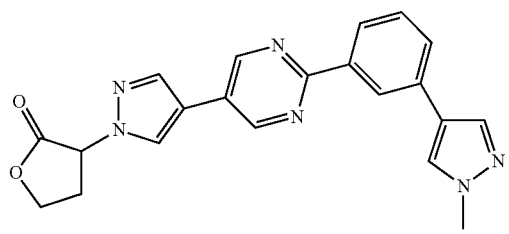 [SMILES: Cn1cc(-c2cccc(-c3ncc(-c4cnn(C5CCOC5=O)c4)cn3)c2)cn1]
HPLC (max plot) 97%; (254 nm) 98%; Rt (min) 3.02; MS: (ESI+) 387.3 |
| 130 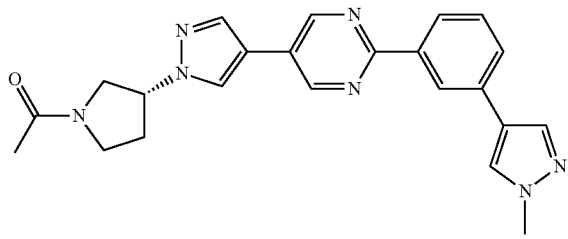 [SMILES: CC(=O)N1CC[C@@H](n2cc(-c3cnc(-c4cccc(-c5cnn(C)c5)c4)nc3)cn2)C1]
HPLC (max plot) 99%; (254 nm) 95%; Rt (min) 2.75; MS: (ESI+) 414.2 |
| 131 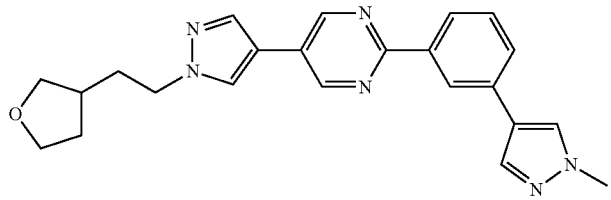 [SMILES: Cn1cc(-c2cccc(-c3ncc(-c4cnn(CCC5CCOC5)c4)cn3)c2)cn1]
HPLC (max plot) 99%; (254 nm) 100%; Rt (min) 3.37; MS: (ESI+) 401.2 |
| 132 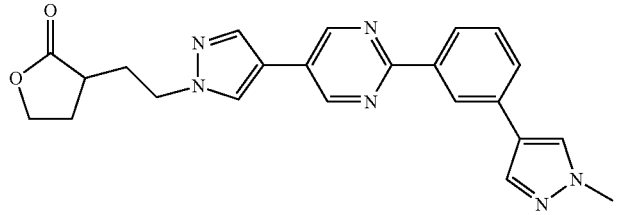 [SMILES: Cn1cc(-c2cccc(-c3ncc(-c4cnn(CCC5CCOC5=O)c4)cn3)c2)cn1]
HPLC (max plot) 98%; (254 nm) 98%; Rt (min) 3.28; MS: (ESI+) 415.2 |
| 133 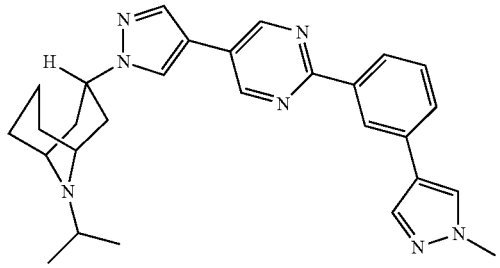 [SMILES: CC(C)N1C2CCCC1CC(n1cc(-c3cnc(-c4cccc(-c5cnn(C)c5)c4)nc3)cn1)C2]
HPLC (max plot) 99%; (254 nm) 99%; Rt (min) 2.89; MS: (ESI+) 468.2 |

| Ex | |
|---|---|
| 134 | 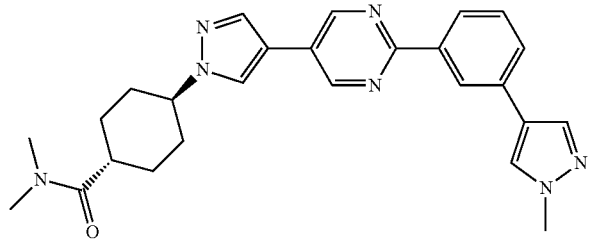 [SMILES: CN(C)C(=O)[C@H]1CC[C@H](n2cc(-c3cnc(-c4cccc(-c5cnn(C)c5)c4)nc3)cn2)CC1] |
| 135 | 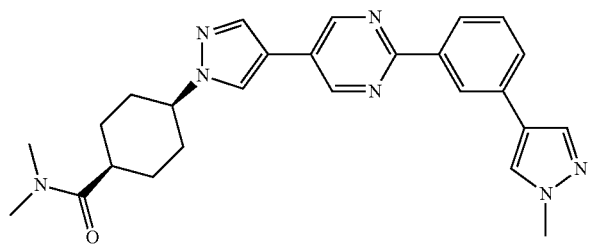 [SMILES: CN(C)C(=O)[C@H]1CC[C@@H](n2cc(-c3cnc(-c4cccc(-c5cnn(C)c5)c4)nc3)cn2)CC1] |
| 136 | <br>HPLC (max plot) 99%; (254 nm) 99%; Rt (min) 2.61; MS: (ESI+) 399.2 |
| 137 | 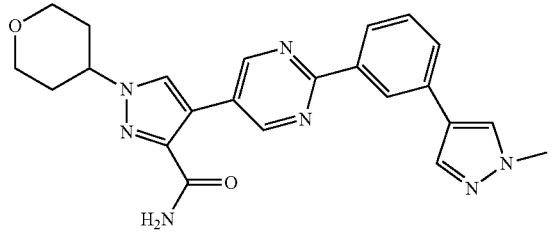 [SMILES: Cn1cc(-c2cccc(-c3ncc(-c4cn(C5CCOCC5)nc4C(N)=O)cn3)c2)cn1]<br>HPLC (max plot) 98%; (254 nm) 98%; Rt (min) 3.03; MS: (ESI+) 430.3 |
| 138 | 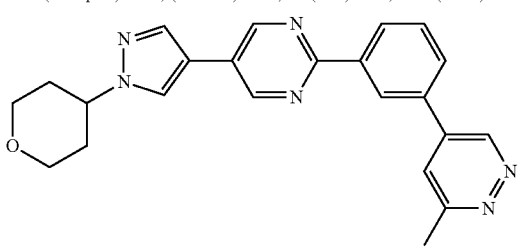<br>HPLC (max plot) 99%; (254 nm) 99%; Rt (min) 2.51; MS: (ESI+) 399.2 |
| 139 | 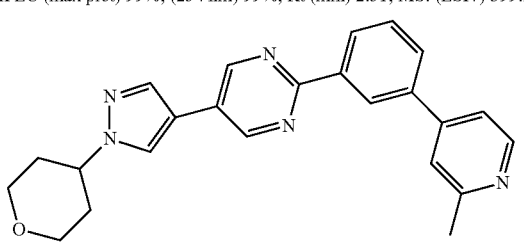<br>HPLC (max plot) 100%; (254 nm) 100%; Rt (min) 2.42; MS: (ESI+) 398.2 |

| Ex | |
|---|---|
| 140 | 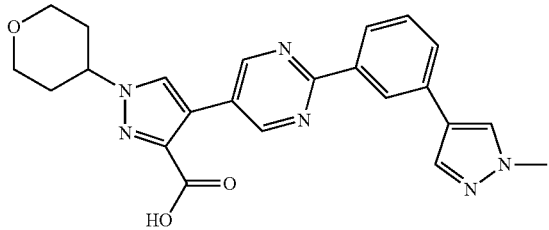 [SMILES: Cn1cc(-c2cccc(-c3ncc(-c4cn(C5CCOCC5)nc4C(=O)O)cn3)c2)cn1] |
HPLC (max plot) 98%; (254 nm) 98%; Rt (min) 2.99; MS: (ESI+) 431.3
| 141 | 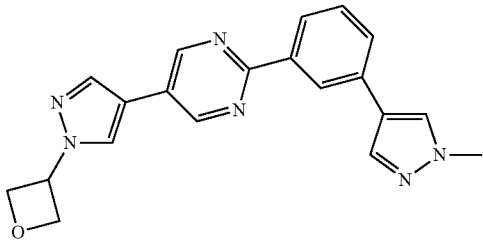 [SMILES: Cn1cc(-c2cccc(-c3ncc(-c4cnn(C5COC5)c4)cn3)c2)cn1] |
HPLC (max plot) 98%; (254 nm) 98%; Rt (min) 3.04; MS: (ESI+) 359.3
| 142 | 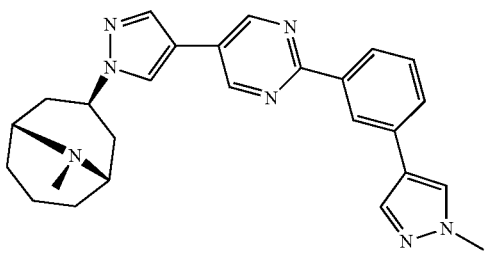 |
HPLC (max plot) 100%; (254 nm) 100%; Rt (min) 2.75; MS: (ESI+) 440.4
| 143 | 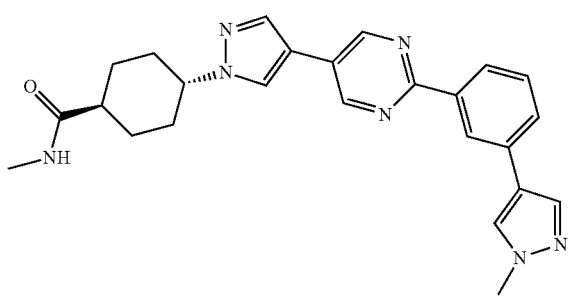 [SMILES: CNC(=O)[C@H]1CC[C@H](n2cc(-c3cnc(-c4cccc(-c5cnn(C)c5)c4)nc3)cn2)CC1] |
HPLC (max plot) 96%; (254 nm) 94%; Rt (min) 2.95; MS: (ESI+) 442.2
| 144 | 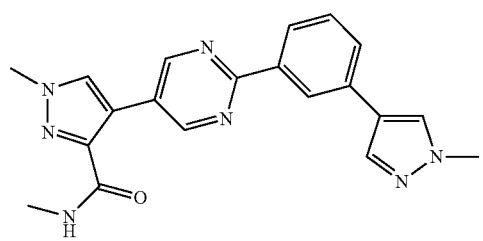 |
HPLC (max plot) 99%; (254 nm) 99%; Rt (min) 2.80; MS: (ESI+) 374.3

| Ex | |
|---|---|
| 145 | 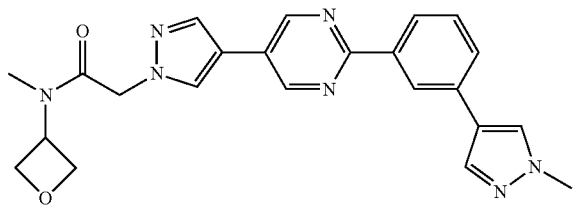<br>HPLC (max plot) 93%; (254 nm) 93%; Rt (min) 2.85; MS: (ESI+) 430.4 |
| 146 | 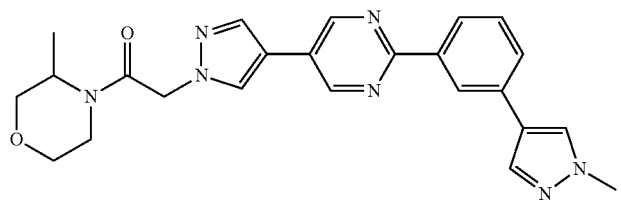<br>HPLC (max plot) 98%; (254 nm) 97%; Rt (min) 2.87; MS: (ESI+) 474.2 |
| 147 | 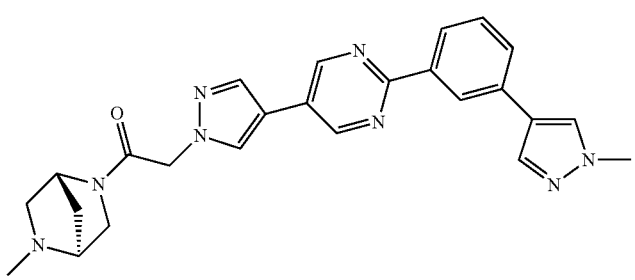<br>HPLC (max plot) 99%; (254 nm) 100%; Rt (min) 2.79; MS: (ESI+) 444.2 |
| 148 | 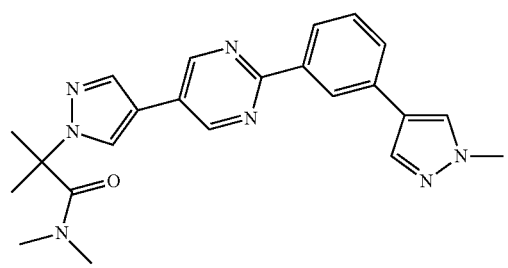<br>HPLC (max plot) 96%; (254 nm) 95%; Rt (min) 2.20; MS: (ESI+) 455.2 |
| 149 | HPLC (max plot) 100%; (254 nm) 100%; Rt (min) 3.10; MS: (ESI+) 416.2 |

| Ex |
|---|
| 150 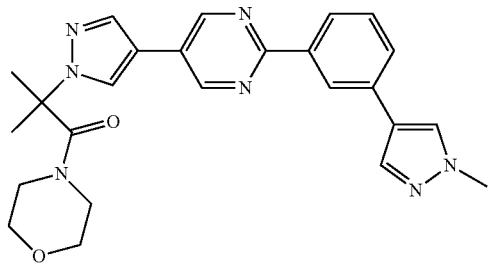 [SMILES: Cn1cc(-c2cccc(-c3ncc(-c4cnn(C(C)(C)C(=O)N5CCOCC5)c4)cn3)c2)cn1]
HPLC (max plot) 100%; (254 nm) 100%; Rt (min) 3.10; MS: (ESI+) 458.2 . |
| 151 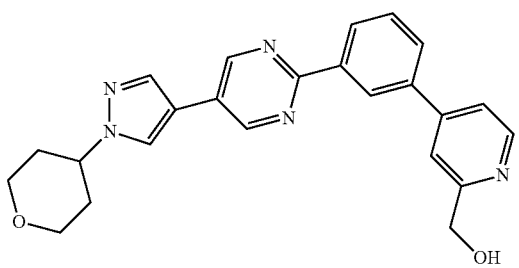 [SMILES: OCc1cc(-c2cccc(-c3ncc(-c4cnn(C5CCOCC5)c4)cn3)c2)ccn1]
HPLC (max plot) 98%; (254 nm) 99%; Rt (min) 2.32; MS: (ESI+) 414.2 |
| 152 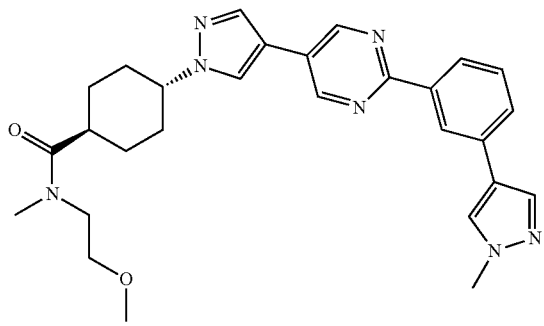 [SMILES: COCCN(C)C(=O)[C@H]1CC[C@H](n2cc(-c3cnc(-c4cccc(-c5cnn(C)c5)c4)nc3)cn2)CC1]
HPLC (max plot) 92%; (254 nm) 91%; Rt (min) 3.32; MS ( ESI+): 500.4. |
| 153 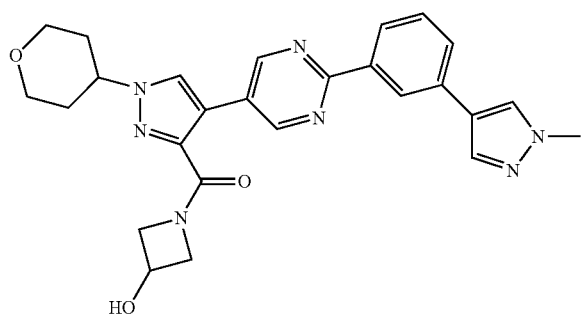 [SMILES: Cn1cc(-c2cccc(-c3ncc(-c4cn(C5CCOCC5)nc4C(=O)N4CC(O)C4)cn3)c2)cn1]
HPLC (max plot) 99%; (254 nm) 99%; Rt (min) 2.83; MS (ESI+) 486.4 |

| Ex | |
|---|---|
| 154 | 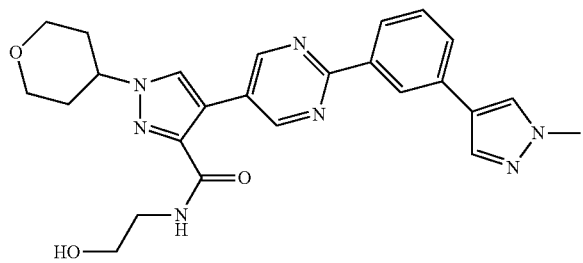 [SMILES: Cn1cc(-c2cccc(-c3ncc(-c4cn(C5CCOCC5)nc4C(=O)NCCO)cn3)c2)cn1] |
HPLC (max plot) 94%; (254 nm) 95%; Rt (min) 2.82; MS (ESI+) 474.4
| 155 | 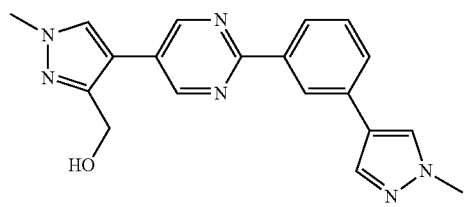 |
HPLC (max plot) 95%; (254 nm) 94%; Rt (min) 2.66; MS (ESI+): 347.3
| 156 | 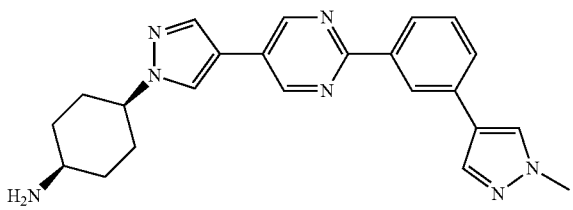 [SMILES: Cn1cc(-c2cccc(-c3ncc(-c4cnn([C@H]5CC[C@@H](N)CC5)c4)cn3)c2)cn1] |
HPLC (max plot) 98%; (254 nm) 95%; Rt (min) 4.23; MS (ESI+) 500.5
| 157 | 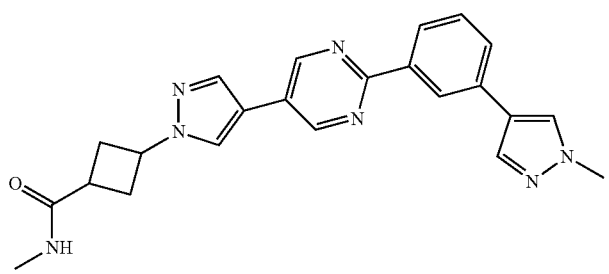 [SMILES: CNC(=O)C1CC(n2cc(-c3cnc(-c4cccc(-c5cnn(C)c5)c4)nc3)cn2)C1] |
HPLC (max plot) 99%; (254 nm) 99%; Rt (min) 2.82; MS (ESI+) 414.4
| 158 | 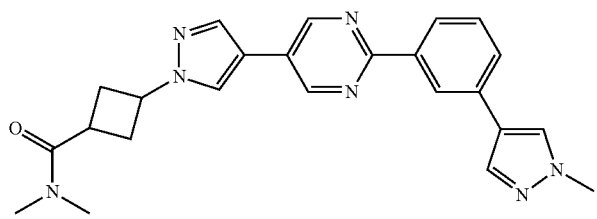 [SMILES: CN(C)C(=O)C1CC(n2cc(-c3cnc(-c4cccc(-c5cnn(C)c5)c4)nc3)cn2)C1] |
HPLC (max plot) 98%; (254 nm) 98%; Rt (min) 2.99; MS (ESI+) 428.3

| Ex | |
|---|---|
| 159 | 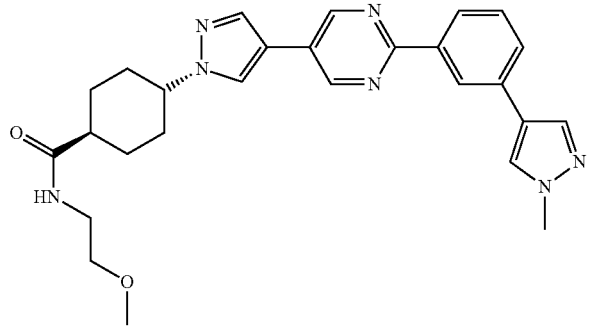 |
HPLC (max plot) 100%; (254 nm) 99%; Rt (min) 3.06; MS (ESI+): 486.2
| 160 | 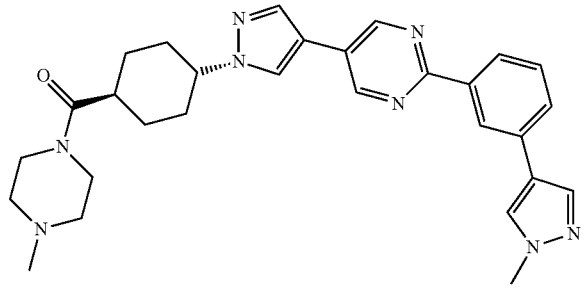 |
HPLC (max plot) 100%; (254 nm) 100%; Rt (min) 2.62; MS (ESI+): 511.4
| 161 | 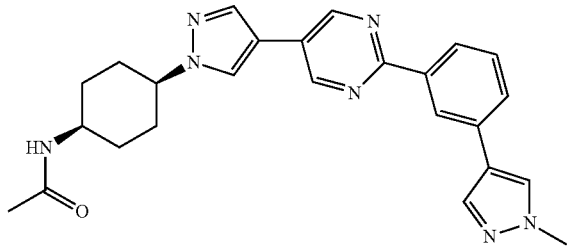 [SMILES: CC(=O)N[C@H]1CC[C@@H](n2cc(-c3cnc(-c4cccc(-c5cnn(C)c5)c4)nc3)cn2)CC1] |
HPLC (max plot) 98%; (254 nm) 98%; Rt (min) 3.01; MS (ESI+): 442.2
| 162 | 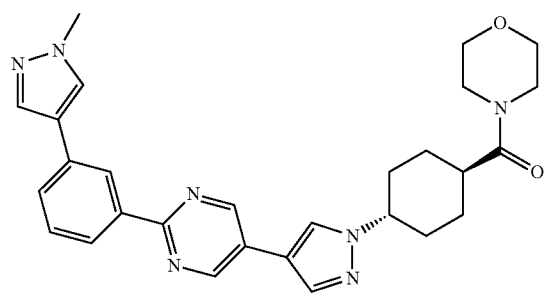 [SMILES: Cn1cc(-c2cccc(-c3ncc(-c4cnn([C@H]5CC[C@H](C(=O)N6CCOCC6)CC5)c4)cn3)c2)cn1] |
HPLC (max plot) 99%; (254 nm) 98%; Rt (min) 3.34; MS (ESI+): 498.4

| Ex | |
|---|---|
| 163 | 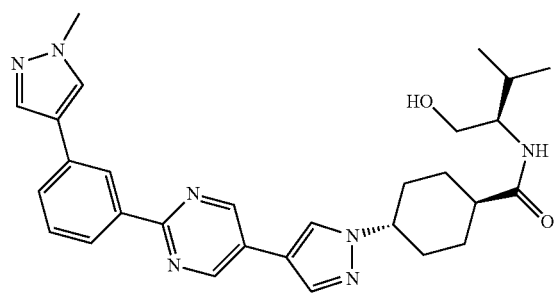 [SMILES: CC(C)[C@H](CO)NC(=O)[C@H]1CC[C@H](n2cc(-c3cnc(-c4cccc(-c5cnn(C)c5)c4)nc3)cn2)CC1] HPLC (max plot) 98%; (254 nm) 97%; Rt (min) 3.26; MS (ESI+) 514.5 |
| 164 | 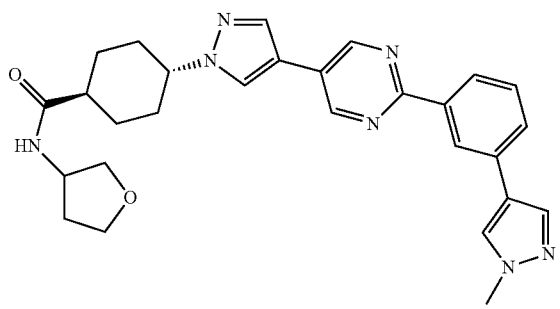 [SMILES: Cn1cc(-c2cccc(-c3ncc(-c4cnn([C@H]5CC[C@H](C(=O)NC6CCOC6)CC5)c4)cn3)c2)cn1] HPLC (max plot) 90%; (254 nm) 90%; Rt (min) 3.02; MS (ESI+) 498.4 |
| 165 | 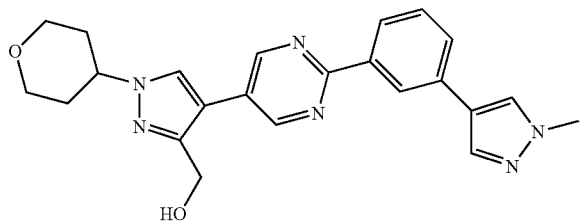 [SMILES: Cn1cc(-c2cccc(-c3ncc(-c4cn(C5CCOCC5)nc4CO)cn3)c2)cn1] HPLC (max plot) 100%; (254 nm) 100%; Rt (min) 2.89; MS (ESI+) 417.4 |
| 166 | 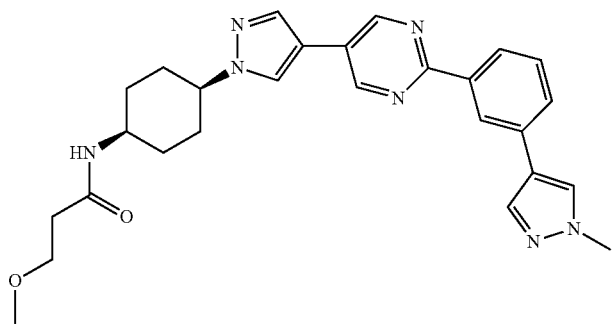 [SMILES: COCCC(=O)N[C@H]1CC[C@@H](n2cc(-c3cnc(-c4cccc(-c5cnn(C)c5)c4)nc3)cn2)CC1] HPLC (max plot) 97.5%; (254 nm) 98.3%; Rt (min) 3.11; MS: (ESI+) 486.4. |
| 167 | 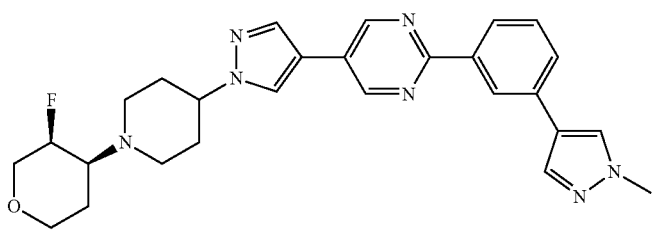 [SMILES: Cn1cc(-c2cccc(-c3ncc(-c4cnn(C5CCN([C@H]6CCOC[C@H]6F)CC5)c4)cn3)c2)cn1] |

| Ex |
|---|
| 168 |
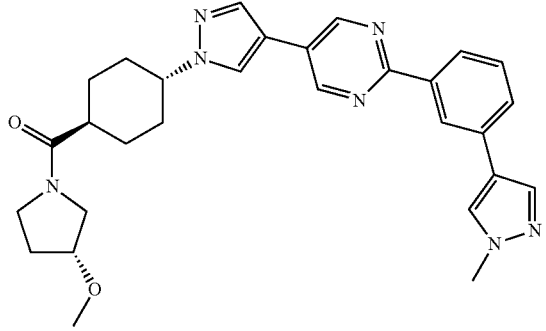 [SMILES: CO[C@@H]1CCN(C(=O)[C@H]2CC[C@H](n3cc(-c4cnc(-c5cccc(-c6cnn(C)c6)c5)nc4)cn3)CC2)C1]
HPLC (max plot) 94%; (254 nm) 95%; Rt (min) 3.24; MS (ESI+): 512.4
169
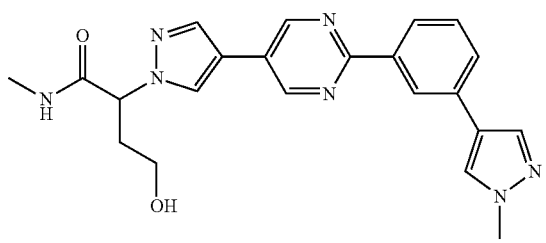 [SMILES: CNC(=O)C(CCO)n1cc(-c2cnc(-c3cccc(-c4cnn(C)c4)c3)nc2)cn1]
HPLC (max plot) 98%; (254 nm) 97%; Rt (min) 2.47; MS (ESI+) 418.4
170
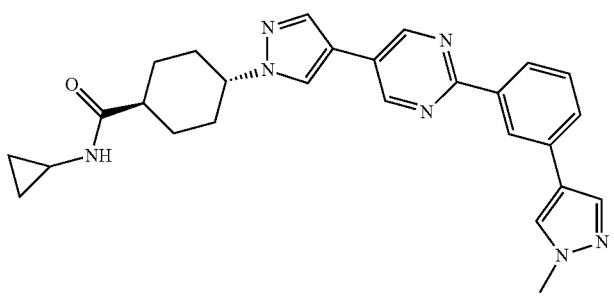 [SMILES: Cn1cc(-c2cccc(-c3ncc(-c4cnn([C@H]5CC[C@H](C(=O)NC6CC6)CC5)c4)cn3)c2)cn1]
HPLC (max plot) 94%; (254 nm) 91%; Rt (min) 3.39; MS (ESI+) 468.2
171
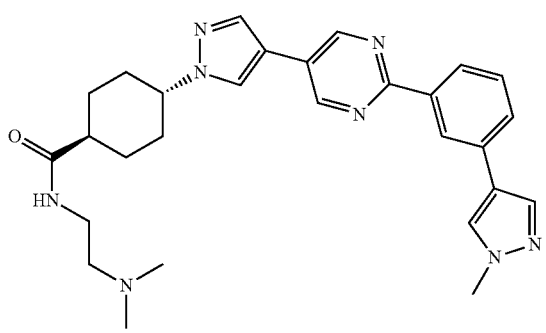 [SMILES: CN(C)CCNC(=O)[C@H]1CC[C@H](n2cc(-c3cnc(-c4cccc(-c5cnn(C)c5)c4)nc3)cn2)CC1]
HPLC (max plot) 98%; (254 nm) 97%; Rt (min) 2.58; MS (ESI+) 499.3

-continued
| Ex | |
|---|---|
| 172 | 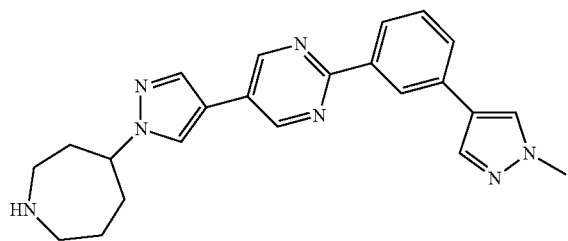 [SMILES: Cn1cc(-c2cccc(-c3ncc(-c4cnn(C5CCCNCC5)c4)cn3)c2)cn1]
HPLC (max plot) 100%; (254 nm) 100%; Rt (min) 2.56; MS (ESI+) 400.2 |
| 173 | 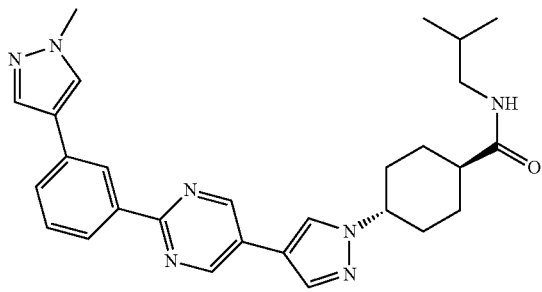 [SMILES: CC(C)CNC(=O)[C@H]1CC[C@H](n2cc(-c3cnc(-c4cccc(-c5cnn(C)c5)c4)nc3)cn2)CC1]
HPLC (max plot) 99%; (254 nm) 98%; Rt (min) 3.66 ; MS (ESI+) 484.3. |
| 174 | 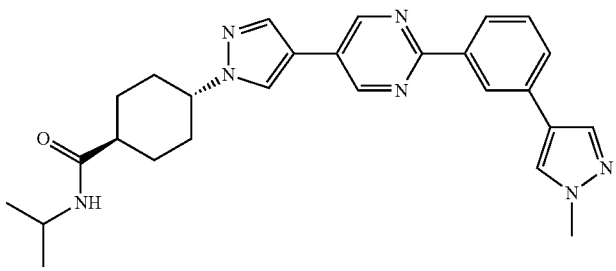 [SMILES: CC(C)NC(=O)[C@H]1CC[C@H](n2cc(-c3cnc(-c4cccc(-c5cnn(C)c5)c4)nc3)cn2)CC1]
HPLC (max plot) 93%; (254 nm) 91%; Rt (min) 3.38; MS (ESI+) 470.2 |
| 175 | 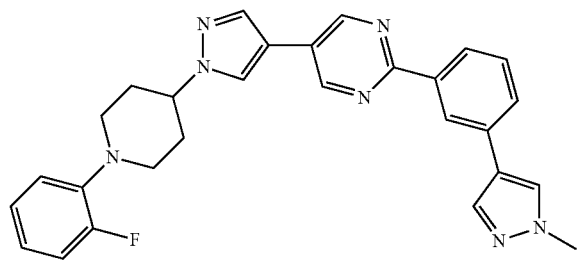 [SMILES: Cn1cc(-c2cccc(-c3ncc(-c4cnn(C5CCN(c6ccccc6F)CC5)c4)cn3)c2)cn1]
HPLC (max plot) 99%; (254 nm) 99%; Rt (min) 4.34; MS (ESI+) 480.4. |
| 176 | 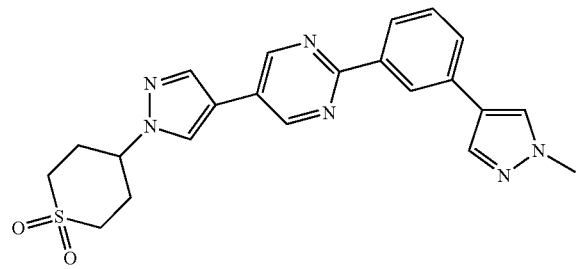 [SMILES: Cn1cc(-c2cccc(-c3ncc(-c4cnn(C5CCS(=O)(=O)CC5)c4)cn3)c2)cn1]
HPLC (max plot) 99%; (254 nm) 99%; Rt (min) 3.14; MS (ESI+) 435.3 |

| Ex | |
|---|---|
| 177 | 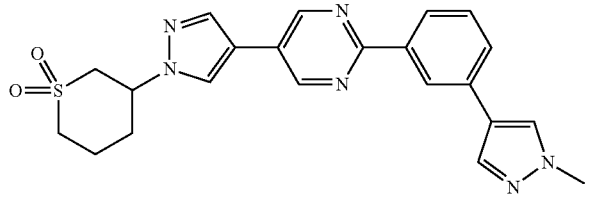 [SMILES: Cn1cc(-c2cccc(-c3ncc(-c4cnn(C5CCCS(=O)(=O)C5)c4)cn3)c2)cn1]
HPLC (max plot) 100%; (254 nm) 100%; Rt (min) 3.21; MS (ESI+) 435.3 |
| 178 | 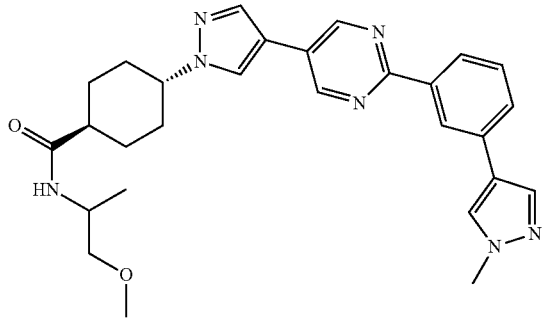 [SMILES: COCC(C)NC(=O)[C@H]1CC[C@H](n2cc(-c3cnc(-c4cccc(-c5cnn(C)c5)c4)nc3)cn2)CC1]
HPLC (max plot) 96%; (254 nm) 93%; Rt (min) 3.25; MS (ESI+) 500.4 |
| 179 | 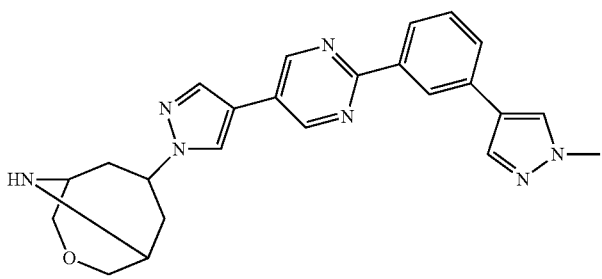 [SMILES: Cn1cc(-c2cccc(-c3ncc(-c4cnn(C5CC6COCC(C5)N6)c4)cn3)c2)cn1]
HPLC (max plot) 100%; (254 nm) 100%; Rt (min) 2.56; MS (ESI+) 428.2 |
| 180 | 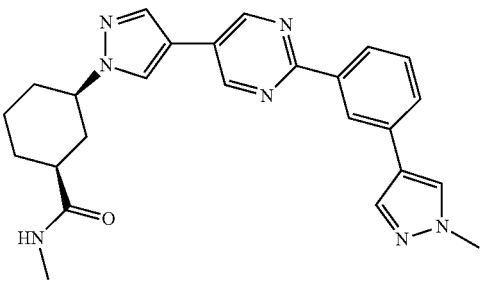 [SMILES: CNC(=O)[C@H]1CCC[C@@H](n2cc(-c3cnc(-c4cccc(-c5cnn(C)c5)c4)nc3)cn2)C1]
HPLC (max plot) 87.6%; (254 nm) 88%; Rt (min) 3.21; MS (ESI+) 442.4. |
| 181 | 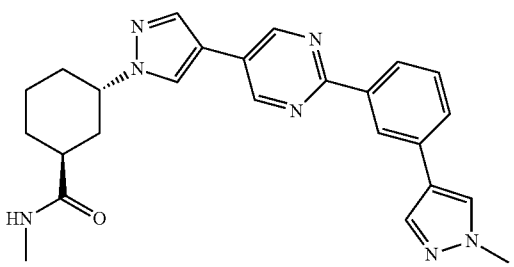 [SMILES: CNC(=O)[C@H]1CCC[C@H](n2cc(-c3cnc(-c4cccc(-c5cnn(C)c5)c4)nc3)cn2)C1]
HPLC (max plot) 99.3%; (254 nm) 99.6%; Rt (min) 3.31; MS (ESI+) 442.4 |

| Ex | |
|---|---|
| 182 | 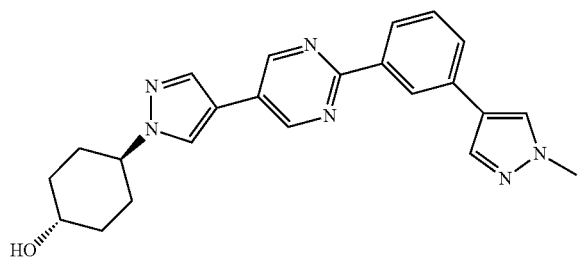 [SMILES: Cn1cc(-c2cccc(-c3ncc(-c4cnn([C@H]5CC[C@H](O)CC5)c4)cn3)c2)cn1] |
| 183 | 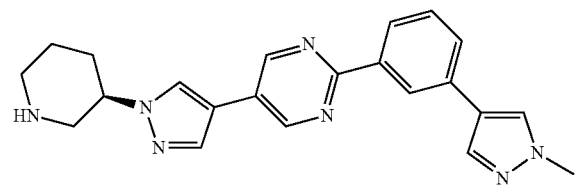 [SMILES: Cn1cc(-c2cccc(-c3ncc(-c4cnn([C@@H]5CCCNC5)c4)cn3)c2)cn1]
HPLC (max plot) 95.6%; (254 nm) 95.2%; Rt (min) 2.51; MS (ESI+) 386.4. |
| 184 | 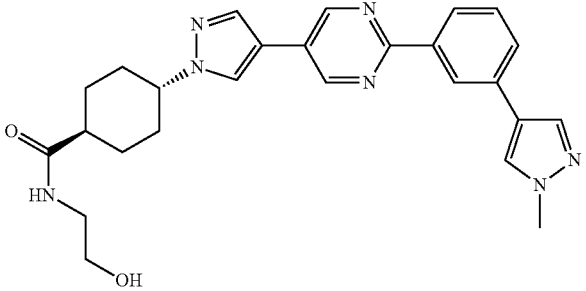 [SMILES: Cn1cc(-c2cccc(-c3ncc(-c4cnn([C@H]5CC[C@H](C(=O)NCCO)CC5)c4)cn3)c2)cn1]
HPLC (max plot) 98.1%; (254 nm) 98%; Rt (min) 2.93; MS: (ESI+) 472.2. |
| 185 | 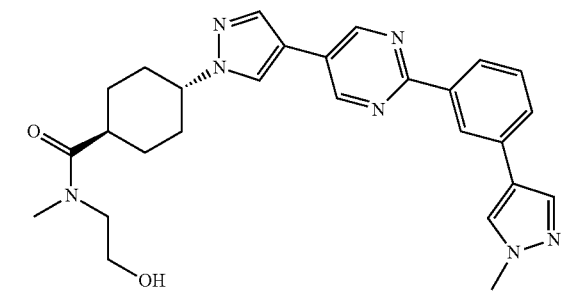 [SMILES: CN(CCO)C(=O)[C@H]1CC[C@H](n2cc(-c3cnc(-c4cccc(-c5cnn(C)c5)c4)nc3)cn2)CC1]
HPLC (max plot) 90.0%; (254 nm) 86.3%; Rt (min) 2.93; MS: (ESI+) 486.4. |
| 186 | 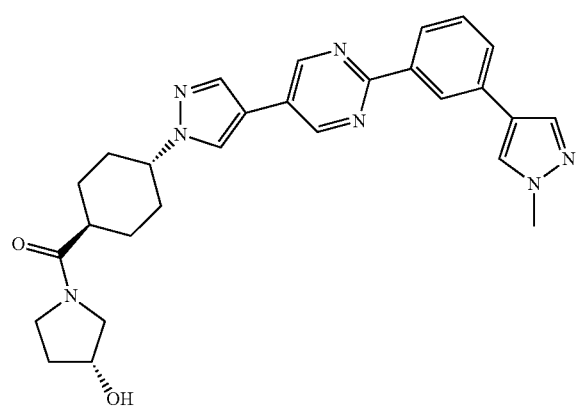 [SMILES: Cn1cc(-c2cccc(-c3ncc(-c4cnn([C@H]5CC[C@H](C(=O)N6CC[C@@H](O)C6)CC5)c4)cn3)c2)cn1]
HPLC (max plot) 91.4%; (254 nm) 88.2%; Rt (min) 2.84; MS: (ESI+) 498.4. |

| Ex |
|---|
| 187 |
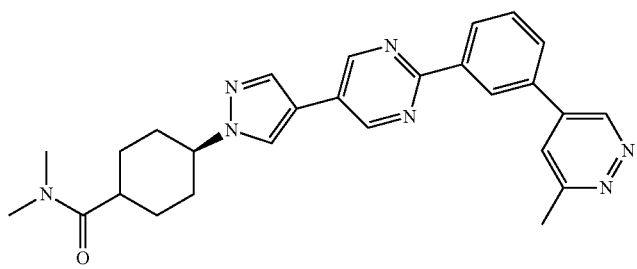
HPLC (max plot) 98.7%; (254 nm) 100%; Rt (min) 2.77; MS: (ESI+) 468.4.
188
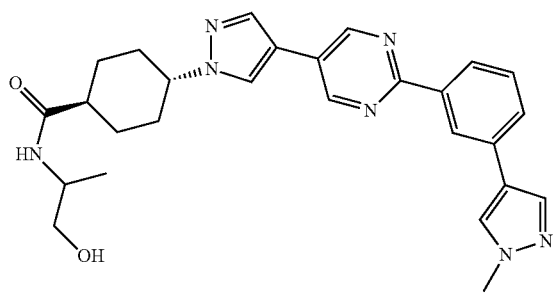 [SMILES: CC(CO)NC(=O)[C@H]1CC[C@H](n2cc(-c3cnc(-c4cccc(-c5cnn(C)c5)c4)nc3)cn2)CC1]
HPLC (max plot) 91.3%; (254 nm) 88.4%; Rt (min) 2.89; MS: (ESI+) 486.4.
189
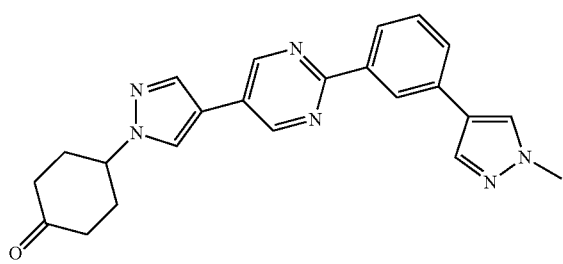 [SMILES: Cn1cc(-c2cccc(-c3ncc(-c4cnn(C5CCC(=O)CC5)c4)cn3)c2)cn1]
.HPLC (max plot) 89.6%; (254 nm) 89.5%; Rt (min) 3.30; MS: (ESI+) 457.4.
190
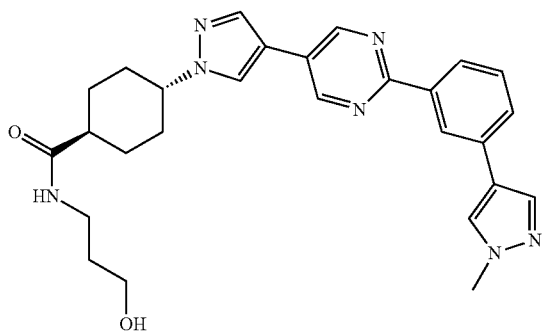 [SMILES: Cn1cc(-c2cccc(-c3ncc(-c4cnn([C@H]5CC[C@H](C(=O)NCCCO)CC5)c4)cn3)c2)cn1]
.HPLC (max plot) 94.0%; (254 nm) 97.9%; Rt (min) 2.86; MS: (ESI+) 486.3

| Ex | |
|---|---|
| 191 | 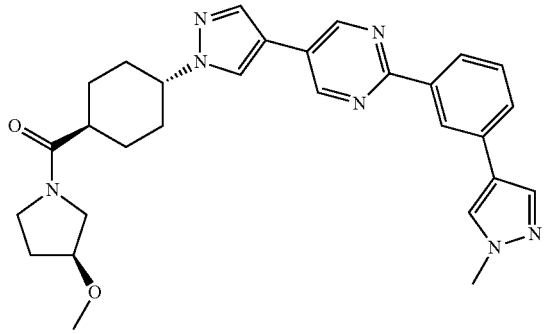 [SMILES: CO[C@H]1CCN(C(=O)[C@H]2CC[C@H](n3cc(-c4cnc(-c5cccc(-c6cnn(C)c6)c5)nc4)cn3)CC2)C1]<br>HPLC (max plot) 94.3%; (254 nm) 97.1%; Rt (min) 3.25; MS: (ESI+) 512.4. |
| 192 | 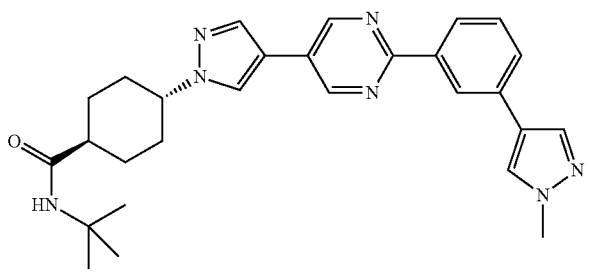 [SMILES: Cn1cc(-c2cccc(-c3ncc(-c4cnn([C@H]5CC[C@H](C(=O)NC(C)(C)C)CC5)c4)cn3)c2)cn1]<br>HPLC (max plot) 93.3%; (254 nm) 93.9%; Rt (min) 3.78; MS: (ESI+) 484.2. |
| 193 | 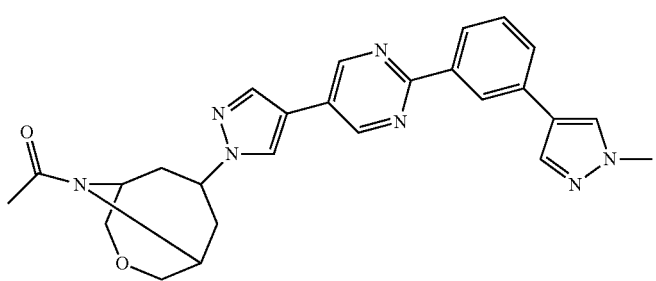 [SMILES: CC(=O)N1C2COCC1CC(n1cc(-c3cnc(-c4cccc(-c5cnn(C)c5)c4)nc3)cn1)C2]<br>HPLC (max plot) 100%; (254 nm) 100%; Rt (min) 3.11; MS: (ESI+) 470.3. |
| 194 | 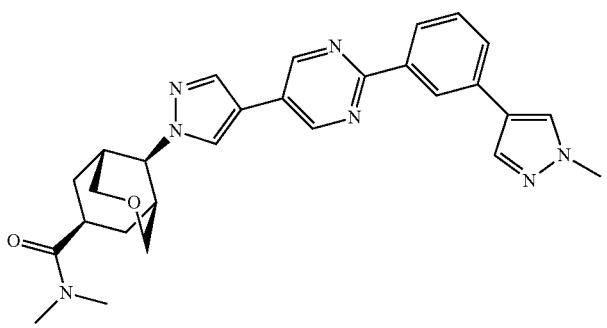 [SMILES: CN(C)C(=O)[C@H]1C[C@H]2COC[C@@H](C1)[C@@H]2n1cc(-c2cnc(-c3cccc(-c4cnn(C)c4)c3)nc2)cn1]<br>HPLC (max plot) 99.2%; (254 nm) 98.0%; Rt (min) 3.33; MS: (ESI+) 498.4. |

| Ex |
|---|
| 195 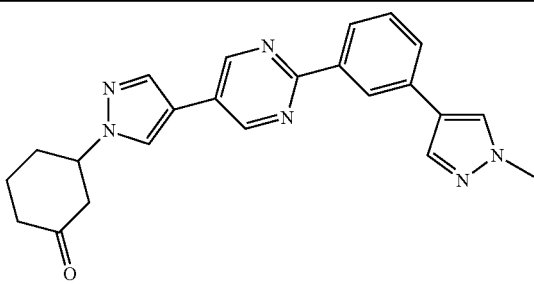
HPLC (max plot) 99.0%; (254 nm) 99.0%; Rt (min) 3.40; MS: (ESI+) 399.3. |
| 196 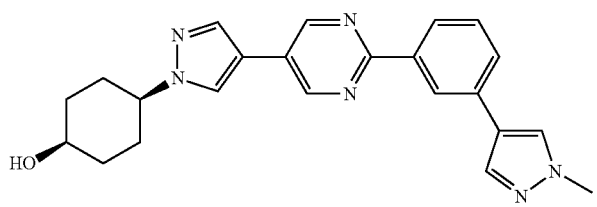 [SMILES: Cn1cc(-c2cccc(-c3ncc(-c4cnn([C@H]5CC[C@@H](O)CC5)c4)cn3)c2)cn1]
HPLC (max plot) 97.1%; (254 nm) 96.3%; Rt (min) 3.19; MS: (ESI+) 401.3. |
| 197 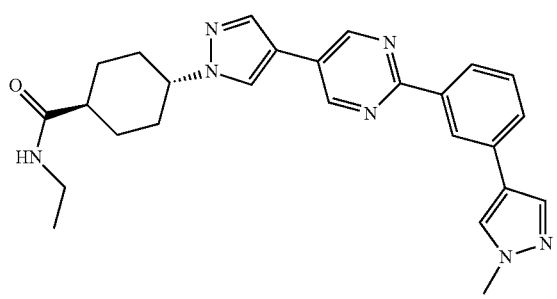 [SMILES: CCNC(=O)[C@H]1CC[C@H](n2cc(-c3cnc(-c4cccc(-c5cnn(C)c5)c4)nc3)cn2)CC1]
HPLC (max plot) 92.7%; (254 nm) 91.5%; Rt (min) 3.16; MS: (ESI+) 456.4 |
| 198 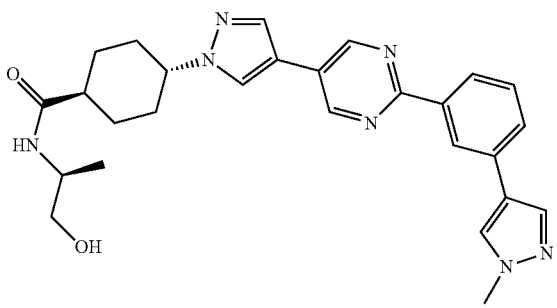 [SMILES: C[C@@H](CO)NC(=O)[C@H]1CC[C@H](n2cc(-c3cnc(-c4cccc(-c5cnn(C)c5)c4)nc3)cn2)CC1]
HPLC (max plot) 93.8%; (254 nm) 94.8%; Rt (min) 2.90; MS: (ESI+) 486.4 |
| 199 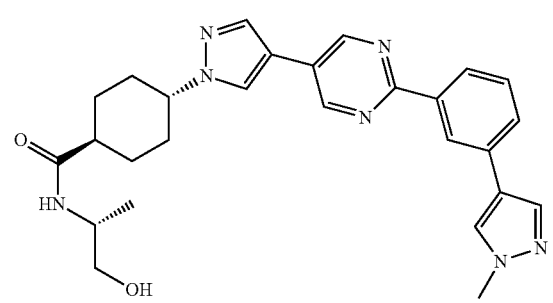 [SMILES: C[C@H](CO)NC(=O)[C@H]1CC[C@H](n2cc(-c3cnc(-c4cccc(-c5cnn(C)c5)c4)nc3)cn2)CC1]
HPLC (max plot) 92.9%; (254 nm) 91.7%; Rt (min) 2.91; MS: (ESI+) 486.4. |

| Ex | |
|---|---|
| 200 | 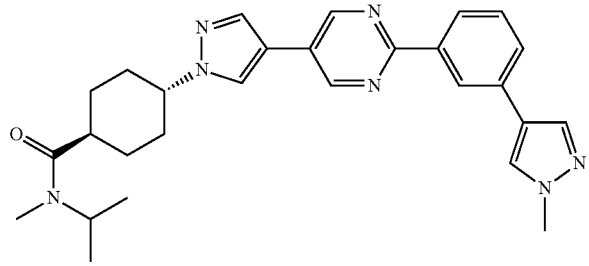 [SMILES: CC(C)N(C)C(=O)[C@H]1CC[C@H](n2cc(-c3cnc(-c4cccc(-c5cnn(C)c5)c4)nc3)cn2)CC1]<br>HPLC (max plot) 88.6%; (254 nm) 88.0%; Rt (min) 3.68; MS: (ESI+) 484.4. |
| 201 | 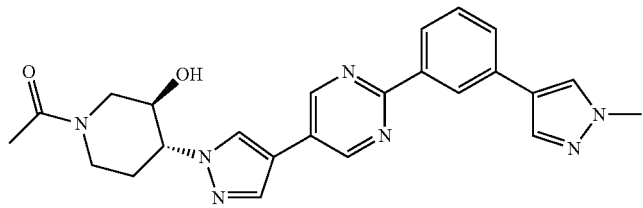 [SMILES: CC(=O)N1CC[C@@H](n2cc(-c3cnc(-c4cccc(-c5cnn(C)c5)c4)nc3)cn2)[C@H](O)C1]<br>HPLC (Chiralpak IC; EtOH:DEA:THF; 95:0.1:5); (220 nm) 100% ; Rt (min) 6.69. |
| 202 | 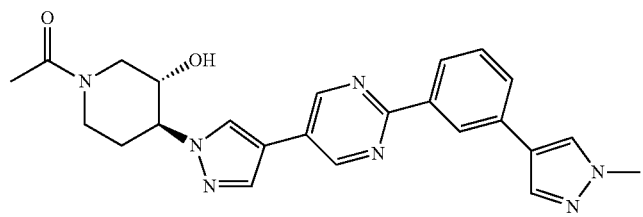 [SMILES: CC(=O)N1CC[C@H](n2cc(-c3cnc(-c4cccc(-c5cnn(C)c5)c4)nc3)cn2)[C@@H](O)C1]<br>HPLC (Chiralpak IC; EtOH:DEA:THF; 95:0.1:5); (max plot) 99.9% ; Rt (min) 8.05. |
| 203 | 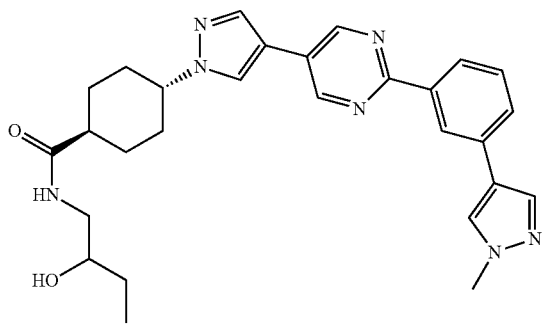 [SMILES: CCC(O)CNC(=O)[C@H]1CC[C@H](n2cc(-c3cnc(-c4cccc(-c5cnn(C)c5)c4)nc3)cn2)CC1]<br>HPLC (max plot) 93.6%; (254 nm) 92.00%; Rt (min) 3.06; MS: (ESI+) 500.4 |
| 204 | 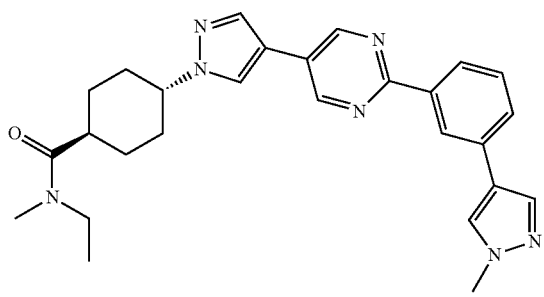 [SMILES: CCN(C)C(=O)[C@H]1CC[C@H](n2cc(-c3cnc(-c4cccc(-c5cnn(C)c5)c4)nc3)cn2)CC1]<br>HPLC (max plot) 89.1%; (254 nm) 89.0%; Rt (min) 3.44; MS: (ESI+) 470.4. |

| Ex |
|---|
| 205 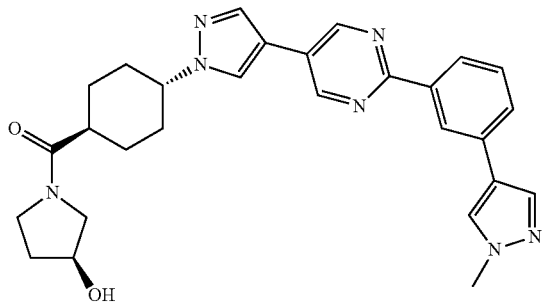 [SMILES: Cn1cc(-c2cccc(-c3ncc(-c4cnn([C@H]5CC[C@H](C(=O)N6CC[C@H](O)C6)CC5)c4)cn3)c2)cn1]
HPLC (max plot) 91.1%; (254 nm) 88.6%; Rt (min) 2.88; MS: (ESI+) 498.3. |
| 206 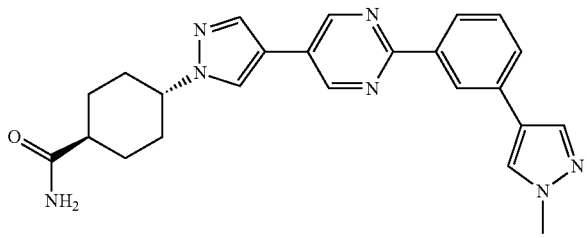 [SMILES: Cn1cc(-c2cccc(-c3ncc(-c4cnn([C@H]5CC[C@H](C(N)=O)CC5)c4)cn3)c2)cn1]
HPLC (max plot) 89.5%; (254 nm) 89.0%; Rt (min) 2.85; MS: (ESI+) 428.3 |
| 207 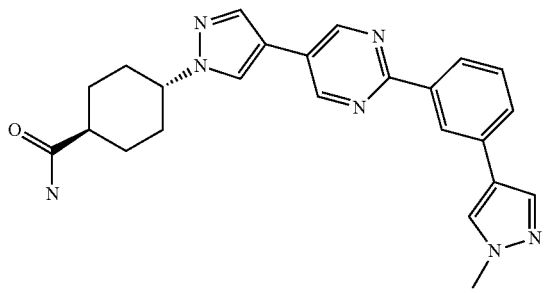 [SMILES: Cn1cc(-c2cccc(-c3ncc(-c4cnn([C@H]5CC[C@H](C(N)=O)CC5)c4)cn3)c2)cn1]
HPLC (max plot) 100%; (254 nm) 100%; Rt (min) 4.03; MS: (ESI+) 403.3 |
| 208 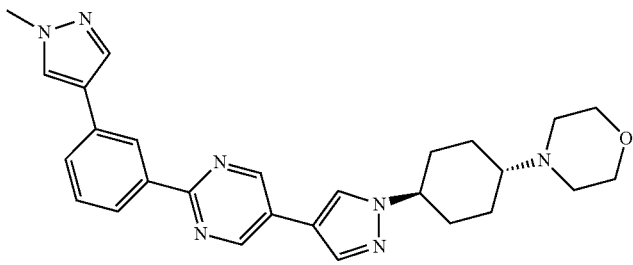 [SMILES: Cn1cc(-c2cccc(-c3ncc(-c4cnn([C@H]5CC[C@H](N6CCOCC6)CC5)c4)cn3)c2)cn1]
HPLC (max plot) 99.4%; (254 nm) 99.0%; Rt (min) 2.66; MS: (ESI+) 470.5. |
| 209 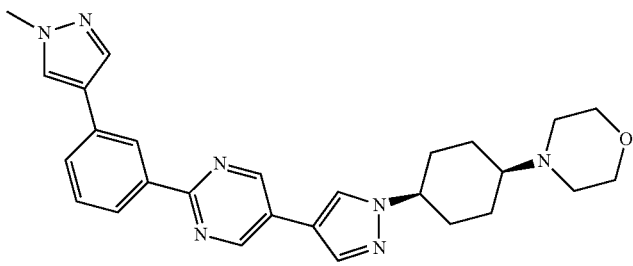 [SMILES: Cn1cc(-c2cccc(-c3ncc(-c4cnn([C@H]5CC[C@@H](N6CCOCC6)CC5)c4)cn3)c2)cn1]
HPLC (max plot) 100%; (254 nm) 100%; Rt (min) 2.65; MS: (ESI+) 470.4. |

| Ex | |
|---|---|
| 210 | 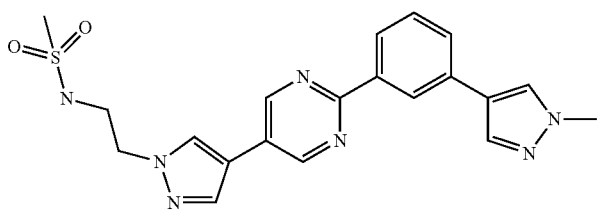 [SMILES: Cn1cc(-c2cccc(-c3ncc(-c4cnn(CCNS(C)(=O)=O)c4)cn3)c2)cn1] HPLC (max plot) 99.9%; (254 nm) 99.9%; Rt (min) 2.91; MS: (ESI+) 424.4. |
| 211 | 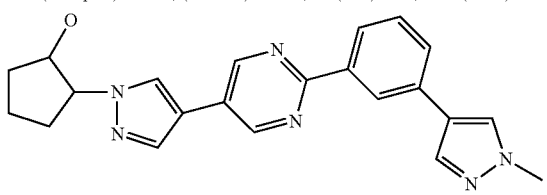 HPLC (max plot) 99.2%; (254 nm) 100%; Rt (min) 3.08; MS: (ESI+) 387.4. |
| 212 | 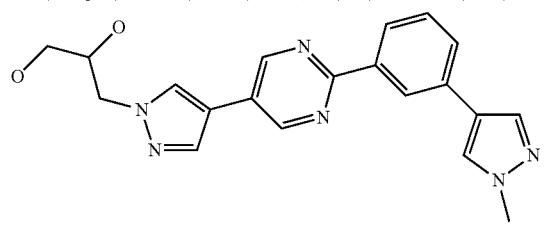 HPLC (max plot) 99.5%; (254 nm) 100%; Rt (min) 2.39; MS: (ESI+) 377.3. |
| 213 | 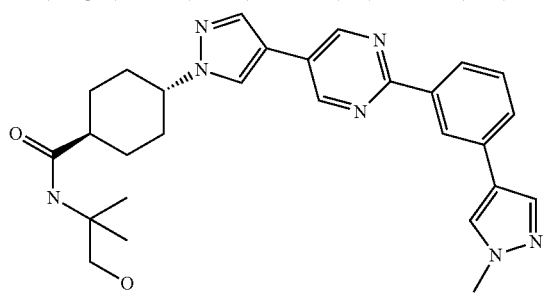 [SMILES: Cn1cc(-c2cccc(-c3ncc(-c4cnn([C@H]5CC[C@H](C(=O)NC(C)(C)CO)CC5)c4)cn3)c2)cn1] HPLC (max plot) 84.7%; (254 nm) 84.0%; Rt (min) 3.17; MS: (ESI+) 500.4. |
| 214 | 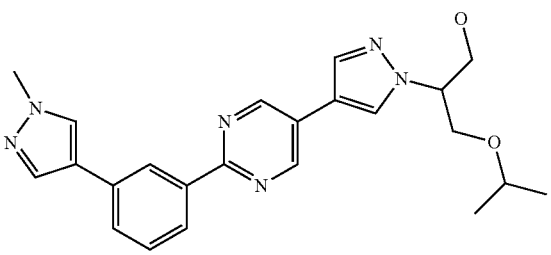 [SMILES: CC(C)OCC(CO)n1cc(-c2cnc(-c3cccc(-c4cnn(C)c4)c3)nc2)cn1] HPLC (max plot) 100%; (254 nm) 100%; Rt (min) 3.23; MS: (ESI+) 419.4. |
| 215 | 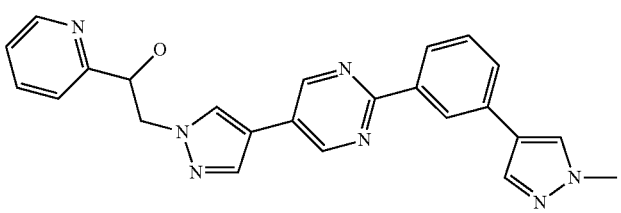 [SMILES: Cn1cc(-c2cccc(-c3ncc(-c4cnn(CC(O)c5ccccn5)c4)cn3)c2)cn1] HPLC (max plot) 95.5%; (254 nm) 94.7%; Rt (min) 2.44; MS: (ESI+) 424.4 |

| Ex | |
|---|---|
| 216 | 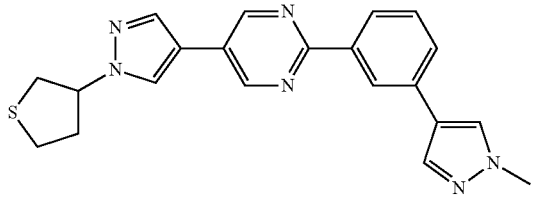 [SMILES: Cn1cc(-c2cccc(-c3ncc(-c4cnn(C5CCSC5)c4)cn3)c2)cn1]
HPLC (max plot) 98.0%; (254 nm) 97.8%; Rt (min) 3.80; MS: (ESI+) 389.4. m.p.: 193.0-195.0 °C. |
| 217 | 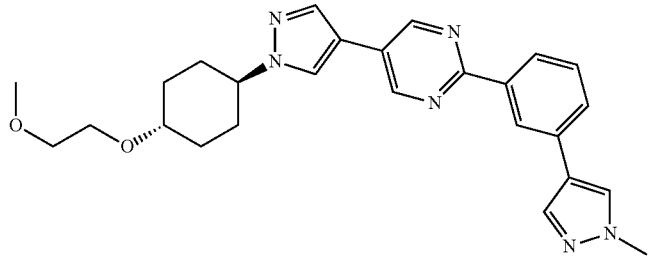 [SMILES: COCCO[C@H]1CC[C@H](n2cc(-c3cnc(-c4cccc(-c5cnn(C)c5)c4)nc3)cn2)CC1]
HPLC (max plot) 99.6%; (254 nm) 100%; Rt (min) 3.66; MS: (ESI+) 459.4. |
| 218 | 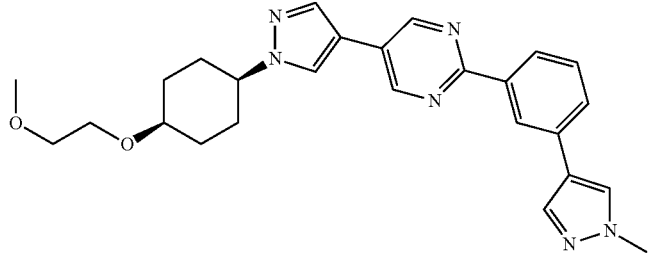 [SMILES: COCCO[C@H]1CC[C@@H](n2cc(-c3cnc(-c4cccc(-c5cnn(C)c5)c4)nc3)cn2)CC1]
HPLC (max plot) 100%; (254 nm) 100%; Rt (min) 3.80; MS: (ESI+) 459.4. |
| 219 | 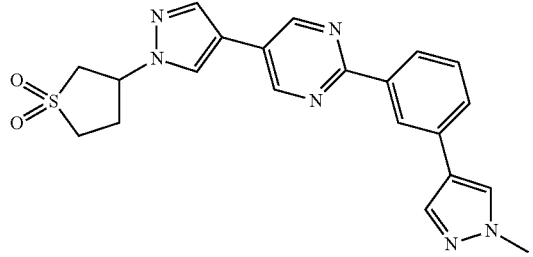 [SMILES: Cn1cc(-c2cccc(-c3ncc(-c4cnn(C5CCS(=O)(=O)C5)c4)cn3)c2)cn1]
HPLC (max plot) 98.1%; (254 nm) 97.2%; Rt (min) 3.16; MS: (ESI+) 479.4; m.p.: 247.0-250.0° C. |
| 220 | 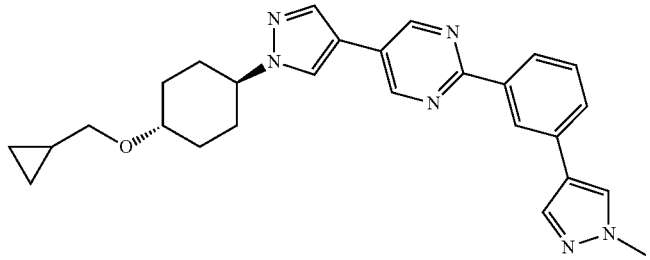 [SMILES: Cn1cc(-c2cccc(-c3ncc(-c4cnn([C@H]5CC[C@H](OCC6CC6)CC5)c4)cn3)c2)cn1]
HPLC (max plot) 99.9%; (254 nm) 99.8%; Rt (min) 4.31; MS: (ESI+) 455.4. |

| Ex | |
|---|---|
| 221 | 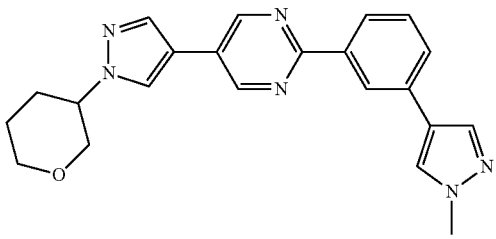 [SMILES: Cn1cc(-c2cccc(-c3ncc(-c4cnn(C5CCCOC5)c4)cn3)c2)cn1]<br>HPLC (max plot) 98.9%; (254 nm) 98.7%; Rt (min) 3.47; MS: (ESI+) 387.4. |
| 222 | 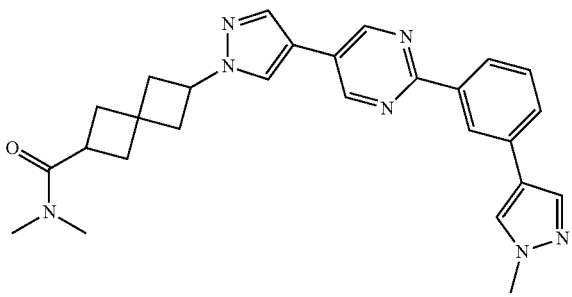 [SMILES: CN(C)C(=O)C1CC2(C1)CC(n1cc(-c3cnc(-c4cccc(-c5cnn(C)c5)c4)nc3)cn1)C2]<br>HPLC (max plot) 89.8%; (254 nm) 83.9%; Rt (min) 3.40; MS: (ESI+) 468.5. |
| 223 | 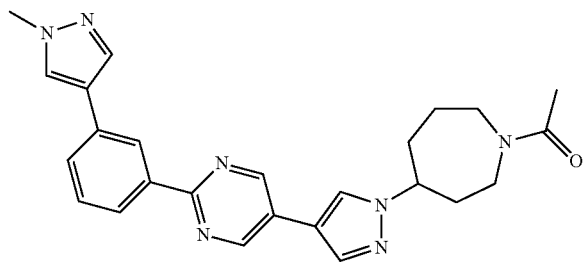 [SMILES: CC(=O)N1CCCC(n2cc(-c3cnc(-c4cccc(-c5cnn(C)c5)c4)nc3)cn2)CC1]<br>HPLC (max plot) 99.4%; (254 nm) 99.5%; Rt (min) 3.20; MS: (ESI+) 442.5. |
| 224 | 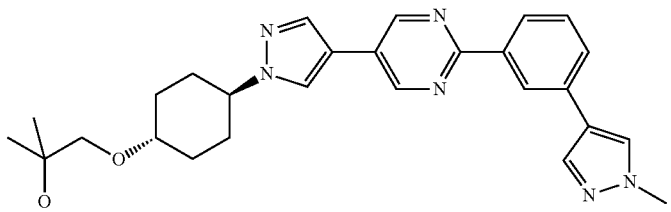 [SMILES: Cn1cc(-c2cccc(-c3ncc(-c4cnn([C@H]5CC[C@H](OCC(C)(C)O)CC5)c4)cn3)c2)cn1]<br>HPLC (max plot) 99.0%; (254 nm) 98.7%; Rt (min) 3.73; MS: (ESI+) 473.6. |
| 225 | 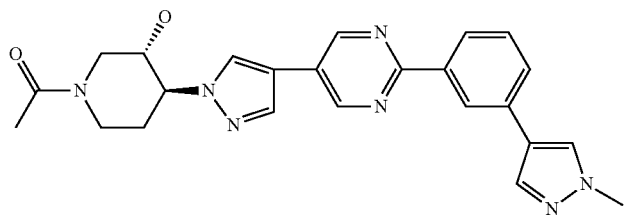 [SMILES: CC(=O)N1CC[C@H](n2cc(-c3cnc(-c4cccc(-c5cnn(C)c5)c4)nc3)cn2)[C@@H](O)C1]<br>HPLC (Chiralpak IC; EtOH:DEA; 100:0.1); (max plot) 99.2%; Rt (min) 11.02. |

| Ex | |
|---|---|
| 226 | 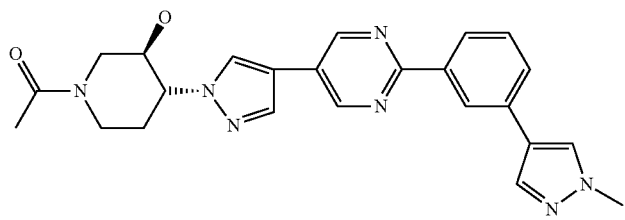<br>HPLC (Chiralpak IC; EtOH:DEA; 100:0.1); (max plot) 98.2%; Rt (min) 13.7. |
| 227 | 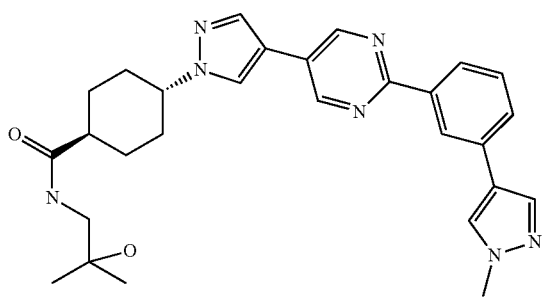 [SMILES: Cn1cc(-c2cccc(-c3ncc(-c4cnn([C@H]5CC[C@H](C(=O)NCC(C)(C)O)CC5)c4)cn3)c2)cn1]<br>HPLC (max plot) 92.3%; (254 nm) 87.7%; Rt (min) 3.00; MS: (ESI−) 498.7. |
| 228 | 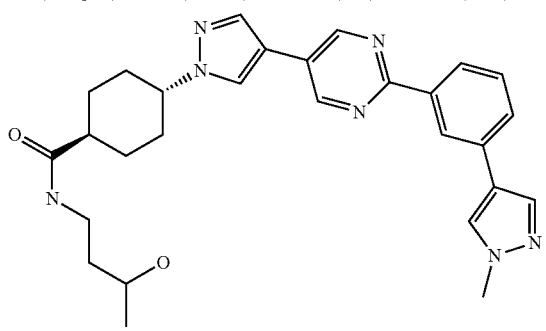<br>HPLC (max plot) 93.2%; (254 nm) 92.3%; Rt (min) 2.99; MS: (ESI+) 500.6. |
| 229 | 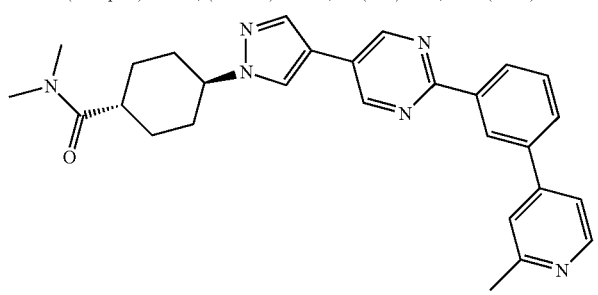<br>HPLC (max plot) 97.1%; (254 nm) 96.4%; Rt (min) 2.60; MS: (ESI+) 467.5. |
| 230 | 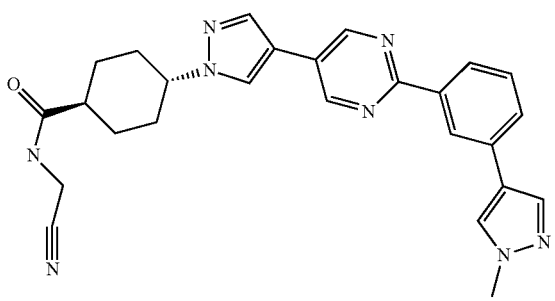 [SMILES: Cn1cc(-c2cccc(-c3ncc(-c4cnn([C@H]5CC[C@H](C(=O)NCC#N)CC5)c4)cn3)c2)cn1]<br>HPLC (max plot) 97.9%; (254 nm) 93.3%; Rt (min) 3.14; MS: (ESI+) 467.4. |

| Ex | |
|---|---|
| 231 | 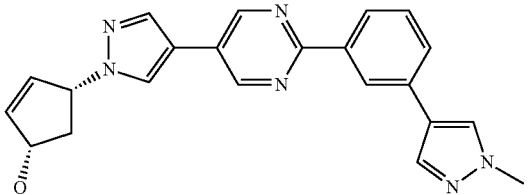 [SMILES: Cn1cc(-c2cccc(-c3ncc(-c4cnn([C@H]5C=C[C@@H](O)C5)c4)cn3)c2)cn1] HPLC (max plot) 100%; (254 nm) 100%; Rt (min) 3.07; MS: (ESI+) 385.4. |
| 232 | 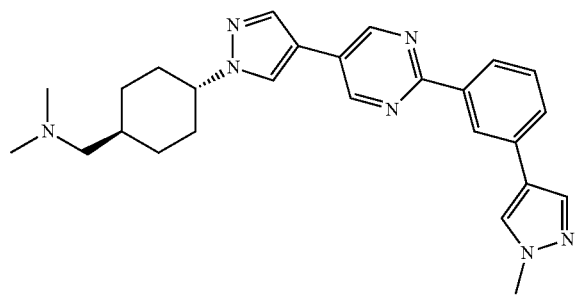 HPLC (max plot) 97.9%; (254 nm) 93.3%; Rt (min) 3.14; MS: (ESI+) 467.4. |
| 233 | 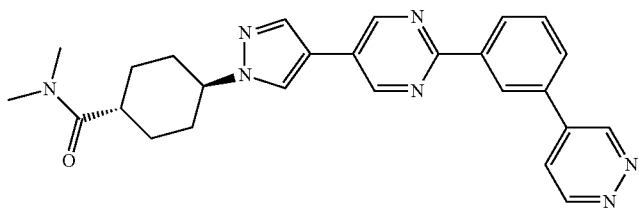 [SMILES: CN(C)C(=O)[C@H]1CC[C@H](n2cc(-c3cnc(-c4cccc(-c5ccnnc5)c4)nc3)cn2)CC1] HPLC (max plot) 90.2%; (254 nm) 86.4%; Rt (min) 2.88; MS: (ESI+) 454.5. |
| 234 | 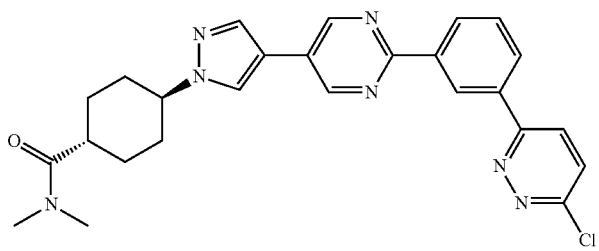 [SMILES: CN(C)C(=O)[C@H]1CC[C@H](n2cc(-c3cnc(-c4cccc(-c5ccc(Cl)nn5)c4)nc3)cn2)CC1] HPLC (max plot) 100%; (254 nm) 89.4%; Rt (min) 3.51; MS: (ESI+) 488.5. |
| 235 | 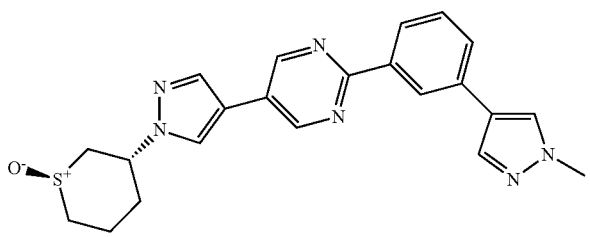 [SMILES: Cn1cc(-c2cccc(-c3ncc(-c4cnn([C@@H]5CCC[S@@+]([O-])C5)c4)cn3)c2)cn1] HPLC (max plot) 100%; (254 nm) 100%; Rt (min) 3.02; MS: (ESI+) 419.5. |

| Ex | |
|---|---|
| 236 | 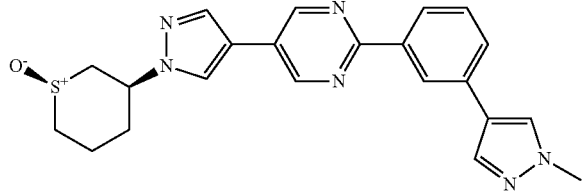 [SMILES: Cn1cc(-c2cccc(-c3ncc(-c4cnn([C@H]5CCC[S@@+]([O-])C5)c4)cn3)c2)cn1]
HPLC (max plot) 98.2%; (254 nm) 98.9%; Rt (min) 2.98; MS: (ESI+) 419.5. |
| 237 | 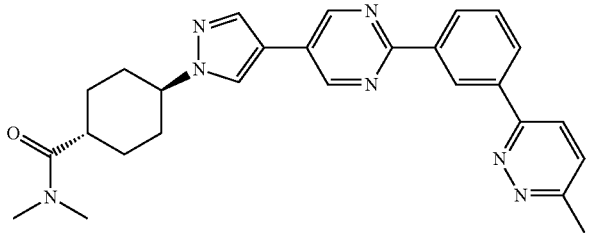 [SMILES: Cc1ccc(-c2cccc(-c3ncc(-c4cnn([C@H]5CC[C@H](C(=O)N(C)C)CC5)c4)cn3)c2)nn1]
HPLC (max plot) 88.5%; (254 nm) 92.0%; Rt (min) 2.72; MS: (ESI+) 468.5. |
| 238 | 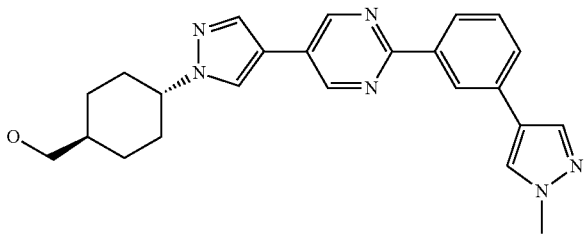 [SMILES: Cn1cc(-c2cccc(-c3ncc(-c4cnn([C@H]5CC[C@H](CO)CC5)c4)cn3)c2)cn1]
HPLC (max plot) 95.5%; (254 nm) 96.4%; Rt (min) 3.22; MS: (ESI+) 415.5. |
| 239 | 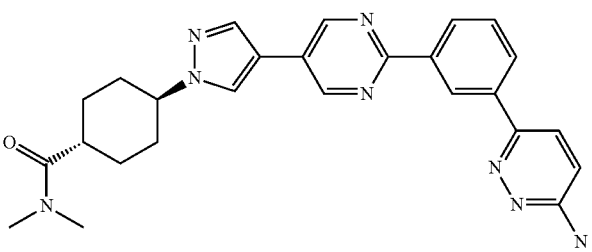 [SMILES: CN(C)C(=O)[C@H]1CC[C@H](n2cc(-c3cnc(-c4cccc(-c5ccc(N)nn5)c4)nc3)cn2)CC1]
HPLC (max plot) 86.8%; (254 nm) 93.3%; Rt (min) 2.61; MS: (ESI+) 469.5. |
| 240 | 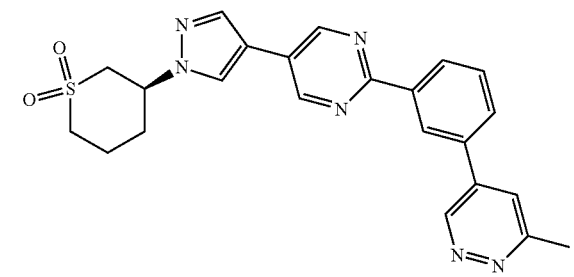 [SMILES: Cc1cc(-c2cccc(-c3ncc(-c4cnn([C@H]5CCCS(=O)(=O)C5)c4)cn3)c2)cnn1]
HPLC (max plot) 97.0%; (254 nm) 97.7%; Rt (min) 2.28; MS: (ESI+) 447.4. |

| Ex | |
|---|---|
| 241 | 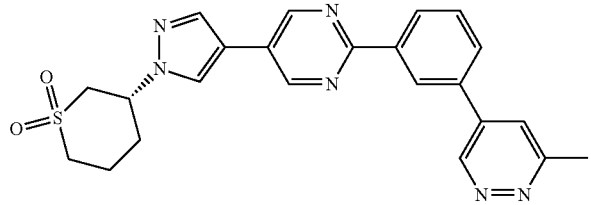 [SMILES: Cc1cc(-c2cccc(-c3ncc(-c4cnn([C@@H]5CCCS(=O)(=O)C5)c4)cn3)c2)cnn1] |
HPLC (max plot) 99.6%; (254 nm) 98.9%; Rt (min) 2.45; MS: (ESI+) 447.5.
| 242 | 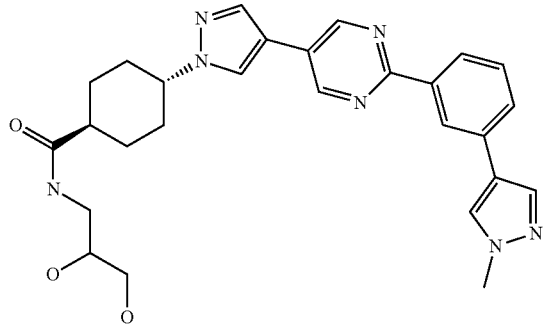 [SMILES: Cn1cc(-c2cccc(-c3ncc(-c4cnn([C@H]5CC[C@H](C(=O)NCC(O)CO)CC5)c4)cn3)c2)cn1] |
HPLC (max plot) 95.0%; (254 nm) 95.9%; Rt (min) 2.73; MS: (ESI+) 502.5.
| 243 | 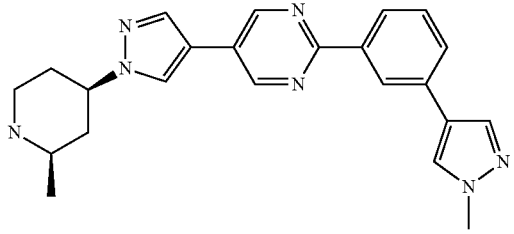 [SMILES: C[C@@H]1C[C@H](n2cc(-c3cnc(-c4cccc(-c5cnn(C)c5)c4)nc3)cn2)CCN1] |
HPLC (max plot) 98.2%; (254 nm) 96.3%; Rt (min) 2.47; MS: (ESI+) 400.5.
| 244 | 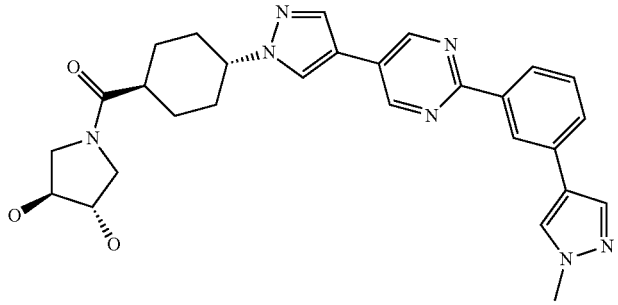 [SMILES: Cn1cc(-c2cccc(-c3ncc(-c4cnn([C@H]5CC[C@H](C(=O)N6C[C@H](O)[C@@H](O)C6)CC5)c4)cn3)c2)cn1] |
HPLC (max plot) 98.3%; (254 nm) 97.8%; Rt (min) 2.74; MS: (ESI+) 514.6.
| 245 | 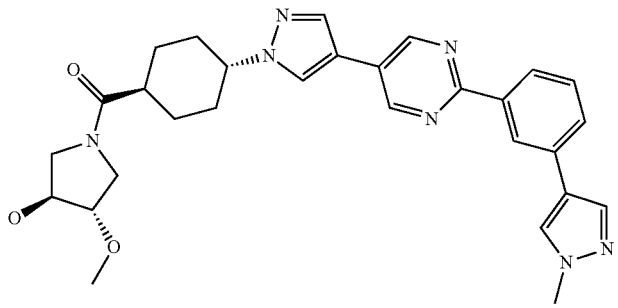 [SMILES: CO[C@H]1CN(C(=O)[C@H]2CC[C@H](n3cc(-c4cnc(-c5cccc(-c6cnn(C)c6)c5)nc4)cn3)CC2)C[C@@H]1O] |
HPLC (max plot) 91.9%; (254 nm) 90.7%; Rt (min) 3.00; MS: (ESI+) 528.6.

| Ex | |
|---|---|
| 246 | 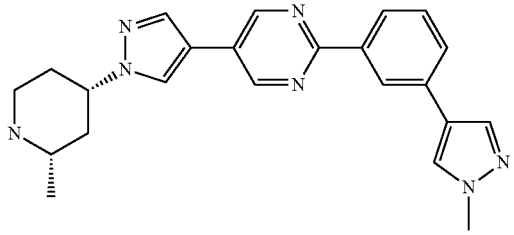 [SMILES: C[C@H]1C[C@@H](n2cc(-c3cnc(-c4cccc(-c5cnn(C)c5)c4)nc3)cn2)CCN1] |
HPLC (max plot) 96.7%; (254 nm) 97.8%; Rt (min) 2.43; MS: (ESI+) 400.4.
| 247 | 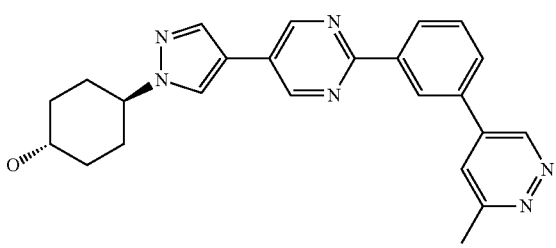 [SMILES: Cc1cc(-c2cccc(-c3ncc(-c4cnn([C@H]5CC[C@H](O)CC5)c4)cn3)c2)cnn1] |
|---|---|
HPLC (max plot) 93.8%; (254 nm) 95.5%; Rt (min) 2.42; MS: (ESI+) 413.4.
| 248 | 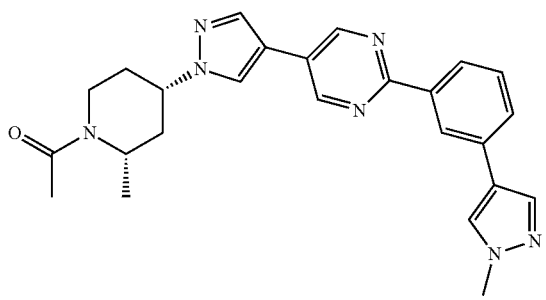 [SMILES: CC(=O)N1CC[C@H](n2cc(-c3cnc(-c4cccc(-c5cnn(C)c5)c4)nc3)cn2)C[C@@H]1C] |
|---|---|
HPLC (max plot) 97.6%; (254 nm) 97.1%; Rt (min) 3.31; MS: (ESI+) 442.5.
| 249 | 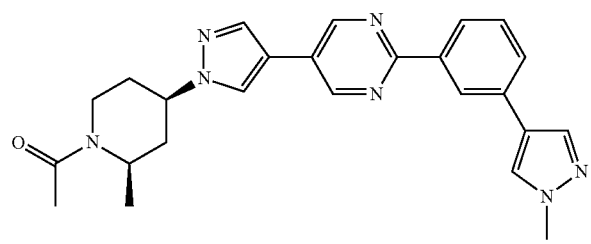 [SMILES: CC(=O)N1CC[C@@H](n2cc(-c3cnc(-c4cccc(-c5cnn(C)c5)c4)nc3)cn2)C[C@H]1C] |
|---|---|
HPLC (max plot) 97.3%; (254 nm) 96.7%; Rt (min) 3.30; MS: (ESI+) 442.5.
| 250 | 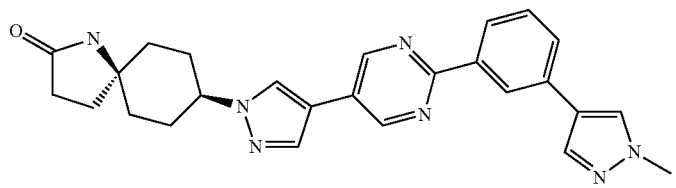 [SMILES: Cn1cc(-c2cccc(-c3ncc(-c4cnn([C@H]5CC[C@]6(CCC(=O)N6)CC5)c4)cn3)c2)cn1] |
|---|---|
| 251 | 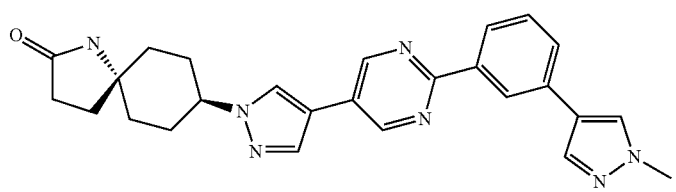 [SMILES: Cn1cc(-c2cccc(-c3ncc(-c4cnn([C@H]5CC[C@@]6(CCC(=O)N6)CC5)c4)cn3)c2)cn1] |

| Ex | |
|---|---|
| 252 | 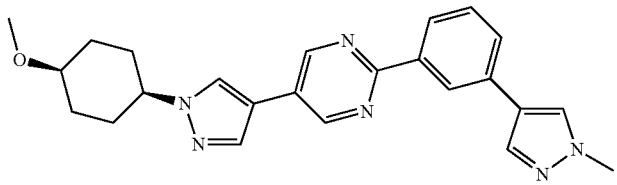<br>HPLC (max plot) 72.6%; (254 nm) 100%; Rt (min) 3.82; MS: (ESI+) 415.4. |
| 253 | 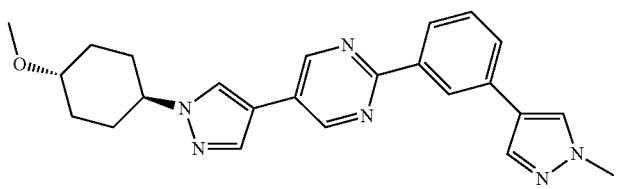<br>HPLC (max plot) 100%; (254 nm) 98.9%; Rt (min) 3.72; MS: (ESI+) 415.4. |
| 254 | 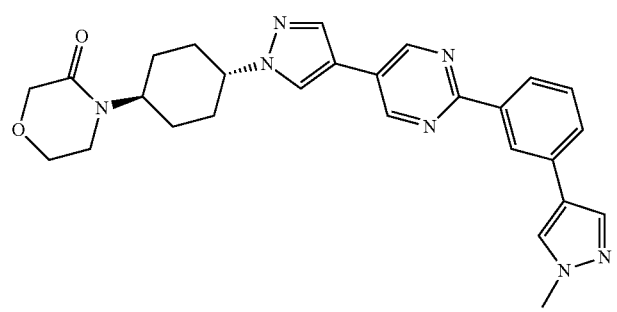 [SMILES: Cn1cc(-c2cccc(-c3ncc(-c4cnn([C@H]5CC[C@H](N6CCOCC6=O)CC5)c4)cn3)c2)cn1] |
| 255 | 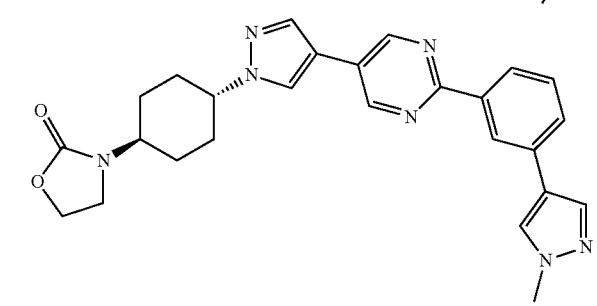 |
| 256 | 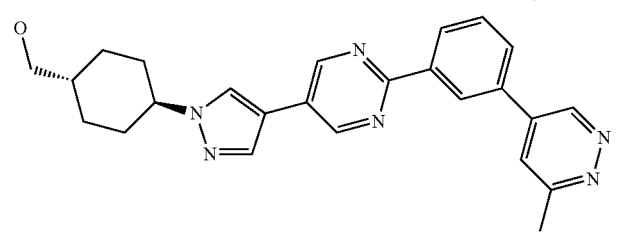 [SMILES: Cc1cc(-c2cccc(-c3ncc(-c4cnn([C@H]5CC[C@H](CO)CC5)c4)cn3)c2)cnn1]<br>HPLC (max plot) 99.1%; (254 nm) 99.2%; Rt (min) 2.70; MS: (ESI+) 427.3. |
| 257 | 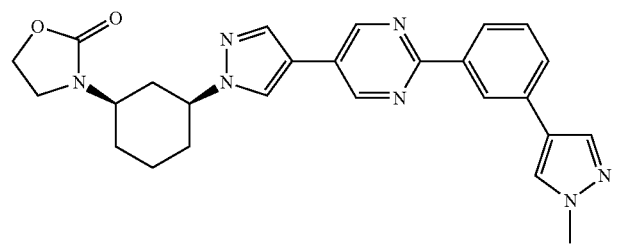 [SMILES: Cn1cc(-c2cccc(-c3ncc(-c4cnn([C@H]5CCC[C@@H](N6CCOC6=O)C5)c4)cn3)c2)cn1]<br>HPLC (max plot) 96.7%; (254 nm) 99.2%; Rt (min) 3.51; MS: (ESI+) 470.3. |

-continued
| Ex |
|---|
| 258 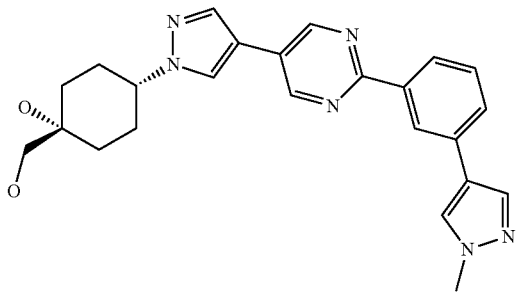 [SMILES: Cn1cc(-c2cccc(-c3ncc(-c4cnn([C@H]5CC[C@](O)(CO)CC5)c4)cn3)c2)cn1] |
| 259 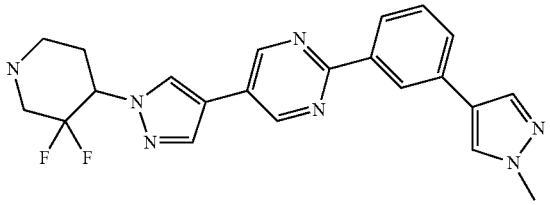 [SMILES: Cn1cc(-c2cccc(-c3ncc(-c4cnn(C5CCNCC5(F)F)c4)cn3)c2)cn1] |
| 260 |
| 261 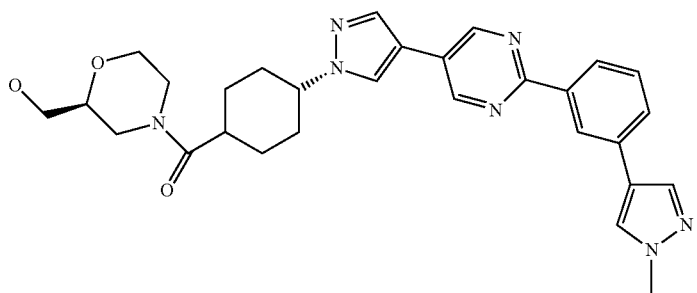
HPLC (max plot) 99.7%; (254 nm) 99.4%; Rt (min) 3.34; MS: (ESI+) 528.3. |
| 262 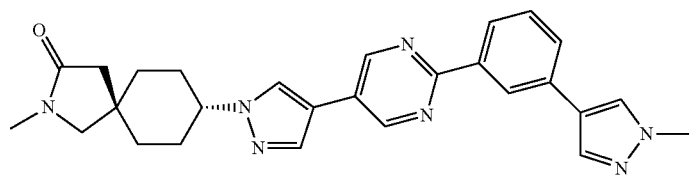 |
| 263 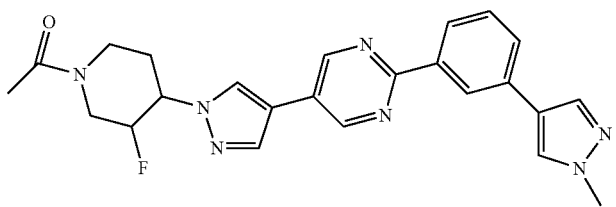 [SMILES: CC(=O)N1CCC(n2cc(-c3cnc(-c4cccc(-c5cnn(C)c5)c4)nc3)cn2)C(F)C1]
HPLC (max plot) 96.1%; (254 nm) 97.4%; Rt (min) 3.37; MS: (ESI+) 446.3. |
| 264 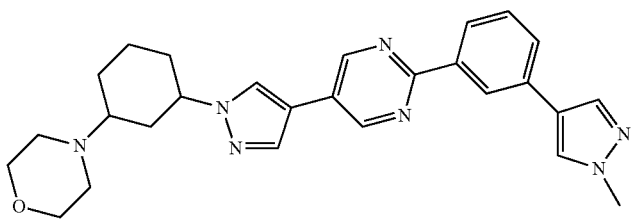 [SMILES: Cn1cc(-c2cccc(-c3ncc(-c4cnn(C5CCCC(N6CCOCC6)C5)c4)cn3)c2)cn1]
HPLC (max plot) 99.0%; (254 nm) 96.6%; Rt (min) 3.80; MS: (ESI+) 457.20. |

-continued
| Ex |  |
|---|---|
| 265 | 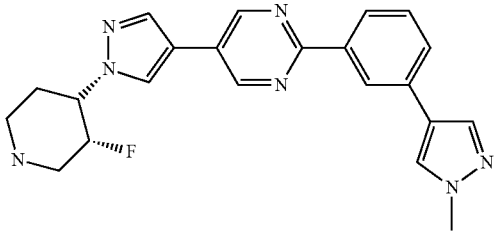 |
| 266 | 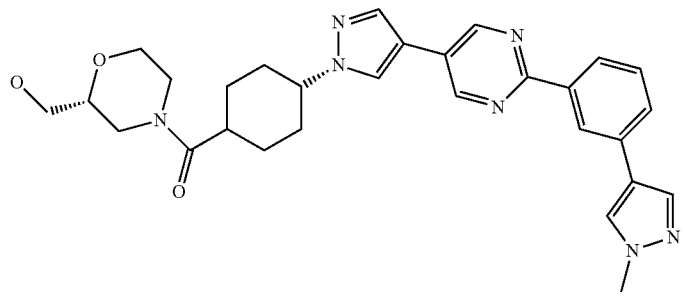 |
HPLC (max plot) 98.7%; (254 nm) 98.2%; Rt (min) 3.37; MS: (ESI+) 528.30.
| 267 | 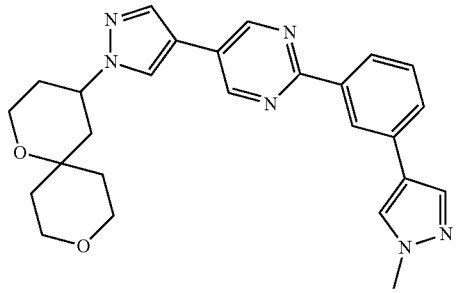 [SMILES: Cn1cc(-c2cccc(-c3ncc(-c4cnn(C5CCOC6(CCOCC6)C5)c4)cn3)c2)cn1] |
HPLC (max plot) 99.0%; (254 nm) 96.6%; Rt (min) 3.80; MS: (ESI+) 457.20.
| 268 | 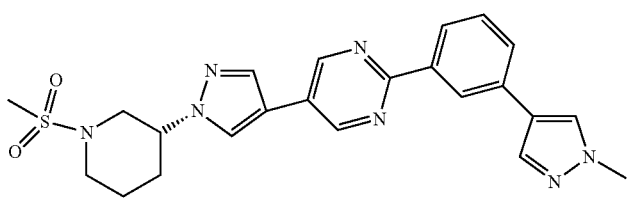 |
HPLC (max plot) 96.4%; (254 nm) 92.1%; Rt (min) 3.78; MS: (ESI+) 464.20.
| 269 | 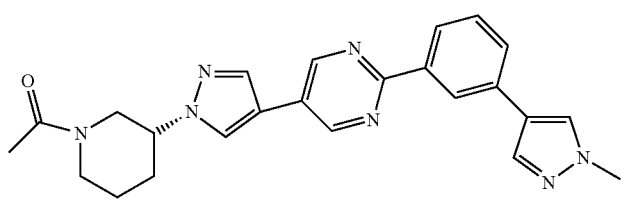 |
HPLC (max plot) 99.2%; (254 nm) 98.0%; Rt (min) 3.52; MS: (ESI+) 428.30.

| Ex | |
|---|---|
| 270 | 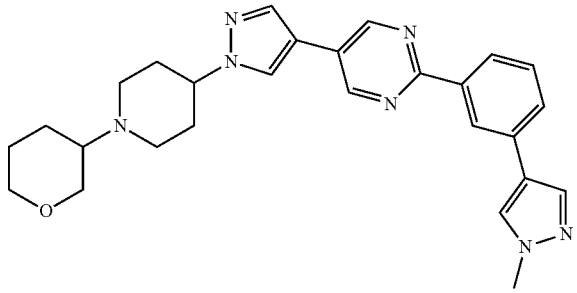 [SMILES: Cn1cc(-c2cccc(-c3ncc(-c4cnn(C5CCN(C6CCCOC6)CC5)c4)cn3)c2)cn1] |
| | HPLC (max plot) 98.3%; (254 nm) 97.1%; Rt (min) 2.90; MS: (ESI+) 470.20. |
| 271 | 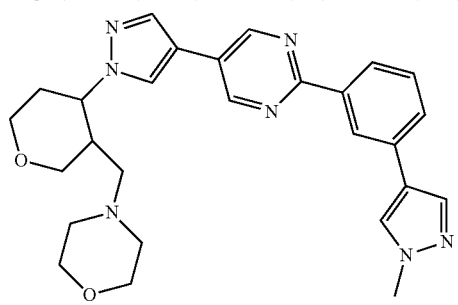 [SMILES: Cn1cc(-c2cccc(-c3ncc(-c4cnn(C5CCOCC5CN5CCOCC5)c4)cn3)c2)cn1] |
| | HPLC (max plot) 96.0%; (254 nm) 95.4%; Rt (min) 2.98; MS: (ESI+) 486.20. |
| 272 | 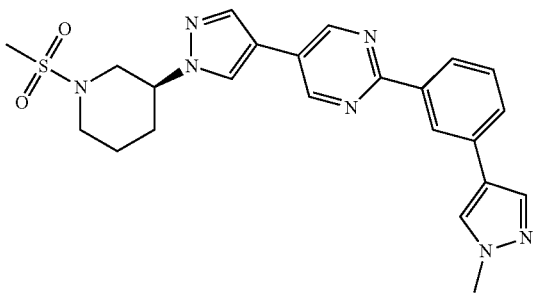 [SMILES: Cn1cc(-c2cccc(-c3ncc(-c4cnn([C@H]5CCCN(S(C)(=O)=O)C5)c4)cn3)c2)cn1] |
| | HPLC (max plot) 96.42%; (254 nm) 92.11%; Rt (min) 3.78; MS: (ESI+) 464.20. |
| 273 | 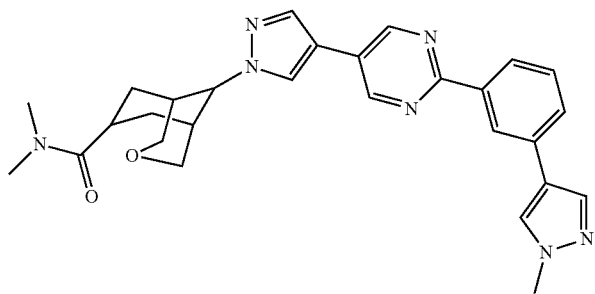 [SMILES: CN(C)C(=O)C1CC2COCC(C1)C2n1cc(-c2cnc(-c3cccc(-c4cnn(C)c4)c3)nc2)cn1] |
| | HPLC (max plot) 95.2%; (254 nm) 95.5%; Rt (min) 4.85; MS: (ESI+) 498.2. contains 10% of the cis isomer (example 194). |
| 274 | 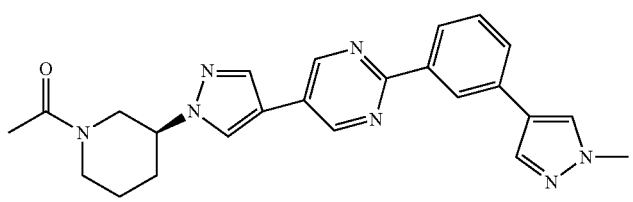 [SMILES: CC(=O)N1CCC[C@H](n2cc(-c3cnc(-c4cccc(-c5cnn(C)c5)c4)nc3)cn2)C1] |
| | HPLC (max plot) 99.23%; (254 nm) 98.04%; Rt (min) 3.52; MS: (ESI+) 428.30. |

| Ex |
|---|
| 275 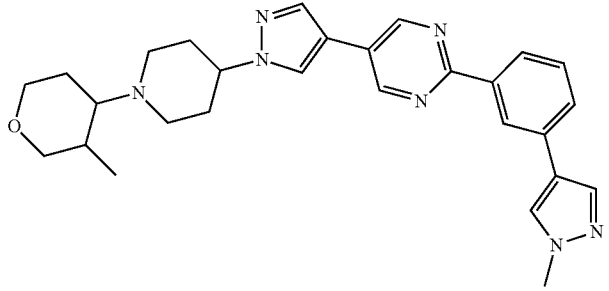 [SMILES: CC1COCCC1N1CCC(n2cc(-c3cnc(-c4cccc(-c5cnn(C)c5)c4)nc3)cn2)CC1]
HPLC (max plot) 99.0%; (254 nm) 98.5%; Rt (min) 3.17; MS: (ESI+) 484.4. m.p.: 176.30-180.80° C. |
| 276 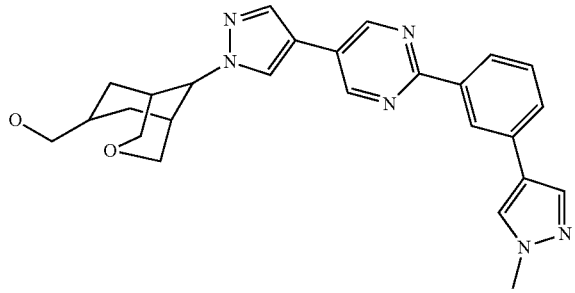 [SMILES: Cn1cc(-c2cccc(-c3ncc(-c4cnn(C5C6COCC5CC(CO)C6)c4)cn3)c2)cn1]
HPLC (max plot) 96.7%; (254 nm) 98.6%; Rt (min) 3.38; MS: (ESI+) 457.30; m.p.: 182.00-214.80° C. |
| 277 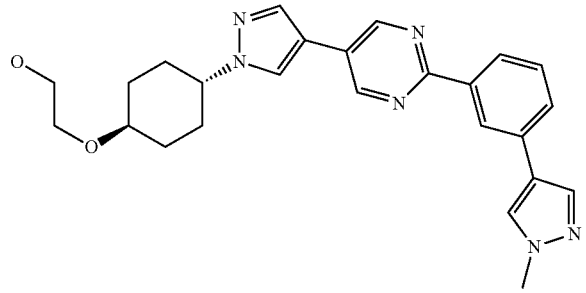 [SMILES: Cn1cc(-c2cccc(-c3ncc(-c4cnn([C@H]5CC[C@H](OCCO)CC5)c4)cn3)c2)cn1]
HPLC (max plot) 97.41%; (254 nm) 96.82%; Rt (min) 3.67; MS: (ESI+) 445.00. m.p.: 218.70-223.30° C. |
| 278 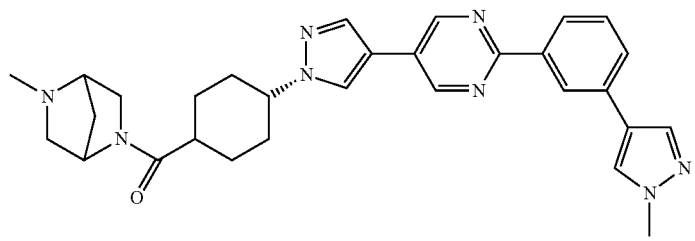
HPLC (max plot) 97.47%; (254 nm) 98.65%; Rt (min) 3.25; MS: (ESI+) 523.20. m.p.: 50.30-55.00° C. |

| Ex | |
|---|---|
| 279 | 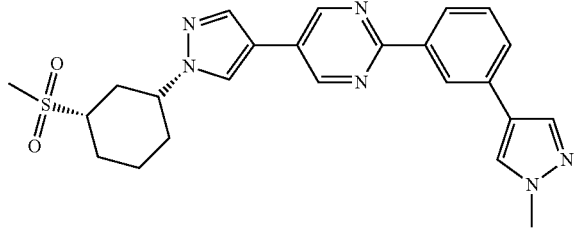<br>HPLC (max plot) 97.2%; (254 nm) 95.3%; Rt (min) 3.64; MS: (ESI+) 463.3. m.p.: 218.5-222.8° C. |
| 280 | 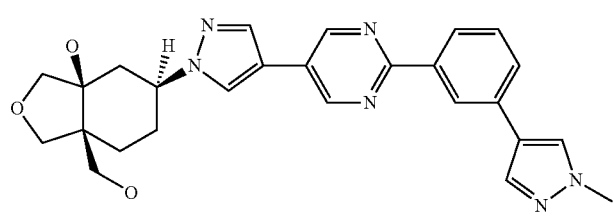 [SMILES: Cn1cc(-c2cccc(-c3ncc(-c4cnn([C@H]5CC[C@]6(CO)COC[C@]6(O)C5)c4)cn3)c2)cn1] |
| 281 | 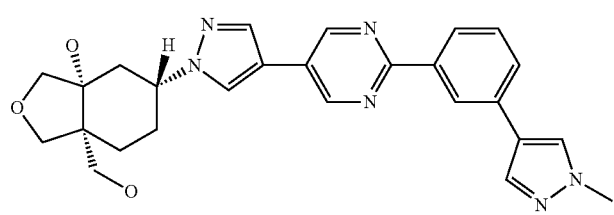 [SMILES: Cn1cc(-c2cccc(-c3ncc(-c4cnn([C@@H]5CC[C@@]6(CO)COC[C@@]6(O)C5)c4)cn3)c2)cn1] |
| 282 | 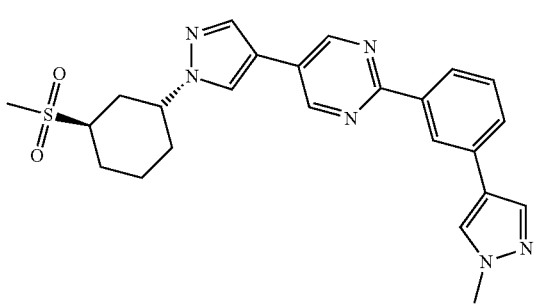<br>HPLC (max plot) 97.5%; (254 nm) 97.3%; Rt (min) 3.93; MS: (ESI+) 463.3. m.p.: 159.0-168.5° C. |
| 283 | 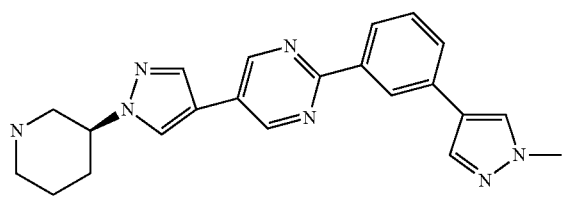 [SMILES: Cn1cc(-c2cccc(-c3ncc(-c4cnn([C@H]5CCCNC5)c4)cn3)c2)cn1]<br>HPLC (max plot) 99.85%; (254 nm) 99.58%; Rt (min) 2.88; MS: (ESI+) 386.20. m.p.: 175.80-180.60° C. |
| 284 | 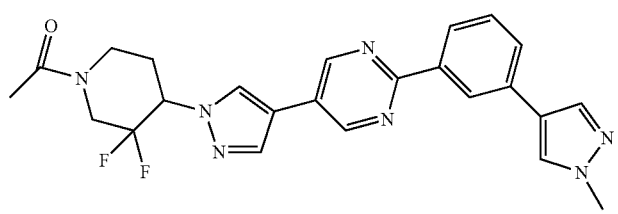 [SMILES: CC(=O)N1CCC(n2cc(-c3cnc(-c4cccc(-c5cnn(C)c5)c4)nc3)cn2)C(F)(F)C1] |

| Ex | |
|---|---|
| 285 | 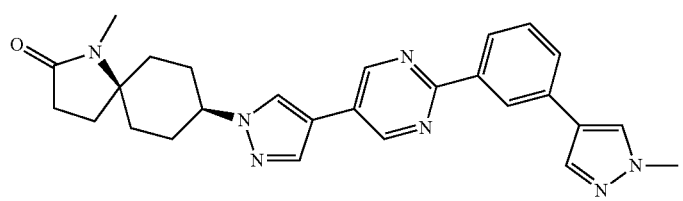 [SMILES: Cn1cc(-c2cccc(-c3ncc(-c4cnn([C@H]5CC[C@]6(CCC(=O)N6C)CC5)c4)cn3)c2)cn1] |
| 286 | 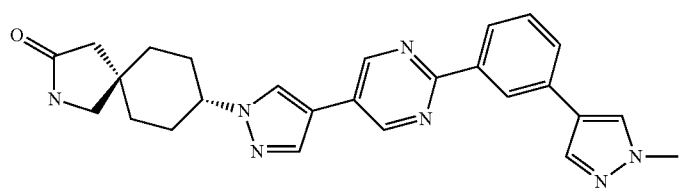 [SMILES: Cn1cc(-c2cccc(-c3ncc(-c4cnn([C@H]5CC[C@@]6(CC5)CNC(=O)C6)c4)cn3)c2)cn1] |
| 287 | 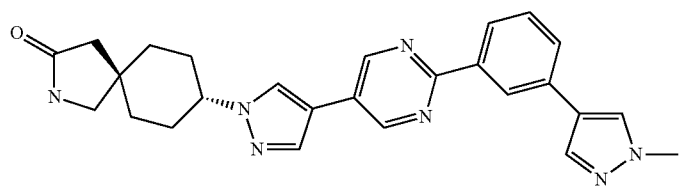 [SMILES: Cn1cc(-c2cccc(-c3ncc(-c4cnn([C@H]5CC[C@]6(CC5)CNC(=O)C6)c4)cn3)c2)cn1] |
| 288 | 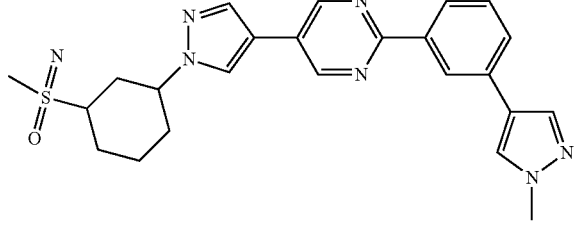<br>HPLC (max plot) 96.3%; (254 nm) 96.6%; Rt (min) 3.14.; MS: (ESI+) 462.3. m.p.: 172.0-179.2° C. |
| 289 | 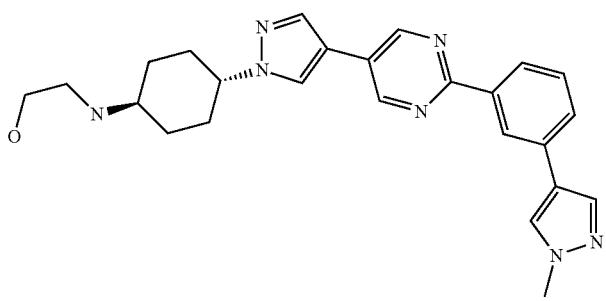 [SMILES: Cn1cc(-c2cccc(-c3ncc(-c4cnn([C@H]5CC[C@H](NCCO)CC5)c4)cn3)c2)cn1]<br>HPLC (max plot) 93.7%; (254 nm) 95.4%; Rt (min) 3.17; MS: (ESI+) 444.2. m.p.: 176.0-180.8° C. |
| 290 | 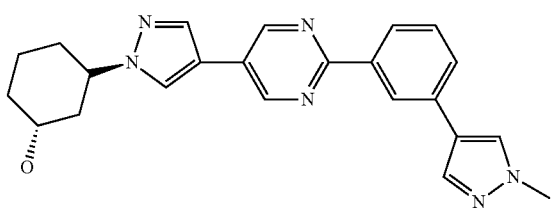<br>HPLC (max plot) 99.49%; (254 nm) 99.65%; Rt (min) 3.48; MS: (ESI+) 401.2. m.p.: 207.5-212.00° C. |

| Ex | |
|---|---|
| 291 | 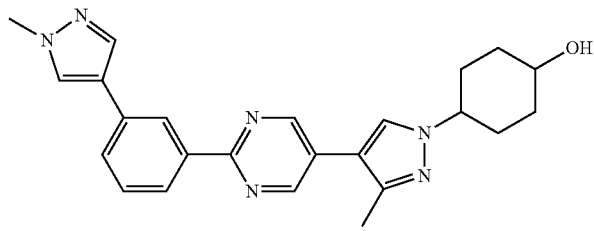<br>HPLC (254 nm) 93.4%; Rt (min) 3.16; MS: (ESI+) 419.2 |
| 292 | 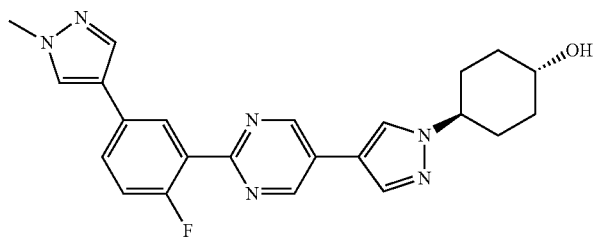<br>HPLC (254 nm) 100%; Rt (min) 3.48; MS: (ESI+) 415.2 |

In another embodiment the most preferred compounds are piperidines as examples 5, 30, 259, 263, 265, and 284.

In a further embodiment the most preferred compounds are amides and spiro-amides as examples 121, 233, 234, 278, 250, 251, 260, 262, 285, 286, and 287.

In another embodiment the most preferred compounds are sulfonyl as examples 279 and 288 and cyclic amides: 254, and 255 and spiro ether from example 267.

"$C_1$-$C_6$-alkyl" or "$C_1$-$C_6$-alkyl group" denotes a linear or branched alkyl chain having 1 to 6 carbon atoms.

"$C_1$-$C_6$-alkyl" or "$C_1$-$C_3$-alkyl" may also include haloalkyl. Halo-alkyl contains 1 to 10 halogen atoms, preferably 1 to 3 halogen atoms. Halo-alkyl contains for example a group —$CF_3$, —$CHF_2$ or —$CH_2F$.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Moreover, A denotes preferably $CH_2OCH_3$, $OCH_2CH_2OCH_3$, $CH_2OH$, $CH_2NH_2$, $NHCH_2CH_2OH$, $CH_2CH_2OH$, $CH_2NHCH_2$ or $NHCH_2CH_3$.

Hal preferably denotes Cl or F.

$R^3$ preferably denotes H oder $CH_3$.

Q preferably is absent or preferably denotes $NR^3COCH_2$, $CH_2CONR^3$, $COCH(CH_3)$, $CH(CH_3)CO$, $COCH_2CH_2$, $CH_2CH_2CO$, $CH_2$, $CH_2CH_2$, $CH_2CO$, $COCH_2$, $CH(OH)CH_2$, $CH_2CH(OH)$, CO—$C(CH_3)_2$ or $(CH_3)_2C$—CO.

A "leaving group" denotes a chemical moiety which can be removed or replaced by another chemical group.

Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N hydroxysuccinimide.

Cyclic alkyl (cycloalkyl) preferably denotes cyclopropyl, cyclobutyl, cyclopentyl, cyclohexyl or cycloheptyl.

Irrespective of further substitutions, Het denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2, 4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothia-diazol-4-, -5-yl or 2,1,3-benzoxadiazol-5-yl, azabicyclo[3.2.1]octyl or dibenzofuranyl. The heterocyclic radicals may also be partially or fully hydrogenated.

Irrespective of further substitutions, Het can thus also denote, for example, 2,3-dihydro-2-, -3-, -4- or -5-furyl, 2,5- dihydro-2-, -3-, -4- or 5-furyl, tetrahydro-2- or -3-furyl, 1,3-di-oxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxyl)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Z preferably denotes isoxazolyl, imidazolyl, thiazolyl, oxazolyl, pyridazinyl, triazolyl, pyridyl, pyrazolyl or furyl, each of which is unsubstituted or mono- or disubstituted by methyl, Hal, $NH_2$, $CH_2COHet^2$ and/or benzyl.

Z very particularly preferably denotes 1-methyl-1H-pyrazol-4-yl or 6-methyl-pyridazin-4-yl, $Het^1$ $Het^2$ preferably denotes piperidinyl or pyrrolidinyl.

$R^2$ preferably denotes H, Het, Q-Het, Cyc or A.

The invention preferably relates to compounds of the formula (I)

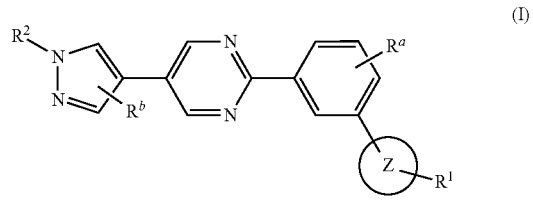

(I)

wherein
$R^1$ is absent,
Z denotes isoxazolyl, imidazolyl, thiazolyl, oxazolyl, pyridazinyl, triazolyl, pyridyl, pyrazolyl or furyl, each of which is unsubstituted or mono- or disubstituted by A, Hal, $N(R^3)_2$, $CH_2COHet^2$ and/or benzyl,
$R^a$ is absent or denotes Hal,
$R^b$ is absent or denotes $CONH_2$, COOH, CONHA, $COHet^1$ or $CH_2OH$
$R^2$ denotes H, Het, Q-Het, Cyc, A, OA, $CH_2COOH$, NHA, $NA_2$, $CH_2CONH_2$, $CH_2CONHA$, CH(A)CONHA or $NR^3SO_2A$,
or denotes phenyl, optionally mono- or disubstituted by OA,
Het denotes tetrahydrothiopyranyl, 2-oxa-6-aza-spiro[3.3]heptyl, 2-oxy-7-aza-spiro[3.5]nonyl, 8-aza-bicyclo[3.2.1]octyl, 2-oxa-5-aza-bicyclo[2.2.1]heptyl, oxetanyl, tetrahydropyranyl, imidazolyl, oxazolyl, piperazinyl, thiazolyl, azepanyl, tetrahydrofuranyl, isoxazolyl, azetidinyl, oxazolidinyl, hexahydroisobenzofuranyl, piperidyl, furyl, pyrrolidinyl, morpholinyl, 1,9-dioxa-spiro[5.5]undecyl, 2,5-diaza-bicyclo[2.2.1]heptyl, 3-oxa-bicyclo[3.3.1]nonyl, tetrahydrothiophenyl, 1-aza-spiro[4.5]decyl, 2-aza-spiro[4.5]decyl, 3-oxa-9-aza-bicyclo[3.3.1]nonyl, [1,4]oxazepanyl, 8-oxa-3-aza-bicyclo[3.2.1]octyl or 9-aza-bicyclo[3.3.1]nonyl, each of which is unsubstituted or mono-, di- or trisubstituted by $CON(R^3)_2$, A, COA, $(CH_2)_nHet^1$, Hal, $Ar^1$, $(CH_2)_nOH$, $(CH_2)_nOA$, $Cyc^1$, $COCyc^1$, $SO_2A$, $COHet^1$ and/or =O, Cyc denotes cyclohexyl, spiro[3.3]heptyl, cyclopentyl or cyclopentenyl, each of which is unsubstituted or mono- or disubstituted by A, $OCH_2Cyc^1$, $CONHCH_2CN$, NHCOA, $(CH_2)_nCONHA$, $(CH_2)_nCONA_2$, COOH, $NH_2$, $COHet^1$, $CONHCyc^1$, $CONHHet^1$, $SO_2A$, $CH_2OH$, =O, $Het^1$ and/or $SR_3$(=O)(=NH), Q is absent or denotes $NR^3COCH_2$, $CH_2CONR^3$, COCH(CH_3), $CH(CH_3)CO$, $COCH_2CH_2$, $CH_2CH_2CO$, $CH_2$, $CH_2CH_2$, $CH_2CO$, $COCH_2$, $CH(OH)CH_2$, $CH_2CH(OH)$, $CO—C(CH_3)_2$ or $(CH_3)_2C—CO$, A denotes a linear or branched alkyl having 1 to 10 carbon atoms wherein 1 to 7 H atoms may be replaced by a group independently selected from $—OR^3$, Hal, $NHSO_2A$, $SO_2A$, SOA, $N(R^3)_2$, and wherein 1, 2 or 3 non-adjacent $—CH_2—$ groups may be replaced by a group independently selected from $—CO—$, $NR^3$ and/or $—O—$, Hal denotes F, Cl, Br or I, $Ar^1$ denotes phenyl, optionally substituted by Hal, $R^3$ denotes H or $C_1$-$C_6$-alkyl wherein 1 H atom may be replaced by a group selected from OH, O—$C_1$-$C_6$-alkyl, and Hal, $Het^1$ denotes 2,5-diaza-bicyclo[2.2.1]heptyl, piperazinyl, morpholinyl, azetidinyl, tetrahydropyranyl, tetrahydrofuranyl, pyrrolidinyl or piperidinyl, each of which is unsubstituted or mono- or disubstituted by $CH_2OH$, OA, Hal and/or A, $Het^2$ denotes piperidinyl or pyrrolidinyl, $Cyc^1$ denotes cycloalkyl with 3-7 atoms, optionally mono-, di- or trisubstituted by A, =O and/or OH, n denotes 0, 1, 2 or 3 and pharmaceutically acceptable derivatives, solvates, tautomers, salts, hydrates and stereoisomers thereof, including mixtures thereof in all ratios.

Chemistry Part

The following abbreviations refer to the abbreviations used below:

Ac (acetyl), BINAP (2,2'-bis(disphenylphosphino)-1,1'-binaphthalene), dba (dibenzylidene acetone), Bu (Butyl), tBu (tert-Butyl), DCE (dichloroethane), DCM (Dichloromethane), DIEA (di-isopropyl ethylamine), DMA (dimethyl acetamide), DMSO (Dimethyl Sulfoxide), DMF (N,N-Dimethylformamide), Dppf (1,1'-bis (diphenyl phosphine ferrocene)), EtOAc (Ethyl acetate), EtOH (Ethanol), g (gram), cHex (Cyclohexane), HATU (N-[(Dimethylamino)(3H-[1,2,3]triazolo[4,5-b]pyridin-3-yloxy)methylene]-N-methylmethanaminiumhexafluoro phosphate), HPLC (High Performance Liquid Chromatography), hr (hour), LDA (lithium diisopropyl amine), LiHMDS (lithium bis(trimethylsilyl)amide), MHz (Megahertz), MeOH (Methanol), min (minute), mL (milliliter), mmol (millimole), mM (millimolar), mp (melting point), MS (Mass Spectrometry), MW (microwave), NMR (Nuclear Magnetic Resonance), O/N (overnight), PBS (Phosphate Buffered Saline), $PPh_3$ (triphenylphosphine), RT (room temperature), TEA (Triethyl amine), TFA (Trifluoroacetic acid), THF (Tetrahydrofuran), TLC (Thin Layer Chromatography), oTol (ortho-tolyl), UV (Ultraviolet).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, N.Y., 1994 and, Theodora W. Greene and Peter G. M. Wuts in "Protective Groups in Organic Synthesis", Wiley Interscience, 3$^{rd}$ Edition 1999.

Depending on the nature of $R^1$, $R^2$, $R^a$, $R^b$ and Z different synthetic strategies may be selected for the synthesis of compounds of Formula (I). In the process illustrated in the following schemes, $R^1$, $R^2$, $R^a$, $R^b$ and Z are as above defined in the description unless otherwise mentioned.

Compounds of formula (I) wherein $R^1$, $R^2$, $R^a$, $R^b$ and Z are as above defined can be prepared by Suzuki-Miyura coupling reaction between a compound of Formula (II), wherein $R^1$, $R^a$ and Z are as above defined and X is an halogen (preferably bromine or iodine) or a triflate group, and a boronic acid or ester of Formula (III) wherein $R^2$ and $R^b$ are as above defined and R is H or an alkyl group as outlined in Scheme 1. General protocols for such coupling are given below in the Examples, using conditions and methods well known to those skilled in the art to perform such coupling (see for example Miyaura, N.; Suzuki, A. Chem. Rev. 1995, 95, 2457; Takahiro I. and Toshiaki M., Tetrahedron Lett. 2005, 46, 3573-3577). In a typical procedure, an aryl halide of Formula (II) and a boronic acid or ester of Formula (III) are heated in a suitable solvent, such as THF, toluene, DMF or dioxane, in the presence or absence of water as a co-solvent, in the presence of a base, such as $Cs_2CO_3$, $K_2CO_3$, CsF, and with an appropriate catalyst such as but not limited to dichlorobis(triphenylphosphine)palladium(II), Pd(PPh$_3$)$_4$ or 1,1'-bis(diphenylphosphino)ferrocenedichloro palladium(II), Pd(OAc)$_2$, Pd$_2$(dba)$_3$, Pd(Cl)$_2$(PPh$_3$)$_2$ or Pd/C in the presence or absence of an additional ligand, such as but not limited to P(tBu)$_3$, P(oTol)$_3$, PPh$_3$, BINAP. This coupling reaction can be carried out at a temperature between about 20° C. to about 150° C., preferably at about 120° C., for a few minutes to a few hours, possibly under microwave irradiation.

Scheme 1

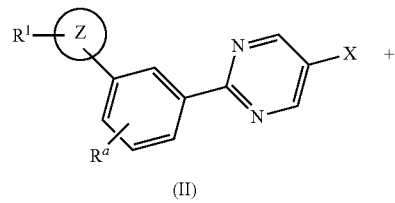

(II)

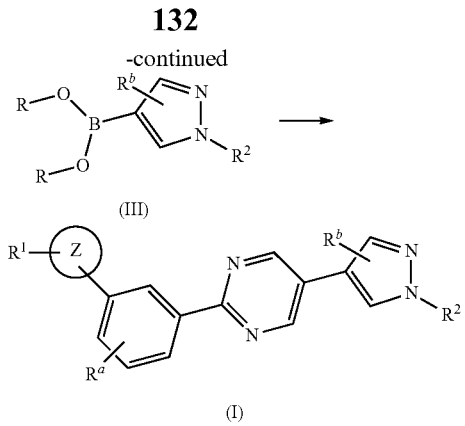

(III)

(I)

Generally, compounds of Formula (IIa), wherein $R^1$, $R^a$ and Z are as above defined and X is bromine, can be obtained as outlined in Scheme 2. Compounds of Formula (IV), wherein $R^1$ and Z are as above defined and R is H or an alkyl group can be coupled with a compound of Formula (V), wherein $R^a$ is as above defined, by a Suzuki-Miyura coupling reaction to give a compound of general formula (VI) wherein $R^1$, $R^a$ and Z are as above defined. General protocols for such coupling are given below in the Examples: in a typical procedure, the aryl halide of Formula (V) and the boronic acid or ester of Formula (IV) are heated in a suitable solvent, such as THF, toluene, DMF or dioxane, in the presence or absence of water as a co-solvent, in the presence of a base, such as as $Cs_2CO_3$, $K_2CO_3$, CsF, and with an appropriate catalyst such as but not limited to dichlorobis(triphenylphosphine)palladium(II), Pd(PPh$_3$)$_4$ or 1,1'-bis(diphenylphosphino)ferrocenedichloro palladium(II), Pd(OAc)$_2$, Pd$_2$(dba)$_3$, Pd(Cl)$_2$(PPh$_3$)$_2$ or Pd/C in the presence or absence of an additional ligand, such as but not limited to P(tBu)$_3$, P(oTol)$_3$, PPh$_3$, BINAP. This coupling reaction can be carried out at a temperature between about 20° C. to about 150° C., preferably at about 120° C., for a few minutes to a few hours, possibly under microwave irradiation.

Compounds of Formula (VI), wherein $R^1$, $R^a$ and Z are as above defined, can be converted in compounds of Formula (VII), wherein $R^1$, $R^a$ and Z are as above defined, by reaction with an appropriate source of boron, such as but not limited to bis(pinacolato)diboron, bis(catecholate)diboron, bis(diethyl-D-tartrate glycolato)diboron, bis(hexyleneglycolato)diboron, bis(neopentylglycolato)diboron, preferably bis(pinacolato)diboron in the presence of a suitable catalyst, such as but not limited to 1,1'bis(diphenylphosphino)ferrocenedichloro palladium(II), dichlorobis(triphenylphosphine)palladium (II), Pd(PPh$_3$)$_4$, Pd(OAc)$_2$, Pd$_2$(dba)$_3$, Pd(Cl)$_2$(PPh$_3$)$_2$, preferably 1,1'bis(diphenylphosphino)ferrocenedichloro palladium(II), in the presence of a suitable base such as but not limited to potassium acetate, cesium fluoride, potassium carbonate, preferably potassium acetate, in the presence of a solvent such as but not limited to THF, dioxane, DCE, DMF, preferably THF or dioxane, at a temperature between about 20° C. to about 150° C., preferably at about 120° C., for a few minutes to a few hours, possibly under microwave irradiation.

The compounds of Formula (VII), wherein $R^1$, $R^a$ and Z are as above defined, can be reacted with 5-bromo-2-iodopyrimidine to give the compounds of Formula (IIa), wherein $R^1$, $R^a$ and Z are as above defined, by a Suzuki-Miyura coupling reaction. General protocols for such coupling are given below in the Examples: in a typical procedure, the 5-bromo-2-iodopyrimidine and the boronic acid or ester (xx) are heated in a suitable solvent, such as THF, toluene or dioxane, in the presence or absence of water as a co-solvent, in the presence of a base, such as as $Cs_2CO_3$, $K_2CO_3$, CsF, and with an appropriate catalyst such as but not limited to dichlorobis(triphenylphosphine)palladium(II), $Pd(PPh_3)_4$ or 1,1'-bis(diphenylphosphino)ferrocenedichloro palladium(II), $Pd(OAc)_2$, $Pd_2(dba)_3$, $Pd(Cl)_2(PPh_3)_2$ or Pd/C in the presence or absence of an additional ligand, such as but not limited to $P(tBu)_3$, $P(oTol)_3$, $PPh_3$, BINAP. This coupling reaction can be carried out at a temperature between about 20° C. to about 150° C., preferably at about 120° C., for a few minutes to a few hours, possibly under microwave irradiation.

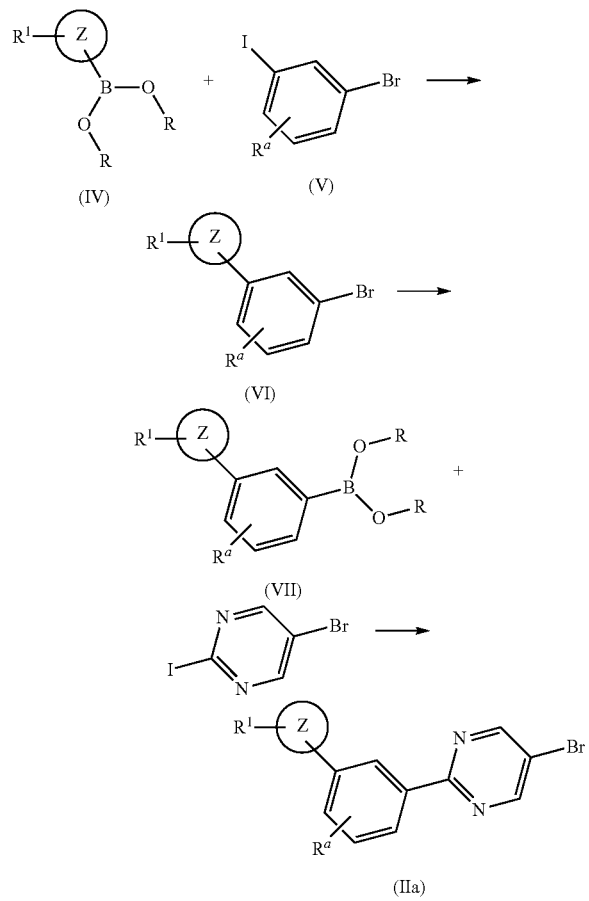

Scheme 2

Alternatively, compounds of formula (I) wherein $R^1$, $R^2$, $R^a$, $R^b$ and Z are as above defined can be prepared by Suzuki-Miyura coupling reaction between a compound of Formula (VIII), wherein $R^1$, $R^a$ and Z are as above defined and R is H or an alkyl group, and a compound of Formula (IX) wherein $R^2$ and $R^b$ are as above defined and X is an halogen (preferably bromine or iodine) or a triflate group as outlined in Scheme 3. General protocols for such coupling are given below in the Examples, using conditions and methods well known to those skilled in the art to perform such coupling (see for example Miyaura, N.; Suzuki, A. Chem. Rev. 1995, 95, 2457; Takahiro I. and Toshiaki M., Tetrahedron Lett. 2005, 46, 3573-3577). In a typical procedure, an aryl halide of Formula (II) and a boronic acid or ester of Formula (III) are heated in a suitable solvent, such as THF, toluene or dioxane, in the presence or absence of water as a co-solvent, in the presence of a base, such as as $Cs_2CO_3$, $K_2CO_3$, CsF, and with an appropriate catalyst such as but not limited to dichlorobis(triphenylphosphine)palladium(II), $Pd(PPh_3)_4$ or 1,1'-bis(diphenylphosphino)ferrocenedichloro palladium(II), $Pd(OAc)_2$, $Pd_2(dba)_3$, $Pd(Cl)_2(PPh_3)_2$ or Pd/C in the presence or absence of an additional ligand, such as but not limited to $P(tBu)_3$, $P(oTol)_3$, $PPh_3$, BINAP. This coupling reaction can be carried out at a temperature between about 20° C. to about 150° C., preferably at about 120° C., for a few minutes to a few hours, possibly under microwave irradiation.

Compounds of Formula (VIII), wherein $R^1$, $R^a$ and Z are as above defined and R is H or an alkyl group, can be prepared from compounds of Formula II, wherein $R^1$, $R^a$ and Z are as above defined and X is an halogen (preferably bromine or iodine) or a triflate group, by reaction with an appropriate diboron derivative, such as but not limited to bis(pinacolato)diboron, bis(catecholate)diboron, bis(diethyl-D-tartrate glycolato)diboron, bis(hexyleneglycolato)diboron, bis(neopentylglycolato)diboron, preferably bis(pinacolato)diboron, in the presence of a suitable catalyst, such as but not limited to 1,1'bis(diphenylphosphino)ferrocenedichloro palladium(II), dichlorobis(triphenylphosphine)palladium(II), $Pd(PPh_3)_4$, $Pd(OAc)_2$, $Pd_2(dba)_3$, $Pd(Cl)_2(PPh_3)_2$, preferably 1,1'bis(diphenylphosphino)ferrocenedichloro palladium(II), in the presence of a suitable base such as but not limited to potassium acetate, cesium fluoride, potassium carbonate, preferably potassium acetate, in the presence of a solvent such as but not limited to THF, dioxane, DCE, DMF, preferably THF or dioxane, at a temperature between about 20° C. to about 150° C., preferably at about 120° C., for a few minutes to a few hours, possibly under microwave irradiation.

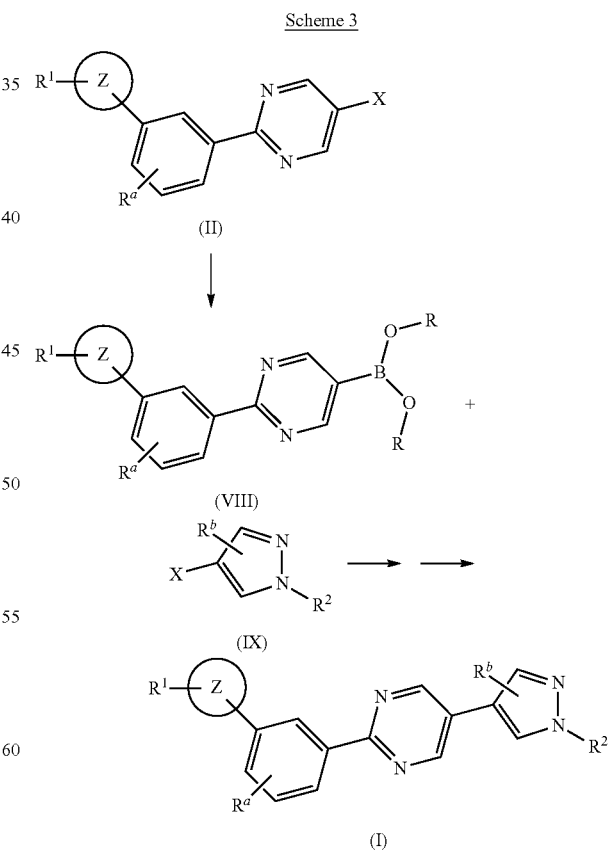

Scheme 3

Alternatively, compounds of Formula I, wherein $R^1$, $R^2$, $R^a$, $R^b$ and Z are as above defined, can be prepared as depicted in Scheme 4. A 2-aminopyrimidine of Formula (X), wherein X is an halogen (preferably iodine or bromine) or a trifluoromethanesulfonate group, is coupled with a boronic acid derivative of Formula (III), wherein $R^2$, $R^b$ are as above defined and R is H or an alkyl group to give a compound of general formula (XI) wherein wherein $R^2$ and $R^b$ are as above defined under Suzuki-Miyaura conditions, well known to those skilled in the art to perform such couplings, as described above. General protocols for such coupling are given below in the Examples, using conditions and methods well known to those skilled in the art to perform such couplings. The resulting 2-aminopyridine of Formula (XI), wherein $R^2$ and $R^b$ are as above defined, can be converted to a 2-iodopyrimidine of Formula (XII), wherein $R^2$ and $R^b$ are as above defined, for example by reaction with a suitable source of iodine, such as but not limited to diiodomethane, iodine, N-iodosuccinimide, in the presence of an alkyl nitrite such as but not limited to tert-butyl nitrite or iso-pentyl nitrite, in the presence of copper (I) iodide, in a suitable solvent, such as but not limited to THF or dioxane, at a temperature between about 20° C. to about 150° C., preferably at about 80-100° C., for a few hours.

Compounds of Formula (XIV), wherein $R^2$, $R^a$, and $R^b$ are as above defined, can be obtained by coupling of a compound of Formula (XII), wherein $R^2$ and $R^b$ are as above defined, with a boronic acid derivative of Formula (XIII), wherein $R^a$ is as above defined and R is H or an alkyl group, under Suzuki-Miyaura conditions, well known to those skilled in the art to perform such couplings, as described above.

Conversion of compounds of Formula (XIV), wherein $R^2$, $R^a$, and $R^b$ are as above defined, to compounds of Formula (XV), wherein $R^2$, $R^a$, and $R^b$ are as above defined, can be accomplished using similar conditions as described above for the conversion of an aromatic or heteroaromatic amine into an aromatic or heteroaromatic iodide, for example by reaction with a suitable source of iodine, such as but not limited to diiodomethane, iodine, N-iodosuccinimide, in the presence of an alkyl nitrite such as but not limited to tert-butyl nitrite or iso-pentyl nitrite, in the presence of copper (I) iodide, in a suitable solvent, such as but not limited to THF or dioxane, at a temperature between about 20° C. to about 150° C., preferably at about 80-100° C., for a few hours.

Finally, compounds of Formula I, wherein $R^1$, $R^2$, $R^a$, $R^b$ and Z are as above defined, can be obtained by coupling of a compound of Formula (XV), wherein $R^2$, $R^a$, and $R^b$ are as above defined, with a boronic acid derivative of Formula (IV), wherein $R^1$ and Z are as above defined and R is H or an alkyl group, under Suzuki-Miyaura conditions, well known to those skilled in the art to perform such couplings, as described above.

Scheme 4

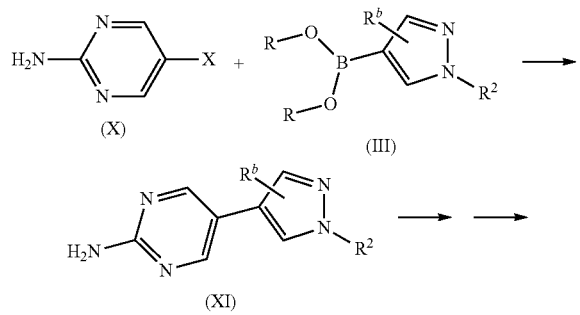

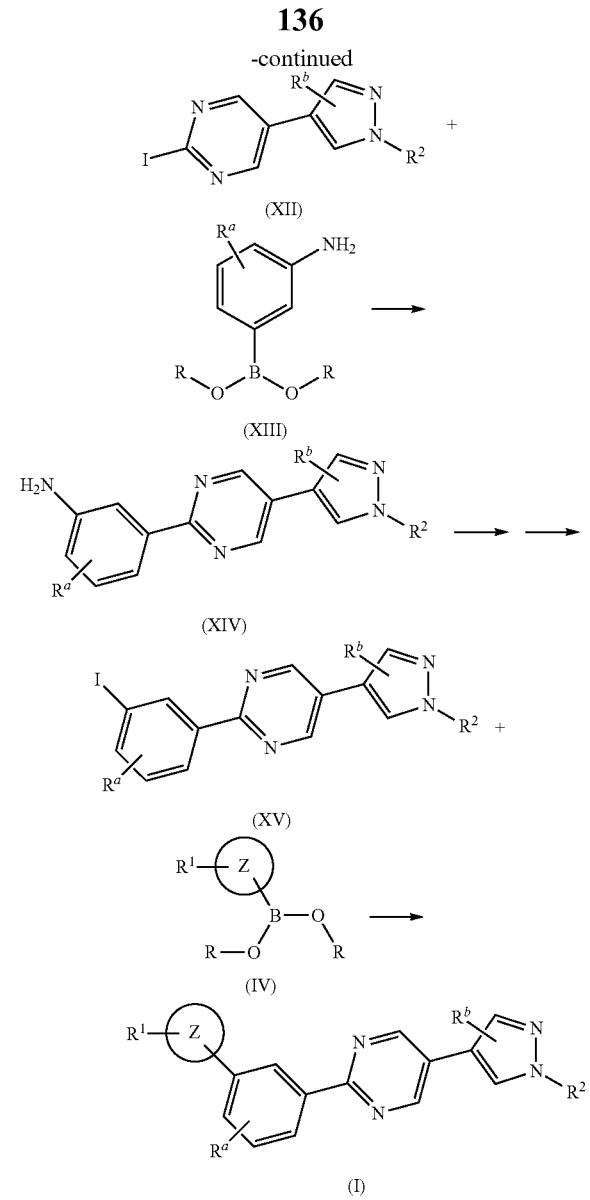

Alternatively, compounds of Formula I, wherein $R^1$, $R^2$, $R^a$, $R^b$ and Z are as above defined, can be prepared as depicted in Scheme 5. Aryl iodides of Formula (XV), wherein $R^2$, $R^a$ and $R^b$ are as above defined, can be converted to compounds of Formula (XVI), wherein $R^2$, $R^a$ and $R^b$ are as above defined and R is H or an alkyl group, by reaction with an appropriate diboron derivative, such as but not limited to bis(pinacolato) diboron, bis(catecholate)diboron, bis(diethyl-D-tartrate glycolato)diboron, bis(hexyleneglycolato)diboron, bis(neopentylglycolato)diboron, preferably bis(pinacolato)diboron, in the presence of a suitable catalyst, such as but not limited to 1,1'bis(diphenylphosphino)ferrocenedichloro palladium(II), dichlorobis(triphenylphosphine)palladium(II), $Pd(PPh_3)_4$, $Pd(OAc)_2$, $Pd_2(dba)_3$, $Pd(Cl)_2(PPh_3)_2$, preferably 1,1'bis (diphenylphosphino)ferrocenedichloro palladium(II), in the presence of a suitable base such as but not limited to potassium acetate, cesium fluoride, potassium carbonate, preferably potassium acetate, in the presence of a solvent such as but not limited to THF, dioxane, DCE, DMF, preferably THF or dioxane, at a temperature between about 20° C. to about 150° C., preferably at about 120° C., for a few minutes to a few hours, possibly under microwave irradiation.

Compounds of Formula I, wherein $R^1$, $R^2$, $R^a$, $R^b$ and Z are as above defined, can be obtained by coupling of a compound of Formula (XVI), wherein $R^2$, R and $R^b$ are as above defined and R is H or an alkyl group, with a compound of Formula (XVII), wherein $R^1$ and Z are as above defined, under Suzuki-Miyaura conditions, well known to those skilled in the art to perform such couplings, as described above.

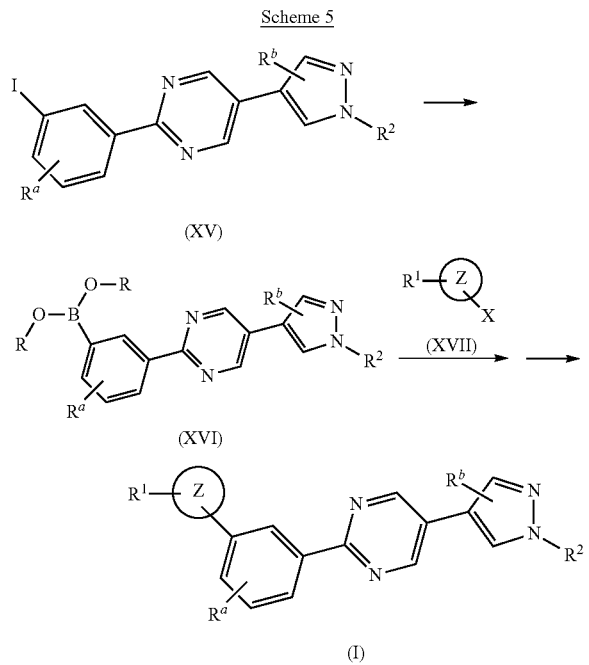

Scheme 5

Alternatively, compounds of formula (I) wherein $R^1$, $R^2$, $R^a$, $R^b$ and Z are as above defined can be prepared by Suzuki-Miyura coupling reaction between a compound of Formula (XII), wherein $R^2$ and $R^b$ are as above defined, and a compound of Formula (VII) wherein $R^1$, $R^a$ and Z are as above defined and R is H or an alkyl group as outlined in Scheme 6. The reaction can be carried out using the general conditions described above. General protocols for such coupling are given below in the Examples, using conditions and methods well known to those skilled in the art to perform such couplings.

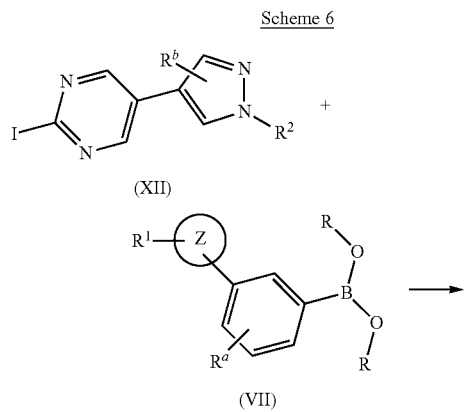

Scheme 6

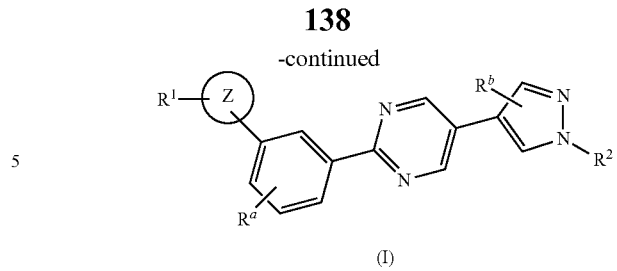

Alternatively, compounds of Formula (I), wherein $R^1$, $R^2$, $R^a$, $R^b$ and Z are as above defined, can be prepared as depicted in Scheme 7 from compounds of Formula (Ia), wherein $R^1$, $R^a$, $R^b$ and Z are as above defined and $R^2$ is H, prepared following one of the routes described above, by reaction with a compound of Formula (XVIII), wherein $R^2$ is as above defined, but not H and LG is a leaving group, such as bromine, chlorine, alkylsulfonate or any other suitable leaving group known to those skilled in the art.

General protocols for such transformation are given below in the Examples, using conditions and methods well known to those skilled in the art. In a typical procedure, a compound of Formula (Ia) is treated with a base, such as but not limited to NaH, $K_2CO_3$, $Cs_2CO_3$, LDA, LHMDS, preferably NaH, and with a compound of Formula (XVIII), in a suitable solvent like THF, dioxane, DMF, DMA, at a temperature between −20° C. to about 150° C., for a time between a few minutes to a few hours.

Alternatively, as depicted in Scheme 7, compounds of Formula (I), wherein $R^1$, $R^2$, $R^a$, $R^b$ and Z are as above defined, can be prepared from compounds of Formula (Ib), wherein $R^1$, $R^a$, $R^b$ and Z are as above defined and $R^2$ is H, prepared following one of the routes described above, by reaction with an alcohol of Formula (XIX), wherein $R^2$ is as above defined, but not H, using conditions well known to those skilled in the art for a Mitsunobu reaction (see for example Hughes, D. L. *Organic Reactions* (New York), 1992, 42, 335-656; Reynolds, A. J.; Kassiou, M. *Current Organic Chemistry*, 2009, 13 (16); 1610-1632). Typically, the reaction takes place in the presence of a phosphine, such as but not limited to $P(tBu)_3$, $PPBu_3$, $P(oTol)_3$, $PPh_3$, in the presence of an azadicarboxylate, such as but not limited to diethylazadicarboxylate, diisopropylazadicarboxylate, Tetramethylazodicarboxamide, in a solvent such as THF, dioxane, DCM, DCE, at a temperature between −20° C. to about 150° C., preferably at room temperature, for a time between a few minutes to a few hours.

Scheme 7

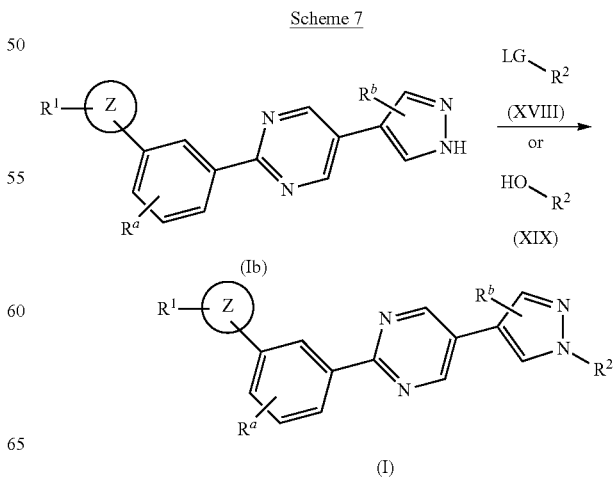

Compounds of this invention can be isolated in association with solvent molecules by crystallization from an appropriate solvent or by evaporation of an appropriate solvent.

The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of an alkali or earth alkali salt (such as sodium ethylhexanoate, magnesium oleate), employing a solvent in which the desired alkali or earth alkali salt of the compounds of formula (I) precipitates, or can be otherwise isolated by concentration and addition of a non-solvent.

Both types of salts may be formed or interconverted using ion-exchange resin techniques.

Depending on the conditions used, the reaction times are generally between a few minutes and 14 days. The reaction temperature is between about −30° C. and about 140° C., normally between −10° C. and 90° C., in particular between about 0° C. and 70° C.

Compounds of the formula (I) and related formulae can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy‑carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy‑carbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, further‑ more CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C. Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl¬ formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

The formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called pro¬ drug compounds.

The term "prodrug derivatives" is taken to mean compounds of the formula I which have been modified with, for example, alkyl or acyl groups, sugars or oligopeptides and which are rapidly cleaved in the organism to form the active compounds. Preferably "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press: New York (1987). It is intended that these references, and any others cited throughout this specification, are incorporated herein by reference.

These also include biodegradable polymer derivatives of the compounds according to the invention, as described, for example, in Int. J. Pharm. 115, 61-67 (1995).

The formula (I) and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, *acacia*, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or drypressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I), and related formulae and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I), and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a IRAK related disorder, comprising administering to said subject an effective amount of a compound of formula I and related formulae. The present invention preferably relates to a method, wherein the IRAK associated disorder is an autoimmune disorder or condition associated with an overactive immune response or cancer. The present invention furthermore relates to a method of treating a subject suffering from an immunoregulatory abnomality, comprising administering to said subject a compound of formula (I), and related formulae in an amount that is effective for treating said immunoregulatory abnormality. The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, *pemphigus*, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular *pemphigus*, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma *vulgaris*, ichthyosis *vulgaris*, photoallergic sensitivity, cutaneous T cell lymphoma, chronic lymphocytic leukemia, arteriosclerosis, atherosclerosis, aortitis syndrome, polyarteritis nodosa, myocardosis, *scleroderma*, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia *senilis* by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

Preferably, disorders associated with IRAK are selected from Rheumatoid Arthritis Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Crohn's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, Cancer.

Preferred compounds of formula (I), and related formulae exhibit a IC50 for the binding to IRAK of less than about 5 µM, preferably less than about 1 µM and even more preferably less than about 0.100 µM.

Compounds according to formula (I), and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In general, the synthesis pathways for any individual compound of formula (I), and related formulae will depend on the specific substitutents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of formula (I), and related formulae which contain a basic center may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I), and related formulae, which contain an acid center, with a suitable base. Both types of salts may be formed or interconverted using ion-exchange resin techniques.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, N.Y., 1994 and, Theodora W. Greene and Peter G. M. Wuts in "Protective Groups in Organic Synthesis", Wiley Interscience, 3rd Edition 1999.

In the following the present invention shall be illustrated by means of some examples, which are not construed to be viewed as limiting the scope of the invention.

EXPERIMENTAL PART

In the following the present invention shall be illustrated by means of some examples, which are not construed to be viewed as limiting the scope of the invention.
General:

The HPLC data provided in the examples described below were obtained as followed.

Condition A: Column Waters Xbridge™ C8 50 mm×4.6 mm at a flow of 2 mL/min; 8 min gradient $H_2O:CH_3CN:TFA$ from 100:0:0.1% to 0:100:0.05%.

UV detection (maxplot) for all conditions.

The MS data provided in the examples described below were obtained as followed: Mass spectrum: LC/MS Waters ZMD (ESI).

The NMR data provided in the examples described below were obtained as followed: 1H-NMR: Bruker DPX-300 MHz or Bruker AV-400 MHz.

Autopreparative LC/MS purifications were performed with a mass directed autopurification Fractionlynx from Waters equipped with a Sunfire Prep C18 OBD column 19×100 mm 5 µm, unless otherwise reported. All HPLC purifications were performed with a gradient of ACN/$H_2O$ or ACN/$H_2O$/HCOOH (0.1%).

The microwave chemistry was performed on a single mode microwave reactor Emrys™ Optimiser or Initiator™ Sixty from Biotage.

The compounds of invention have been named according to the standards used in the program Autonom.

The compounds according to formula (I) can be prepared from readily available starting materials by several synthetic approaches, using both solution-phase and solid-phase chemistry protocols or mixed solution and solid phase protocols. Examples of synthetic pathways are described below in the examples. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich or Sigma or ABCR unless otherwise reported. SPE cartridges were purchased from IST and used following supplier recommendations.

Intermediate 1: 1-methyl-4-[3-(4,4,5,5-tetramethyl-1,3,2-dioxaborolan-2-yl)phenyl]-1H-pyrazole

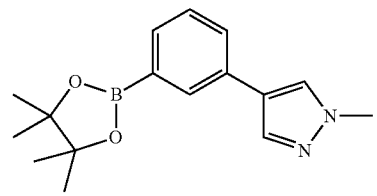

To a solution of 4-(3-Bromo-phenyl)-1-methyl-1H-pyrazole (Otava, 410 mg, 1.7 mmol) in dry DMF (10 mL) was added bis(pinacolato)diborane (525 mg, 2.0 mmol) and dried KOAc (340 mg, 3.4 mmol). The reaction mixture was degassed for 20 min before the addition of dppf (48 mg, 0.09 mmol) and (dppf) $PdCl_2.CH_2Cl_2$ (71 mg, 0.09 mmol). The reaction mixture was then heated at 80° C. O/N. It was filtered through celite and the filtrate was concentrated under reduced pressure to give the title compound as a yellow oil (550 mg, 92%). $^1$H NMR (300 MHz, DMSO-d6) δ 8.24-8.15 (s, 1H), 7.89-7.82 (d, J=0.9 Hz, 1H), 7.82-7.76 (t, J=1.3 Hz, 1H), 7.73-7.64 (m, 1H), 7.53-7.45 (m, 1H), 7.42-7.29 (m, 1H), 3.89-3.82 (s, 3H), 1.34-1.26 (s, 12H).

Intermediate 2: 5-bromo-2-[3-(1-methyl-1H-pyrazol-4-yl)phenyl]pyrimidine

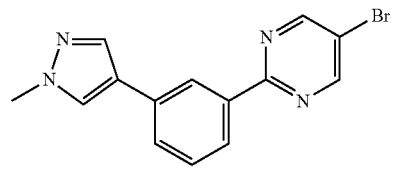 [SMILES: Cn1cc(-c2cccc(-c3ncc(Br)cn3)c2)cn1]

To a solution of 1-Methyl-4-[3-(4,4,5,5-tetramethyl-[1,3,2]dioxaborolan-2-yl)-phenyl]-1H-pyrazole (intermediate 1, 5.0 g, 17.5 mmol) in 1,4-dioxane (80 mL) was added 5-Bromo-2-iodo-pyrimidine (6.0 g, 21.0 mmol) and potassium carbonate (7.3 g, 5.25 mmol) in a sealed tube. The reaction mixture was purged with nitrogen for 30 min. Then Tetrakis(triphenyl phospine)Palladium(0) (2.02 g, 0.17 mmol) was added and the reaction mixture was heated at 100° C. O/N. It was filtered through a celite pad and the filtrate was concentrated under reduced pressure. Purification by flash chromatography on silica (EtOAc/hexane) afforded the title compound as a yellow solid (2.5 g, 45%). $^1$H NMR (400 MHz, DMSO-d6): δ 9.09 (s, 1H), 8.49 (t, J=1.64 Hz, 1H), 8.25 (s, 1H), 8.18 (dd, J=1.2, 4.74 Hz, 1H), 7.90 (d, J=1.2 Hz, 1H), 7.75-7.73 (m, 1H), 7.52 (t, J=4.0 Hz, 1H), 3.88 (s, 3H). HPLC (Condition A): Rt 4.19 min (purity 98.9%). MS (ESI+): 317.0.

Intermediate 3:
5-Bromo-2-(3-pyridin-3-yl-phenyl)-pyrimidine

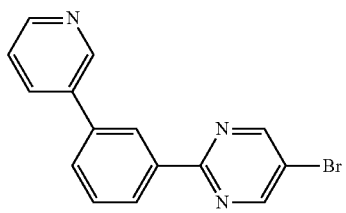 [SMILES: Brc1cnc(-c2cccc(-c3cccnc3)c2)nc1]

The title compound was obtained following procedure described for intermediate 2, but starting from 5-Bromo-2-iodo-pyrimidine and 3-[3-(4,4,5,5-Tetramethyl-[1,3,2]dioxaborolan-2-yl)-phenyl]-pyridine (prepared as described in Chemical Communications, 2008, 7, 889-890) as a yellow solid. MS (ESI+): 312.0.

Intermediate 4: 3-(5-bromopyrimidin-2-yl)aniline

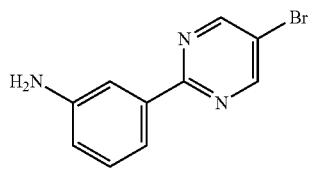 [SMILES: Nc1cccc(-c2ncc(Br)cn2)c1]

A mixture of 5-Bromo-2-iodo-pyrimidine (9.0 g; 31.6 mmol; 1.0 eq.), 3-aminophenyl boronic acid (4.3 g; 31.6 mmol; 1.0 eq.), K$_2$CO$_3$ (17.5 g; 126.4 mmol; 4.0 eq.) and Pd(PPh$_3$)$_4$ (1.83 g; 1.58 mmol; 0.05 eq.) in water/dioxane (67:135 mL) was heated overnight at 100° C. The reaction mixture was then diluted with EtOAc and organic phase was washed with water, dried over magnesium sulfate, filtered and concentrated to give the title compound as a beige solid (7.6 g; 96%). HPLC (Condition A): Rt 1.90 min (purity 78.0%). MS (ESI+): 250.1.

Intermediate 5: tert-butyl 4-{4-[2-(3-iodophenyl) pyrimidin-5-yl]-1H-pyrazol-1-yl}piperidine-1-carboxylate Step 1: Formation of tert-butyl 4-{4-[2-(3-aminophenyl)pyrimidin-5-yl]-1H-pyrazol-1-yl}piperidine-1-carboxylate

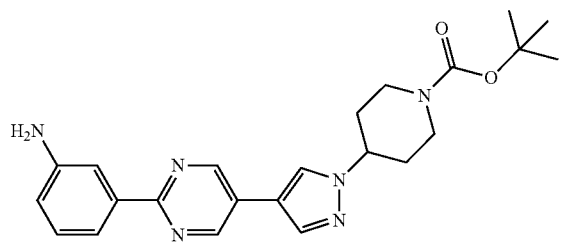 [SMILES: CC(C)(C)OC(=O)N1CCC(n2cc(-c3cnc(-c4cccc(N)c4)nc3)cn2)CC1]

A mixture of 3-(5-bromopyrimidin-2-yl)aniline (intermediate 4, 220 mg; 0.88 mmol; 1.0 eq.), 1-(1-Boc-piperidino) pyrazole-4-boronic acid (389 mg; 1.3 mmol; 1.5 eq.), Pd(PPh$_3$)$_4$ (51 mg; 0.04 mmol; 0.05 eq.) and K$_2$CO$_3$ (365 mg; 2.6 mmol; 3.0 eq.) in dioxane/water (3.3: 1.65 mL) was heated at 12000 for 30 min in a sealed tube in MW. The reaction mixture was then diluted with EtOAc. The two phases were separated and aqueous phase was extracted with EtOAc. Combined organic phases were dried over magnesium sulfate, filtered and concentrated. Flash chromatography on silica (EtOAc:heptane, gradient from 50:50 to 100:0) afforded the title compound a beige solid (240 mg; 65%). $^1$H NMR (300 MHz, DMSO-d6) δ 9.09 (s, 2H), 8.52 (s, 1H), 8.11 (s, 1H), 7.67 (t, J=2.0 Hz, 1H), 7.57-7.53 (m, 1H), 7.14 (t, J=7.8 Hz, 1H), 6.69-6.66 (m, 1H), 5.25 (s, 2H), 4.46-4.36 (m, 1H), 4.08-4.04 (m, 2H), 2.94 (m, 2H), 2.08-2.04 (m, 2H), 1.87-1.75 (m, 2H), 1.43 (s, 9H). HPLC (ConditionA): Rt 3.03 min (purity 99.0%). MS (ESI+): 421.4.

Step 2: Formation of tert-butyl 4-{4-[2-(3-iodophenyl)pyrimidin-5-yl]-1H-pyrazol-1-yl}piperidine-1-carboxylate

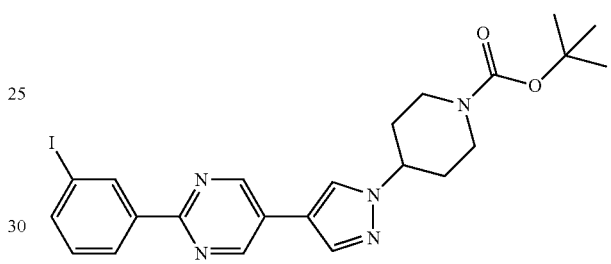

Isopentyl nitrite (192 μl; 1.43 mmol; 3.0 eq.) was added to a solution of tert-butyl 4-4-[2-(3-aminophenyl)pyrimidin-5-yl]-1H-pyrazol-1-ylpiperidine-1-carboxylate (intermediate 5, step 1, 200 mg; 0.48 mmol; 1.0 eq.), Copper(I) iodide (91 mg; 0.48 mmol; 1.0 eq.) and diiodomethane (193 μl; 2.38 mmol; 5.0 eq.) in dry THF (8.0 mL) and the reaction mixture was refluxed for 2 hours. The reaction mixture was filtered through a Celite pad and the filtrate was concentrated to dryness. Purification by flash chromatography (EtOAc:heptane, gradient from 20:80 to 50:50) afforded the title compound as a white solid (200 mg; 67%). $^1$H NMR (300 Mz, DMSO-d6) δ 9.17 (s, 2H), 8.71 (t, J=1.7 Hz, 1H), 8.56 (s, 1H), 8.40-8.37 (m, 1H), 8.15 (s, 1H), 7.90-7.86 (m, 1H), 7.35 (t, J=7.9 Hz, 1H), 4.48-4.38 (m, 1H), 4.08-4.03 (m, 2H), 2.95 (m, 2H), 2.08-2.05 (m, 2H), 1.87-1.73 (m, 2H), 1.43 (s, 9H). HPLC (Condition A): Rt 5.47 min (purity 91.0%). MS (ESI+): 532.4

Intermediate 6: tert-butyl 4-[4-(2-iodopyrimidin-5-yl)-1H-pyrazol-1-yl]piperidine-1-carboxylate Step 1: Formation of tert-butyl 4-[4-(2-aminopyrimidin-5-yl)-1H-pyrazol-1-yl]piperidine-1-carboxylate

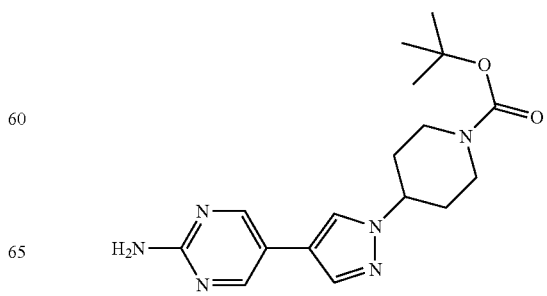

The title compound was obtained following procedure described for intermediate 5, step 1, but starting from 2-amino-5-bromopyrimidine (1.28 g; 7.36 mmol; 1.0 eq.) and 4-[4-(4,4,5,5-tetramethyl-[1,3,2]dioxaborolan-2-yl)-pyrazol-1-yl]-piperidine-1-carboxylic acid tert-butyl ester (2.57 g; 6.81 mmol; 1.00 eq.), as a yellow solid (1.39 g, 49%1H NMR (300 MHz, DMSO-d6) δ 8.47 (s, 2H), 8.19 (s, 1H), 7.82 (s, 1H), 6.58 (s, 2H), 4.41-4.27 (m, 1H), 4.04 (m, 2H), 2.91 (m, 2H), 2.08-1.95 (m, 2H), 1.86-1.67 (m, 2H), 1.42 (s, 9H). MS (ESI+): 345.5.

Step 2: Formation of tert-butyl 4-[4-(2-iodopyrimidin-5-yl)-1H-pyrazol-1-yl]piperidine-1-carboxylate

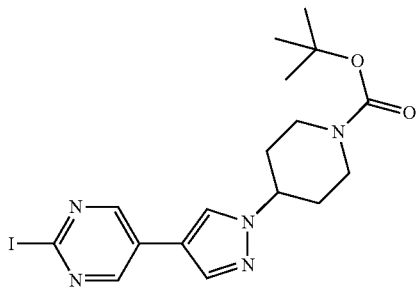 [SMILES: CC(C)(C)OC(=O)N1CCC(n2cc(-c3cnc(I)nc3)cn2)CC1]

The title compound was obtained following procedure described for intermediate 5, step 2, but starting from tert-butyl 4-[4-(2-aminopyrimidin-5-yl)-1H-pyrazol-1-yl]piperidine-1-carboxylate (1.4 g; 3.31 mmol; 1.0 eq.) as a yellow solid (980 mg, 61%). 1H NMR (300 MHz, DMSO-d6) δ 8.84 (s, 2H), 8.52 (s, 1H), 8.09 (s, 1H), 4.48-4.32 (m, 1H), 4.15-3.95 (m, 2H), 3.07-2.76 (m, 2H), 2.08-2.00 (m, 2H), 1.87-1.68 (m, 2H), 1.42 (s, 9H). MS (ESI+): 456.4.

Intermediate 7: 1-Pyrrolidin-1-yl-2-[4-(4,4,5,5-tetramethyl-[1,3,2]dioxaborolan-2-yl)-pyrazol-1-yl]-ethanone

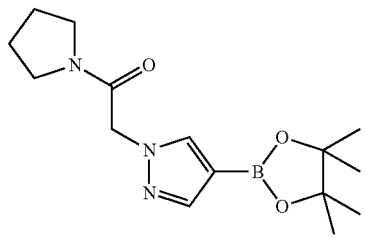 [SMILES: CC1(C)OB(c2cnn(CC(=O)N3CCCC3)c2)OC1(C)C]

A solution of 1-(bromoacetyl)pyrrolidine (Chemical Diversity Labs; 3.0 g, 15.6 mmol, 1.2 eq.) in acetonitrile (15 mL) was slowly added over a suspension of pyrazole-4-boronic acid pinacol ester (2.5 g, 12.9 mmol, 1 eq.) in acetonitrile and stirred overnight at RT. The reaction mixture was filtered and the filtrate was diluted with DCM and washed with water then brine. Separated organic phase was dried over magnesium sulfate, filtered and concentrated to give the title compound as a yellow oil (2.72 g, 100%).

Intermediate 8: 1-[2-fluoro-1-(fluoromethyl)ethyl]-4-(4,4,5,5-tetramethyl-1,3,2-dioxaborolan-2-yl)pyrazole

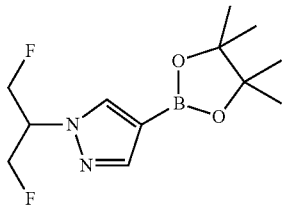 [SMILES: CC1(C)OB(c2cnn(C(CF)CF)c2)OC1(C)C]

To a stirred solution of Pyrazole-4-boronic acid pinacol ester (6.6 g, 34 mmol, 1 eq.) in dry THF (150 mL) was added 1,3-Difluoro-2-propanol (5.1 g, 51 mmol, 1.5 eq.) followed by triphenylphosphine (13.5 g, 51 mmol, 1.5 eq.) and Diisopropyl azodicarboxylate (10.5 g, 51 mmol, 1.5 eq.) at 0° C. under nitrogen atmosphere. After the addition, the reaction mixture was stirred at RT for 48 h. The reaction mixture was concentrated under vacuum and the residue was solubilized in EtOAc, washed with water (three times), dried over sodium sulfate, filtered and concentrated. The crude product was redissolved in EtOAc and Pet. Ether was added. The precipitate obtained was filtered off and the filtrate concentrated under reduced pressure to give the title compound as a oil (contaminated with triphenyl phosphine oxide).

Intermediate 9: tert-butyl-trans-3-fluoro-4-[(methylsulfonyl)oxy]piperidine-1-carboxylate Step 1: Formation of tert-Butyl-trans-3-fluoro-4-hydroxypiperidine-1-carboxylate

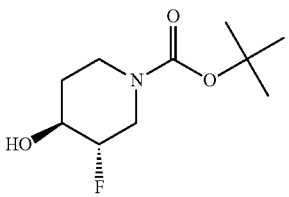

Sodium borohydride (1.53 g, 40.5 mmol) was added to a stirred solution of tert-butyl 3-fluoro-4-oxopiperidine-1-carboxylate (OmegaChem, 8 g, 36.8 mmol) in dry methanol (100 mL) maintained at 0° C. The reaction mixture was stirred at same temperature for 45 min, it was then quenched with dry acetone (20 mL) and evaporated under reduced pressure. The residue was diluted with EtOAc and washed with water and brine. It was dried over sodium sulfate, filtered and concentrated. Purification by flash chromatography on silica (Pet. Ether: EtOAc, 80:20) afforded the titled compound as white solid (4.0 g, 50%). 1H NMR (400 MHz, DMSO-d6) δ 4.61 (ddd, J=39, 8.6, 3.2 Hz, 1H), 3.93 (m, 2H), 3.71 (bs, 1H), 3.42 (brs, 1H), 3.06-3.00 (m, 1H), 1.88-1.83 (m, 2H), 1.45 (s, 9H). HPLC (Condition A): Rt 2.7 min (purity 97%).

Step 2: Formation of tert-butyl-cis 3-fluoro-4-[(methylsulfonyl)oxy]piperidine-1-carboxylate

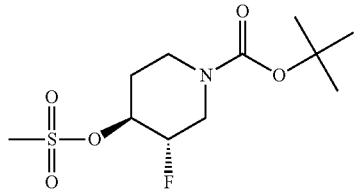 [SMILES: CC(C)(C)OC(=O)N1CC[C@H](OS(C)(=O)=O)[C@@H](F)C1]

Methane sulfonyl chloride (142 µl; 1.84 mmol; 1.2 eq.) was added to a solution of tert-butyl ester-trans-3-Fluoro-4-hydroxy-piperidine-1-carboxylic acid (336 mg; 1.53 mmol; 1.0 eq.) in DCM (5 mL) and TEA (320 µl, 2.3 mmol, 1.5 eq.) maintained at 00° C. under nitrogen atmosphere. The reaction mixture was then stirred at RT for 3 h. It was poured into a saturated solution of NH$_4$Cl. The phases were separated and aqueous phase was extracted twice with DCM. Combined organic phases were washed with sta. NaHCO$_3$ and brine, dried over magnesium sulfate, filtered and concentrated to give the title compound as a white solid (432 mg, 95%). 1H NMR (300 MHz, DMSO) δ 4.81-4.95 (m, 2H), 4.05 (m, 1H), 3.84 (m, 1H), 3.25 (s, 3H), 3.13 (m, 1H), 2.94 (m, 1H), 1.84 (m, 2H), 1.38 (s, 9H).

Intermediate 10: 3-Bromo-5-(1-methyl-1H-pyrazol-4-yl)-phenol

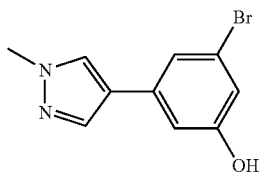

1-Methyl-4-(4,4,5,5-tetramethyl-[1,3,2]dioxaborolan-2-yl)-1H-pyrazole (750 mg; 3.6 mmol; 1.0 eq.), 3,5-Dibromophenol (4.54 g; 18.0 mmol; 5.0 eq.), bis(triphenylphosphine) palladium(II) chloride (253 mg; 0.36 mmol; 0.1 eq.) and potassium carbonate (2.49 g; 18.02 mmol; 5 eq.) were suspended in DMF (80 mL) and water (1 mL). The reaction mixture was then heated at 800° C. for 16 h in a sealed tube. It was filtered through Celite and the filtrate was concentrated under reduced pressure. Purification by flash chromatography on silica (n-heptane:EtOAc, gradient from 95:5 to 10:90) afforded the title compound as a clear oil (337 mg, 30%). 1H NMR (300 MHz, DMSO-d6) δ 10.01 (brs, 1H), 8.14 (s, 1H), 7.83 (d, J=0.7 Hz, 1H), 6.96 (d, J=1.7 Hz, 1H), 6.92 (dd, J=2.1, 1.5 Hz, 1H), 6.76 (t, J=2.0 Hz, 1H), 3.84 (s, 3H).

Intermediate 11: 2-(3-Iodo-phenyl)-5-(1H-pyrazol-4-yl)-pyrimidine

Step 1: Formation of 3-[5-(1H-Pyrazol-4-yl)-pyrimidin-2-yl]-phenylamine

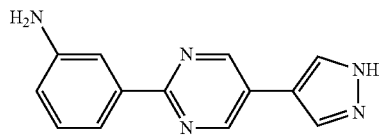 [SMILES: Nc1cccc(-c2ncc(-c3cn[nH]c3)cn2)c1]

4-(4,4,5,5-Tetramethyl-[1,3,2]dioxaborolan-2-yl)-pyrazole-1-carboxylic acid tert-butyl ester (20.7 g; 70.4 mmol; 1.0 eq.), 3-(5-Bromo-pyrimidin-2-yl)-phenylamine (intermediate 4, 17.6 g; 70.4 mmol; 1.0 eq.), bis(triphenylphosphine) palladium(II) chloride (4.94 g; 7.04 mmol; 0.10 eq.) and potassium carbonate (14.6 g; 105 mmol; 1.5 eq.) were suspended in dioxane (540 mL) and water (273 mL). The reaction mixture was then heated at 90° C. for 16 h. It was filtered through Celite and the filtrate was extracted with EtOAc. Organic phase was washed with brine, dried over magnesium sulfate, filtered and concentrated. The gum obtained was then triturated Et$_2$O (100 mL). The resulting solid was filtered off and dried under high vacuum to give the title compound as a beige solid (14 g, 87%). 1H NMR (300 MHz, DMSO-d6) δ 13.21 (brs, 1H), 9.12 (s, 2H), 8.44 (m, 1H), 8.14 (m, 1H), 7.67 (t, J=2.0 Hz, 1H), 7.57-7.54 (m, 1H), 7.14 (t, J=7.8 Hz, 1H), 5.25 (s, 2H), 6.68 (ddd, J=7.8 Hz, 2.0 Hz, 1.0 Hz, 1H). HPLC (Condition A): Rt 1.24 min (purity 72.1%). MS (ESI+): 238.2.

Step 2: Formation of 2-(3-Iodo-phenyl)-5-(1H-pyrazol-4-yl)-pyrimidine

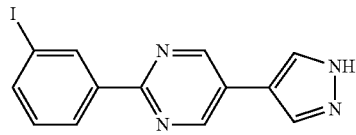 [SMILES: Ic1cccc(-c2ncc(-c3cn[nH]c3)cn2)c1]

To a suspension of 3-[5-(1H-Pyrazol-4-yl)-pyrimidin-2-yl]-phenylamine (12.6 g; 53.2 mmol; 1.0 eq.) in Dioxane (500 mL) were added diiodomethane (21.6 mL; 266 mmol; 5.0 eq.), Copper(I) iodide (10.1 g; 53.2 mmol; 1.0 eq.) and isopentyl nitrite (21.5 mL; 159 mmol; 3.0 eq.). The reaction mixture was stirred at 100° C. for 2 hours and filtered. The filtrate was kept in a flask. The resulting green solid was suspended in dioxane (100 mL) and stirred at 100° C. for 30 minutes. The solid was then filtered off and the two filtrates were combined and concentrated under reduced pressure. The dark brown residue was sonicated in EtOAc (20 mL) and pentane (80 mL). The resulting brown solid was filtered, further washed with pentane and dried few hours under high vacuum to give the title compound as a brown solid (7.0 g; 38%). 1H NMR (300 MHz, DMSO-d6) δ 13.27 (brs, 1H), 9.20 (s, 2H), 8.71 (t, J=1.5 Hz, 1H), 8.52 (m, 1H), 8.39 (dt, J=8.0 Hz, 1.5 Hz, 1H), 8.21 (m, 1H), 7.89-7.86 (m, 1H), 7.35 (t, J=8.0 Hz, 1H). HPLC (Condition A): Rt 3.86 min (purity 67.6%). MS (ESI+): 349.3

Intermediate 12: 2-{4-[2-(3-Iodo-phenyl)-pyrimidin-5-yl]-pyrazol-1-}-1-pyrrolidin-1-yl-ethanone

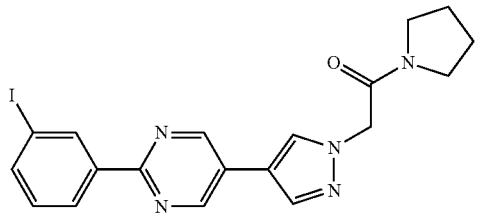 [SMILES: O=C(Cn1cc(-c2cnc(-c3cccc(I)c3)nc2)cn1)N1CCCC1]

A solution of cesium carbonate (17.3 g; 53 mmol; 2.5 eq.) and 2-(3-Iodo-phenyl)-5-(1H-pyrazol-4-yl)-pyrimidine (intermediate 11, 7.4 g; 21 mmol; 1.0 eq.) in DMF (150 mL) was stirred at RT for 30 minutes before the addition of a solution of 2-Bromo-1-pyrrolidin-1-yl-ethanone (Chemical Diversity Labs; 4.08 g; 21.3 mmol; 1.0 eq.) in DMF (65 mL). The reaction mixture was then stirred at RT O/N. It was diluted with DCM and washed with water and brine (three times). Organic phase was dried over magnesium sulfate, filtered and concentrated. The resulting residue was sonicated in DCM and the solid obtained was filtered, washed with EtOAc and pentane and dried under vacuum to give the title compound as a beige solid (3.70 g; 38%). 1H NMR (300 MHz, DMSO-d6) δ 9.19 (s, 2H), 8.72 (t, J=1.7 Hz, 1H), 8.41-8.38 (m, 2H), 8.14 (d, J=0.5 Hz, 1H), 7.89 (ddd, J=7.8 Hz, 1.7 Hz, 1.0 Hz, 1H), 7.35 (t, J=7.8 Hz, 1H), 5.12 (s, 2H), 3.53 (t, J=6.7 Hz, 2H), 3.32 (t, J=6.7 Hz, 2H), 1.93 (quint., J=6.7 Hz, 2H), 1.80 (quint., J=6.7 Hz, 2H). HPLC (Condition A): Rt 3.97 min (purity 95.9%). MS (ESI+): 460.4.

Intermediate 13: 2-Methanesulfonyloxymethyl-morpholine-4-carboxylic acid tert-butyl ester

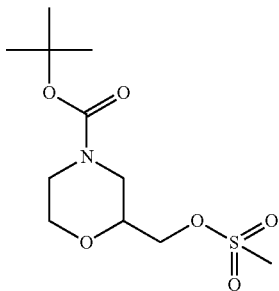 [SMILES: CC(C)(C)OC(=O)N1CCOC(COS(C)(=O)=O)C1]

Methane sulfonyl chloride (71 μl; 0.92 mmol; 1.0 eq.) was added to a solution of 2-hydroxymethyl-morpholine-4-carboxylic acid tert-butyl ester (200 mg; 0.92 mmol; 1.0 eq.) and TEA (190 uL; 1.38 mmol; 1.5 eq.) in anhydrous DCM (3 mL) maintained at 0° C. and under nitrogen atmosphere. The reaction mixture was stirred at RT O/N. The reaction mixture was washed with 10% citric acid solution and brine. Organic phase was dried over magnesium sulfate, filtered and concentrated to give the title compound as a brown oil (250 mg, 92%). $^1$H NMR (300 MHz, DMSO) δ 4.33-4.13 (m, 2H), 3.91-3.78 (m, 2H), 3.75-3.55 (m, 4H), 3.42 (td, J=11.6, 2.8 Hz, 1H), 3.20 (s, 3H), 1.41 (s, 9H).

Intermediate 14: 2-(4-{2-[3-(1H-Pyrazol-4-yl)-phenyl]-pyrimidin-5-yl}-pyrazol-1-yl)-1-pyrrolidin-1-yl-ethanone

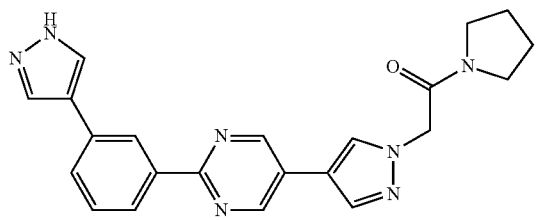 [SMILES: O=C(Cn1cc(-c2cnc(-c3cccc(-c4cn[nH]c4)c3)nc2)cn1)N1CCCC1]

The title compound was obtained following procedure described for intermediate 5, step 1, but starting from 2-{4-[2-(3-Iodo-phenyl)-pyrimidin-5-yl]-pyrazol-1-yl}-1-pyrrolidin-1-yl-ethanone (Intermediate 12, 1.0 g; 2.18 mmol; 1.0 eq.) and 4-(4,4,5,5-Tetramethyl-[1,3,2]dioxaborolan-2-yl)-pyrazole-1-carboxylic acid tert-butyl ester (704 mg; 2.4 mmol; 1.1 eq.) as a beige solid (695 mg; 80%). 1H NMR (300 MHz, DMSO-d6): 9.15 (s, 2H), 8.57-8.56 (m, 1H), 8.37 (s, 1H), 8.21 (dt, J=8.0 Hz, 1.5 Hz, 1H), 8.14-8.13 (m, 3H), 7.75 (dt, J=8.0 Hz, 1.5 Hz, 1H), 7.51 (t, J=8.0 Hz, 1H), 5.12 (s, 2H), 3.53 (t, J=6.8 Hz, 2H), 3.33 (t, J=6.8 Hz, 2H), 1.93 (quint., J=6.8 Hz, 2H), 1.80 (quint., J=6.8 Hz, 2H). MS (ESI+): 400.5.

Intermediate 15: 2-[3-(1-Methyl-1H-pyrazol-4-yl)-phenyl]-5-(4,4,5,5-tetramethyl-[1,3,2]dioxaborolan-2-yl)-pyrimidine

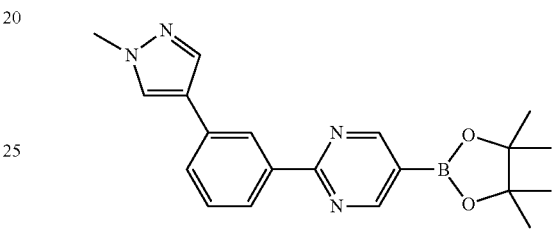

A mixture of 5-bromo-2-[3-(1-methyl-1H-pyrazol-4-yl)phenyl]pyrimidine (intermediate 2, 700 mg; 2.22 mmol; 1.0 eq.), bis(pinacolato)diboron (508 mg; 2.00 mmol; 0.9 eq.), potassium acetate (436 mg; 4.44 mmol; 2.0 eq.) and (dppf)PdC$_2$.CH$_2$Cl$_2$ (162 mg; 0.22 mmol; 0.10 eq.) in Dioxane-1,4 (4 mL) was heated at 1000 for 1 h in the MW. Reaction mixture was diluted with a saturated solution of NaHCO$_3$ and extracted with EtOAc (three times). Combined organic phases were washed with brine, dried over magnesium sulfate, filtered and concentrated to give the title compound as a dark oil (1 g, 89%) which was used in the next steps without further purification. $^1$H NMR (300 MHz, DMSO) δ 9.03 (s, 2H), 8.56 (s, 1H), 8.34-8.18 (m, 2H), 7.92 (s, 1H), 7.76 (d, J=7.6 Hz, 1H), 7.53 (t, J=7.7 Hz, 1H), 3.89 (s, 3H), 1.35 (s, 12H).

Intermediate 16: exo-3-(4-Iodo-1H-pyrazol-1-yl)-8-methyl-8-azabicyclo[3.2.1]octane

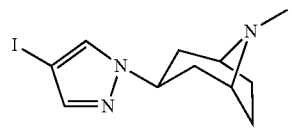

To a stirred solution of 4-Iodopyrazole (50 g, 0.257 mol) in dry THF (500 mL) was added Tropine (40 g, 0.283 mol) followed by triphenylphosphine (135 g, 0.5154 mol) and Diisopropyl azodicarboxylate (104 g, 0.5154 mol) at 0° C. under nitrogen atmosphere. After the addition, the reaction mixture was stirred at RT for 48 h. The reaction mixture was concentrated under vacuum. The crude product was purified by flash column chromatography (HCCl$_3$:MeOH, gradient from 95:5 to 92:8) to afford the titled compound as white crystalline solid (8.5 g, 10%). $^1$H NMR (400 MHz, CDCl$_3$): δ

7.50 (s, 1H), 7.46 (s, 1H), 4.54 (m, 1H), 3.32 (brs, 2H), 2.39 (s, 3H), 2.15-2.11 (m, 4H), 1.97-1.93 (m, 2H), 1.74-1.70 (m, 2H).

Intermediate 17: 2-{4-[2-(3-Iodo-phenyl)-pyrimidin-5-yl]-pyrazol-1-yl}-1-morpholin-4-yl-ethanone

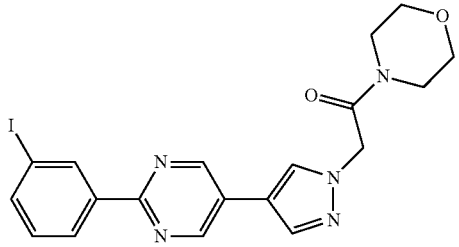 [SMILES: O=C(Cn1cc(-c2cnc(-c3cccc(I)c3)nc2)cn1)N1CCOCC1]

The title compound was obtained following procedure described for intermediate 12, but starting from 2-(3-Iodo-phenyl)-5-(1H-pyrazol-4-yl)-pyrimidine (intermediate 11, 850 mg; 2.44 mmol; 1.0 eq.) and 2-Chloro-1-morpholin-4-yl-ethanone (599 mg; 3.66 mmol; 1.5 eq.) as a beige solid (730 mg, 63%). 1H NMR (300 MHz, DMSO-d6) d 9.18 (s, 2H), 8.72 (t, J=1.6 Hz, 1H), 8.41-8.37 (m, 2H), 8.15 (s, 1H), 7.90-7.87 (m, 1H), 7.35 (t, J=7.8 Hz, 1H), 5.25 (s, 2H), 3.64-3.45 (m 8H). HPLC (Condition A): Rt 3.76 min (purity 94.6%). MS (ESI+): 476.3.

Intermediate 18: tert-butyl 4-{4-[2-(3-iodophenyl)pyrimidin-5-yl]-1H-pyrazol-1-yl}piperidine-1-carboxylate Step 1: Formation of tert-butyl 4-{4-[2-(3-aminophenyl)pyrimidin-5-yl]-1H-pyrazol-1-yl}piperidine-1-carboxylate

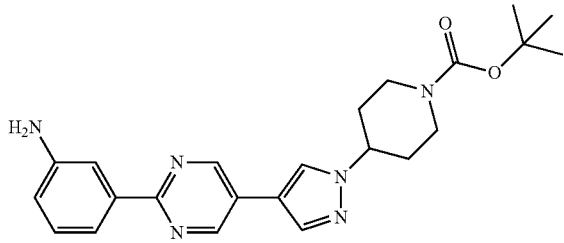 [SMILES: CC(C)(C)OC(=O)N1CCC(n2cc(-c3cnc(-c4cccc(N)c4)nc3)cn2)CC1]

The title compound was obtained following procedure described for intermediate 11, step 1, but starting from 3-(5-bromopyrimidin-2-yl)aniline (intermediate 4, 7.50 g; 21 mmol; 1.0 eq.) and 4-[4-(4,4,5,5-Tetramethyl-[1,3,2]dioxaborolan-2-yl)-pyrazol-1-yl]-piperidine-1-carboxylic acid tert-butyl ester (11.9 g; 31.5 mmol; 1.5 eq.) as a yellow powder (5 g, 51%). ¹H NMR (300 MHz, DMSO) δ 9.09 (s, 2H), 8.52 (s, 1H), 8.12 (s, 1H), 7.75-7.49 (m, 2H), 7.23-7.09 (m, 1H), 6.69 (ddd, J=7.9, 2.5, 1.1 Hz, 1H), 5.26 (s, 2H), 4.42 (td, J=7.3, 3.5 Hz, 1H), 4.05 (dd, J=13.2, 7.7 Hz, 2H), 2.95 (s, 2H), 2.07 (dd, J=13.3, 3.7 Hz, 2H), 1.91-1.70 (m, 2H), 1.43 (s, 9H). MS, (ESI+) 421.5

Step 2: Formation of tert-butyl 4-{4-[2-(3-iodophenyl)pyrimidin-5-yl]-1H-pyrazol-1-yl}piperidine-1-carboxylate

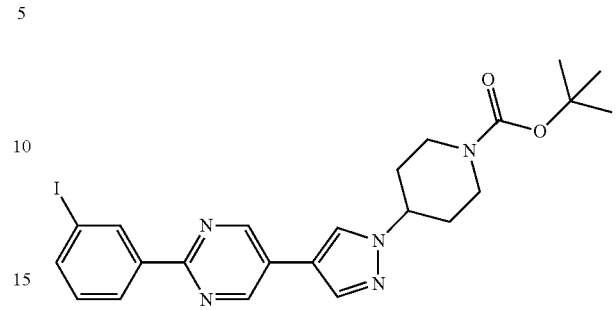

The title compound was obtained following procedure described for intermediate 11, step 2, but starting from tert-butyl 4-4-[2-(3-aminophenyl)pyrimidin-5-yl]-1H-pyrazol-1-ylpiperidine-1-carboxylate (4.50 g; 10.70 mmol; 1.00 eq.) as a beige solid (3.3 g; 58%). 1H NMR (300 MHz, DMSO-d6) δ 9.16 (s, 2H), 8.71 (t, J=1.5 Hz, 1H), 8.56 (s, 1H), 8.38 (dt, J=7.8 Hz, 1.5 Hz, 1H), 8.15 (s, 1H), 7.88 (dt, J=7.8 Hz, 1.5 Hz, 1H), 7.34 (t, J=7.8 Hz, 1H), 4.46-4.37 (m, 1H), 4.08 (m, 2H), 2.94 (m, 2H), 2.08-2.04 (m, 2H), 1.87-1.74 (m, 2H), 1.43 (s, 9H). HPLC (Condition A): Rt 5.48 min (purity 85.8%). MS (ESI+): 532.5.

Intermediate 19: 4-{4-[2-(3-Trimethylsilanylethynyl-phenyl)-pyrimidin-5-yl]-pyrazol-1-yl}-piperidine-1-carboxylic acid tert-butyl ester

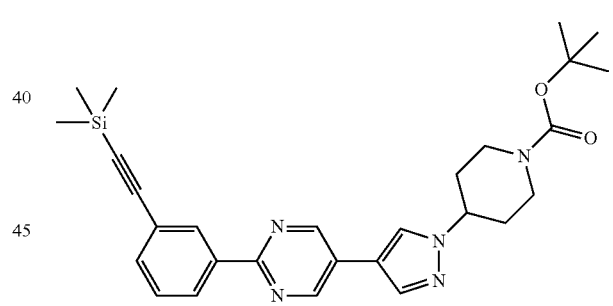

A mixture of tert-butyl 4-{4-[2-(3-iodophenyl)pyrimidin-5-yl]-1H-pyrazol-1-yl}piperidine-1-carboxylate (intermediate 18, 315 mg; 0.59 mmol; 1.0 eq.), Ethynyl-trimethyl-silane (83 µl; 0.59 mmol; 1.0 eq.), (dppf)PdCl$_2$.CH$_2$Cl$_2$ (26 mg; 0.04 mmol; 0.06 eq.), CuI (7 mg; 0.04 mmol; 0.06 eq.) and TEA (115 µl; 0.89 mmol; 1.5 eq.) in dry THF (3.6 mL) and dry DMF (1 mL) was heated in a sealed vial at 80° C. for 48 h. The reaction mixture was then diluted with EtOAc and washed with sat. NH$_4$Cl and brine. Organic phase was dried over magnesium sulfate, filtered and concentrated. Purification by flash chromatography on silica (heptanes:EtOAC, gradient form 90:10 to 50:50) afforded the title compound as a beige solid (115 mg, 39%). 1H NMR (300 MHz, DMSO-d6) d 9.17 (s, 2H), 8.57 (s, 1H), 8.41-8.38 (m, 1H), 8.15 (s, 2H), 7.61-7.54 (m, 2H), 4.08-4.03 (m, 2H), 2.96 (m, 2H9, 2.08-2.05 (m, 2H), 1.83-1.77 (m, 2H), 1.43 (s, 9H), 0.26 (s, 9H). MS (ESI+): 502.5.

Intermediate 20: 4-(4-Iodo-pyrazol-1-yl)-cyclohexanone

Step 1: Formation of Toluene-4-sulfonic acid 1,4-dioxa-spiro[4.5]dec-8-yl ester

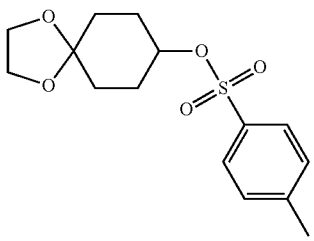 [SMILES: Cc1ccc(S(=O)(=O)OC2CCC3(CC2)OCCO3)cc1]

4-Methyl-benzenesulfonyl chloride (5.51 g; 29 mmol; 1.0 eq.) was added portionwise to a solution of 1,4-Dioxa-spiro[4.5]decan-8-ol (4.44 g; 28 mmol; 1.0 eq.) in anhydrous Pyridine (13.5 mL) maintained at 5° C. with an ice bath. The reaction mixture was then allowed to warm to RT and stirred O/N. It was then quenched by addition of water and diluted with EtOAc. Organic phase was washed with a 1N HCl solution, saturated NaHCO3 solution and brine. It was dried over magnesium sulfate, filtered and concentrated under reduced pressure to give 6.9 g of a pale yellow oil. Purification by flash chromatography on silica (heptane/EtOAc 60:40) afforded the title compound as a white powder (4.7 g, 52%). HPLC (Condition A): Rt 4.04 min (purity 100%). MS (ESI+): 330.3

Step 2: Formation of 1-(1,4-Dioxa-spiro[4.5]dec-8-yl)-4-iodo-1H-pyrazole

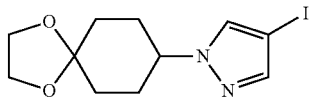 [SMILES: Ic1cnn(C2CCC3(CC2)OCCO3)c1]

A mixture of Toluene-4-sulfonic acid 1,4-dioxa-spiro[4.5]dec-8-yl ester (4.47 g; 13.9 mmol; 1.0 eq.), 4-Iodo-1H-pyrazole (2.69 g; 13.9 mmol; 1.0 eq.) and cesium carbonate (6.78 g; 20.8 mmol; 1.5 eq.) was heated in DMA (50.0 mL) at 100° C. for 3 h. It was then allowed to cool to RT, diluted with EtOAc and washed with water and brine. Aqueous phases were back-extracted with EtOAc. Combined organic phases were finally dried over sodium sulfate, filtered and concentrated to give 6.32 g of a yellow oil. Recrystallisation in iPrOH afforded the title compound as a white powder (2.81 g, 61%). HPLC (Condition A): Rt 3.46 min (purity 100%). MS (ESI+): 335.1.

Step 3: Formation of 4-(4-Iodo-pyrazol-1-yl)-cyclohexanone

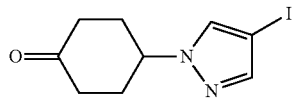 [SMILES: O=C1CCC(n2cc(I)cn2)CC1]

A solution of 1-(1,4-Dioxa-spiro[4.5]dec-8-yl)-4-iodo-1H-pyrazole (2.81 g; 8.41 mmol; 1.00 eq.) and pyridinium para-toluenesulfonate (4.23 g; 16.8 mmol; 2.0 eq.) in acetone (40 mL) and water (40 mL) was heated at reflux O/N. It was then allowed to cool to RT and diluted with EtOAc. Aqueous phase was extracted with EtOAc (twice) and combined organic phases were washed with water and brine, dried over sodium sulftate, filtered and concentrated to give the title compound as a white powder (2.34 g, 96%). HPLC (Condition A): Rt 2.83 min (purity 99.2%). MS (ESI+): 291.1.

Intermediate 21 and 22: cis and trans-4-(4-Iodo-pyrazol-1-yl)-cyclohexanol

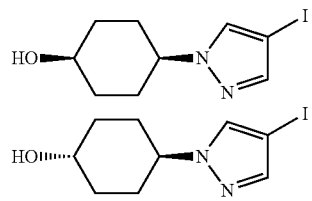

Sodium borohydride (86 mg; 2.27 mmol; 0.5 eq.) was added portionwise to a suspension of 4-(4-Iodo-pyrazol-1-yl)-cyclohexanone (1.33 g; 4.55 mmol; 1.0 eq.) in EtOH (10 mL). The reaction mixture was stirred at RT for 30 min and concentrated under vacuum. The residue was taken up with EtOAc (50 mL) and washed with NH4Cl aq sat (50 mL). The aqueous phase was back-extracted with EtOAc (twice). Combined organic layers were washed with brine, dried over sodium sulfate, filtered and concentrated to give 1.42 g of an oil. Purification by flash chromatography on silica (heptane/EtOAc, gradient from 80:20 to 40:60) afforded the title compounds.

1st eluting compound: colorless glue (234 mg, 18%). Cis-4-(4-Iodo-pyrazol-1-yl)-cyclohexanol. HPLC (Condition A): Rt 2.69 min (purity 99.7%). MS (ESI+): 293.1.

2nd eluting compound: white powder (730 mg, 55%). Trans-4-(4-Iodo-pyrazol-1-yl)-cyclohexanol. HPLC (Condition A): Rt 2.65 min (purity 100%). MS (ESI+): 293.1.

Intermediates 23 and 24: Cis-8-(4-Bromo-pyrazol-1-yl)-1-aza-spiro[4.5]decan-2-one

Step 1: Formation of N'-(2-Oxo-1-aza-spiro[4.5]dec-8-yl)-hydrazinecarboxylic acid tert-butyl ester

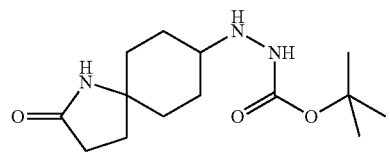 [SMILES: CC(C)(C)OC(=O)NNC1CCC2(CCC(=O)N2)CC1]

A solution of 1-Aza-spiro[4.5]decane-2,8-dione (Chembridge corporation, 800 mg; 4.78 mmol; 1.0 eq.) and hydrazinecarboxylic acid tert-butyl ester (309 mg; 2.34 mmol; 1.1 eq.) in AcOH (5 mL) was stirred at RT for 5 min. Sodium cyanoborohydride (133 mg; 2.13 mmol; 1.0 eq.) was then added and the reaction mixture was stirred O/N at RT. It was then diluted with water and basified to pH 9 by addition of a 5N solution of NaOH. During the addition, the reaction mixture was maintained at 20° C. by addition of crushed ice. It was extracted with DCM and the combined organic phases were washed with brine, dried over magnesium sulfate, filtered and concentrated to give the title compound as a yellow oil (1.0 g, 98%) which was used without further purification.

Step 2: Formation of 8-(4-Bromo-pyrazol-1-yl)-1-aza-spiro[4.5]decan-2-one

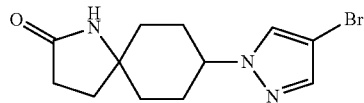

Hydrobromic acid (1.04 mL of a 48 wt % solution in water; 9.18 mmol; 2.0 eq.) was added to a solution of N'-(2-Oxo-1-aza-spiro[4.5]dec-8-yl)-hydrazinecarboxylic acid tert-butyl ester (1.30 g; 4.59 mmol; 1.0 eq.) and 2-Bromo-malonaldehyde (865 mg; 5.51 mmol; 1.2 eq.) in AcOH (13 mL). The reaction mixture was stirred at RT for 2 hour. It was then basified to pH 5 by addition of a 5N NaOH solution and extracted with DCM (three times). Combined organic phases were washed with brine, dried over magnesium sulfate, filtered and concentrated. Purification by autopreparative LC/MS afforded the title compound as the pure cis-isomer (1.0 g, 94%).

Separation by chiral preparative HPLC (Chiralpak IC 250× 4.6 mm); EtOH/DEA) afforded the two pure isomers (attributed arbitrarily).

First eluting isomer (174 mg, Rt=4.68 min): intermediate 23

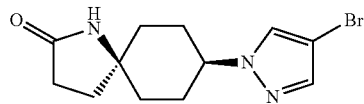 [SMILES: O=C1CC[C@]2(CC[C@H](n3cc(Br)cn3)CC2)N1]

Second eluting isomer (224 mg, Rt=6.22 min): Intermediate 24

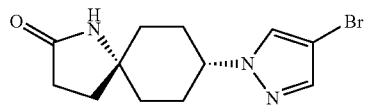 [SMILES: O=C1CC[C@]2(CC[C@H](n3cc(Br)cn3)CC2)N1]

Intermediate 25: 2-[4-(4-Iodo-pyrazol-1-yl)-cyclohexylamino]-ethanol

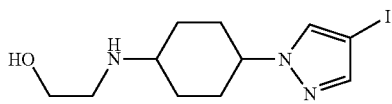 [SMILES: OCCNC1CCC(n2cc(I)cn2)CC1]

2-Amino-ethanol (0.30 mL; 4.96 mmol; 1.4 eq.) was added in one portion to a solution of 4-(4-Iodo-pyrazol-1-yl)-cyclohexanone (intermediate 20; 1.00 g; 3.45 mmol; 1.0 eq.) in EtOH. After 1 h the reaction solution was cooled to 0° C. and NaBH$_4$ (290 mg; 7.67 mmol; 2.2 eq.) added portionwise over 1 min. After a further 1 h the reaction suspension was poured into 1 N NaOH solution and extracted with DCM. Combined organic phases were washed with brine, dried over magnesium sulfate, filtered and concentrated. Purification using a SCX-2 cartridge afforded the title compound as a white solid (1.00 g; 84%). 1H NMR (300 MHz, DMSO) δ 7.94 (s, 1H), 7.49 (s, 1H), 4.47 (brs, 1H), 4.12 (m, 1H), 3.45 (m, 2H), 2.60 (t, J=5.8 Hz, 2H), 2.41 (m, 1H), 2.95 (m, 4H), 1.72 (m, 2H), 1.13 (m, 2H).

Intermediate 26: trans-4-[4-(4-Iodo-pyrazol-1-yl)-cyclohexyl]-morpholin-3-one

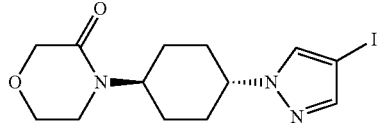 [SMILES: O=C1COCCN1[C@H]1CC[C@H](n2cc(I)cn2)CC1]

Chloro-acetyl chloride (0.25 mL; 3.14 mmol; 1.1 eq.) was added dropwise over 2 min to a solution of 2-[4-(4-Iodo-pyrazol-1-yl)-cyclohexylamino]-ethanol (intermediate 25; 1.0 g; 2.89 mmol; 1.0 eq.) and DIEA (2.00 ml; 11.45 mmol; 3.96 eq.) in THF (80.00 mL) at −30° C. The reaction solution was allowed to warm slowly to RT and stirred for 16 h. It was then poured into a 1 N HCl solution and extracted with DCM. Combined organic phases were washed with saturated NaHCO$_3$ solution, dried over magnesium sulfate, filtrated and concentrated to give 2-Chloro-N-(2-hydroxy-ethyl)-N-[4-(4-iodo-pyrazol-1-yl)-cyclohexyl]-acetamide as a brown oil. This oil was redissolved in THF (30 mL; 370 mmol; 128 eq.) and sodium tert-butoxide (2M solution in THF; 30 mL; 60.0 mmol; 21 eq.) was added in one portion. The reaction solution was heated at 40° C. for 1 h then cooled to RT and poured into 1 N HCl solution. It was extracted with DCM (twice). Combined organic phases were washed with brine, dried over magnesium sulfate, filtered and concentrated. The residue was triturated sequentially with EtOAc and Et$_2$O, filtered and dried to give the title compound as a yellow solid (275 mg; 21%). 1H NMR (300 MHz, DMSO) δ 7.98 (s, 1H), 7.50 (s, 1H), 4.40-4.25 (m, 1H), 4.25-4.10 (m, 1H), 4.03 (s, 2H), 3.87-3.75 (m, 2H), 3.32-3.23 (m, 2H), 2.14-1.99 (m, 2H), 1.93-1.60 (m, 6H). MS (ESI+): 376.2.

Intermediate 27: trans-3-[4-(4-Iodo-pyrazol-1-yl)-cyclohexyl]-oxazolidin-2-one

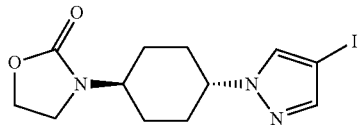 [SMILES: O=C1OCCN1[C@H]1CC[C@H](n2cc(I)cn2)CC1]

Di-imidazol-1-yl-methanone (1.32 g; 8.14 mmol; 2.9 eq.) was added in one portion to a solution of 2-[4-(4-Iodo-pyrazol-1-yl)-cyclohexylamino]-ethanol (intermediate 25; 997 mg; 2.83 mmol; 1.0 eq.) and Dimethyl-pyridin-4-yl-amine (60 mg; 0.49 mmol; 0.17 eq.) in CHCl3 (30 mL). The reaction suspension was heated at 60° C. for 20 min then cooled and poured into a 1 N HCl solution. It was extracted with DCM (twice), combined organic phases were washed with brine, dried over magnesium sulfate, filtered and concentrated. Purification by flash chromatography on silica (DCM: MeOH; 96:4) followed by a trituration in Acetonitrile afforded the title compound as a white solid (239 mg; 23%). 1H NMR (300 MHz, DMSO) δ 7.96 (d, J=0.5 Hz, 1H), 7.51 (d, J=0.5 Hz, 1H), 4.30-4.12 (m, 3H), 3.63-3.46 (m, 3H), 2.11-2.00 (m, 2H), 1.91-1.58 (m, 6H). HPLC (Condition A): Rt 2.98 min (purity 99.0%). MS (ESI+): 362.2.

Intermediate 28: 4-Iodo-1-(1-oxa-spiro[2.5]oct-6-yl)-1H-pyrazole

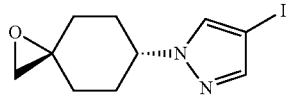 [SMILES: Ic1cnn([C@H]2CC[C@@]3(CC2)CO3)c1]

2-Methyl-propan-2-ol potassium (466 mg; 4.15 mmol; 1.2 eq.) was added in one portion to a solution of 4-(4-Iodo-pyrazol-1-yl)-cyclohexanone (1.02 g; 3.50 mmol; 1.0 eq.) and trimethylsulfoxonium chloride (531 mg; 4.13 mmol; 1.2 eq.) in DMSO (50 mL). The reaction mixture was stirred at RT for 16 h. It was then poured into EtOAc. Organic phase was separated and washed with brine (three times), dried over magnesium sulfate, filtered and concentrated to give the title compound a white solid (813 mg, 76%). 1H NMR (300 MHz, DMSO) δ 8.01 (d, J=0.5 Hz, 1H), 7.52 (d, J=0.5 Hz, 1H), 4.41-4.26 (m, 1H), 2.66 (s, 2H), 2.13-1.85 (m, 6H), 1.34-1.21 (m, 2H). MS (ESI+): 305.1.

Intermediate 29:
4-(4-Bromo-pyrazol-1-yl)-3,3-difluoro-piperidine

Step 1: Formation of 4-(N'-tert-Butoxycarbonyl-hydrazino)-3,3-difluoro-piperidine-1-carboxylic acid tert-butyl ester

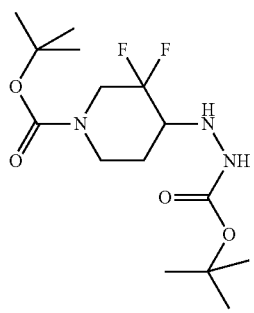

The title compound was obtained following procedure described for Intermediate 23, step 1 but starting from 3,3-Difluoro-4-oxo-piperidine-1-carboxylic acid tert-butyl ester (OmegaChem; 500 mg; 2.06 mmol; 1.0 eq.) as a white solid (495 mg; 1.40 mmol; 68%). 1H NMR (400 MHz, DMSO; 1H) δ 8.33 (s, 1H), 4.72 (s, 1H), 3.97-3.91 (m, 1H), 3.72-3.60 (m, 1H), 3.56-3.44 (m, 2H), 3.32-3.28 (m, 1H), 1.78-1.71 (m, 1H), 1.37 (s, 18H). HPLC (Condition A): Rt 4.75 min (purity 99.5%).

Step 2: Formation of 4-(4-Bromo-pyrazol-1-yl)-3,3-difluoro-piperidine

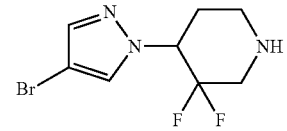 [SMILES: FC1(F)CNCCC1n1cc(Br)cn1]

The title compound was obtained following procedure described for Intermediate 23, step 2 but starting from 4-(N'-tert-Butoxycarbonyl-hydrazino)-3,3-difluoro-piperidine-1-carboxylic acid tert-butyl ester (490 mg; 1.39 mmol; 1.0 eq.) as a yellow solid (152 mg, 36%). HPLC (Condition A): Rt 2.09 min (purity 88.0%). MS (ESI+): 268.0.

Intermediate 30 and 31: Cis and trans-8-(4-bromo-1H-pyrazol-1-yl)-2-azaspiro[4.5]decan-3-one Step 1: Formation of Methyl 1,4-dioxaspiro[4.5]dec-8-ylideneacetate

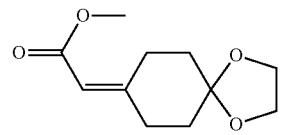

A solution of methyl (triphenylphosphoranylidene) acetate (13.9 g, 41.6 mmol) and cyclohexanedionemonoethylene-acetal (5 g, 32 mmol, 1.0 eq.) in dry toluene (50 mL) was heated at reflux under nitrogen atmosphere for 18 h. The solvent was removed under reduced pressure and the crude was purified by flash chromatography on silica (pet. ether: ethyl acetate). The title compound was isolated as a colorless liquid (4 g, 60%). 1H NMR (400 MHz, DMSO) δ 5.7 (s, 1H), 3.88 (s, 1H), 3.59 (s, 3H), 3.32-2.84 (m, 2H), 2.32-2.29 (m, 2H), 1.69-1.65 (m, 4H).

Step 2: Formation of Methyl [8-(nitromethyl)-1,4-dioxaspiro[4.5]dec-8-yl]acetate

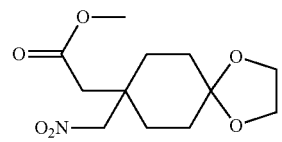 [SMILES: COC(=O)CC1(C[N+](=O)[O-])CCC2(CC1)OCCO2]

A solution of Methyl 1,4-dioxaspiro[4.5]dec-8-ylideneacetate (4 g, 18.8 mmol) in dry THF (20 mL) was treated by nitromethane (1.5 mL, 28.3 mmol) followed by tertbutylammonium fluoride (18.8 mLot a 1M solution in THF, 0.0188 mol). The resulting mixture was stirred at reflux for 18 h under nitrogen. After cooling to RT, the mixture was diluted with water and extracted with MTBE (3×100 mL). Combined organic layers were washed with 10% sodium bicarbonate solution (20 mL), water (100 mL) and brine (50 mL), dried over sodium sulphate filtered and concentrated. Purification by flash chromatography on silica (Pet.Ether:EtOAc) afforded the title compound as a colorless liquid (2.5 g, 49%). 1H NMR (400 MHz, DMSO) δ 4.7 (s, 2H), 3.94 (s, 4H), 3.69 (s, 3H), 2.57 (s, 2H), 1.74 (m, 8H).

Step 3: Formation of 1,4-Dioxa-10-azadispiro[4.2.4.2]tetradecan-11-one

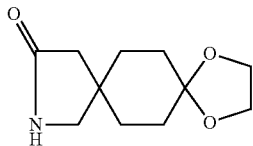 [SMILES: CNCC1(CC(C)=O)CCC2(CC1)OCCO2]

To a slurry of Methyl [8-(nitromethyl)-1,4-dioxaspiro[4.5] dec-8-yl]acetate (1 g, 4.7 mmol) in Methanol (20 mL) was added Pd/C (1 g, 10%) under $N_2$ atmosphere. The reaction mixture was stirred at room temperature under 5 kg/cm$^2$ $H_2$ pressure for 12 h. After completion, the reaction mixture was filtered through celite pad, washed with methanol and the filtrate was concentrated under reduced pressure to afford the title compound as a white solid (0.7 g, 70%). $^1$H NMR (400 MHz, DMSO-$d_6$) δ 7.46 (s, 1H), 3.83 (s, 4H), 3.00 (s, 2H), 2.00 (s, 2H), 1.56-1.51 (m, 8H).

Step 4: Formation of 2-Azaspiro[4.5]decane-3,8-dione

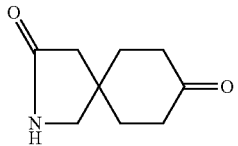

A solution of 1,4-dioxa-10-azadispiro[4.2.4.2]tetradecan-11-one (10.5 g, 49.8 mmol) in aq.HCl (2N, 20 mL) was stirred at RT for 2 h. The reaction mixture was then concentrated under reduced pressure and diluted with water. It was extracted with ethyl acetate (Three times) and the combined organic phases were washed with water, brine, dried over sodium sulfate, filtered and concentrated. Purification by flash chromatography on silica (Pet.Ether:EtOAc) afforded the title compound as a white solid (7.5 g, 92%). $^1$H NMR (400 MHz, DMSO-$d_6$) δ 7.58 (m, 1H), 3.15-3.15 (s, 2H), 2.30 (s, 4H), 2.28-2.25 (m, 2H), 1.82-1.79 (m, 4H).

Step 5: Formation of tert-butyl 2-(3-oxo-2-azaspiro[4.5]dec-8-yl) hydrazinecarboxylate

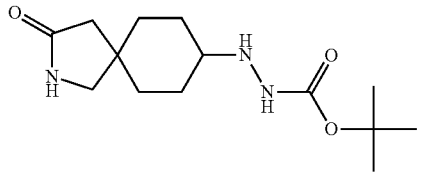 [SMILES: CC(C)(C)OC(=O)NNC1CCC2(CC1)CNC(=O)C2]

The title compound was obtained following procedure described for Intermediate 23, step 1 but starting from 2-azaspiro[4.5]decane-3,8-Dione (3.8 g, 22.7 mmol) as a white solid (4.6 g, 72%). $^1$H NMR (400 MHz, DMSO-$d_6$) δ 8.17 (s, 1H), 7.46-7.44 (m, 1H), 4.20 (s, 1H), 2.97-2.93 (m, 2H), 2.64 (bs, 1H), 1.96-1.93 (m, 2H), 1.61-1.58 (m, 4H), 1.36 (s, 9H), 1.28-1.24 (m, 2H), 1.22-1.09 (m, 2H).

Step 5: Formation of 8-(4-bromo-1H-pyrazol-1-yl)-2-azaspiro[4.5]decan-3-one

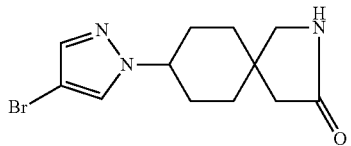 [SMILES: O=C1CC2(CCC(n3cc(Br)cn3)CC2)CN1]

The title compound was obtained following procedure described for Intermediate 23, step 1 but starting from tert-butyl 2-(3-oxo-2-azaspiro[4.5]dec-8-yl) hydrazinecarboxylate (4 g, 14.1 mmol) as a white solid (2 g, 48%). $^1$H NMR (400 MHz, DMSO-$d_6$) δ 8.04-8.04 (d, 1H), 7.52-7.50 (m, 2H), 4.15-4.09 (m, 1H), 3.12 (s, 1H), 2.98 (s, 1H), 2.12 (s, 1H), 1.98 (s, 1H), 1.88-1.86 (m, 2H), 1.78-1.69 (m, 4H), 1.50-1.45 (m, 2H).

Step 7: separation isomers of 8-(4-bromo-1H-pyrazol-1-yl)-2-azaspiro[4.5]decan-3-one The mixture obtained in step 6 was separated by preparative HPLC (Chiralpak AD-H, hexane:IPA:DEA 80:20:0.1).
First eluting compound: intermediate 30, Rt=19.32 min

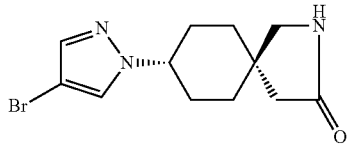 [SMILES: O=C1C[C@]2(CC[C@@H](n3cc(Br)cn3)CC2)CN1]

Second eluting compound: intermediate 31, Rt=22.69 min

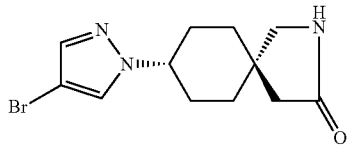 [SMILES: O=C1C[C@]2(CC[C@H](n3cc(Br)cn3)CC2)CN1]

Intermediate 32 and 33: cis and trans-8-(4-bromo-1H-pyrazol-1-yl)-2-methyl-2-azaspiro[4.5]decan-3-one

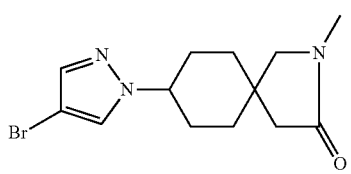 [SMILES: CN1CC2(CCC(n3cc(Br)cn3)CC2)CC1=O]

Step 1: Formation of 8-(4-bromo-1H-pyrazol-1-yl)-2-methyl-2-azaspiro[4.5]decan-3-one To a solution of 8-(4-bromo-1H-pyrazol-1-yl)-2-azaspiro[4.5]decan-3-one (mixture of intermediate 30 and 31 obtained in step 5; 4 g, 13.4 mmol) in DMF (10 mL) was added sodium hydride (60%) (0.8 g, 0.0116 mol) followed by methyl iodide (2.2 mL, 14.8 mmol) at 0° C. The reaction mixture was slowly allowed to warm to RT and stirred for 1 h. The reaction mixture was quenched with water and extracted with ethyl acetate. Combined organic phases were washed with water (50 mL) and brine (50 mL), dried over sodium sulphate, filtered and concentrated. Purification by flash chromatography on silica (Pet. ether: ethyl acetate) afforded the title compound (mixture of two isomers) as an off white solid (1.8 g, 43%). 1H NMR (400 MHz, DMSO-d6) δ 8.04-8.03 (m, 1H), 7.51-7.50 (m, 1H), 4.16-4.10 (m, 1H), 3.24 (s, 1H), 3.09 (s, 1H), 2.70-2.69 (m, 3H), 2.21 (s, 1H), 2.09 (s, 1H), 1.90-1.86 (m, 6H), 1.79-1.54 (m, 2H).

Step 2: Separation Cis and trans 8-(4-bromo-1H-pyrazol-1-yl)-2-methyl-2-azaspiro[4.5]decan-3-one The mixture obtained in step 1 was separated by preparative HPLC (Zorbax RX—SIL, hexane:EtOH:DEA; 90:10:0.1)
First eluting compound: intermediate 32; Rt=12.87 min

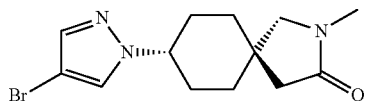

Second eluting compound: intermediate 33; Rt=13.87 min

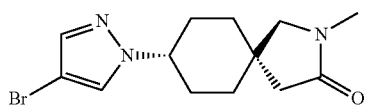

Intermediate 34: Cis-8-(4-Bromo-pyrazol-1-yl)-1-methyl-1-aza-spiro[4.5]decan-2-one

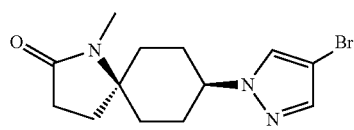 [SMILES: CN1C(=O)CC[C@]12CC[C@H](n1cc(Br)cn1)CC2]

The title compound was obtained following procedure described for intermediate 32 and 33, step 1 but starting from 8-(4-Bromo-pyrazol-1-yl)-1-aza-spiro[4.5]decan-2-one (intermediate 23; 150 mg; 0.50 mmol; 1.0 eq.) as a brown gum (130 mg, 82%). HPLC (max plot) 98.8% (ELSD); (220 nm) 69.4%; Rt (min) 3.29; MS: (ESI+) 314.0 (M+H2).

Intermediates 35 and 36: (3aS,5S,7aS) and (3aR,5R,7aR)-5-(4-bromopyrazol-1-yl)-7a-(hydroxymethyl)-1,3,4,5,6,7-hexahydroisobenzofuran-3a-ol Step 1: Formation of Methyl-6-(2-tert-butoxycarbonylhydrazino)-cis-7a-hydroxy-1,3,4,5,6,7-hexahydroisobenzofuran-3a-carboxylate

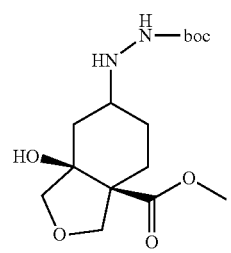

The title compound was obtained following procedure described for Intermediate 23, step 1 but starting from Methyl cis-7a-hydroxy-6-oxo-3,4,5,7-tetrahydro-1H-isobenzofuran-3a-carboxylate (prepared as described in Synthesis, 2010, p 895, 1.0 g, 4.6 mmol) as a brown oil (0.85 g, 55%). 1H NMR (400 MHz, DMSO): δ 12.00 (brs, 1H), 8.20 (brs, 1H), 4.91 (s, 1H), 4.17-4.10 (m, 1H), 4.08-3.58 (m, 1H), 3.57 (s, 3H), 3.56-3.32 (m, 1H), 1.91-1.61 (m, 10 H), 1.37 (s, 9H). HPLC (Condition A): Rt 2.40; 2.47 min (purity 11.6, 86.7%). MS (ESI+): 331.2.

Step 2: Formation of methyl-6-(4-bromopyrazol-1-yl)-cis-7a-hydroxy-1,3,4,5,6,7-hexahydroisobenzofuran-3a-carboxylate

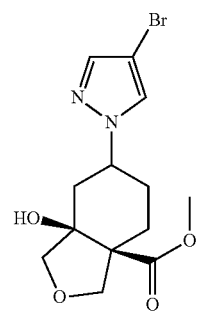

The title compound was obtained following procedure described for Intermediate 23, step 2 but starting from Methyl-6-(2-tert-butoxycarbonylhydrazino)-cis-7a-hydroxy-1,3,4,5,6,7-hexahydroisobenzofuran-3a-carboxylate (0.8 g, 2.4 mmol) as a colorless oil (0.2 g, 24%). 1H NMR (400 MHz, DMSO): δ 7.48-7.46 (m, 2H), 4.55 (m, 1H), 4.30-4.24 (m, 2H), 4.13-4.08 (m, 2H), 3.92 (s, 3H), 3.76-3.60 (m, 1H), 2.36-2.24 (m, 3H), 2.12-2.01 (m, 3H). HPLC (Condition A): Rt 3.14 min (purity 95.4%). MS (ESI+): 345.0.

Step 3: Formation of 5-(4-bromopyrazol-1-yl)-cis-7a-(hydroxymethyl)-1,3,4,5,6,7-hexahydroisobenzofuran-3a-ol

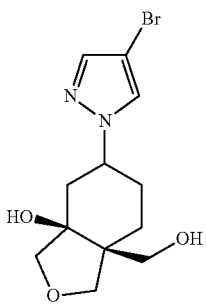 [SMILES: OC[C@]12CCC(n3cc(Br)cn3)C[C@@]1(O)COC2]

Lithium borohydride (2M in THF, 4.13 mL of a 2M solution in THF, 8.6 mmol) was added slowly over 10 minutes to a solution of methyl-6-(4-bromopyrazol-1-yl)-cis-7a-hydroxy-1,3,4,5,6,7-hexahydroisobenzofuran-3a-carboxylate (1.2 g, 3.4 mmol) in THF (10 mL) at 0-5° C. under nitrogen atmosphere. The reaction mixture was allowed to warm to 25-26° C. and stirred for 8 h. It was then quenched with ice (50 g) and acetic acid (5 mL) and extracted with DCM (3 times). Combined organic phases were washed with water, brine, dried over sodium sulfate, filtered and concentrated to give the title compound as light yellow liquid (0.8 g) containing the cis and trans isomers (95:5) which were separated by preparative HPLC.

Minor isomer: 50 mg; HPLC (Condition A): Rt 3.72 min (purity 93.8%)

Major isomer: 0.5 g. 1H NMR (400 MHz; DMSO): δ 7.47 (s, 2H), 4.48-4.44 (m, 1H), 4.22-4.20 (d, J=11.08 Hz, 1H), 3.99-3.93 (m, 2H), 3.70-3.68 (d, J=8.32 Hz, 1H), 3.54-3.51 (d, J=10.0 Hz, 2H), 2.28-2.10 (m, 4H), 2.02-1.95 (m, 1H), 1.64-1.59 (m, 1H). HPLC (Condition A): Rt 2.95 min (purity 99.9%). MS (ESI+): 319.0. Cis-cis isomer as shown by NOE experiments performed on compound described in example Step 4: Enantiomers separation of cis-5-(4-bromopyrazol-1-yl)-cis-7a-(hydroxymethyl)-1,3,4,5,6,7-hexahydroisobenzofuran-3a-ol

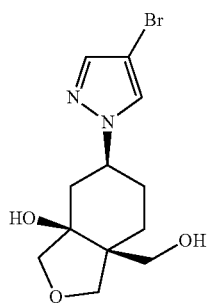 [SMILES: OC[C@]12CC[C@H](n3cc(Br)cn3)C[C@@]1(O)COC2]

The enantiomers of major isomer obtained in step 3 were separated by SFC (Lux A2, CO2:MeOH).

First eluting enantiomer: intermediate 35; 200 mg; Rt=15.6 min (Chiralcel OD-H, 250×4.6 mm; 5 uM; eluant: hexane:IPA:TFA, 90:10:0.1).

Second eluting enantiomer: intermediate 36; 200 mg; Rt=16.78 min (Chiralcel OD-H, 250×4.6 mm; 5 uM; eluant: hexane:IPA:TFA, 90:10:0.1).

Intermediate 37:
4-(4-Bromo-pyrazol-1-yl)-3-fluoro-piperidine

Step 1: Formation of 4-(N'-tert-Butoxycarbonyl-hydrazino)-3-fluoro-piperidine-1-carboxylic acid tert-butyl ester

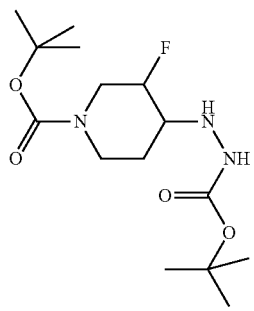 [SMILES: CC(C)(C)OC(=O)NNC1CCN(C(=O)OC(C)(C)C)CC1F]

The title compound was obtained following procedure described for Intermediate 23, step 1 but starting from 3-Fluoro-4-oxo-piperidine-1-carboxylic acid tert-butyl ester (OmegaChem; 1.00 g; 4.47 mmol; 1.0 eq.) as a white solid (1.0 g, 73%). MS (ESI+): 222.2.

Step 2: Formation of
4-(4-Bromo-pyrazol-1-yl)-3-fluoro-piperidine

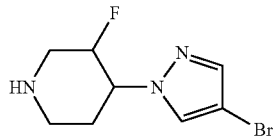

The title compound was obtained following procedure described for Intermediate 23, step 2 but starting from 4-(N'-tert-Butoxycarbonyl-hydrazino)-3-fluoro-piperidine-1-carboxylic acid tert-butyl ester (1.10 g; 3.25 mmol; 1.0 eq.) a white solid (mixture of cis:trans isomer, 7:3; 600 mg, 74%). 1H NMR (400 MHz, DMSO-d6) δ 8.06 (s, 0.3H), 7.97 (s, 0.7H), 7.59 (brs, 1H), 4.82 (d, J=52 Hz, 0.7H), 4.70 (m, 0.3H), 4.45 (m, 0.7H), 4.30 (m, 0.3H), 3.31-2.62 (m, 3.3H), 2.45 (m, 1H), 2.10 (m, 0.7H), 1.93-1.82 (m, 2H).

Example 1

2-[3-(1-Methyl-1H-pyrazol-4-yl)-phenyl]-5-(1-piperidin-4-yl-1H-pyrazol-4-yl)-pyrimidine hydrochloride Step 1: Formation of tert-butyl 4-(4-{2-[3-(1-methyl-1H-pyrazol-4-yl)phenyl]pyrimidin-5-yl}-1H-pyrazol-1-yl)piperidine-1-carboxylate

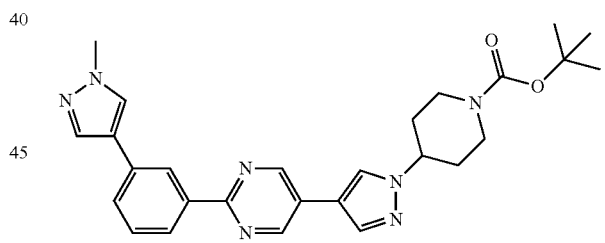

A solution of 5-bromo-2-[3-(1-methyl-1H-pyrazol-4-yl)-phenyl]-pyrimidine (intermediate 2, 160 mg, 0.50 mmol), 4-[4-(4,4,5,5-Tetramethyl-[1,3,2]dioxaborolan-2-yl)-pyrazol-1-yl]-piperidine-1-carboxylic acid tert-butyl ester (Combi-blocks, 287 mg, 0.76 mmol) and Na2CO3 (140 mg, 0.12 mmol) in dry Toluene: Ethanol (1:1) (5 mL) was purged with nitrogen for 30 min before the addition of Pd(PPh3)4 (60 mg, 0.05 mmol). The reaction mixture was then heated at 100° C. O/N and filtered through a celite pad. The filtrate was concentrated under reduced pressure to give the crude product. Purification by Flash chromatography on silica (hexane: EtOAc) afforded the title compound as a yellow solid (230 mg, 93%). ¹H NMR (400 MHz, DMSO-d6): δ 9.15 (s, 2H), 8.53 (d, J=8.0 Hz, 2H), 8.25 (s, 1H), 8.21 (d, J=7.76 Hz, 1H), 8.14 (s, 1H), 7.91 (s, 1H), 7.91-7.48 (m, 10H), 4.45-4.44 (m, 1H), 4.07-4.04 (m, 2H), 3.88 (s, 3H), 2.12 (s, 2H), 2.70 (d, J=3.44 Hz, 1H), 2.08-2.05 (m, 2H), 1.86-1.76 (m, 2H), 1.42 (s, 9H). HPLC (Condition A): Rt 4.68 min (purity 87%). MS (ESI+): 486.2.

Step 2: Formation of 2-[3-(1-Methyl-1H-pyrazol-4-yl)-phenyl]-5-(1-piperidin-4-yl-1H-pyrazol-4-yl)-pyrimidine hydrochloride

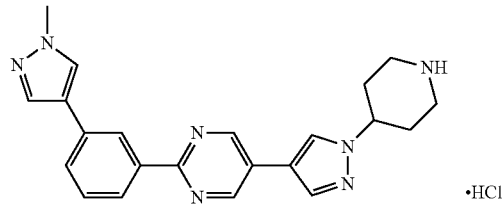 [SMILES: Cn1cc(-c2cccc(-c3ncc(-c4cnn(C5CCNCC5)c4)cn3)c2)cn1 ; Cl]

A solution of HCl/dioxane (4N solution in dioxane, 10 mL) was added slowly to a solution of tert-butyl 4-[4-[2-[3-(3-pyridyl) phenyl]pyrimidin-5-yl]pyrazol-1-yl]piperidine-1-carboxylate (200 mg, 0.63 mmol) at 0° C. under nitrogen atmosphere. After 2 h, the reaction mixture was concentrated under reduced pressure. The residue was washed with ether and dried under reduced pressure to afford the title compound as a beige solid (32 mg, 81%). $^1$H NMR (400 MHz, DMSO-$d_6$): δ 9.19 (s, 3H), 8.52 (t, J=4.0 Hz, 2H), 8.25-8.19 (m, 3H), 7.91-7.89 (m, 1H), 7.72-7.69 (m, 1H), 7.51 (t, J=7.72 Hz, 1H), 3.89 (s, 3H), 3.41-3.37 (m, 2H), 3.11-3.08 (m, 2H), 2.27-2.14 (m, 4H). HPLC (Condition A): Rt 2.97 min (purity 95%). MS (ESI+): 386.3.

Example 2

5-(1-(piperidin-4-yl)-1H-pyrazol-4-yl)-2-(3-(pyridin-3-yl)phenyl)pyrimidine hydrochloride Step 1: Formation of 4-{4-[2-(3-Pyridin-3-yl-phenyl)-pyrimidin-5-yl]-pyrazol-1-yl}-piperidine-1-carboxylic acid tert-butyl ester

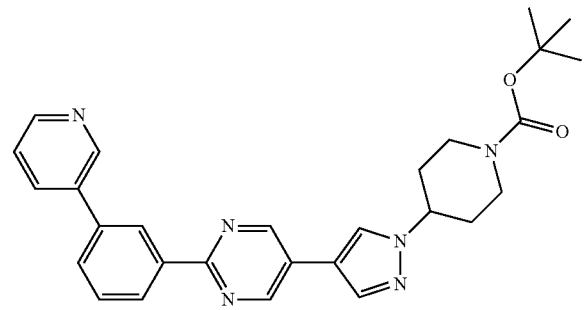 [SMILES: CC(C)(C)OC(=O)N1CCC(n2cc(-c3cnc(-c4cccc(-c5cccnc5)c4)nc3)cn2)CC1]

The title compound was obtained following procedure described for example 1, step 1, but starting from 5-Bromo-2-(3-pyridin-3-yl-phenyl)-pyrimidine (intermediate 3) and 1-(1-Boc-4-piperidyl)pyrazole-4-boronic acid pinacol ester (combi-Blocks) as a yellow solid. MS (ESI+): 483.2.

Step 2: Formation of 5-(1-(piperidin-4-yl)-1H-pyrazol-4-yl)-2-(3-(pyridin-3-yl)phenyl)pyrimidine hydrochloride

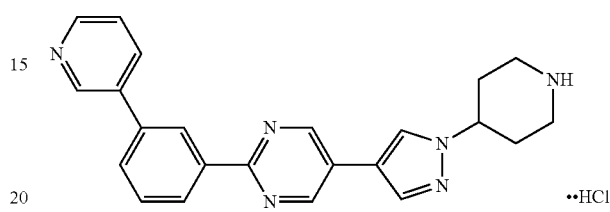

The title compound was obtained following procedure described for example 1, step 2, but starting from 4-{4-[2-(3-Pyridin-3-yl-phenyl)-pyrimidin-5-yl]-pyrazol-1-yl}-piperidine-1-carboxylic acid tert-butyl ester as a yellow oil. $^1$H NMR (400 MHz, DMSO-$d_6$): δ 9.21-9.18 (m, 2H), 9.00-8.95 (m, 1H), 8.74-8.67 (m, 3H), 8.57-8.44 (m, 2H), 8.24-8.20 (m, 2H), 7.90 (d, J=7.80 Hz, 1H), 7.70-7.60 (m, 2H), 4.59-4.53 (m, 1H), 3.45-3.43 (m, 2H), 3.15-3.10 (m, 2H), 2.30-2.10 (m, 4H). HPLC (Condition A): Rt 2.18 min (purity 98%). MS (ESI+): 383.3.

Example 3

2-[3-(1-methyl-1H-pyrazol-4-yl)phenyl]-5-(1H-pyrazol-4-yl)pyrimidine

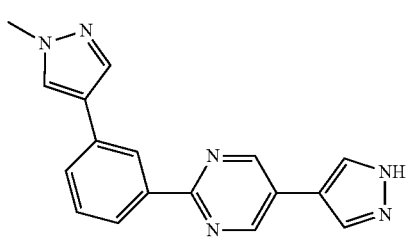 [SMILES: Cn1cc(-c2cccc(-c3ncc(-c4cn[nH]c4)cn3)c2)cn1]

The title compound was obtained following procedure described for intermediate 4, but starting from 5-bromo-2-[3-(1-methyl-1H-pyrazol-4-yl)phenyl]pyrimidine (intermediate 2, 5.0 g; 15.9 mmol; 1.0 eq.) and 4-(4,4,5,5-Tetramethyl-[1,3,2]dioxaborolan-2-yl)-pyrazole-1-carboxylic acid tert-butyl ester (5.1 g; 17.4 mmol; 1.1 eq.) as a beige solid (4 g, 85%). 1H NMR (300 MHz, DMSO-d6) δ 13.25 (s, 1H), 9.20 (s, 2H), 8.59-8.40 (m, 2H), 8.30-8.11 (m, 3H), 7.93 (d, J=0.9 Hz, 1H), 7.71 (ddd, J=7.6, 1.8, 1.1 Hz, 1H), 7.51 (t, J=7.8 Hz, 1H), 3.90 (s, 3H). HPLC (Condition A): Rt 2.94 min (purity 95.5%). MS (ESI+): 303.1, (ESI−): 301.1.

Example 4

2,2,2-Trifluoro-1-[4-(4-{2-[3-(1-methyl-1H-pyrazol-4-yl)-phenyl]-pyrimidin-5-yl}-pyrazol-1-yl)-piperidin-1-yl]-ethanone

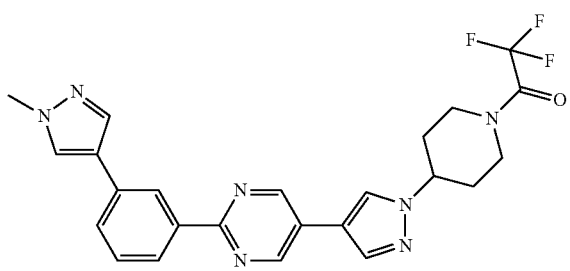 [SMILES: Cn1cc(-c2cccc(-c3ncc(-c4cnn(C5CCN(C(=O)C(F)(F)F)CC5)c4)cn3)c2)cn1]

Trifluoroacetic anhydride (44 µl; 0.31 mmol; 1.0 eq.) was added to a solution of 2-[3-(1-Methyl-1H-pyrazol-4-yl)-phenyl]-5-(1-piperidin-4-yl-1H-pyrazol-4-yl)-pyrimidine (example 1, 200 mg; 0.31 mmol; 1.0 eq.) in DCM (3 mL) and TEA (130 µl; 0.93 mmol; 3.0 eq.) maintained at 0° C. The reaction mixture was then stirred at RT for 3 h. It was quenched by addition of a saturated solution of NaHCO₃ at 0° C. The aqueous phase was extracted with DCM (twice) and the combined organic phases were washed with sat. NH₄Cl and brine, dried over magnesium sulfate, filtered and concentrated. Purification by autopreparative LC/MS afforded the title compound as a white foam (61 mg, 41%). 1H NMR (300 MHz, DMSO-d6) δ 9.17 (s, 2H), 8.61-8.55 (m, 1H), 8.53 (t, J=1.6 Hz, 1H), 8.29-8.25 (m, 1H), 8.22 (dt, J=7.8, 1.4 Hz, 1H), 8.19-8.16 (m, 1H), 7.93 (d, J=0.8 Hz, 1H), 7.75-7.68 (m, 1H), 7.52 (t, J=7.7 Hz, 1H), 4.70-4.56 (m, 1H), 4.47-4.35 (m, 1H), 4.06-3.94 (m, 1H), 3.89 (s, 3H), 3.58-3.42 (m, 1H), 3.24-3.10 (m, 1H), 2.32-2.14 (m, 2H), 2.07-1.86 (m, 2H). HPLC (Condition A): Rt 4.02 min (purity 98.7%). MS (ESI+): 482.2.

Example 5

1-[4-(4-{2-[3-(1-Methyl-1H-pyrazol-4-yl)-phenyl]-pyrimidin-5-yl}-pyrazol-1-yl)-piperidin-1-yl]-ethanone

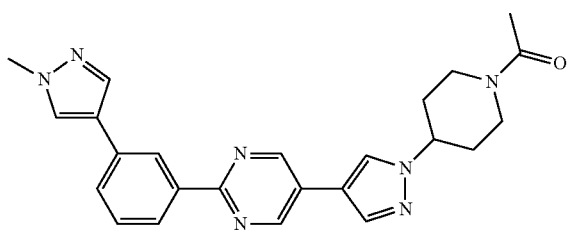 [SMILES: CC(=O)N1CCC(n2cc(-c3cnc(-c4cccc(-c5cnn(C)c5)c4)nc3)cn2)CC1]

Acetyl chloride (222 µl; 3.1 mmol; 2.0 eq.) was added to a solution of 2-[3-(1-Methyl-1H-pyrazol-4-yl)-phenyl]-5-(1-piperidin-4-yl-1H-pyrazol-4-yl)-pyrimidine hydrochloride (example 1, 655 mg; 1.55 mmol; 1.0 eq.) and TEA (503 µl; 3.88 mmol; 2.5 eq.) in dry DMF (12 mL) and the reaction mixture was stirred at RT and under nitrogen for 2 h. The reaction mixture was diluted with DCM and washed with water. Organic phase was washed with brine, dried over magnesium sulfate, filtered and concentrated. Purification by flash chromatography on silica (DCM: MeOH, gradient 100:0 to 80:20) afforded the title compound as a white solid (370 mg, 56%). 1H NMR (300 MHz, DMSO-d6) δ 9.16 (s, 2H), 8.58-8.50 (m, 2H), 8.26 (s, 1H), 8.21 (dt, J=8.0, 1.5 Hz, 1H), 8.15 (s, 1H), 7.92 (s, 1H), 7.71 (dt, J=8.0, 1.5 Hz, 1H), 7.51 (t, J=8.0 Hz, 1H), 4.58-4.43 (m, 2H), 4.01-3.83 (m, 4H), 3.29-3.17 (m, 1H), 2.74 (dd, J=14.1, 9.2 Hz, 1H), 2.19-2.02 (m, 5H), 1.98-1.69 (m, 2H). HPLC (Condition A): Rt 2.90 min (purity 98.0%). MS (ESI+): 428.36.

Example 6

5-[1-(1-Methyl-piperidin-4-yl)-1H-pyrazol-4-yl]-2-[3-(1-methyl-1H-pyrazol-4-yl)-phenyl]-pyrimidine

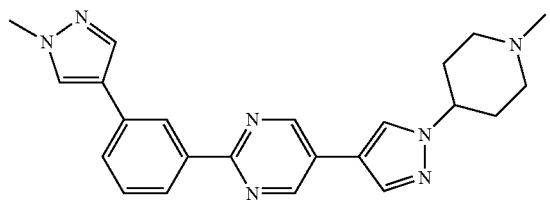

Sodium triacetoxyborohydride (50 mg; 0.24 mmol; 2.0 eq.) was added to a solution of 2-[3-(1-methyl-1H-pyrazol-4-yl)phenyl]-5-(1-piperidin-4-yl-1H-pyrazol-4-yl)pyrimidine (example 1, 50 mg; 0.12 mmol; 1.0 eq.), formaldehyde (16 µl of a 36% aq. solution; 0.21 mmol; 1.8 eq.) and DIEA (24 µl; 0.14 mmol; 1.2 eq.) in DCE (2 mL). The reaction mixture was heated at 50° C. for 1 hour. It was then diluted with DCM and poured into a saturated solution of NaHCO₃. The organic phase was washed with brine, dried over magnesium sulfate, filtered and concentrated to give the title compound as a white solid (25 mg; 53%). ¹H NMR (300 MHZ, DMSO-d6) δ 9.17 (s, 2H), 8.54-8.52 (m, 2H), 8.26 (s, 1H), 8.22 (dt, J=7.8 Hz, 1.5 Hz, 1H), 8.15 (s, 1H), 7.92 (d, J=1.5 Hz, 1H), 7.51 (dt, J=7.8 Hz, 1.5 Hz, 1H), 7.51 (t, J=7.8 Hz, 1H), 4.31-4.20 (m, 1H), 3.89 (s, 3H), 3.04-3.01 (m, 2H), 2.36-2.23 (m, 5H), 2.10-2.03 (m, 4H). HPLC (Condition A): Rt 2.48 min (purity 99.3%). MS (ESI+): 400.50.

Example 7

2-(3-Furan-3-yl-phenyl)-5-(1-piperidin-4-yl-1H-pyrazol-4-yl)-pyrimidine Hydrochloride Step 1: Formation of tert-butyl 4-(4-{2-[3-(3-furyl)phenyl]pyrimidin-5-yl}-1H-pyrazol-1-yl)piperidine-1-carboxylate

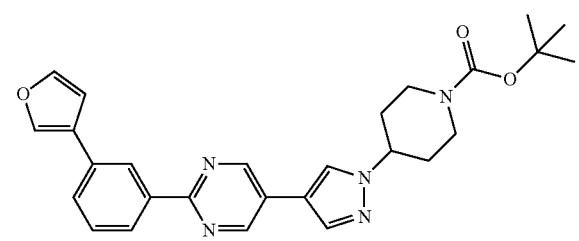 [SMILES: CC(C)(C)OC(=O)N1CCC(n2cc(-c3cnc(-c4cccc(-c5ccoc5)c4)nc3)cn2)CC1]

Tert-butyl 4-4-[2-(3-iodophenyl)pyrimidin-5-yl]-1H-pyrazol-1-ylpiperidine-1-carboxylate (intermediate 5; 100 mg; 0.19 mmol; 1.0 eq.), furan-3-boronic acid (25 mg; 0.23 mmol; 1.2 eq.), Pd(Ph₃)₄ (11 mg; 0.01 mmol; 0.05 eq.) and potassium carbonate (78 mg; 0.56 mmol; 3.0 eq.) were flushed with nitrogen before the addition of dioxane: water (1.5:0.75 mL). The reaction mixture was heated in MW at 120° C. for 30 min. It was then diluted with EtOAc and water. Aqueous phase was extracted with EtOAc (three times) and combined organic phases were dried over magnesium sulfate, filtered and concentrated. Purification by flash chromatography (heptane:EtOAc, gradient from 80:20 to 50:50 afforded the title compound as a white solid (92 mg; 100%). ¹H NMR (300 MHz, DMSO-d6) δ 9.17 (s, 2H), 8.57-8.54 (m, 2H), 8.30-8.27 (m, 2H), 8.15 (s, 1H), 7.75 (t, J=1.7 Hz, 1H), 7.78-7.74 (m, 1H), 7.55 (t, J=7.8 Hz, 1H), 7.03 (dd, J=1.7 Hz, 1.0 Hz, 1H), 4.47-4.40 (m, 1H), 4.09-4.05 (m, 2H), 2.94 (m, 2H), 2.09-2.05 (m, 2H), 1.88-1.74 (m, 2H), 1.43 (s, 9H). HPLC (Condition A): Rt 5.13 min (purity 92.1%). MS (ESI+): 472.3.

Step 2: Formation of 2-(3-Furan-3-yl-phenyl)-5-(1-piperidin-4-yl-1H-pyrazol-4-yl)-pyrimidine hydrochloride

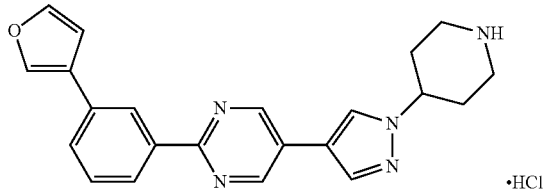 [SMILES: c1cc(-c2ccoc2)cc(-c2ncc(-c3cnn(C4CCNCC4)c3)cn2)c1 ; Cl]

A solution of HCl/dioxane (4N solution in dioxane, 0.76 mL, 3.0 mmol, 15 eq.) was added slowly to a solution of tert-butyl 4-(4-2-[3-(3-furyl)phenyl]pyrimidin-5-yl-1H-pyrazol-1-yl)piperidine-1-carboxylate (95 mg; 0.20 mmol; 1.0 eq.) in DCM (0.95 mL) and MeOH (0.95 mL) at 0° C. under nitrogen atmosphere. The reaction mixture was stirred at RT for 1 h and concentrated under reduced pressure. Purification by autopreparative LC/MS afforded the title compound a as a white powder (40 mg; 49%). ¹H NMR (300 MHz, DMSO-d6) δ 9.21 (s, 2H), 8.78 (bs, 2H), 8.57 (t, J=1.6 Hz, 1H), 8.52 (s, 1H), 8.31-8.27 (m, 2H), 8.21 (s, 1H), 7.80 (t, J=1.6 Hz, 1H), 7.79-7.75 (m, 1H), 7.56 (t, J=7.8 Hz, 1H), 7.03-7.02 (m, 1H), 4.58-4.52 (m, 1H), 3.46-3.38 (m, 2H), 3.16-3.06 (m, 2H), 2.28-2.11 (m, 4H). HPLC (Condition A): Rt 3.11 min (purity 99.8%). MS (ESI+): 372.4.

Example 8

4-{2-[3-(1-Methyl-1H-pyrazol-4-yl)-phenyl]-pyrimidin-5-yl}-pyrazol-1-yl)-acetic acid

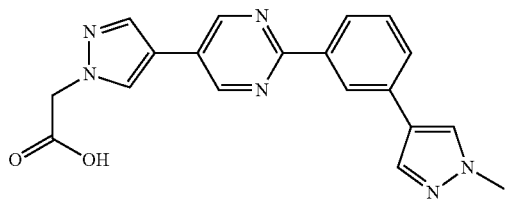 [SMILES: Cn1cc(-c2cccc(-c3ncc(-c4cnn(CC(=O)O)c4)cn3)c2)cn1]

The title compound was obtained following procedure described for example 7, step 1, but starting from 5-bromo-2-[3-(1-methyl-1H-pyrazol-4-yl)phenyl]pyrimidine (intermediate 2; 80 mg; 0.25 mmol; 1.0 eq.) and 1-(Ethoxycarbonylmethyl)-1H-pyrazole-4-boronic acid, pinacol ester (71 mg; 0.25 mmol; 1.0 eq.) as a white solid (21 mg, 23%). ¹H NMR (300 MHz, DMSO-d6) δ 13.22 (s, 1H), 9.18 (s, 2H), 8.54 (s, 1H), 8.44 (s, 1H), 8.27 (s, 1H), 8.23 (d, J=7.8 Hz, 1H), 8.17 (s, 1H), 7.93 (s, 1H), 7.72 (d, J=7.8 Hz, 1H), 7.52 (t, J=7.8 Hz, 1H), 5.05 (s, 2H), 3.90 (s, 3H). HPLC (Condition A): Rt 2.61 min (purity 97.5%). MS (ESI+): 361.3

Example 9

2-(4-{2-[3-(1-Methyl-1H-pyrazol-4-yl)-phenyl]-pyrimidin-5-yl}-pyrazol-1-yl)-1-pyrrolidin-1-yl-ethanone

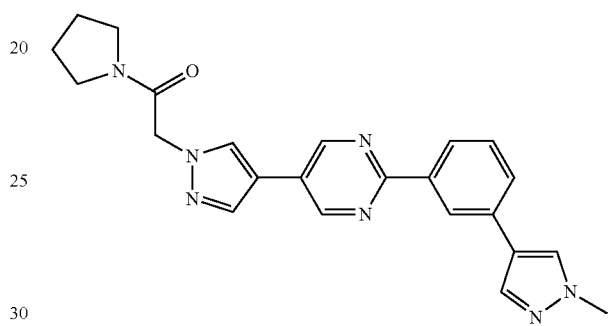

The title compound was obtained following procedure described for example 7, step 1, but starting from 5-bromo-2-[3-(1-methyl-1H-pyrazol-4-yl)phenyl]pyrimidine (intermediate 2, 80 mg; 0.25 mmol; 1.0 eq.) and 1-Pyrrolidin-1-yl-2-[4-(4,4,5,5-tetramethyl-[1,3,2]dioxaborolan-2-yl)-pyrazol-1-yl]-ethanone (intermediate 7, 77 mg; 0.25 mmol; 1.00 eq.) as a yellow powder (57 mg; 54%). ¹H NMR (300 MHz, DMSO-d6) δ 9.18 (s, 2H), 8.54 (t, J=1.6 Hz, 1H), 8.38 (s, 1H), 8.27 (s, 1H), 8.25-8.17 (m, 1H), 8.15 (s, 1H), 7.93 (s, 1H), 7.77-7.67 (m, 1H), 7.52 (t, J=7.7 Hz, 1H), 5.13 (s, 2H), 3.90 (s, 3H), 3.53 (t, J=6.7 Hz, 2H), 3.34 (t, 2H), 2.02-1.69 (m, 4H). HPLC (Condition A): Rt 2.83 min (purity 96.3%). MS (ESI+): 414.3

Example 10

4-[2-(4-{2-[3-(1-Methyl-1H-pyrazol-4-yl)-phenyl]-pyrimidin-5-yl}-pyrazol-1-yl)-ethyl]-morpholine

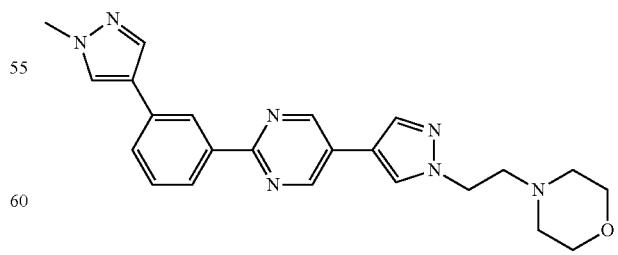

The title compound was obtained following procedure described for example 7, step 1, but starting from 5-bromo-2-[3-(1-methyl-1H-pyrazol-4-yl)phenyl]pyrimidine (intermediate 2, 80 mg; 0.25 mmol; 1.0 eq.) and 1-(2-Morpholinoethyl)-1H-pyrazole-4-boronic acid pinacol ester (78 mg; 0.25 mmol; 1.0 eq.) as a white powder (71 mg; 68%). ¹H NMR (300 MHz, DMSO-d6) δ 9.16 (s, 2H), 8.53 (t, J=1.6 Hz, 1H), 8.46 (s, 1H), 8.26 (s, 1H), 8.25-8.19 (m, 1H), 8.13 (s, 1H), 7.92 (d, J=0.6 Hz, 1H), 7.76-7.66 (m, 1H), 7.52 (t, J=7.8 Hz, 1H), 4.30 (t, J=6.5 Hz, 2H), 3.90 (s, 3H), 3.63-3.51 (m, 4H), 2.76 (t, J=6.6 Hz, 2H), 2.48-2.34 (m, 4H).). HPLC (Condition A): Rt 2.31 min (purity 98.3%). MS (ESI+): 416.3

Example 11

Dimethyl-[2-(4-{2-[3-(1-methyl-1H-pyrazol-4-yl)-phenyl]-pyrimidin-5-yl}-pyrazol-1-yl)-ethyl]-amine

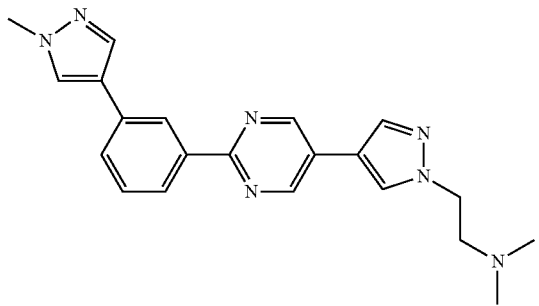

The title compound was obtained following procedure described for example 7, step 1, but starting from 5-bromo-2-[3-(1-methyl-1H-pyrazol-4-yl)phenyl]pyrimidine (intermediate 2, 80 mg; 0.25 mmol; 1.0 eq.) and dimethyl-2-[4-(4,4,5,5-tetramethyl-[1,3,2]dioxaborolan-2-yl)-pyrazol-1-yl]-ethyl-amine (67 mg; 0.25 mmol; 1.0 eq.) as a white solid (69 mg, 73%). ¹H NMR (300 MHz, DMSO-d6) δ 9.16 (s, 2H), 8.53 (t, J=1.6 Hz, 1H), 8.46 (s, 1H), 8.27 (s, 1H), 8.25-8.17 (m, 1H), 8.13 (s, 1H), 7.92 (d, J=0.6 Hz, 1H), 7.77-7.66 (m, 1H), 7.52 (t, J=7.8 Hz, 1H), 4.27 (t, J=6.5 Hz, 2H), 3.90 (s, 3H), 2.72 (t, J=6.5 Hz, 2H), 2.19 (d, J=10.3 Hz, 6H). HPLC (Condition A): Rt 2.23 min (purity 97.3%). MS (ESI+): 374.3

Example 12

2-[3-(1-Methyl-1H-pyrazol-4-yl)-phenyl]-5-[1-(tetrahydro-furan-3-yl)-1H-pyrazol-4-yl]-pyrimidine

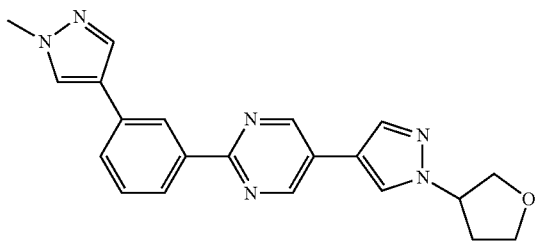 [SMILES: Cn1cc(-c2cccc(-c3ncc(-c4cnn(C5CCOC5)c4)cn3)c2)cn1]

The title compound was obtained following procedure described for example 7, step 1, but starting from 5-bromo-2-[3-(1-methyl-1H-pyrazol-4-yl)phenyl]pyrimidine (intermediate 2, 150 mg; 0.48 mmol; 1.0 eq.) and 1-(Tetrahydro-furan-3-yl)-4-(4,4,5,5-tetramethyl-[1,3,2]dioxaborolan-2-yl)-1H-pyrazole (CombiPhos Catalysts, Inc.; 126 mg; 0.48 mmol; 1.0 eq.) as a white solid (113 mg; 64%). ¹H NMR (300 MHz, DMSO-d6) δ 9.18 (s, 2H), 8.53 (s, 2H), 8.34-8.14 (m, 3H), 7.94 (s, 1H), 7.71 (d, J=7.8 Hz, 1H), 7.52 (t, J=7.7 Hz, 1H), 5.15-5.04 (m, 1H), 4.15-3.75 (m, 7H), 2.48-2.24 (m, 2H). HPLC (Condition A): Rt 3.16 min (purity 95.0%). MS (ESI+): 373.3

Example 13

2-(3-Isoxazol-4-yl-phenyl)-5-(1-piperidin-4-yl-1H-pyrazol-4-yl)-pyrimidine hydrochloride Step 1: Formation of tert-butyl 4-{4-[2-(3-isoxazol-4-ylphenyl)pyrimidin-5-yl]-1H-pyrazol-1-yl}piperidine-1-carboxylate

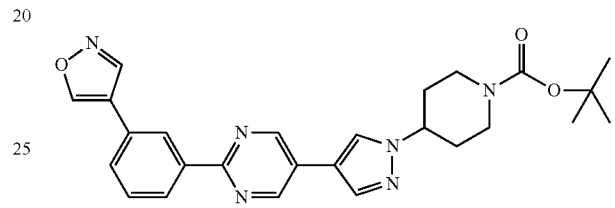

Tert-butyl 4-4-[2-(3-iodophenyl)pyrimidin-5-yl]-1H-pyrazol-1-ylpiperidine-1-carboxylate (intermediate 5, 150 mg; 0.24 mmol; 1.0 eq.), 4-Isoxazoleboronic acid pinacol ester (47 mg; 0.24 mmol; 1.0 eq.), bis(triphenylphosphine)palladium(II)chloride (17 mg; 0.02 mmol; 0.10 eq.) and cesium fluoride (109 mg; 0.72 mmol; 3.0 eq.) were flushed with nitrogen before the addition of dioxane: water (2.25:1.1 mL). The reaction mixture was heated in MW at 120° C. for 30 min. It was then diluted with EtOAc and water. Aqueous phase was extracted with EtOAc and combined organic phases were dried over magnesium sulfate, filtered and concentrated. Purification by flash chromatography (cyclohexane:EtOAc, gradient from 80:20 to 30:70) afforded the title compound as a white beige solid (70 mg; 62%). ¹H NMR (300 MHz, DMSO-d6) δ 9.60 (s, 1H), 9.27 (s, 1H), 9.17 (s, 2H), 8.64 (t, J=1.5 Hz, 1H), 8.56 (s, 1H), 8.35 (dt, J=8.0 Hz, 1.5 Hz, 1H), 8.16 (s, 1H), 7.87-7.83 (m, 1H), 7.61 (t, J=8.0 Hz, 1H), 4.47-4.35 (m, 1H), 4.09-4.04 (m, 2H), 2.95 (m, 2H), 2.09-2.06 (m, 2H), 1.87-1.72 (m, 2H), 1.43 (s, 9H). HPLC (Condition A): Rt 4.70 min (purity 97.4%). MS (ESI+): 473.5.

Step 2: Formation of 2-(3-Isoxazol-4-yl-phenyl)-5-(1-piperidin-4-yl-1H-pyrazol-4-yl)-pyrimidine hydrochloride

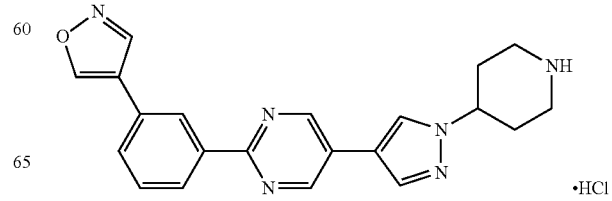

A solution of HCl/dioxane (4N solution in dioxane, 0.55 mL, 2.2 mmol, 15 eq.) was added slowly to a solution tert-butyl 4-4-[2-(3-isoxazol-4-ylphenyl)pyrimidin-5-yl]-1H-pyrazol-1-ylpiperidine-1-carboxylate (70 mg; 0.15 mmol; 1.0 eq.) in DCM (0.7 mL) and MeOH (0.7 mL). The reaction mixture was stirred at RT for 3 h and concentrated under reduced pressure. The solid obtained was suspended in DCM (3 mL), sonicated, filtered off and dried overnight under reduced pressure to give the title compound as a yellow solid (60 mg; 99%). $^1$H NMR (300 MHz, DMSO-d6): 9.61 (s, 1H), 9.27 (s, 1H), 9.25-9.21 (m, 3H), 8.98 (brs, 1H), 8.64 (t, J=1.5 Hz, 1H), 8.55 (s, 1H), 8.36 (dt, J=8.0 Hz, 1.5 Hz, 1H), 8.22 (s, 1H), 7.86 (dt, J=8.0 Hz, 1.5 Hz, 1H), 7.62 (t, J=8.0 Hz, 1H), 3.43-3.30 (m, 3H), 3.17-3.06 (m, 2H), 2.29-2.13 (m, 4H). HPLC (Condition A): Rt 2.62 min (purity 98.1%). MS (ESI+): 373.3.

Example 14

2-[3-(1,3-Dimethyl-1H-pyrazol-4-yl)-phenyl]-5-(1-piperidin-4-yl-1H-pyrazol-4-yl)-pyrimidine hydrochloride Step 1: Formation of tert-butyl 4-(4-{2-[3-(1,3-dimethyl-1H-pyrazol-4-yl)phenyl]pyrimidin-5-yl}-1H-pyrazol-1-yl)piperidine-1-carboxylate

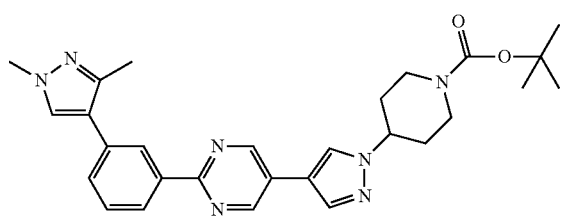 [SMILES: Cc1nn(C)cc1-c1cccc(-c2ncc(-c3cnn(C4CCN(C(=O)OC(C)(C)C)CC4)c3)cn2)c1]

The title compound was obtained following procedure described for example 7, step 1, but starting from tert-butyl 4-4-[2-(3-iodophenyl)pyrimidin-5-yl]-1H-pyrazol-1-ylpiperidine-1-carboxylate (intermediate 5, 150 mg; 0.28 mmol; 1.0 eq.) and 1,3-dimethyl-1H-pyrazole-4-boronic acid, pinacolester (63 mg; 0.28 mmol; 1.0 eq.) as a brown gum (120 mg, 85%). HPLC (Condition A): Rt 4.37 min (purity 89.4%). MS (ESI+): 500.5.

Step 2: Formation of 2-[3-(1,3-Dimethyl-1H-pyrazol-4-yl)-phenyl]-5-(1-piperidin-4-yl-1H-pyrazol-4-yl)-pyrimidine hydrochloride

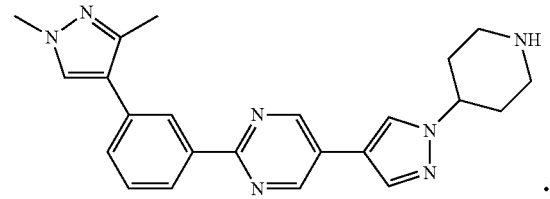

The title compound was obtained following procedure described for example 13, step 2, but starting from tert-butyl 4-(4-2-[3-(1,3-dimethyl-1H-pyrazol-4-yl)phenyl]pyrimidin-5-yl-1H-pyrazol-1-yl)piperidine-1-carboxylate (120 mg; 0.24 mmol; 1.0 eq.) as a brown solid (60 mg; 57%). $^1$H NMR (300 MHz, DMSO-d6) δ 9.20 (m, 3H), 8.95 (brs, 1H), 8.52 (s, 1H), 8.47-8.46 (m, 1H), 8.25 (dt, J=7.0 Hz, 1.8 Hz, 1H), 8.20 (s, 1H), 8.03 (s, 1H), 7.60-7.51 (m, 2H), 4.60-4.52 (m, 1H), 3.82 (s, 3H), 3.42-3.38 (m, 2H), 3.15-3.05 (m, 2H), 2.36 (s, 3H), 2.28-2.11 (m, 4H). HPLC (Condition A): Rt 2.49 min (purity 99.9%). MS (ESI+): 400.5.

Example 15

2-[3-(1,5-Dimethyl-1H-pyrazol-4-yl)-phenyl]-5-(1-piperidin-4-yl-1H-pyrazol-4-yl)-pyrimidine hydrochloride Step 1: Formation of tert-butyl 4-(4-{2-[3-(1,5-dimethyl-1H-pyrazol-4-yl)phenyl]pyrimidin-5-yl}-1H-pyrazol-1-yl)piperidine-1-carboxylate

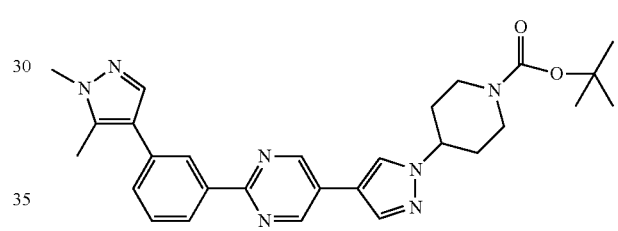

The title compound was obtained following procedure described for example 7, step 1, but starting from tert-butyl 4-4-[2-(3-iodophenyl)pyrimidin-5-yl]-1H-pyrazol-1-ylpiperidine-1-carboxylate (intermediate 5, 150 mg; 0.28 mmol; 1.0 eq.) and 1,5-dimethyl-1H-pyrazole-4-boronic acid, pinacolester (63 mg; 0.28 mmol; 1.0 eq.) as a beige solid (96 mg; 68%). $^1$H NMR (300 MHz, DMSO-d6) δ 9.17 (s, 2H), 8.54 (s, 1H), 8.41 (s, 1H), 8.28-8.25 (m, 1H), 8.14 (s, 1H), 7.64 (s, 1H), 7.59-7.54 (m, 2H), 4.47-4.37 (m, 1H), 4.08-4.04 (m, 2H), 3.81 (s, 3H), 2.96 (m, 2H), 2.43 (s, 3H), 2.09-2.05 (m, 2H), 1.88-1.74 (m, 2H), 1.43 (s, 9H). HPLC (Condition A): Rt 4.25 min (purity 98.5%). MS (ESI+): 500.6.

Step 2: formation of 2-[3-(1,5-Dimethyl-1H-pyrazol-4-yl)-phenyl]-5-(1-piperidin-4-yl-1H-pyrazol-4-yl)-pyrimidine hydrochloride

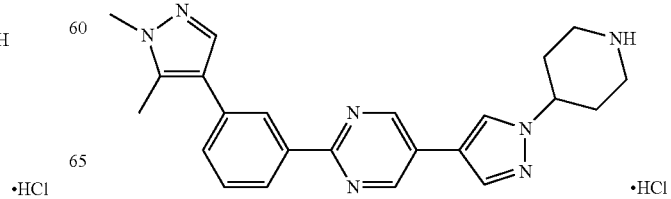

The title compound was obtained following procedure described for example 13, step 2, but starting from tert-butyl 4-(4-2-[3-(1,5-dimethyl-1H-pyrazol-4-yl)phenyl]pyrimidin-5-yl-1H-pyrazol-1-yl)piperidine-1-carboxylate (intermediate 5, 95 mg; 0.19 mmol; 1.0 eq.) as a yellow solid (80 mg; 96%). ¹H NMR (300 MHz, DMSO-d6) δ 9.27-9.21 (m, 3H), 9.05-8.86 (m, 1H), 8.52 (s, 1H), 8.43-8.41 (m, 1H), 8.29-8.24 (m, 1H), 8.20 (s, 1H), 7.67 (s, 1H), 7.59-7.53 (m, 2H), 4.62-4.49 (m, 1H), 3.82 (s, 3H), 3.42-3.38 (m, 2H), 3.16-3.05 (m, 2H), 2.43 (s, 3H), 2.28-2.12 (m, 4H). HPLC (Condition A): Rt 2.54 min (purity 99.7%). MS (ESI+): 400.5.

Example 16

2-{3-[1-(2-Fluoro-1-fluoromethyl-ethyl)-1H-pyrazol-4-yl]-phenyl}-5-(1-piperidin-4-yl-1H-pyrazol-4-yl)-pyrimidine hydrochloride Step 1: Formation of tert-butyl 4-{4-[2-(3-{1-[2-fluoro-1-(fluoromethyl)ethyl]-1H-pyrazol-4-yl}phenyl)pyrimidin-5-yl]-1H-pyrazol-1-yl}piperidine-1-carboxylate

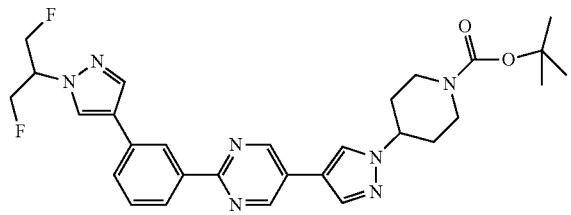 [SMILES: CC(C)(C)OC(=O)N1CCC(n2cc(-c3cnc(-c4cccc(-c5cnn(C(CF)CF)c5)c4)nc3)cn2)CC1]

The title compound was obtained following procedure described for example 7, step 1, but starting from tert-butyl 4-4-[2-(3-iodophenyl)pyrimidin-5-yl]-1H-pyrazol-1-ylpiperidine-1-carboxylate (Intermediate 5, 150 mg; 0.28 mmol; 1.0 eq.) and 1-[2-fluoro-1-(fluoromethyl)ethyl]-4-(4,4,5,5-tetramethyl-1,3,2-dioxaborolan-2-yl)pyrazole (intermediate 8, 77 mg; 0.28 mmol; 1.0 eq.) as a white solid (120 mg; 77%). ¹H NMR (300 MHz, DMSO-d6): 9.16 (s, 2H), 8.57 (t, J=1.5 Hz, 1H), 8.55 (s, 1H), 8.48 (s, 1H), 8.24 (dt, J=8.0 Hz, 1.5 Hz, 1H), 8.15 (s, 1H), 8.07 (s, 1H), 7.76 (dt, J=8.0 Hz, 1.5 Hz, 1H), 7.52-7.55 (m, 1H), 5.08-4.92 (m, 3H), 4.88-4.77 (m, 2H), 4.47-4.40 (m, 1H), 4.09-4.04 (m, 2H), 2.95 (m, 2H), 2.09-2.05 (m, 2H), 1.88-1.75 (m, 2H), 1.43 (s, 9H). HPLC (Condition A): Rt 4.77 min (purity 84.5%). MS (ESI+): 550.7.

Step 2: Formation of 2-{3-[1-(2-Fluoro-1-fluoromethyl-ethyl)-1H-pyrazol-4-yl]-phenyl}-5-(1-piperidin-4-yl-1H-pyrazol-4-yl)-pyrimidine hydrochloride

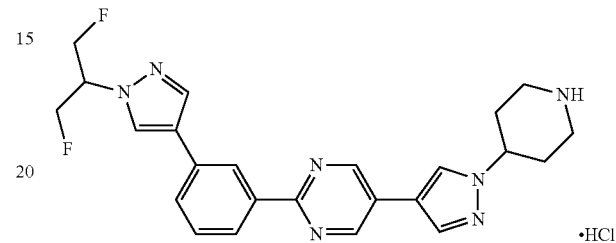

The title compound was obtained following procedure described for example 7, step 2, but starting from tert-butyl 4-4-[2-(3-1-[2-fluoro-1-(fluoromethyl)ethyl]-1H-pyrazol-4-ylphenyl)pyrimidin-5-yl]-1H-pyrazol-1-ylpiperidine-1-carboxylate (120 mg; 0.22 mmol; 1.0 eq.) as a white amorphous solid (30 mg; 28%). ¹H NMR (300 MHz, DMSO-d6) δ 9.20 (s, 2H), 8.72 (bs, 2H), 8.57 (t, J=1.5 Hz, 1H), 8.52 (s, 1H), 8.47 (s, 1H), 8.25 (dt, J=8.0 Hz, 1.5 Hz, 1H), 8.21 (s, 1H), 8.07 (s, 1H), 7.76 (dt, J=8.0 Hz, 1.5 Hz, 1H), 7.54 (t, J=8.0 Hz, 1H), 5.11-4.92 (m, 3H), 4.87-4.77 (m, 2H), 4.60-4.52 (m, 1H), 3.45-3.40 (m, 2H), 3.16-3.07 (m, 2H), 2.29-2.11 (m, 4H). HPLC (Condition A): Rt 2.83 min (purity 98.8%). MS (ESI+): 450.4.

Example 17

2-(4-{3-[5-(1-Piperidin-4-yl-1H-pyrazol-4-yl)-pyrimidin-2-yl]-phenyl}-pyrazol-1-yl)-1-pyrrolidin-1-yl-ethanone hydrochloride Step 1: Formation of tert-butyl 4-[4-(2-{3-[1-(2-oxo-2-pyrrolidin-1-ylethyl)-1H-pyrazol-4-yl]phenyl}pyrimidin-5-yl)-1H-pyrazol-1-yl]piperidine-1-carboxylate

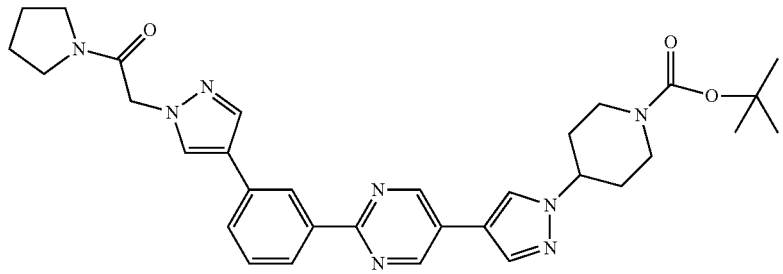 [SMILES: CC(C)(C)OC(=O)N1CCC(n2cc(-c3cnc(-c4cccc(-c5cnn(CC(=O)N6CCCC6)c5)c4)nc3)cn2)CC1]

The title compound was obtained following procedure described for example 7, step 1, but starting from tert-butyl 4-4-[2-(3-iodophenyl)pyrimidin-5-yl]-1H-pyrazol-1-ylpiperidine-1-carboxylate (intermediate 5, 150 mg; 0.28 mmol; 1.0 eq.) and 1-Pyrrolidin-1-yl-2-[4-(4,4,5,5-tetramethyl-[1,3,2]dioxaborolan-2-yl)-pyrazol-1-yl]-ethanone (Intermediate 7; 103 mg; 0.34 mmol; 1.2 eq.) as a grey solid (148 mg; 90%). ¹H NMR (300 MHz, DMSO-d6) δ 9.18 (s, 2H), 8.55-8.54 (m, 2H), 8.24-8.21 (m, 2H), 8.15 (s, 1H), 7.94 (s, 1H), 7.73 (dt, J=8.0 Hz, 1.5 Hz, 1H), 7.52 (t, J=8.0 Hz, 1H), 5.06 (s, 2H), 4.48-4.39 (m, 1H), 4.09-4.01 (m, 2H), 3.52 (t, J=6.6 Hz, 2H), 3.35-3.31 (m, 2H), 2.94 (m, 2H), 2.09-2.06 (m, 2H), 1.98-1.76 (m, 6H), 1.43 (s, 9H). HPLC (Condition A): Rt 4.20 min (purity 98.6%). MS (ESI+): 583.7.

Step 2) Formation of 2-(4-{3-[5-(1-Piperidin-4-yl-1H-pyrazol-4-yl)-pyrimidin-2-yl]-phenyl}-pyrazol-1-yl)-1-pyrrolidin-1-yl-ethanone hydrochloride

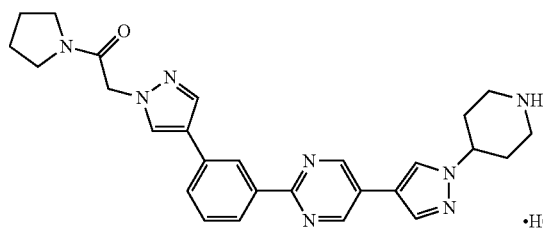

·HCl

The title compound was obtained following procedure described for example 13, step 2, but starting from tert-butyl 4-[4-(2-3-[1-(2-oxo-2-pyrrolidin-1-ylethyl)-1H-pyrazol-4-yl]phenylpyrimidin-5-yl)-1H-pyrazol-1-yl]piperidine-1-carboxylate (145 mg; 0.25 mmol; 1.0 eq.) as a yellow solid (85.00 mg; 65.81%). ¹H NMR (300 MHz, DMSO-d6) δ 9.20 (s, 2H), 9.12 (m, 1H), 8.86 (m, 1H), 8.55 (t, J=1.7 Hz, 1H), 8.53 (s, 1H), 8.25-8.21 (m, 3H), 7.95 (d, J=0.8 Hz, 1H), 7.75-7.71 (m, 1H), 7.53 (t, J=8.0 Hz, 1H), 5.06 (s, 2H), 4.61-4.51 (m, 1H), 3.52 (t, J=6.8 Hz, 2H), 3.43-3.39 (m, 2H), 3.33 (t, J=6.8 Hz, 2H), 3.16-3.05 (m, 2H), 2.30-2.12 (m, 4H), 1.93 (quint., J=6.8 Hz, 2H), 1.80 (quint., J=6.8 Hz, 2H).). HPLC (Condition A): Rt 2.41 min (purity 99.4%). MS (ESI+): 483.6.

Example 18

5-(1-Piperidin-4-yl-1H-pyrazol-4-yl)-2-[3-(1H-pyrazol-4-yl)-phenyl]-pyrimidine hydrochloride Step 1: Formation of tert-butyl 4-(4-{2-[3-(1H-pyrazol-4-yl)phenyl]pyrimidin-5-yl}-1H-pyrazol-1-yl)piperidine-1-carboxylate

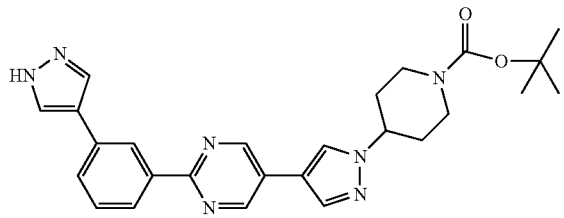 [SMILES: CC(C)(C)OC(=O)N1CCC(n2cc(-c3cnc(-c4cccc(-c5cn[nH]c5)c4)nc3)cn2)CC1]

The title compound was obtained following procedure described for example 7, step 1, but starting from tert-butyl 4-4-[2-(3-iodophenyl)pyrimidin-5-yl]-1H-pyrazol-1-ylpiperidine-1-carboxylate (intermediate 5; 200 mg; 0.38 mmol; 1.0 eq.) and 1-Boc-4-(4,4,5,5-tetramethyl-1,3,2-dioxaborolan-2-yl)pyrazole (133 mg; 0.45 mmol; 1.2 eq.) as a beige solid (177 mg; 99%). ¹H NMR (300 MHz, DMSO) δ 13.03 (bs, 1H), 9.17 (s, 2H), 8.59-8.52 (m, 2H), 8.29 (s, 1H), 8.22 (dt, J=8.0, 1.5 Hz, 1H), 8.15 (s, 1H), 7.96 (s, 1H), 7.75 (dt, J=8.0, 1.5 Hz, 1H), 7.51 (t, J=8.0 Hz, 1H), 4.51-4.36 (m, 1H), 4.15-4.01 (m, 2H), 3.07-2.80 (m, 2H), 2.15-2.03 (m, 2H), 1.90-1.72 (m, 2H), 1.43 (s, 9H). HPLC (Condition A): Rt 4.06 min (purity 88.0%). MS (ESI+): 472.4.

Step 2: Formation of 5-(1-Piperidin-4-yl-1H-pyrazol-4-yl)-2-[3-(1H-pyrazol-4-yl)-phenyl]-pyrimidine hydrochloride

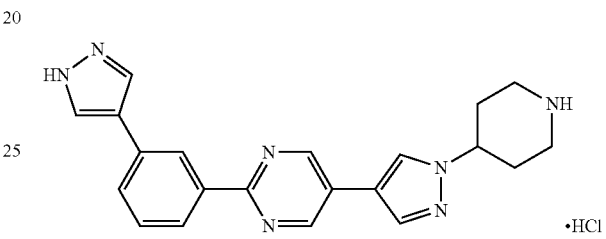

·HCl

The title compound was obtained following procedure described for example 7, step 2, but starting from tert-butyl 4-[4-(2-3-[1-(tert-butoxycarbonyl)-1H-pyrazol-4-yl]phenylpyrimidin-5-yl)-1H-pyrazol-1-yl]piperidine-1-carboxylate (215 mg; 0.38 mmol; 1.0 eq.) as a white amorphous solid (50 mg; 33%). ¹H NMR (300 MHz, DMSO-d6) δ 13.05 (brs, 1H), 9.20 (s, 2H), 8.90 (brs, 2H), 8.56 (t, J=1.7 Hz, 1H), 8.52 (s, 1H), 8.30 (brs, 1H), 8.24-8.21 (m, 2H), 7.98 (brs, 1H), 7.76 (dt, J=7.8 Hz, 1.7 Hz, 1H), 7.52 (t, J=7.8 Hz, 1H), 4.62-4.52 (m, 1H), 3.47-3.39 (m, 2H), 3.15-3.06 (m, 2H), 2.29-2.08 (m, 4H). HPLC (Condition A): Rt 2.08 min (purity 100.0%). MS (ESI+): 372.4.

Example 19

5-(1-Piperidin-4-yl-1H-pyrazol-4-yl)-2-[3-(1-propyl-1H-pyrazol-4-yl)-phenyl]-pyrimidine hydrochloride Step 1: Formation of tert-butyl 4-(4-{2-[3-(1-propyl-1H-pyrazol-4-yl)phenyl]pyrimidin-5-yl}-1H-pyrazol-1-yl)piperidine-1-carboxylate

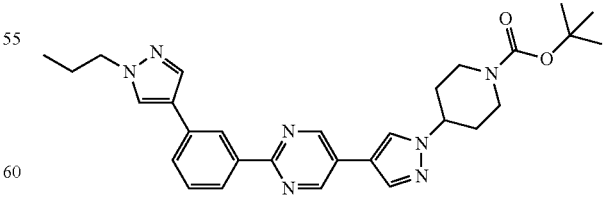

The title compound was obtained following procedure described for example 7, step 1, but starting from tert-butyl 4-4-[2-(3-iodophenyl)pyrimidin-5-yl]-1H-pyrazol-1-ylpiperidine-1-carboxylate (intermediate 5, 200 mg; 0.38 mmol; 1.0 eq.) and 1-propyl-1H-pyrazole-4-boronic acid, pinacol ester (89 mg; 0.38 mmol; 1.0 eq.) as a beige solid (160 mg, 83%). 1H NMR (300 MHz, DMSO-d6) δ 9.16 (s, 2H), 8.55 (s, 1H), 8.54 (t, J=1.5 Hz, 1H), 8.30 (s, 1H), 8.21 (dt, J=8.0 Hz, 1.5 Hz, 1H), 8.15 (s, 1H), 7.93 (s, 1H), 7.72 (dt, J=8.0 Hz, 1.5 Hz, 1H), 7.51 (t, J=8.0 Hz, 1H), 4.47-4.38 (m, 1H), 4.13-4.00 (m, 4H), 2.94 (m, 2H), 2.09-2.05 (m, 2H), 1.90-1.75 (m, 4H), 1.43 (s, 9H), 0.86 (t, J=7.5 Hz, 3H). HPLC (Condition A): Rt 4.85 min (purity 91.2%). MS (ESI+): 514.6.

Step 2: Formation of 5-(1-Piperidin-4-yl-1H-pyrazol-4-yl)-2-[3-(1-propyl-1H-pyrazol-4-yl)-phenyl]-pyrimidine hydrochloride

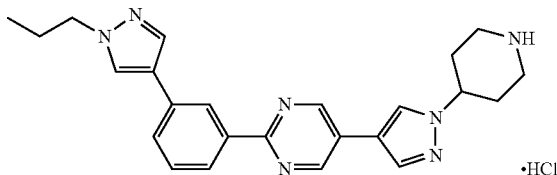 [SMILES: CCCn1cc(-c2cccc(-c3ncc(-c4cnn(C5CCNCC5)c4)cn3)c2)cn1 ; Cl]

The title compound was obtained following procedure described for example 13, step 2, but starting from tert-butyl 4-(4-2-[3-(1-propyl-1H-pyrazol-4-yl)phenyl]pyrimidin-5-yl-1H-pyrazol-1-yl)piperidine-1-carboxylate (160 mg; 0.31 mmol; 1.00 eq.) as a Pale yellow solid (126 mg; 90%). 1H NMR (300 MHZ, DMSO-d6) δ 9.28-9.20 (m, 3H), 9.01-8.98 (m, 1H), 8.55-8.53 (m, 2H), 8.31 (s, 1H), 8.23-8.21 (m, 2H), 7.94 (s, 1H), 7.73 (dt, J=7.8 Hz, 1.6 Hz, 1H), 7.51 (t, J=7.8 Hz, 1H), 4.57 (quint., J=5.0 Hz, 1H), 4.11 (t, J=7.0 Hz, 2H), 3.42-3.38 (m, 2H), 3.16-3.04 (m, 2H), 2.29-2.13 (m, 4H), 1.84 (sext., J=7.0 Hz, 2H), 0.86 (t, J=7.0 Hz, 3H). HPLC (Condition A): Rt 2.82 min (purity 100.0%). MS (ESI+): 414.5.

Example 20

2-[3-(1-Isopropyl-1H-pyrazol-4-yl)-phenyl]-5-(1-piperidin-4-yl-1H-pyrazol-4-yl)-pyrimidine hydrochloride Step 1: Formation of tert-butyl 4-(4-{2-[3-(1-isopropyl-1H-pyrazol-4-yl)phenyl]pyrimidin-5-yl}-1H-pyrazol-1-yl)piperidine-1-carboxylate

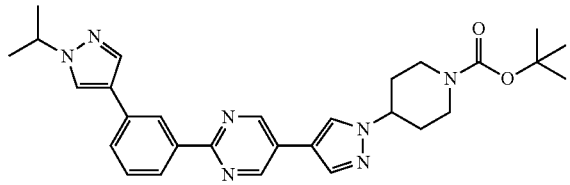 [SMILES: CC(C)n1cc(-c2cccc(-c3ncc(-c4cnn(C5CCN(C(=O)OC(C)(C)C)CC5)c4)cn3)c2)cn1]

The title compound was obtained following procedure described for example 7, step 1, but starting from tert-butyl 4-4-[2-(3-iodophenyl)pyrimidin-5-yl]-1H-pyrazol-1-ylpiperidine-1-carboxylate (intermediate 5; 200 mg; 0.38 mmol; 1.0 eq.) and 1-Isopropyl-4-(4,4,5,5-tetramethyl-[1,3,2]dioxaborolan-2-yl)-1H-pyrazole (98 mg; 0.41 mmol; 1.1 eq.) as a yellow solid (153 mg; 79%). 1H NMR (300 MHz, DMSO-d6) δ 9.18 (s, 2H), 8.55-8.53 (m, 2H), 8.34 (s, 1H), 8.21 (dt, J=8.0 Hz, 1.5 Hz, 1H), 8.15 (s, 1H), 7.92 (s, 1H), 7.73 (dt, J=8.0 Hz, 1.5 Hz, 1H), 7.51 (t, J=8.0 Hz, 1H), 4.54 (sept., J=6.7 Hz, 1H), 4.47-4.38 (m, 1H), 4.09-4.00 (m, 2H), 2.94 (m, 2H), 2.09-2.06 (m, 2H), 1.88-1.75 (m, 2H), 1.47 (d, J=6.7 Hz, 6H), 1.43 (s, 9H) HPLC (Condition A): Rt 4.83 min (purity 98.1%). MS (ESI+): 514.6.

Step 2: Formation of 2-[3-(1-Isopropyl-1H-pyrazol-4-yl)-phenyl]-5-(1-piperidin-4-yl-1H-pyrazol-4-yl)-pyrimidine hydrochloride

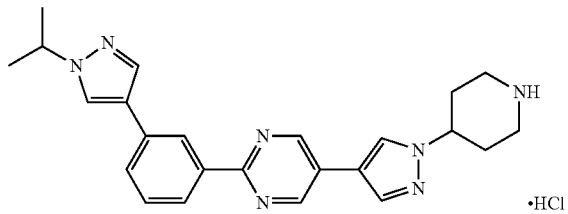 [SMILES: CC(C)n1cc(-c2cccc(-c3ncc(-c4cnn(C5CCNCC5)c4)cn3)c2)cn1 ; Cl]

The title compound was obtained following procedure described for example 13, step 2, but starting from tert-butyl 4-(4-2-[3-(1-isopropyl-1H-pyrazol-4-yl)phenyl]pyrimidin-5-yl-1H-pyrazol-1-yl)piperidine-1-carboxylate (150 mg; 0.29 mmol; 1.0 eq.) as a yellow solid (95 mg; 72%). 1H NMR (300 MHz, DMSO-d6) δ 9.26-9.20 (m, 3H), 8.99-8.95 (m, 1H), 8.55 (t, J=1.6 Hz, 1H), 8.53 (s, 1H), 8.34 (s, 1H), 8.23-8.21 (m, 2H), 7.93 (s, 1H), 7.73 (dt, J=7.8 Hz, 1.6 Hz, 1H), 7.51 (t, J=7.8 Hz, 1H), 4.60-4.50 (m, 2H), 3.43-3.38 (m, 2H), 3.16-3.06 (m, 2H), 2.28-2.22 (m, 4H), 1.47 (d, J=6.6 Hz, 6H). HPLC (Condition A): Rt 2.81 min (purity 99.0%). MS (ESI+): 414.4.

Example 21

2-[3-(1-Benzyl-1H-pyrazol-4-yl)-phenyl]-5-(1-piperidin-4-yl-1H-pyrazol-4-yl)-pyrimidine hydrochloride Step 1: Formation of tert-butyl 4-(4-{2-[3-(1-benzyl-1H-pyrazol-4-yl)phenyl]pyrimidin-5-yl}-1H-pyrazol-1-yl)piperidine-1-carboxylate

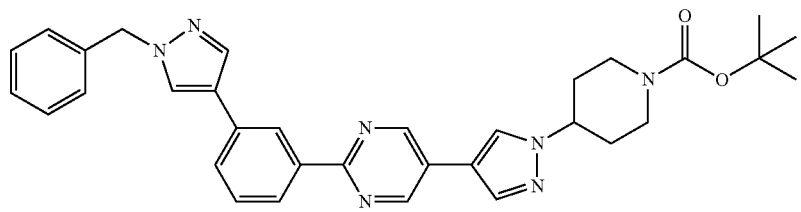 [SMILES: CC(C)(C)OC(=O)N1CCC(n2cc(-c3cnc(-c4cccc(-c5cnn(Cc6ccccc6)c5)c4)nc3)cn2)CC1]

The title compound was obtained following procedure described for example 7, step 1, but starting from tert-butyl 4-4-[2-(3-iodophenyl)pyrimidin-5-yl]-1H-pyrazol-1-ylpiperidine-1-carboxylate (intermediate 5; 200 mg; 0.38 mmol; 1.0 eq.), 1-benzyl-4-(4,4,5,5-tetramethyl-1,3,2-dioxaborolan-2-yl)-1H-pyrazole (107 mg; 0.38 mmol; 1.0 eq.) as a beige solid (165 mg; 78%). 1H NMR (300 MHz, DMSO-d6): 9.18 (s, 2H), 8.55-8.53 (m, 2H), 8.44 (s, 1H), 8.21 (dt, J=7.8 Hz, 1.5 Hz, 1H), 8.15 (s, 1H), 7.94 (d, J=0.8 Hz, 1H), 7.73 (dt, J=8.0 Hz, 1.5 Hz, 1H), 7.73 (m, 1H), 7.51 (t, J=8.0 Hz, 1H), 7.40-7.28 (m, 5H), 5.37 (s, 2H), 4.47-4.39 (m, 1H), 4.08 (m, 2H), 2.94 (m, 2H), 2.09-2.05 (m, 2H), 1.87-1.74 (m, 2H), 1.43 (s, 9H). HPLC (Condition A): Rt 5.15 min (purity 88.9%). MS (ESI+): 562.5.

Step 2: Formation of 2-[3-(1-Benzyl-1H-pyrazol-4-yl)-phenyl]-5-(1-piperidin-4-yl-1H-pyrazol-4-yl)-pyrimidine hydrochloride

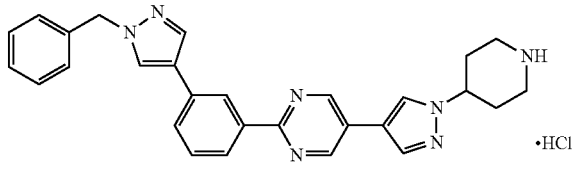 [SMILES: c1ccc(Cn2cc(-c3cccc(-c4ncc(-c5cnn(C6CCNCC6)c5)cn4)c3)cn2)cc1 ; Cl]

The title compound was obtained following procedure described for example 13, step 2, but starting from tert-butyl 4-(4-2-[3-(1-benzyl-1H-pyrazol-4-yl)phenyl]pyrimidin-5-yl-1H-pyrazol-1-yl)piperidine-1-carboxylate (165 mg; 0.29 mmol; 1.0 eq.) as a yellow solid (125 mg; 85%). 1H NMR (300 MHz, DMSO-d6) δ 9.34-9.30 (m, 1H), 9.19 (s, 2H), 9.08-9.05 (m, 1H), 8.57-8.53 (m, 2H), 8.44 (s, 1H), 8.24-8.20 (m, 2H), 7.98 (d, J=0.8 Hz, 1H), 7.73 (dt, J=7.8 Hz, 1.5 Hz, 1H), 7.52 (t, J=7.8 Hz, 1H), 7.40-7.27 (m, 5H), 5.38 (s, 2H), 4.57 (quint., J=5.0 Hz, 1H), 3.42-3.37 (m, 2H), 3.15-3.08 (m, 2H), 2.30-2.13 (m, 4H). HPLC (Condition A): Rt 3.30 min (purity 99.6%). MS (ESI+): 462.6.

Example 22

2-[3-(1-Methyl-1H-pyrazol-4-yl)-phenyl]-5-(1-pyridin-3-ylmethyl-1H-pyrazol-4-yl)-pyrimidine

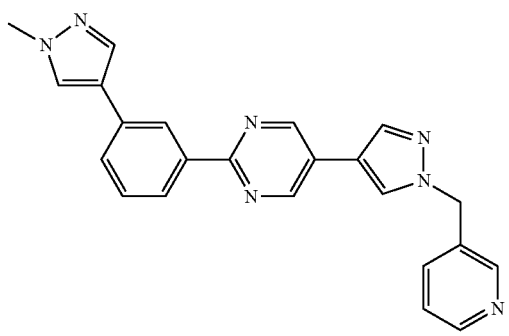 [SMILES: Cn1cc(-c2cccc(-c3ncc(-c4cnn(Cc5cccnc5)c4)cn3)c2)cn1]

The title compound was obtained following procedure described for example 7, step 1, but starting from 5-bromo-2-[3-(1-methyl-1H-pyrazol-4-yl)phenyl]pyrimidine (intermediate 2, 100 mg; 0.32 mmol; 1.0 eq.) and 1-(Pyridin-3-ylmethyl)-1H-pyrazole-4-boronic acid, pinacol ester (90 mg; 0.32 mmol; 1.0 eq.) as a white solid (14 mg; 12%). 1H NMR (300 MHz, DMSO-d6) δ 9.17 (s, 2H), 8.60 (s, 2H), 8.56-8.49 (m, 2H), 8.30-8.17 (m, 3H), 7.92 (s, 1H), 7.72 (d, J=7.7 Hz, 2H), 7.52 (t, J=7.7 Hz, 1H), 7.41 (dd, J=7.9, 4.8 Hz, 1H), 5.48 (s, 2H), 3.89 (s, 3H). HPLC (Condition A): Rt 2.33 min (purity 100%). MS (ESI+): 394.3

Example 23

2-(4-{2-[3-(1-Methyl-1H-pyrazol-4-yl)-phenyl]-pyrimidin-5-yl}-pyrazol-1-yl)-ethanol Step 1: Formation of 5-[1-(2-{[tert-butyl(dimethyl)silyl]oxy}ethyl)-1H-pyrazol-4-yl]-2-[3-(1-methyl-1H-pyrazol-4-yl)phenyl]pyrimidine

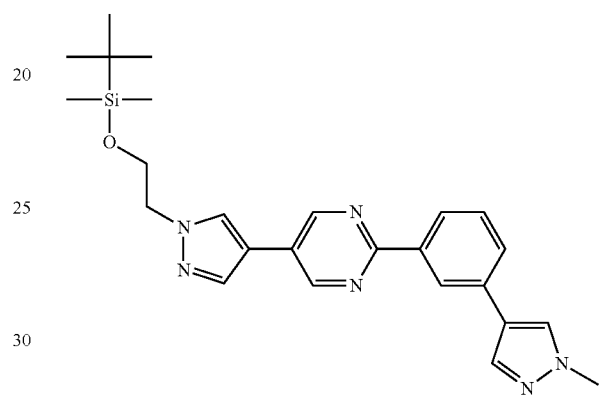

The title compound was obtained following procedure described for example 7, step 1, but starting from 5-bromo-2-[3-(1-methyl-1H-pyrazol-4-yl)phenyl]pyrimidine (intermediate 2; 100 mg; 0.32 mmol; 1.0 eq.) and 1-(Tetrahydrofuran-3-yl)-4-(4,4,5,5-tetramethyl-[1,3,2]dioxaborolan-2-yl)-1H-pyrazole (112 mg; 0.32 mmol; 1.0 eq.) as a beige oil (116 mg; 79%). MS (ESI+): 461.4

Step 2: Formation of 2-(4-{2-[3-(1-Methyl-1H-pyrazol-4-yl)-phenyl]-pyrimidin-5-yl}-pyrazol-1-yl)-ethanol

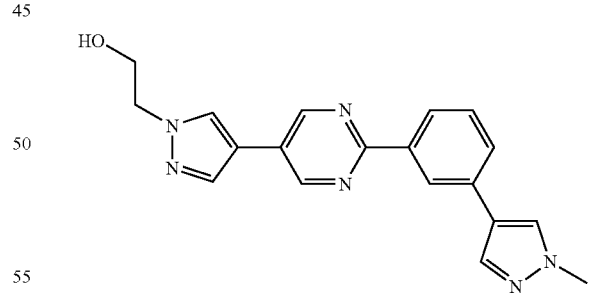

The title compound was obtained following procedure described for example 13, step 2, but starting from 5-[1-(2-{[tert-butyl(dimethyl)silyl]oxy}ethyl)-1H-pyrazol-4-yl]-2-[3-(1-methyl-1H-pyrazol-4-yl)phenyl]pyrimidine (116 mg; 0.25 mmol; 1.0 eq.) as a white powder (59 mg; 68%). 1H NMR (300 MHz, DMSO-d6) δ 9.17 (s, 2H), 8.53 (t, J=1.6 Hz, 1H), 8.44 (s, 1H), 8.27 (s, 1H), 8.25-8.18 (m, 1H), 8.15 (d, J=0.5 Hz, 1H), 7.93 (d, J=0.7 Hz, 1H), 7.76-7.66 (m, 1H), 7.52 (t, J=7.8 Hz, 1H), 4.99 (brs, 1H), 4.21 (t, J=5.5 Hz, 2H), 3.90 (s, 3H), 3.79 (d, J=4.0 Hz, 2H). HPLC (Condition A): Rt 2.68 min (purity 97.7%). MS (ESI+): 347.3. mp=234-236° C.

Example 24

2-[3-Fluoro-5-(1-methyl-1H-pyrazol-4-yl)-phenyl]-5-(1-piperidin-4-yl-1H-pyrazol-4-yl)-pyrimidine hydrochloride

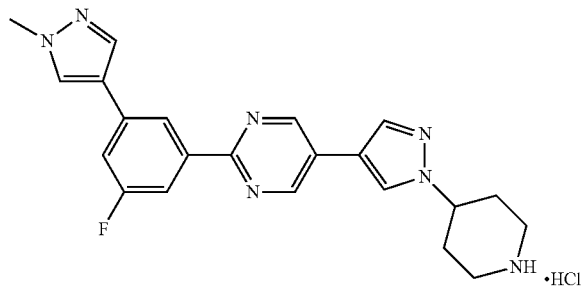 [SMILES: Cn1cc(-c2cc(F)cc(-c3ncc(-c4cnn(C5CCNCC5)c4)cn3)c2)cn1 ; Cl]

tert-butyl 4-[4-(2-iodopyrimidin-5-yl)-1H-pyrazol-1-yl]piperidine-1-carboxylate (intermediate 6; 104 mg; 0.23 mmol; 1.0 eq.), 3-bromo-5-fluorophenyl boronic acid (527 mg; 2.41 mmol; 1.1 eq.), bis(triphenylphosphine)palladium(II) chloride (14 mg; 0.02 mmol; 0.09 eq.) and cesium fluoride (272 mg; 1.79 mmol; 1.0 eq.) were suspended in DMF (4 mL) and water (1 mL). The reaction mixture was then heated in MW at 100° C. for 30 min. 1-methyl-4-(4,4,5,5-tetramethyl-1,3,2-dioxaborolan-2-yl)-1H-pyrazole (1.37 g; 6.58 mmol; 3.0 eq.) and bis(triphenylphosphine)palladium(II) chloride (80 mg; 0.11 mmol; 0.05 eq.) were added to the reaction suspension and heating continued for a further 30 min. On cooling the reaction suspension was filtered through celite, then poured into a 1 N HCl solution and extracted with EtOAc. Combined organic phases were washed with brine, dried over magnesium sulfate, filtered and concentrated. The crude obtained was purified by flash chromatography on silica (DCM:MeOH, gradient from 95:5 to 50:50). The pure residue was redissolved in HCl/dioxane (4 mL of a 1N solution; 16 mmol; 70 eq.) and MeOH (4 mL) and the resulting solution was stirred at RT for 1 h. It was then concentrated and triturated with acetonitrile. The solid was finally filtered and dried under vacuum to give the title compound as an orange solid. (0.72 g; 69%), $^1$H NMR (300 MHz, DMSO) δ 9.22 (s, 2H), 9.16 (br, 1H), 8.92 (br, 1H), 8.55 (s, 1H), 8.38 (t, J=1.4 Hz, 1H), 8.35 (s, 1H), 8.23 (s, 1H), 8.00 (d, J=0.7 Hz, 1H), 7.95-7.86 (m, 1H), 7.66-7.57 (m, 1H), 4.58-4.46 (m, 1H), 3.89 (s, 3H), 3.47-3.35 (m, 2H), 3.19-3.02 (m, 2H), 2.34-2.12 (m, 4H). HPLC (Condition A): Rt 2.60 min (purity 92.6%). MS (ESI+): 404.5.

Example 25

2-(4-{2-[3-(1-Methyl-1H-pyrazol-4-yl)-phenyl]-pyrimidin-5-yl}-pyrazol-1-yl)-1-piperidin-1-yl-ethanone

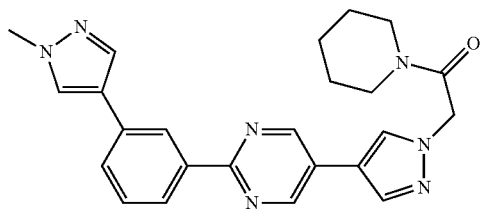 [SMILES: Cn1cc(-c2cccc(-c3ncc(-c4cnn(CC(=O)N5CCCCC5)c4)cn3)c2)cn1]

A mixture of (4-{2-[3-(1-methyl-1H-pyrazol-4-yl)phenyl]pyrimidin-5-yl}-1H-pyrazol-1-yl)acetic acid (example 9, 110 mg; 0.31 mmol; 1.0 eq.), piperidine (52 mg; 0.61 mmol; 2.0 eq.), HATU (174 mg; 0.46 mmol; 1.50 eq.) and DIEA (152 µl; 0.92 mmol; 3.0 eq.) in DMF (2 mL) was stirred at 50° C. O/N. The reaction mixture was poured into water and extracted with DCM (three times). Combined organic phases were then concentrated under reduced pressure and the residue was recrystallised in MeOH/Ether. The solid obtained was filtered and dried under reduced pressure to give the title compound as a white solid (20 mg, 15%). $^1$H NMR (300 MHz, DMSO) δ 9.18 (s, 2H), 8.54 (t, J=1.6 Hz, 1H), 8.37 (s, 1H), 8.27 (s, 1H), 8.25-8.19 (m, 1H), 8.14 (s, 1H), 7.93 (s, 1H), 7.77-7.66 (m, 1H), 7.52 (t, J=7.8 Hz, 1H), 5.22 (s, 2H), 3.90 (s, 3H), 3.55-3.39 (m, 4H), 1.69-1.39 (m, 6H).HPLC (Condition A): Rt 3.16 min (purity 99.9%). MS (ESI+): 428.3

Example 26

5-(1-Azetidin-3-yl-1H-pyrazol-4-yl)-2-[3-(1-methyl-1H-pyrazol-4-yl)-phenyl]-pyrimidine hydrochloride Step 1: Formation of tert-butyl 3-(4-{2-[3-(1-methyl-1H-pyrazol-4-yl)phenyl]pyrimidin-5-yl}-1H-pyrazol-1-yl)azetidine-1-carboxylate

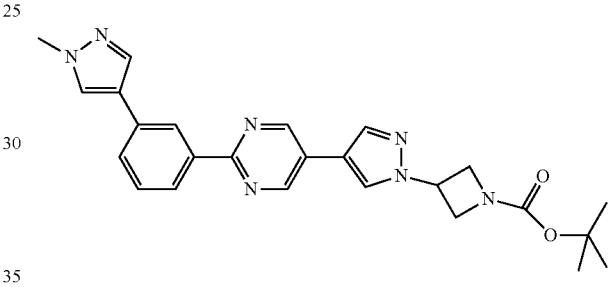

The title compound was obtained following procedure described for example 7, step 1, but starting from 5-bromo-2-[3-(1-methyl-1H-pyrazol-4-yl)phenyl]pyrimidine (intermediate 2; 100 mg; 0.32 mmol; 1.00 eq.) and 3-[4-(4,4,5,5-Tetramethyl-[1,3,2]dioxaborolan-2-yl)-pyrazol-1-yl]-azetidine-1-carboxylic acid tert-butyl ester (111 mg; 0.32 mmol; 1.0 eq.) as a beige solid (150 mg; 100%). HPLC (Condition A): Rt 4.01 min (purity 86.3%). MS (ESI+): 458.3

Step 2: Formation of 5-(1-Azetidin-3-yl-1H-pyrazol-4-yl)-2-[3-(1-methyl-1H-pyrazol-4-yl)-phenyl]-pyrimidine hydrochloride

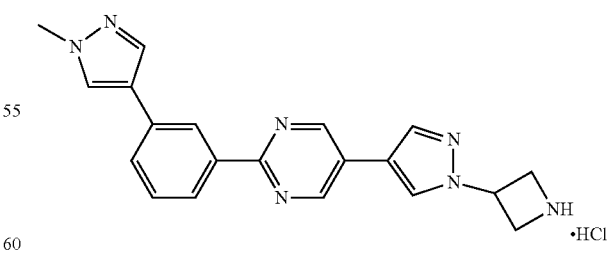

The title compound was obtained following procedure described for example 13, step 2, but starting from tert-butyl 3-(4-{2-[3-(1-methyl-1H-pyrazol-4-yl)phenyl]pyrimidin-5-yl}-1H-pyrazol-1-yl)azetidine-1-carboxylate (150 mg; 0.32 mmol; 1.0 eq.) as a white solid (3 mg, 3%). 1H NMR (300 MHz, DMSO-d6) δ 9.36 (brs, 2H), 9.20 (s, 2H), 8.64 (s, 1H), 8.54 (t, J=1.6 Hz, 1H), 8.38 (s, 1H), 8.30-8.18 (m, 2H), 7.93 (d, J=0.7 Hz, 1H), 7.72 (d, J=8.1 Hz, 1H), 7.52 (t, J=7.8 Hz, 1H), 5.59-5.38 (m, 1H), 4.49-4.21 (m, 4H), 3.90 (s, 3H). HPLC (Condition A): Rt 2.23 min (purity 98.6%). MS (ESI+): 358.3

Example 27

5-[1-(3-Methoxy-propyl)-1H-pyrazol-4-yl]-2-[3-(1-methyl-1H-pyrazol-4-yl)-phenyl]-pyrimidine

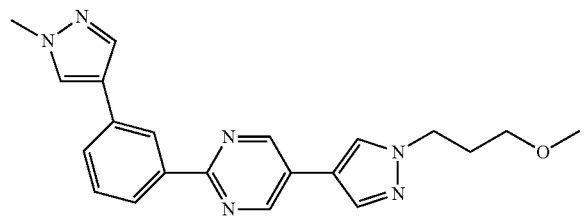

A solution of 2-[3-(1-methyl-1H-pyrazol-4-yl)phenyl]-5-(1H-pyrazol-4-yl)pyrimidine (example 3, 130 mg; 0.43 mmol; 1.0 eq.) in dry DMF (1 mL) was added over a suspension of NaH (60% in oil, 21 mg; 0.86 mmol; 2.0 eq.) in dry DMF (1 mL) maintained at 0° C. under nitrogen atmosphere. The resulting mixture was stirred for one hour at 0° C. then heated at 100° C. O/N after the addition of a solution of 1-chloro-3-methoxypropane (47 mg; 0.43 mmol; 1.0 eq.) in DMF (2 mL). Reaction mixture was then cooled down to RT, quenched with water and extracted with EtOAc (three times). Combined organic phases were washed with water, brine, dried over magnesium sulfate, filtered and concentrated. The resulting solid was dried O/N at 60° C. under reduced pressure to give the title compound a beige powder (165 mg; 75%). 1H NMR (300 MHz, DMSO-d6) δ 9.16 (s, 2H), 8.58-8.49 (m, 1H), 8.46 (s, 1H), 8.30-8.17 (m, 2H), 8.17-8.11 (m, 1H), 7.96-7.89 (m, 1H), 7.75-7.68 (m, 1H), 7.51 (t, J=7.8 Hz, 1H), 4.22 (t, J=7.0 Hz, 2H), 3.90 (s, 3H), 3.39-3.30 (m, 2H), 3.25 (s, 3H), 2.15-1.97 (m, 2H). HPLC (Condition A): Rt 3.34 min (purity 97.1%). MS (ESI+): 375.5.

Example 28

2-[3-(1-Methyl-1H-pyrazol-4-yl)-phenyl]-5-[1-(1-oxetan-3-yl-piperidin-4-yl)-1H-pyrazol-4-yl]-pyrimidine

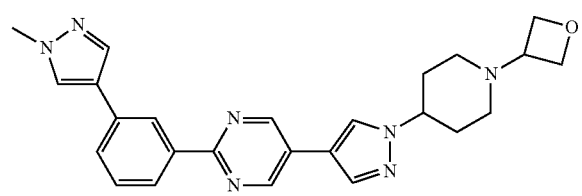 [SMILES: Cn1cc(-c2cccc(-c3ncc(-c4cnn(C5CCN(C6COC6)CC5)c4)cn3)c2)cn1]

Sodium triacetoxyborohydride (0.13 g; 0.62 mmol; 2.0 eq.) was slowly added to a solution of 2-[3-(1-methyl-1H-pyrazol-4-yl)phenyl]-5-(1-piperidin-4-yl-1H-pyrazol-4-yl) pyrimidine (example 1,200 mg; 0.31 mmol; 1.0 eq.), DIEA (53 μl; 0.31 mmol; 1.0 eq.) and 3-oxetanone (39 μl; 0.62 mmol; 2.0 eq.) in DCE (4 mL). The reaction mixture was then stirred at 50° C. for 3 h. It was then quenched by addition of water. Aqueous phase was basified to pH 12 and extracted with EtOAc (three times). Combined organic phases were washed with brine, dried over magnesium sulfate, filtered and concentrated to give the title compound as a beige powder (100 mg, 73%). 1H NMR (300 MHz, DMSO-d6) δ 9.17 (s, 2H), 8.59-8.50 (m, 2H), 8.27 (s, 1H), 8.25-8.18 (m, 1H), 8.18-8.11 (m, 1H), 7.96-7.89 (m, 1H), 7.77-7.66 (m, 1H), 7.52 (t, J=7.7 Hz, 1H), 4.56 (t, J=6.5 Hz, 2H), 4.46 (t, J=6.1 Hz, 2H), 4.23 (s, 1H), 3.90 (s, 3H), 3.51-3.40 (m, 1H), 2.87-2.73 (m, 2H), 2.17-1.90 (m, 6H). HPLC (Condition A): Rt 2.49 min (purity 97.2%). MS (ESI+): 442.5.

Example 29

2-[3-(1-Methyl-1H-pyrazol-4-yl)-phenyl]-5-(1-piperidin-4-ylmethyl-1H-pyrazol-4-yl)-pyrimidine hydrochloride Step 1: Formation of 4-(4-{2-[3-(1-Methyl-1H-pyrazol-4-yl)-phenyl]-pyrimidin-5-yl}-pyrazol-1-ylmethyl)-piperidine-1-carboxylic acid tert-butyl ester

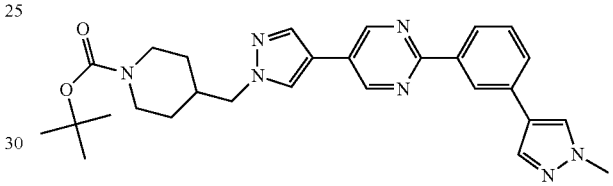

The title compound was obtained following procedure described for example 27, but starting from 2-[3-(1-methyl-1H-pyrazol-4-yl)phenyl]-5-(1H-pyrazol-4-yl)pyrimidine (example 3, 150 mg; 0.50 mmol; 1.0 eq.) and tert-butyl 4-{[(methylsulfonyl)oxy]methyl}piperidine-1-carboxylate (145 mg; 0.50 mmol; 1.0 eq.) as a beige powder (200 mg, 81%). HPLC (Condition A): Rt 4.44 min (purity 97.2%). MS (ESI+): 500.5

Step 2: Formation of 2-[3-(1-Methyl-1H-pyrazol-4-yl)-phenyl]-5-(1-piperidin-4-ylmethyl-1H-pyrazol-4-yl)-pyrimidine hydrochloride

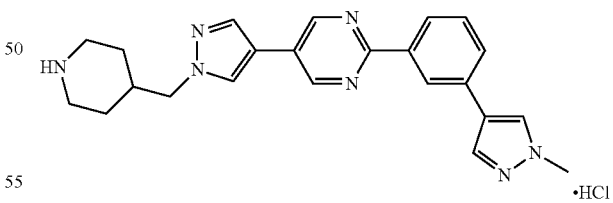

The title compound was obtained following procedure described for example 13, step 2, but starting from of 4-(4-{2-[3-(1-Methyl-1H-pyrazol-4-yl)-phenyl]-pyrimidin-5-yl}-pyrazol-1-ylmethyl)-piperidine-1-carboxylic acid tert-butyl ester (200 mg; 0.40 mmol; 1.0 eq.) as a yellow powder (160 mg, 92%). 1H NMR (300 MHz, DMSO-d6) δ 9.17 (s, 2H), 9.10-8.96 (m, 1H), 8.84-8.68 (m, 1H), 8.53 (t, J=1.6 Hz, 1H), 8.49 (s, 1H), 8.27 (s, 1H), 8.25-8.16 (m, 2H), 7.93 (d, J=0.7 Hz, 1H), 7.75-7.68 (m, 1H), 7.52 (t, J=7.8 Hz, 1H), 4.17-4.07 (m, 2H), 3.90 (s, 3H), 3.31-3.17 (m, 2H), 2.93-2.75

(m, 2H), 2.24-2.06 (m, 1H), 1.76-1.62 (m, 2H), 1.55-1.33 (m, 2H). HPLC (Condition A): Rt 2.50 min (purity 97.5%). MS (ESI+): 400.4.

Example 30 trans-5-[1-(3-Fluoro-piperidin-4-yl)-1H-pyrazol-4-yl]-2-[3-(1-methyl-1H-pyrazol-4-yl)-phenyl]-pyrimidine hydrochloride Step 1: Formation of Trans-3-Fluoro-4-(4-{2-[3-(1-methyl-1H-pyrazol-4-yl)-phenyl]-pyrimidin-5-yl}-pyrazol-1-yl)-piperidine-1-carboxylic acid tert-butyl ester

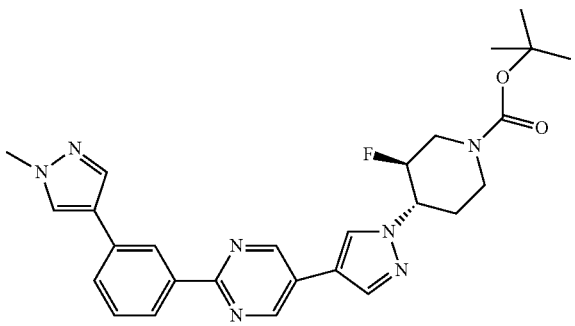 [SMILES: Cn1cc(-c2cccc(-c3ncc(-c4cnn([C@H]5CCN(C(=O)OC(C)(C)C)C[C@@H]5F)c4)cn3)c2)cn1]

The title compound was obtained following procedure described for example 27, but starting from 2-[3-(1-methyl-1H-pyrazol-4-yl)phenyl]-5-(1H-pyrazol-4-yl)pyrimidine (example 3, 150 mg; 0.50 mmol; 1.0 eq.) and tert-butyl 3-fluoro-4-[(methylsulfonyl)oxy]piperidine-1-carboxylate (intermediate 9; 147 mg; 0.50 mmol; 1.0 eq.) as an off-white solid (110 mg, 44%). HPLC (Condition A): Rt 4.53 min (purity 87.5%). MS (ESI+): 504.4

Step 2: Formation of Trans-5-[1-(3-Fluoro-piperidin-4-yl)-1H-pyrazol-4-yl]-2-[3-(1-methyl-1H-pyrazol-4-yl)-phenyl]-pyrimidine hydrochloride

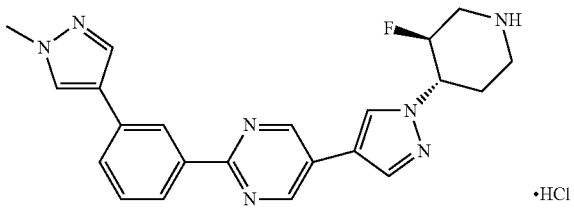 [SMILES: Cn1cc(-c2cccc(-c3ncc(-c4cnn([C@H]5CCNC[C@@H]5F)c4)cn3)c2)cn1 ; Cl]

The title compound was obtained following procedure described for example 13, step 2, but starting from Trans-3-Fluoro-4-(4-{2-[3-(1-methyl-1H-pyrazol-4-yl)-phenyl]-pyrimidin-5-yl}-pyrazol-1-yl)-piperidine-1-carboxylic acid tert-butyl ester (320 mg; 0.64 mmol; 1.0 eq.). After the first precipitation, a purification by autopreparative LC/MS afforded the title compound as a white foam (67 mg, 24%). 1H NMR (300 MHz, DMSO-d6) δ 9.87 (brs, 1H), 9.63 (brs, 1H), 9.21 (s, 2H), 8.55 (d, J=8.1 Hz, 2H), 8.35-8.17 (m, 3H), 7.93 (s, 1H), 7.72 (d, J=7.8 Hz, 1H), 7.52 (t, J=7.7 Hz, 1H), 5.38-5.08 (m, 1H), 4.89-4.72 (m, 1H), 3.90 (s, 3H), 3.79-3.64 (m, 1H), 3.49-3.33 (m, 1H), 3.32-3.01 (m, 2H), 2.46-2.18 (m, 2H). HPLC (Condition A): Rt 2.58 min (purity 98.4%). MS (ESI+): 404.3.

Example 31

1,1,1-Trifluoro-3-[4-(4-{2-[3-(1-methyl-1H-pyrazol-4-yl)-phenyl]-pyrimidin-5-yl}-pyrazol-1-yl)-piperidin-1-yl]-propan-2-ol

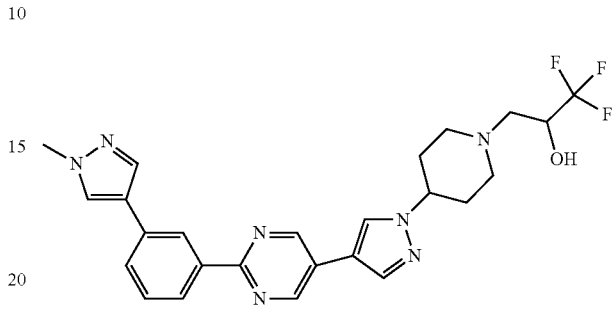

1,2-Epoxy-3,3,3-trifluoropropane (84 mg; 0.72 mmol; 2.4 eq.) was added to a solution of 2-[3-(1-methyl-1H-pyrazol-4-yl)phenyl]-5-(1-piperidin-4-yl-1H-pyrazol-4-yl)pyrimidine (example 1, 200 mg; 0.31 mmol; 1.0 eq.) and DIEA (53 µl; 0.31 mmol; 1.0 eq.) in DMF (4 mL). The reaction mixture was stirred at 50° C. O/N. It was then diluted with water and extracted with EtOAc (three times). Combined organic phases were washed with water and brine, dried over magnesium sulfate, filtered and concentrated. Purification by flash chromatography on silica (DCM:EtOAc, gradient from 40:60 to 0:100) afforded the title compound as a beige powder (56 mg, 36%). 1H NMR (300 MHz, DMSO-d6) δ 9.17 (s, 2H), 8.59-8.49 (m, 2H), 8.27 (s, 1H), 8.25-8.18 (m, 1H), 8.14 (s, 1H), 7.93 (s, 1H), 7.75-7.67 (m, 1H), 7.52 (t, J=7.7 Hz, 1H), 6.24-6.13 (m, 1H), 4.28-4.08 (m, 2H), 3.90 (s, 3H), 3.12-2.97 (m, 2H), 2.66-2.53 (m, 2H), 2.36-2.17 (m, 2H), 2.12-1.86 (m, 4H). HPLC (Condition A): Rt 2.85 min (purity 98.4%). MS (ESI+): 498.4.

Example 32

5-(1-Methyl-1H-pyrazol-4-yl)-2-[3-(1-methyl-1H-pyrazol-4-yl)-phenyl]-pyrimidine

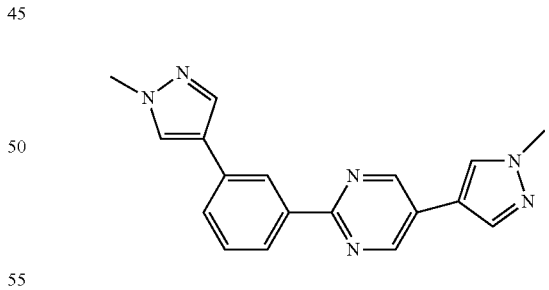

The title compound was obtained following procedure described for example 7, step 1, but starting from 5-bromo-2-[3-(1-methyl-1H-pyrazol-4-yl)phenyl]pyrimidine (intermediate 2, 100 mg; 0.32 mmol; 1.0 eq.) and 1-Methyl-4-(4,4,5,5-tetramethyl-[1,3,2]dioxaborolan-2-yl)-1H-pyrazole (99 mg; 0.48 mmol; 1.5 eq.) as a white powder (56 mg; 55%). 1H NMR (300 MHz, DMSO-d6) δ 9.15 (s, 2H), 8.53 (t, J=1.6 Hz, 1H), 8.41 (s, 1H), 8.26 (s, 1H), 8.24-8.16 (m, 1H), 8.12 (d, J=0.7 Hz, 1H), 7.92 (d, J=0.7 Hz, 1H), 7.76-7.66 (m, 1H), 7.51 (t, J=7.8 Hz, 1H), 3.92 (s, 3H), 3.90 (s, 3H). HPLC (Condition A): Rt 2.86 min (purity 97.4%). MS (ESI+): 317.3, mp=199-200° C.

Example 33

5-(1-Piperidin-4-yl-1H-pyrazol-4-yl)-2-(3-pyridin-4-yl-phenyl)-pyrimidine hydrochloride Step 1: Formation of 4-{4-[2-(3-Pyridin-4-yl-phenyl)-pyrimidin-5-yl]-pyrazol-1-yl}-piperidine-1-carboxylic acid tert-butyl ester

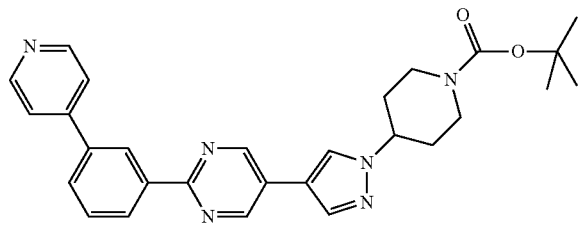 [SMILES: CC(C)(C)OC(=O)N1CCC(n2cc(-c3cnc(-c4cccc(-c5ccncc5)c4)nc3)cn2)CC1]

The title compound was obtained following procedure described for example 7, step 1, but starting from tert-butyl 4-{4-[2-(3-iodophenyl)pyrimidin-5-yl]-1H-pyrazol-1-yl}piperidine-1-carboxylate (intermediate 5, 200 mg; 0.38 mmol; 1.0 eq.) and 4-Pyridineboronic acid (93 mg; 0.75 mmol; 2.0 eq.) as a yellow solid (121 mg, 67%). HPLC (Condition A): Rt 3.31 min (purity 99.6%). MS (ESI+): 483.5

Step 2: Formation of 5-(1-Piperidin-4-yl-1H-pyrazol-4-yl)-2-(3-pyridin-4-yl-phenyl)-pyrimidine hydrochloride

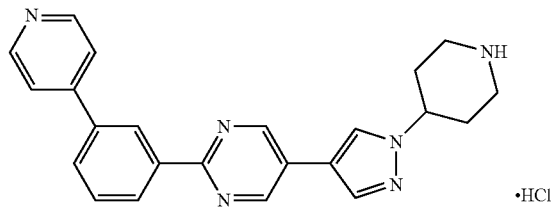 [SMILES: c1cc(-c2ccncc2)cc(-c2ncc(-c3cnn(C4CCNCC4)c3)cn2)c1 ; Cl]

The title compound was obtained following procedure described for example 13, step 2, but starting from 4-{4-[2-(3-Pyridin-4-yl-phenyl)-pyrimidin-5-yl]-pyrazol-1-yl}-piperidine-1-carboxylic acid tert-butyl ester (120 mg; 0.25 mmol; 1.0 eq.) as a beige solid (100 mg, 97%).

1H NMR (300 MHz, DMSO-d6) δ 9.41-9.26 (m, 1H), 9.25 (s, 2H), 9.20-9.10 (m, 1H), 8.99 (d, J=6.8 Hz, 2H), 8.89 (t, J=1.5 Hz, 1H), 8.62 (dt, J=8.0 Hz, 1.5 Hz, 1H), 8.57 (s, 1H), 8.44 (d, J=6.8 Hz, 2H), 8.23 (s, 1H), 8.18-8.14 (m, 1H), 7.81 (t, J=8.0 Hz, 1H), 4.61-4.52 (m, 1H), 3.42-3.37 (m, 2H), 3.16-3.04 (m, 2H), 2.29-2.17 (m, 4H). HPLC (Condition A): Rt 1.69 min (purity 99.2%). MS (ESI+): 383.3.

Example 34

3-(1-Methyl-1H-pyrazol-4-yl)-5-[5-(1-piperidin-4-yl-1H-pyrazol-4-yl)-pyrimidin-2-yl]-phenol Formate

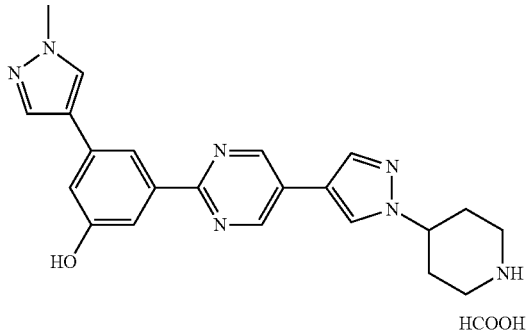 [SMILES: Cn1cc(-c2cc(O)cc(-c3ncc(-c4cnn(C5CCNCC5)c4)cn3)c2)cn1 ; "HCOOH"]

3-Bromo-5-(1-methyl-1H-pyrazol-4-yl)-phenol (337 mg; 1.09 mmol; 1.0 eq.), bis(pinacolato)diborane (245 mg; 0.96 mmol; 0.9 eq.), 1,1-Bis(diphenylphosphino)ferrocenedichloropalladium(II) (98 mg; 0.13 mmol; 0.12 eq.) and Potassium acetate (432 mg; 4.40 mmol; 4.0 eq.) were suspended in 1,4 dioxane (8 mL). The reaction suspension was degassed with argon and heated in MW at 80° C. for 30 min. A further portion of bis(pinacolato)diborane (108 mg; 0.43 mmol; 0.4 eq.) was added and heating repeated (80° C. for 30 min in MW). Tert-butyl 4-[4-(2-iodopyrimidin-5-yl)-1H-pyrazol-1-yl]piperidine-1-carboxylate (intermediate 6, 265 mg; 0.58 mmol; 0.53 eq.), bis(triphenylphosphine)palladium(II) chloride (100 mg; 0.14 mmol; 0.13 eq.) and potassium carbonate (446 mg; 3.23 mmol; 3.0 eq.) were added in one portion and the reaction solution diluted with water (3 mL), degassed with argon and heated again in MW at 100° C. for 30 min. The reaction mixture was cooled down to RT and diluted with DCM. It was filtered through celite. Organic phase was washed sequentially with a 1 N HCl solution and brine, dried over magnesium sulfate, filtered and concentrated. This crude was purified by flash chromatography on silica (n-heptane: EtOAc, gradient from 95:5 to 75:25) and then redissolved in MeOH and HCl/dioxane (10 mL of a 4N solution; 40 mmol; 37 eq.). Reaction mixture was stirred at RT for 2 h and concentrated under reduced pressure. Purification by autopreparative LC/MS afforded the title compound as a white foam (11 mg, 4%). 1H NMR (300 MHz, DMSO-d6) δ 9.67 (s, 1H), 9.16 (s, 2H), 8.50 (s, 1H), 8.18 (d, J=4.1 Hz, 2H), 8.00 (t, J=1.5 Hz, 1H), 7.83 (d, J=0.7 Hz, 1H), 7.71-7.67 (m, 1H), 7.10-7.05 (m, 1H), 4.62-4.48 (m, 1H), 3.88 (s, 3H), 3.47-3.35 (m, 2H), 3.15-3.01 (m, 2H), 2.32-2.04 (m, 4H). HPLC (Condition A): Rt 1.86 min (purity 91.2%). MS (ESI+): 402.5.

Example 35

1-Methoxy-3-(4-{2-[3-(1-methyl-1H-pyrazol-4-yl)-phenyl]-pyrimidin-5-yl}-pyrazol-1-yl)-propan-2-ol

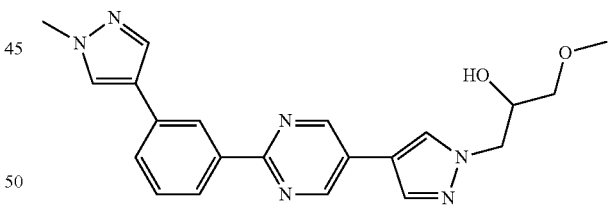

The title compound was obtained following procedure described for example 7, step 1, but starting from 5-bromo-2-[3-(1-methyl-1H-pyrazol-4-yl)phenyl]pyrimidine (intermediate 2, 100 mg; 0.32 mmol; 1.0 eq.) and 1-Methoxy-3-[4-(4,4,5,5-tetramethyl-[1,3,2]dioxaborolan-2-yl)-pyrazol-1-yl]-propan-2-ol (prepared as described in Bioorganic & Medicinal Chemistry Letters, 18(19), 5299-5302; 2008; 134 mg; 0.48 mmol; 1.5 eq.) as a white solid (27 mg, 22%). 1H NMR (300 MHz, DMSO-d6) δ 9.17 (s, 2H), 8.53 (s, 1H), 8.41 (s, 1H), 8.27 (s, 1H), 8.22 (d, J=8.0 Hz, 1H), 8.15 (s, 1H), 7.93 (s, 1H), 7.71 (d, J=7.9 Hz, 1H), 7.52 (t, J=7.8 Hz, 1H), 5.24 (d, J=5.2 Hz, 1H), 4.25 (dd, J=13.3, 3.6 Hz, 1H), 4.15-3.95 (m, 2H), 3.90 (s, 3H), 3.40-3.23 (m, 5H). HPLC (Condition A): Rt 2.68 min (purity 96.6%). MS (ESI+): 391.3

Example 36

2-(4-{2-[3-(1-Methyl-1H-pyrazol-4-yl)-phenyl]-pyrimidin-5-yl}-pyrazol-1-yl)-1-morpholin-4-yl-ethanone

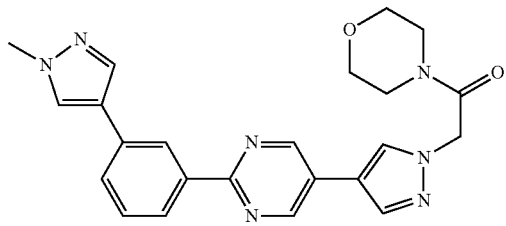 [SMILES: Cn1cc(-c2cccc(-c3ncc(-c4cnn(CC(=O)N5CCOCC5)c4)cn3)c2)cn1]

The title compound was obtained following procedure described for example 25 but starting from 4-{2-[3-(1-Methyl-1H-pyrazol-4-yl)-phenyl]-pyrimidin-5-yl}-pyrazol-1-yl)-acetic acid (example 8, 100 mg; 0.28 mmol; 1.0 eq.) and Morpholine (24 mg; 0.28 mmol; 1.0 eq.) as a white solid (45 mg, 38%). 1H NMR (300 MHz, DMSO-d6) δ 9.18 (s, 2H), 8.54 (t, J=1.6 Hz, 1H), 8.37 (s, 1H), 8.27 (s, 1H), 8.25-8.18 (m, 1H), 8.15 (s, 1H), 7.93 (d, J=0.6 Hz, 1H), 7.77-7.67 (m, 1H), 7.52 (t, J=7.8 Hz, 1H), 5.26 (s, 2H), 3.90 (s, 3H), 3.71-3.42 (m, 8H). HPLC (Condition A): Rt 2.60 min (purity 97.6%). MS (ESI+): 430.3.

Example 37

2-(4-{2-[3-(3-Methyl-3H-imidazol-4-yl)-phenyl]-pyrimidin-5-yl}-pyrazol-1-yl)-1-pyrrolidin-1-yl-ethanone Step 1: Formation of 1-Pyrrolidin-1-yl-2-(4-{2-[3-(4,4,5,5-tetramethyl-[1,3,2]dioxaborolan-2-yl)-phenyl]-pyrimidin-5-yl}-pyrazol-1-yl)-ethanone

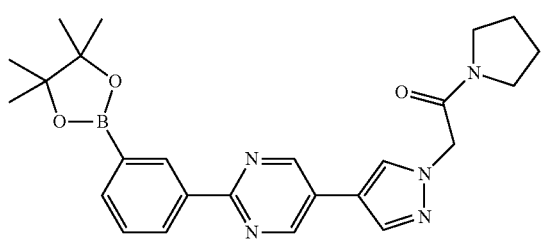 [SMILES: CC1(C)OB(c2cccc(-c3ncc(-c4cnn(CC(=O)N5CCCC5)c4)cn3)c2)OC1(C)C]

A mixture of 2-{4-[2-(3-Iodo-phenyl)-pyrimidin-5-yl]-pyrazol-1-yl}-1-pyrrolidin-1-yl-ethanone (intermediate 12, 700 mg; 1.52 mmol; 1.0 eq.), bis(pinacolato)diborane (426 mg; 1.68 mmol; 1.10 eq.), (dppf)PdCl₂.CH₂Cl₂ (111 mg; 0.15 mmol; 0.1 eq.) and Potassium acetate (449 mg; 4.57 mmol; 3.0 eq.) in THF (15 mL) and DMF (5 mL) was heated in MW at 100° C. for 2 h. The reaction mixture solution was used as it in the next step.

Step 2: Formation of 2-(4-{2-[3-(3-Methyl-3H-imidazol-4-yl)-phenyl]-pyrimidin-5-yl}-pyrazol-1-yl)-1-pyrrolidin-1-yl-ethanone

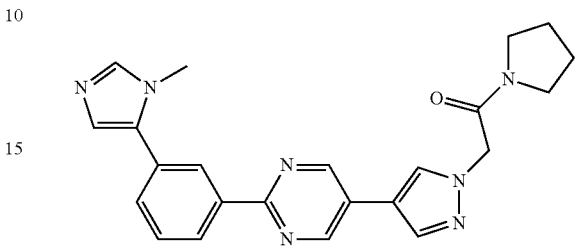

A mixture of 1-Pyrrolidin-1-yl-2-(4-{2-[3-(4,4,5,5-tetramethyl-[1,3,2]dioxaborolan-2-yl)-phenyl]-pyrimidin-5-yl}-pyrazol-1-yl)-ethanone (4 mL of the solution obtained in step 1), 5-bromo-1-methyl-1H-imidazole (35 mg; 0.22 mmol; 1.0 eq.), Pd(Ph₃)₄ (13 mg; 0.01 mmol; 0.05 eq.) and potassium carbonate (90 mg; 0.65 mmol; 3.0 eq.) in water (0.73 mL) was heated at 120° C. in MW for 30 min. Addition of 5-bromo-1-methyl-1H-imidazole (35 mg; 0.22 mmol; 1.0 eq.) and heating at 120° C. for 30 min had to be repeated twice to complete the reaction. The reaction mixture was then diluted with water and extracted twice with EtOAc. Combined organic phases were washed with brine, dried over magnesium sulfate, filtered and concentrated. Purification by flash chromatography on silica (DCM:MeOH, gradient from 100:0 to 80:20) gave a black gum which was redissolved in DCM. Addition of cyclohexane afforded a brown precipitate which was filtered and dried under vacuum to give the title compound as a beige solid (40 mg, 44%). 1H NMR (300 MHz, DMSO-d6) δ 9.20 (s, 2H), 8.47-8.46 (m, 1H), 8.41-8.37 (m, 2H), 8.14 (d, J=0.6 Hz, 1H), 7.76 (s, 1H), 7.68-7.60 (m, 2H), 7.15 (s, 1H), 5.12 (s, 2H), 3.74 (s, 3H), 3.52 (t, J=6.8 Hz, 2H), 3.32 (t, J=6.8 Hz, 2H), 1.93 (quint., J=6.8 Hz, 2H), 1.80 (quint., J=6.8 Hz, 2H). HPLC (Condition A): Rt 2.21 min (purity 96.2%). MS (ESI+): 414.4.

Example 38

N,N-Dimethyl-2-(4-{2-[3-(1-methyl-1H-pyrazol-4-yl)-phenyl]-pyrimidin-5-yl}-pyrazol-1-yl)-acetamide

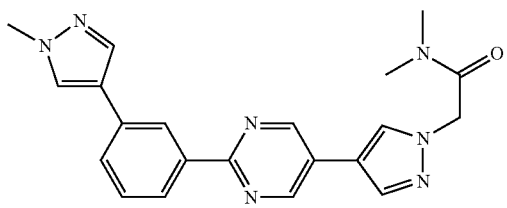 [SMILES: CN(C)C(=O)Cn1cc(-c2cnc(-c3cccc(-c4cnn(C)c4)c3)nc2)cn1]

The title compound was obtained following procedure described for example 25 but starting from (4-{2-[3-(1-Methyl-1H-pyrazol-4-yl)-phenyl]-pyrimidin-5-yl}-pyrazol-1-yl)-acetic acid (example 8 and dimethylamine as a white solid (18 mg, 47%). 1H NMR (300 MHz, DMSO-d6) δ 9.18 (s, 2H), 8.54 (t, J=1.6 Hz, 1H), 8.35 (s, 1H), 8.27 (s, 1H), 8.25-8.17 (m, 1H), 8.14 (d, J=0.6 Hz, 1H), 7.93 (d, J=0.8 Hz, 1H), 7.77-7.66 (m, 1H), 7.52 (t, J=7.8 Hz, 1H), 5.21 (s, 2H), 3.90 (s, 3H), 3.07 (s, 3H), 2.88 (s, 3H). HPLC (Condition A): Rt 2.59 min (purity 99.3%). MS (ESI+): 388.3.

Example 39

2-[3-(1-Methyl-1H-pyrazol-4-yl)-phenyl]-5-{1-[1-(tetrahydro-pyran-4-yl)-piperidin-4-yl]-1H-pyrazol-4-yl}-pyrimidine

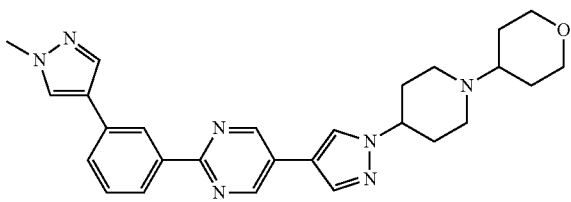 [SMILES: Cn1cc(-c2cccc(-c3ncc(-c4cnn(C5CCN(C6CCOCC6)CC5)c4)cn3)c2)cn1]

The title compound was obtained following procedure described for example 28 but starting from 2-[3-(1-methyl-1H-pyrazol-4-yl)phenyl]-5-(1-piperidin-4-yl-1H-pyrazol-4-yl)pyrimidine (example 1, 200 mg; 0.31 mmol; 1.0 eq.) and tetrahydro-4H-pyran-4-one (62 mg; 0.62 mmol; 2.0 eq.) as a white powder (25 mg, 17%). 1H NMR (300 MHz, DMSO-d6) δ 9.16 (s, 2H), 8.59-8.49 (m, 2H), 8.27 (s, 1H), 8.20 (dt, J=8, 3 Hz, 1H), 8.13 (s, 1H), 7.93 (d, J=0.6 Hz, 1H), 7.76-7.66 (m, 1H), 7.51 (t, J=7.7 Hz, 1H), 4.25-4.10 (m, 1H), 3.95-3.84 (m, 2H), 3.89 (s, 3H), 3.33-3.21 (m, 2H), 3.08-2.94 (m, 2H), 2.59-2.43 (m, 1H), 2.37-2.21 (m, 2H), 2.14-1.84 (m, 4H), 1.77-1.63 (m, 2H), 1.56-1.36 (m, 2H). HPLC (Condition A): Rt 2.55 min (purity 97.6%). MS (ESI+): 470.4.

Example 40

1-(3-Methoxy-azetidin-1-yl)-2-(4-{2-[3-(1-methyl-1H-pyrazol-4-yl)-phenyl]-pyrimidin-5-yl}-pyrazol-1-yl)-ethanone

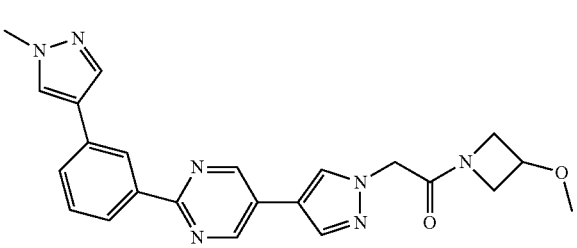

The title compound was obtained following procedure described for example 27 but starting from 2-[3-(1-methyl-1H-pyrazol-4-yl)phenyl]-5-(1H-pyrazol-4-yl)pyrimidine (example 3, 80 mg; 0.26 mmol; 1.0 eq.) and 2-Chloro-1-(3-methoxy-azetidin-1-yl)-ethanone (from Butt Park Ltd., 86 mg; 0.53 mmol; 2.0 eq.) as a white foam (25 mg, 21%). 1H NMR (300 MHz, DMSO-d6) δ 9.18 (s, 2H), 8.56-8.51 (m, 1H), 8.40 (s, 1H), 8.27 (s, 1H), 8.25-8.19 (m, 1H), 8.17 (s, 1H), 7.93 (s, 1H), 7.75-7.68 (m, 1H), 7.52 (t, J=7.7 Hz, 1H), 4.97 (s, 2H), 4.40-4.31 (m, 1H), 4.30-4.20 (m, 1H), 4.15-3.99 (m, 2H), 3.89 (s, 3H), 3.72 (dd, J=10.3, 3.6 Hz, 1H), 3.23 (s, 3H). HPLC (Condition A): Rt 2.87 min (purity 94.1%). MS (ESI+): 430.3.

Example 41

2-(4-{2-[3-(1-Methyl-1H-pyrazol-4-yl)-phenyl]-pyrimidin-5-yl}-pyrazol-1-ylmethyl)-morpholine hydrochloride Step 1: Formation of 2-(4-{2-[3-(1-Methyl-1H-pyrazol-4-yl)-phenyl]-pyrimidin-5-yl}-pyrazol-1-ylmethyl)-morpholine-4-carboxylic acid tert-butyl ester

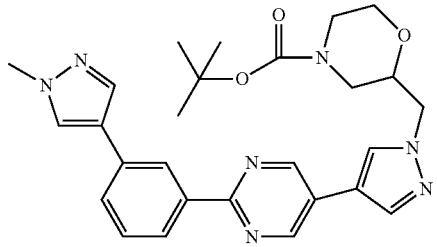 [SMILES: Cn1cc(-c2cccc(-c3ncc(-c4cnn(CC5CN(C(=O)OC(C)(C)C)CCO5)c4)cn3)c2)cn1]

The title compound was obtained following procedure described for example 27 but starting from 2-[3-(1-methyl-1H-pyrazol-4-yl)phenyl]-5-(1H-pyrazol-4-yl)pyrimidine (example 3, 150 mg; 0.50 mmol; 1.0 eq and 2-Methanesulfonyloxymethyl-morpholine-4-carboxylic acid tert-butyl ester (intermediate 13, 146 mg; 0.50 mmol; 1.0 eq.) as a white powder (110 mg, 44%). MS (ESI+): 502.3.

Step 2: Formation of 2-(4-{2-[3-(1-Methyl-1H-pyrazol-4-yl)-phenyl]-pyrimidin-5-yl}-pyrazol-1-ylmethyl)-morpholine hydrochloride

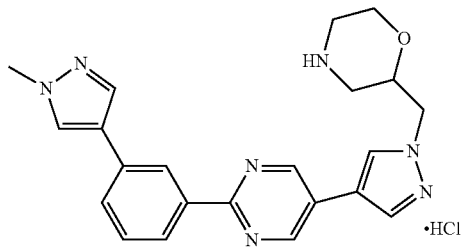 [SMILES: Cn1cc(-c2cccc(-c3ncc(-c4cnn(CC5CNCCO5)c4)cn3)c2)cn1 ; Cl]

The title compound was obtained following procedure described for example 13, step 2 but starting from 2-(4-{2-[3-(1-Methyl-1H-pyrazol-4-yl)-phenyl]-pyrimidin-5-yl}-pyrazol-1-ylmethyl)-morpholine-4-carboxylic acid tert-butyl ester (105 mg; 0.22 mmol; 1.0 eq.) as a yellow powder (50 mg, 52%). 1H NMR (300 MHz, DMSO-d6) δ 9.50 (brs, 2H), 9.19 (s, 2H), 8.54 (t, J=1.6 Hz, 1H), 8.44 (s, 1H), 8.30-8.17 (m, 3H), 7.93 (d, J=0.6 Hz, 1H), 7.75-7.67 (m, 1H), 7.52 (t, J=7.8 Hz, 1H), 4.48-4.23 (m, 2H), 4.23-4.10 (m, 1H), 4.05-3.91 (m, 1H), 3.90 (s, 3H), 3.81-3.64 (m, 1H), 3.36-3.28 (m, 1H), 3.25-3.12 (m, 1H), 3.04-2.74 (m, 2H). HPLC (Condition A): Rt 2.57 min (purity 100.0%). MS (ESI+): 402.3.

Example 42

2-[4-(2-{3-[1-(3-Amino-propyl)-1H-pyrazol-4-yl]-phenyl}-pyrimidin-5-yl)-pyrazol-1-yl]-1-pyrrolidin-1-yl-ethanone hydrochloride

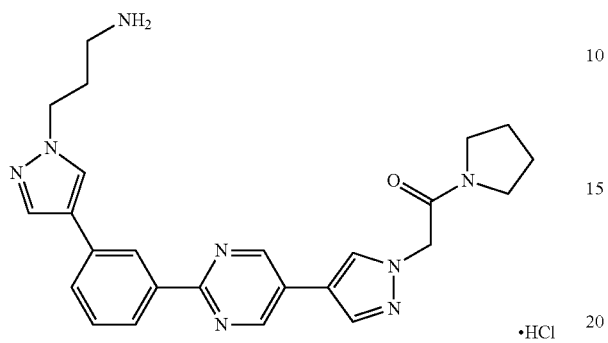

A solution of 2-(4-{2-[3-(1H-Pyrazol-4-yl)-phenyl]-pyrimidin-5-yl}-pyrazol-1-yl)-1-pyrrolidin-1-yl-ethanone (intermediate 14, 100 mg; 0.25 mmol; 1.0 eq.) in dry DMF (1 mL) was added over a suspension of NaH (60% in oil, 21 mg; 0.86 mmol; 2.0 eq.) in dry DMF (1 mL) maintained at 0° C. under nitrogen atmosphere. The resulting mixture was stirred for one hour at 0° C. then heated at 100° C. O/N after the addition of a solution of (3-Bromo-propyl)-carbamic acid tert-butyl ester (60 mg; 0.25 mmol; 1.0 eq.) in DMF (2 mL). Reaction mixture was then cooled down to RT, quenched with water and extracted with EtOAc (three times). Combined organic phases were washed with water, brine, dried over magnesium sulfate, filtered and concentrated. This crude was directly redissolved in DCM (1 mL) and treated with HCl/dioxane (0.94 mL of a 4N solution; 3.76 mmol; 15.0 eq.). The resulting reaction mixture was stirred at RT for 1 hour, concentrated under reduced pressure and purified by auto-preparative LC/MS to give the title compound as a white solid 1H NMR (300 MHz, DMSO-d6) δ 9.18 (s, 2H), 8.55 (t, J=1.5 Hz, 1H), 8.43 (brs, 1H), 8.37 (s, 1H), 8.34 (s, 1H), 8.23 (dt, J=7.8 Hz, 1.6 Hz, 1H), 8.14 (s, 1H), 7.98 (s, 1H), 7.73 (dt, J=7.8 Hz, 1.6 Hz, 1H), 7.52 (t, J=7.8 Hz, 1H), 5.12 (s, 2H), 4.24 (t, J=6.6 Hz, 2H), 3.53 (t, J=6.6 Hz, 2H), 3.33 (t, J=6.8 Hz, 2H), 2.71 (t, J=6.8 Hz, 2H), 2.05 (quint., J=6.6 Hz, 2H), 1.93 (quint., J=6.8 Hz, 2H), 1.80 (quint., J=6.8 Hz, 2H). HPLC (Condition A): Rt 2.39 min (purity 95.6%). MS (ESI+): 457.5.

Example 43

2-{4-[2-(3-Pyridin-4-yl-phenyl)-pyrimidin-5-yl]-pyrazol-1-yl}-1-pyrrolidin-1-yl-ethanone

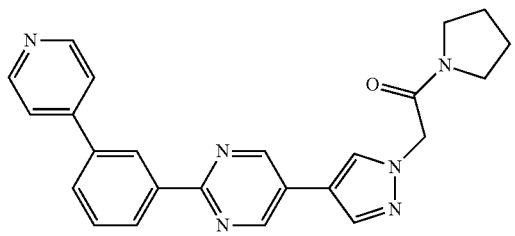 [SMILES: O=C(Cn1cc(-c2cnc(-c3cccc(-c4ccncc4)c3)nc2)cn1)N1CCCC1]

The title compound was obtained following procedure described for intermediate 5, step 1 but starting from 2-{4-[2-(3-Iodo-phenyl)-pyrimidin-5-yl]-pyrazol-1-yl}-1-pyrrolidin-1-yl-ethanone (intermediate 12, 150 mg; 0.33 mmol; 1.0 eq.) and 4-Pyridineboronic acid (80 mg; 0.65 mmol; 2.0 eq.) as a white solid (15 mg, 11%). 1H NMR (300 MHz, DMSO-d6) δ 9.21 (s, 2H), 8.75 (t, J=1.5 Hz, 1H), 8.69 (d, J=6.0 Hz, 2H), 8.50 (dt, J=8.0 Hz, 1.5 Hz, 1H), 8.38 (s, 1H), 8.15 (s, 1H), 7.95 (dt, J=8.0 Hz, 1.5 Hz, 1H), 7.79 (d, J=6.0 Hz, 2H), 7.70 (t, J=8.0 Hz, 1H), 5.12 (s, 2H), 3.52 (t, J=6.6 Hz, 2H), 3.32 (m, 2H), 1.93 (quint., J=6.6 Hz, 2H), 1.80 (quint., J=6.6 Hz, 2H). HPLC (Condition A): Rt 2.17 min (purity 99.1%). MS (ESI+): 411.4.

Example 44

1-(4-{2-[3-(1-Methyl-1H-pyrazol-4-yl)-phenyl]-pyrimidin-5-yl}-pyrazol-1-yl)-propan-2-one

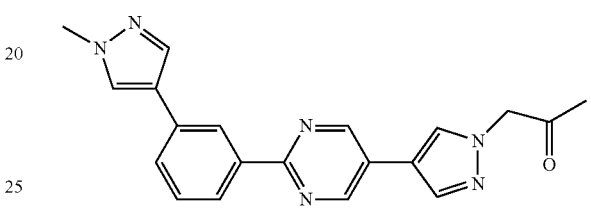

The title compound was obtained following procedure described for example 27 but starting from 2-[3-(1-methyl-1H-pyrazol-4-yl)phenyl]-5-(1H-pyrazol-4-yl)pyrimidine (example 3, 75 mg; 0.25 mmol; 1.0 eq.) and 1-Chloro-propan-2-one (59 μl; 0.74 mmol; 3.0 eq.) as a white powder (25 mg, 28%). 1H NMR (300 MHz, DMSO-d6): 9.17 (s, 2H), 8.53 (s, 1H), 8.34 (s, 1H), 8.25 (s, 1H), 8.21 (d, J=8.2 Hz, 1H), 8.17 (s, 1H), 7.92 (s, 1H), 7.70 (d, J=7.9 Hz, 1H), 7.51 (t, J=7.5 Hz, 1H), 5.23 (s, 2H), 3.89 (s, 3H), 2.16 (s, 3H). HPLC (Condition A): Rt 3.08 min (purity 98.3%). MS (ESI+): 359.4, (ESI−): 357.4.

Example 45

2-[3-(1-Methyl-1H-pyrazol-4-yl)-phenyl]-5-[1-(tetrahydro-furan-3-ylmethyl)-1H-pyrazol-4-yl]-pyrimidine

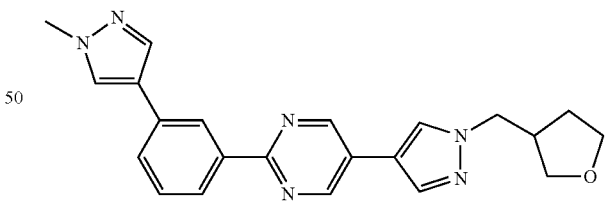

The title compound was obtained following procedure described for example 27 but starting from 2-[3-(1-methyl-1H-pyrazol-4-yl)phenyl]-5-(1H-pyrazol-4-yl)pyrimidine (example 3, 100 mg; 0.33 mmol; 1.0 eq.) and 3-Chloromethyl-tetrahydro-furan (39.88 mg; 0.33 mmol; 1.00 eq.) as a beige powder (32 mg, 25%). 1H NMR (300 MHz, DMSO-d6) δ 9.16 (s, 2H), 8.59-8.45 (m, 2H), 8.33-8.11 (m, 3H), 7.93 (s, 1H), 7.77-7.66 (m, 1H), 7.51 (t, J=7.7 Hz, 1H), 4.17 (d, J=7.5 Hz, 2H), 3.89 (s, 3H), 3.85-3.74 (m, 1H), 3.74-3.60 (m, 2H), 3.52 (dd, J=8.7, 5.4 Hz, 1H), 2.85-2.68 (m, 1H), 2.04-1.88 (m, 1H), 1.73-1.56 (m, 1H). HPLC (Condition A): Rt 3.34 min (purity 98.0%). MS (ESI+): 387.4.

Example 46

2-[3-(1-Methyl-1H-pyrazol-4-yl)-phenyl]-5-(1-ox-azol-2-ylmethyl-1H-pyrazol-4-yl)-pyrimidine

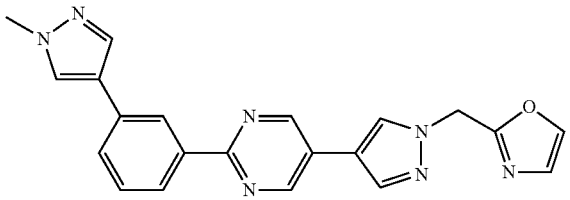 [SMILES: Cn1cc(-c2cccc(-c3ncc(-c4cnn(Cc5ncco5)c4)cn3)c2)cn1]

The title compound was obtained following procedure described for example 27 but starting from 2-[3-(1-methyl-1H-pyrazol-4-yl)phenyl]-5-(1H-pyrazol-4-yl)pyrimidine (example 3, 100 mg; 0.33 mmol; 1.0 eq.) and 2-Chloromethyl-oxazole (39 mg; 0.33 mmol; 1.0 eq) as a beige powder (27 mg, 21%). 1H NMR (300 MHz, DMSO-d6) δ 9.19 (s, 2H), 8.57 (d, J=16.9 Hz, 2H), 8.35-8.09 (m, 4H), 7.93 (s, 1H), 7.72 (d, J=7.4 Hz, 1H), 7.52 (t, J=7.7 Hz, 1H), 7.26 (s, 1H), 5.63 (s, 2H), 3.89 (s, 3H). HPLC (Condition A): Rt 3.09 min (purity 98.9%). MS (ESI+): 384.4.

Example 47

2-[3-(1-Methyl-1H-pyrazol-4-yl)-phenyl]-5-[1-(2-pyridin-2-yl-ethyl)-1H-pyrazol-4-yl]-pyrimidine

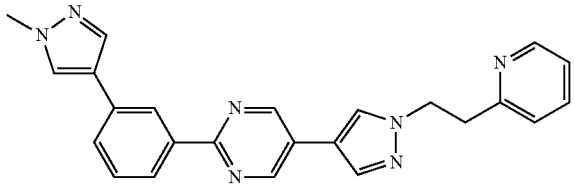 [SMILES: Cn1cc(-c2cccc(-c3ncc(-c4cnn(CCc5ccccn5)c4)cn3)c2)cn1]

The title compound was obtained following procedure described for example 27 but starting from 2-[3-(1-methyl-1H-pyrazol-4-yl)phenyl]-5-(1H-pyrazol-4-yl)pyrimidine (example 3, 100 mg; 0.33 mmol; 1.0 eq.) and 2-(2-Chloro-ethyl)-pyridine (47 mg; 0.33 mmol; 1.0 eq.) as a beige powder (6 mg, 4%). 1H NMR (300 MHz, DMSO-d6) δ 9.12 (s, 2H), 8.57-8.50 (m, 2H), 8.41 (s, 1H), 8.26 (s, 1H), 8.24-8.18 (m, 1H), 8.13 (d, J=0.6 Hz, 1H), 7.92 (d, J=0.7 Hz, 1H), 7.74-7.65 (m, 2H), 7.51 (t, J=7.7 Hz, 1H), 7.30-7.19 (m, 2H), 4.58 (t, J=7.3 Hz, 2H), 3.89 (s, 3H), 3.36-3.27 (m, 2H). HPLC (Condition A): Rt 2.62 min (purity 95.5%). MS (ESI+): 408.4.

Example 48

2-[2-Fluoro-3-(1-methyl-1H-pyrazol-4-yl)-phenyl]-5-(1-piperidin-4-yl-1H-pyrazol-4-yl)-pyrimidine Formate

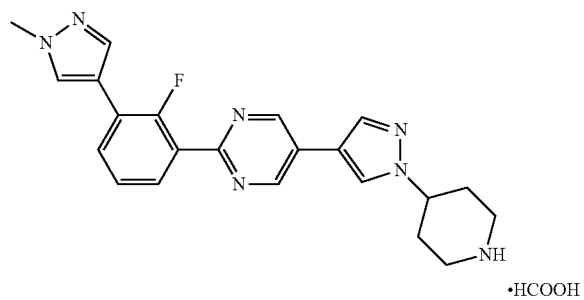 [SMILES: Cn1cc(-c2cccc(-c3ncc(-c4cnn(C5CCNCC5)c4)cn3)c2F)cn1 ; "·HCOOH"]

The title compound was obtained following procedure described for example 24 but starting from tert-butyl 4-[4-(2-iodopyrimidin-5-yl)-1H-pyrazol-1-yl]piperidine-1-carboxylate (intermediate 6, 249 mg; 0.55 mmol; 1.0 eq.), 3-bromo-2-fluorophenylboronic acid (155 mg; 0.71 mmol; 1.3 eq.) and 1-methyl-4-(4,4,5,5-tetramethyl-1,3,2-dioxaborolan-2-yl)-1H-pyrazole (308 mg; 1.48 mmol; 2.7 eq.) as an orange solid (40 mg, 16%). 1H NMR (300 MHz, DMSO-d6) δ 9.21 (s, 2H), 8.54 (s, 1H), 8.29 (s, 1H), 8.22 (d, J=2.2 Hz, 1H), 8.17 (s, 1H), 7.96 (s, 1H), 7.88-7.77 (m, 2H), 7.33 (t, J=7.7 Hz, 1H), 4.41-4.27 (m, 1H), 3.91 (s, 3H), 3.22-3.10 (m, 2H), 2.82-2.67 (m, 2H), 2.15-2.01 (m, 2H), 1.99-1.79 (m, 2H). HPLC (Condition A): Rt 2.17 min (purity 95.5%). MS (ESI+): 404.5.

Example 49

2-(4-{2-[3-(1-Methyl-1H-pyrazol-4-yl)-phenyl]-pyrimidin-5-yl}-pyrazol-1-yl)-acetamide

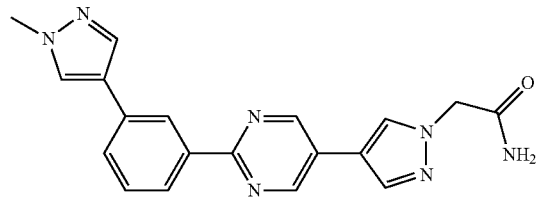 [SMILES: Cn1cc(-c2cccc(-c3ncc(-c4cnn(CC(N)=O)c4)cn3)c2)cn1]

The title compound was obtained following procedure described for example 27 but starting from 2-[3-(1-methyl-1H-pyrazol-4-yl)phenyl]-5-(1H-pyrazol-4-yl)pyrimidine (example 3, 100 mg; 0.33 mmol; 1.0 eq.) and 2-Bromo-acetamide (46 mg; 0.33 mmol; 1.0 eq.) as a beige powder (4 mg, 3%). HPLC (Condition A): Rt 2.65 min (purity 97.9%). MS (ESI+): 360.4.

Example 50

2-[4-(2-{3-[1-(2-Amino-ethyl)-1H-pyrazol-4-yl]-phenyl}-pyrimidin-5-yl)-pyrazol-1-yl]-1-pyrrolidin-1-yl-ethanone hydrochloride Step 1: formation of {2-[4-(3-{5-[1-(2-Oxo-2-pyrrolidin-1-yl-ethyl)-1H-pyrazol-4-yl]-pyrimidin-2-yl}-phenyl)-pyrazol-1-yl]-ethyl}-carbamic acid tert-butyl ester

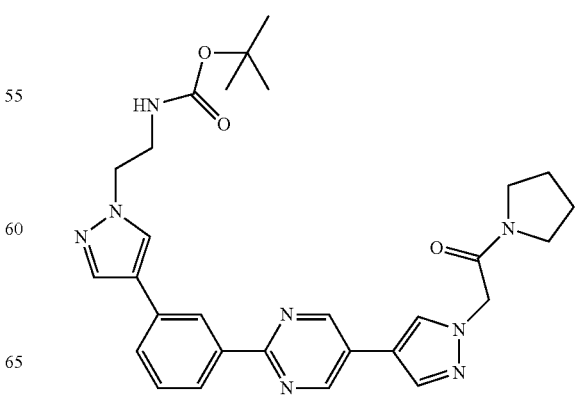

The title compound was obtained following procedure described for example 27 but starting from 2-(4-{2-[3-(1H-Pyrazol-4-yl)-phenyl]-pyrimidin-5-yl}-pyrazol-1-yl)-1-pyrrolidin-1-yl-ethanone (intermediate 14, 150 mg; 0.38 mmol; 1.0 eq.) and (2-Bromo-ethyl)-carbamic acid tert-butyl ester (17 mg; 0.08 mmol; 0.2 eq.) as a white solid (70 mg, 34%). 1H NMR (300 MHz, DMSO-d6) δ 9.18 (s, 2H), 8.55 (t, J=1.5 Hz, 1H), 8.37 (s, 1H), 8.24-8.21 (m, 2H), 8.14 (s, 1H), 7.95 (s, 1H), 7.71 (dt, J=7.8 Hz, 1.5 Hz, 1H), 7.52 (t, J=7.8 Hz, 1H), 6.99 (t, J=6.0 Hz, 1H), 5.12 (s, 2H), 4.18 (t, J=6.0 Hz, 2H), 3.53 (t, J=6.6 Hz, 2H), 3.40-3.31 (m, 4H), 1.93 (quint., J=6.6 Hz, 2H), 1.80 (quint., J=6.6 Hz, 2H), 1.36 (s, 9H). HPLC (Condition A): Rt 3.58 min (purity 95.0%). MS (ESI+): 543.6.

Step 2: Formation of 2-[4-(2-{3-[1-(2-Amino-ethyl)-1H-pyrazol-4-yl]-phenyl}-pyrimidin-5-yl)-pyrazol-1-yl]-1-pyrrolidin-1-yl-ethanone hydrochloride

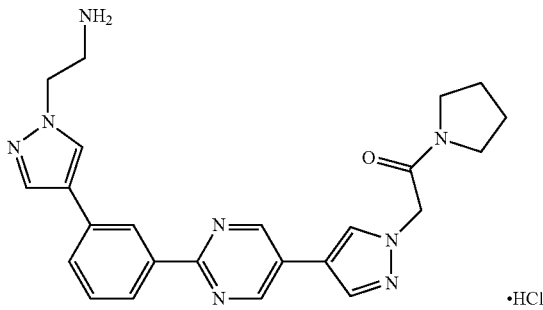 [SMILES: NCCn1cc(-c2cccc(-c3ncc(-c4cnn(CC(=O)N5CCCC5)c4)cn3)c2)cn1 ; Cl]

The title compound was obtained following procedure described for example 13, step 2 but starting from {2-[4-(3-{5-[1-(2-Oxo-2-pyrrolidin-1-yl-ethyl)-1H-pyrazol-4-yl]-pyrimidin-2-yl}-phenyl)-pyrazol-1-yl]-ethyl}-carbamic acid tert-butyl ester (70 mg; 0.13 mmol; 1.0 eq.) as a yellow solid (57 mg, 86%). 1H NMR (300 MHz, DMSO-d6) δ 9.18 (s, 2H), 8.58 (t, J=1.6 Hz, 1H), 8.39-8.38 (m, 2H), 8.24 (dt, J=7.8 Hz, 1.6 Hz, 1H), 8.23-8.06 (m, 6H), 7.75 (dt, J=7.8 Hz, 1.6 Hz, 1H), 7.54 (t, J=7.8 Hz, 1H), 5.13 (s, 2H), 4.44 (t, J=6.0 Hz, 2H), 3.53 (t, JO 6.7 Hz, 2H), 3.33 (m, 4H), 1.93 (quint., J=6.7 Hz, 2H), 1.80 (quint., J=6.7 Hz, 2H). HPLC (Condition A): Rt 2.31 min (purity 99.0%). MS (ESI+): 443.5.

Example 51

1-(4-Methyl-piperazin-1-yl)-2-(4-{2-[3-(1-methyl-1H-pyrazol-4-yl)-phenyl]-pyrimidin-5-yl}-pyrazol-1-yl)-ethanone hydrochloride

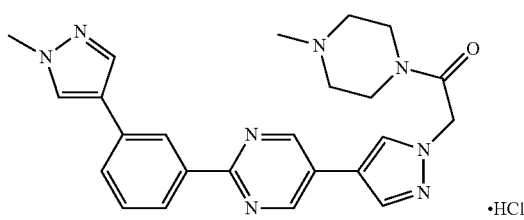 [SMILES: CN1CCN(C(=O)Cn2cc(-c3cnc(-c4cccc(-c5cnn(C)c5)c4)nc3)cn2)CC1 ; Cl]

The title compound was obtained following procedure described for example 25 but starting from (4-{2-[3-(1-Methyl-1H-pyrazol-4-yl)-phenyl]-pyrimidin-5-yl}-pyrazol-1-yl)-acetic acid (example 8, 100 mg; 0.28 mmol; 1.00 eq.) and 1-Methyl-piperazine (55 mg; 0.55 mmol; 2.0 eq.) as a white solid (20 mg, 15%). 1H NMR (300 MHz, DMSO-d6+D2O) d 9.16 (s, 2H), 8.52 (t, J=1.6 Hz, 1H), 8.31 (s, 1H), 8.25-8.18 (m, 2H), 8.15 (d, J=0.5 Hz, 1H), 7.91 (d, J=0.7 Hz, 1H), 7.76-7.66 (m, 1H), 7.52 (t, J=7.8 Hz, 1H), 5.29 (d, J=11.3 Hz, 2H), 4.52-4.29 (m, 1H), 4.24-4.08 (m, 1H), 3.88 (s, 3H), 3.56-3.29 (m, 3H), 3.21-2.89 (m, 3H), 2.84 (s, 3H). HPLC (Condition A): Rt 2.36 min (purity 98.4%). MS (ESI+): 443.5

Example 52

1-(3-Hydroxy-piperidin-1-I)-2-(4-{2-[3-(1-methyl-1H-pyrazol-4-yl)-phenyl]-pyrimidin-5-yl}-pyrazol-1-yl)-ethanone

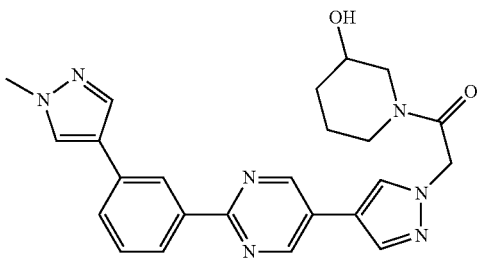 [SMILES: Cn1cc(-c2cccc(-c3ncc(-c4cnn(CC(=O)N5CCCC(O)C5)c4)cn3)c2)cn1]

The title compound was obtained following procedure described for example 25 but starting from (4-{2-[3-(1-Methyl-1H-pyrazol-4-yl)-phenyl]-pyrimidin-5-yl}-pyrazol-1-yl)-acetic acid (example 8, 100 mg; 0.28 mmol; 1.0 eq.) and [Dimethylamino-([1,2,3]triazolo[4,5-b]pyridin-3-yloxy)-methylene]-dimethyl-ammonium; hexafluoro phosphate (158.3 mg; 0.42 mmol; 1.50 eq.) as a white solid (75 mg, 61%). 1H NMR (300 MHz, DMSO-d6) δ 9.18 (s, 2H), 8.54 (s, 1H), 8.37 (d, J=3.7 Hz, 1H), 8.31-8.20 (m, 2H), 8.14 (s, 1H), 7.93 (s, 1H), 7.72 (d, J=7.8 Hz, 1H), 7.52 (t, J=7.7 Hz, 1H), 5.33-5.12 (m, 2H), 4.95 (d, J=4.0 Hz, 1H), 4.15-4.01 (m, 0.6H), 3.90 (s, 3H), 3.74-3.62 (m, 1H), 3.62-3.48 (m, 0.6H), 3.48-3.37 (m, 1H), 3.37-3.20 (m, 0.4H), 3.20-2.99 (m, 0.8H), 2.78-2.61 (m, 0.6H), 1.97-1.20 (m, 4H). HPLC (Condition A): Rt 2.70 min (purity 97.8%). MS (ESI+): 444.5, mp=198-200° C.

Example 53

2-[3-(1-Methyl-1H-pyrazol-4-yl)-phenyl]-5-[1-(2-pyridin-4-yl-ethyl)-1H-pyrazol-4-yl]-pyrimidine

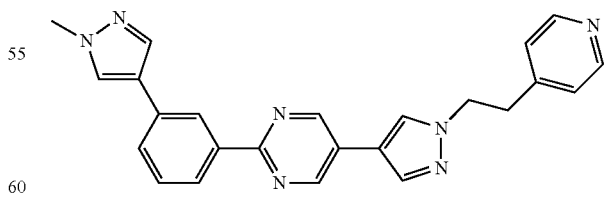

A solution of 2-[3-(1-methyl-1H-pyrazol-4-yl)phenyl]-5-(1H-pyrazol-4-yl)pyrimidine (example 3, 120 mg; 0.40 mmol; 1.0 eq.) in dry DMA (1 mL) was added over a suspension of NaH (60% in oil, 28 mg; 1.19 mmol; 3.0 eq.) in dry DMA (2 mL) maintained at 0° C. under nitrogen atmosphere. The resulting mixture was stirred for one hour at 0° C. then heated at 100° C. O/N after the addition of a solution of 14-(2-Bromo-ethyl)-pyridine hydrobromide (159 mg; 0.60 mmol; 1.5 eq.) in DMA (2 mL). Cesium carbonate (388 mg; 1.19 mmol; 3.00 eq.) and 4-(2-Bromo-ethyl)-pyridine hydrobromide (159 mg; 0.60 mmol; 1.5 eq.) were added and the reaction mixture was heated again at 100° C. O/N. Reaction mixture was then cooled down to RT and quenched with water and extracted with DCM (three times). Combined organic phases were washed with water, brine, dried over magnesium sulfate, filtered and concentrated. The resulting oil was purified by autopreparative LC/MS to give the title compound a white foam (80 mg, 49%). 1H NMR (300 MHz, DMSO-d6) δ 9.12 (s, 2H), 8.56-8.50 (m, 1H), 8.50-8.41 (m, 2H), 8.38 (s, 1H), 8.26 (s, 1H), 8.24-8.17 (m, 1H), 8.15 (s, 1H), 7.92 (s, 1H), 7.77-7.66 (m, 1H), 7.51 (t, J=7.7 Hz, 1H), 7.29-7.19 (m, 2H), 4.48 (t, J=7.1 Hz, 2H), 3.89 (s, 3H), 3.21 (t, J=7.0 Hz, 2H). HPLC (Condition A): Rt 2.47 min (purity 99.6%). MS (ESI+): 408.4.

Example 54

2-(4-{2-[3-(1-Methyl-1H-pyrazol-4-yl)-phenyl]-pyrimidin-5-yl}-pyrazol-1-yl)-N-(tetrahydro-pyran-4-yl)-acetamide

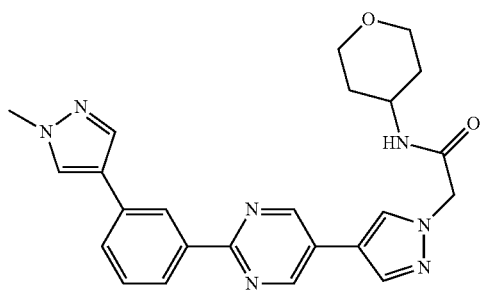 [SMILES: Cn1cc(-c2cccc(-c3ncc(-c4cnn(CC(=O)NC5CCOCC5)c4)cn3)c2)cn1]

The title compound was obtained following procedure described for example 25 but starting from (4-{2-[3-(1-Methyl-1H-pyrazol-4-yl)-phenyl]-pyrimidin-5-yl}-pyrazol-1-yl)-acetic acid (example 8, 100 mg; 0.28 mmol; 1.0 eq.) and tetrahydro-pyran-4-ylamine (56 mg; 0.55 mmol; 2.0 eq.) as a white powder (9 mg, 14%). 1H NMR (300 MHz, DMSO-d6) δ 9.19 (s, 2H), 8.54 (s, 1H), 8.43 (s, 1H), 8.37-8.18 (m, 3H), 8.15 (s, 1H), 7.93 (s, 1H), 7.77-7.67 (m, 1H), 7.52 (t, J=7.7 Hz, 1H), 5.21 (s, 0.3H), 4.86 (s, 1.7H), 3.98-3.69 (m, 6H), 3.46-3.26 (m, 2H), 1.82-1.66 (m, 2H), 1.53-1.30 (m, 2H). HPLC (Condition A): Rt 2.64 min (purity 96.6%). MS (ESI+): 444.3.

Example 55

2-(4-{2-[3-(1-Methyl-1H-pyrazol-4-yl)-phenyl]-pyrimidin-5-yl}-pyrazol-1-yl)-1-(2-oxa-6-aza-spiro[3.3]hept-6-yl)-ethanone

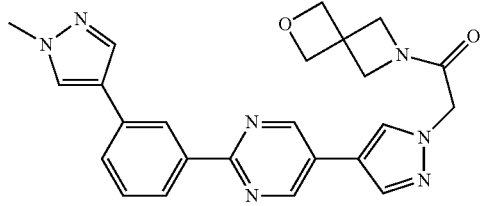 [SMILES: Cn1cc(-c2cccc(-c3ncc(-c4cnn(CC(=O)N5CC6(COC6)C5)c4)cn3)c2)cn1]

The title compound was obtained following procedure described for example 25 but starting from 4-{2-[3-(1-Methyl-1H-pyrazol-4-yl)-phenyl]-pyrimidin-5-yl}-pyrazol-1-yl)-acetic acid (example 8, 100 mg; 0.28 mmol; 1.0 eq.) and 2-Oxa-6-aza-spiro[3.3]heptane oxalate (105 mg; 0.55 mmol; 2.0 eq.) as a white powder (40 mg, 33%). 1H NMR (300 MHz, DMSO-d6) δ 9.18 (s, 1H), 8.54 (s, 1H), 8.38 (s, 1H), 8.27 (s, 1H), 8.22 (d, J=8.0 Hz, 1H), 8.16 (s, 1H), 7.93 (s, 1H), 7.72 (d, J=7.9 Hz, 1H), 7.52 (t, J=7.8 Hz, 1H), 4.92 (s, 2H), 4.69 (s, 4H), 4.36 (s, 2H), 4.10 (s, 2H), 3.90 (s, 3H). HPLC (Condition A): Rt 2.50 min (purity 98.3%). MS (ESI+): 442.3.

Example 56

2-(4-{2-[3-(2-Methyl-thiazol-5-yl)-phenyl]-pyrimidin-5-yl}-pyrazol-1-yl)-1-pyrrolidin-1-yl-ethanone

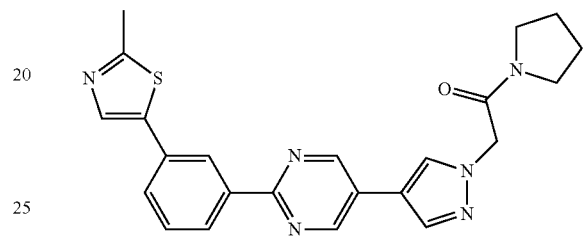

The title compound was obtained following procedure described for example 37 but starting from 2-{4-[2-(3-Iodo-phenyl)-pyrimidin-5-yl]-pyrazol-1-yl}-1-pyrrolidin-1-yl-ethanone (intermediate 12, 200 mg; 0.44 mmol; 1.0 eq.) and 5-Bromo-2-methyl-thiazole (77 mg; 0.44 mmol; 1.0 eq.) as a white solid (30 mg, 16%). 1H NMR (300 MHz, DMSO-d6) d 9.21 (s, 2H), 8.55 (t, J=1.5 Hz, 1H), 8.37-8.34 (m, 2H), 8.14-8.13 (m, 2H), 7.82 (ddd, J=7.8 Hz, 2.0 Hz, 1.5 Hz, 1H), 7.60 (t, J=7.8 Hz, 1H), 5.12 (s, 2H), 3.53 (t, J=6.8 Hz, 2H), 3.32 (t, J=6.8 Hz, 2H), 2.71 (s, 3H), 1.93 (quint., J=6.8 Hz, 2H), 1.80 (quint., J=6.8 Hz, 2H). HPLC (Condition A): Rt 3.17 min (purity 97.4%). MS (ESI+): 431.4.

Example 57

2-[3-(1-Methyl-1H-pyrazol-4-yl)-phenyl]-5-[1-(2-piperidin-1-yl-ethyl)-1H-pyrazol-4-yl]-pyrimidine

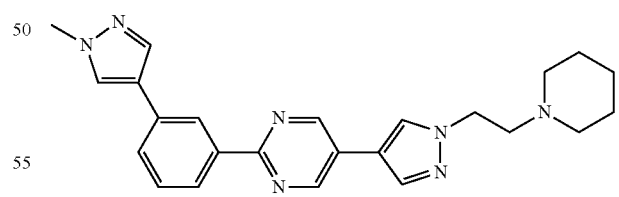

The title compound was obtained following procedure described for example 27 but starting from 2-[3-(1-methyl-1H-pyrazol-4-yl)phenyl]-5-(1H-pyrazol-4-yl)pyrimidine (example 3, 120 mg; 0.40 mmol; 1.0 eq.) and 1-(2-Chloro-ethyl)-piperidine hydrochloride (110 mg; 0.60 mmol; 1.5 eq.) as a white solid (80 mg, 49%). 1H NMR (300 MHz, DMSO-d6) δ 9.15 (s, 2H), 8.53 (t, J=1.5 Hz, 1H), 8.45 (s, 1H), 8.26 (s, 1H), 8.25-8.17 (m, 1H), 8.12 (s, 1H), 7.92 (d, J=0.6 Hz, 1H), 7.77-7.66 (m, 1H), 7.52 (t, J=7.8 Hz, 1H), 4.27 (t, J=6.7 Hz, 2H), 3.90 (s, 3H), 2.71 (t, J=6.7 Hz, 2H), 2.46-2.33 (m, 4H), 1.56-1.29 (m, 6H). HPLC (Condition A): Rt 2.59 min (purity 98.1%). MS (ESI+): 414.5.

Example 58

2-[3-(1-Methyl-1H-pyrazol-4-yl)-phenyl]-5-[1-(2-pyrrolidin-1-yl-ethyl)-1H-pyrazol-4-yl]-pyrimidine

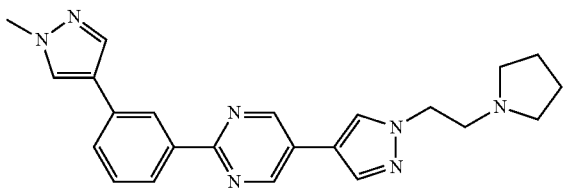 [SMILES: Cn1cc(-c2cccc(-c3ncc(-c4cnn(CCN5CCCC5)c4)cn3)c2)cn1]

The title compound was obtained following procedure described for example 27 but starting from 2-[3-(1-methyl-1H-pyrazol-4-yl)phenyl]-5-(1H-pyrazol-4-yl)pyrimidine (example 3, 120 mg; 0.40 mmol; 1.0 eq.) and 1-(2-Chloro-ethyl)-pyrrolidine hydrochloride (101 mg; 0.60 mmol; 1.5 eq.) as a beige foam (75 mg, 47%). 1H NMR (300 MHz, DMSO-d6) δ 9.15 (s, 2H), 8.53 (t, J=1.6 Hz, 1H), 8.46 (s, 1H), 8.26 (s, 1H), 8.24-8.18 (m, 1H), 8.12 (s, 1H), 7.92 (d, J=0.6 Hz, 1H), 7.77-7.68 (m, 1H), 7.51 (t, J=7.8 Hz, 1H), 4.27 (t, J=6.6 Hz, 2H), 3.89 (s, 3H), 2.87 (t, J=6.6 Hz, 2H), 2.50-2.40 (m, 4H), 1.73-1.58 (m, 4H). MS (ESI+): 400.4.

Example 59

2-[4-(2-{3-[1-(2-Hydroxy-ethyl)-1H-pyrazol-4-yl]-phenyl}-pyrimidin-5-yl)-pyrazol-1-yl]-1-pyrrolidin-1-yl-ethanone

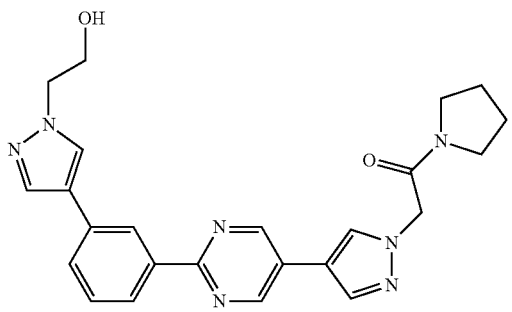 [SMILES: O=C(Cn1cc(-c2cnc(-c3cccc(-c4cnn(CCO)c4)c3)nc2)cn1)N1CCCC1]

The title compound was obtained following procedure described for intermediate 5, step 1 but starting from 2-{4-[2-(3-Iodo-phenyl)-pyrimidin-5-yl]-pyrazol-1-yl}-1-pyrrolidin-1-yl-ethanone (intermediate 12, 130 mg; 0.28 mmol; 1.0 eq.) and 2-[4-(4,4,5,5-Tetramethyl-[1,3,2]dioxaborolan-2-yl)-pyrazol-1-yl]-ethanol (101 mg; 0.42 mmol; 1.5 eq.) as a white solid (45 mg, 36%). 1H NMR (300 MHz, DMSO-d6) δ 9.18 (s, 2H), 8.55 (t, J=1.6 Hz, 1H), 8.37 (s, 1H), 8.26 (s, 1H), 8.22 (dt, J=7.8 Hz, 1.6 Hz, 1H), 8.14 (d, J=0.6 Hz, 1H), 7.95 (d, J=0.6 Hz, 1H), 7.74-7.70 (m, 1H), 7.52 (t, J=7.8 Hz, 1H), 5.12 (s, 2H), 4.96 (t, J=5.6 Hz, 1H), 4.19 (t, J=5.6 Hz, 2H), 3.79 (q, J=5.6 Hz, 2H), 3.53 (t, J=6.6 Hz, 2H), 3.32 (t, J=6.6 Hz, 2H), 1.91 (quint., J=6.6 Hz, 2H), 1.80 (quint., J=6.8 Hz, 2H). HPLC (Condition A): Rt 2.64 min (purity 97.7%). MS (ESI+): 444.4.

Example 60

N-(1-Hydroxymethyl-propyl)-2-(4-{2-[3-(1-methyl-1H-pyrazol-4-yl)-phenyl]-pyrimidin-5-yl}-pyrazol-1-yl)-acetamide

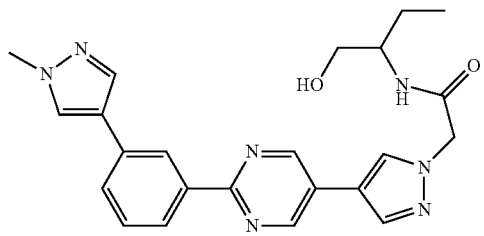 [SMILES: CCC(CO)NC(=O)Cn1cc(-c2cnc(-c3cccc(-c4cnn(C)c4)c3)nc2)cn1]

The title compound was obtained following procedure described for example 25 but starting from (4-{2-[3-(1-Methyl-1H-pyrazol-4-yl)-phenyl]-pyrimidin-5-yl}-pyrazol-1-yl)-acetic acid (example 8, 100 mg; 0.28 mmol; 1.0 eq.) and 2-Amino-butan-1-ol (49 mg; 0.55 mmol; 2.0 eq.) as a white powder (14 mg, 12%). 1H NMR (300 MHz, DMSO-d6) δ 9.18 (s, 2H), 8.54 (t, J=1.6 Hz, 1H), 8.43 (s, 1H), 8.27 (s, 1H), 8.25-8.19 (m, 1H), 8.15 (d, J=0.6 Hz, 1H), 8.00 (d, J=8.5 Hz, 1H), 7.93 (d, J=0.7 Hz, 1H), 7.75-7.68 (m, 1H), 7.52 (t, J=7.8 Hz, 1H), 4.88 (d, J=2.0 Hz, 2H), 3.90 (s, 3H), 3.72-3.58 (m, 1H), 3.42-3.27 (m, 3H), 1.68-1.51 (m, 1H), 1.42-1.25 (m, 1H), 0.86 (t, J=7.4 Hz, 3H). HPLC (Condition A): Rt 2.60 min (purity 98.0%).

MS (ESI+): 432.3, (ESI−): 430.2.

Example 61

(3-exo)-8-Methyl-3-(4-{2-[3-(1-methyl-1H-pyrazol-4-yl)-phenyl]-pyrimidin-5-yl}-pyrazol-1-yl)-8-aza-bicyclo[3.2.1]octane

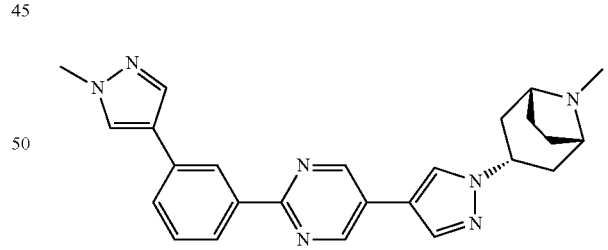

The title compound was obtained following procedure described for example 13, step 1, but starting from 2-[3-(1-Methyl-1H-pyrazol-4-yl)-phenyl]-5-(4,4,5,5-tetramethyl-[1,3,2]dioxaborolan-2-yl)-pyrimidine (intermediate 15, 150 mg; 0.25 mmol; 1.0 eq.) and (3-exo)-3-(4-Iodo-pyrazol-1-yl)-8-methyl-8-aza-bicyclo[3.2.1]octane (intermediate 16, 79 mg; 0.25 mmol; 1.0 eq.) as a beige foam (45 mg, 43%). 1H NMR (300 MHz, DMSO-d6) δ 9.15 (s, 2H), 8.57-8.47 (m, 2H), 8.27 (s, 1H), 8.24-8.19 (m, 1H), 8.13 (s, 1H), 7.93 (s, 1H), 7.74-7.68 (m, 1H), 7.51 (t, J=7.8 Hz, 1H), 4.57 (tt, J=11.4, 5.7 Hz, 1H), 3.89 (s, 3H), 3.37-3.24 (m, 2H), 2.33 (s, 3H), 2.24-2.10 (m, 2H), 2.10-2.00 (m, 2H), 1.96-1.84 (m, 2H), 1.80-1.69 (m, 2H). HPLC (Condition A): Rt 2.55 min (purity 98.9%). MS (ESI+): 426.3.

Example 62

4-(4-{2-[3-(1-Methyl-1H-pyrazol-4-yl)-phenyl]-pyrimidin-5-yl}-pyrazol-1-yl)-cyclohexanecarboxylic acid Step 1: formation of 4-(4-{2-[3-(1-Methyl-1H-pyrazol-4-yl)-phenyl]-pyrimidin-5-yl}-pyrazol-1-yl)-cyclohexanecarboxylic acid ethyl ester

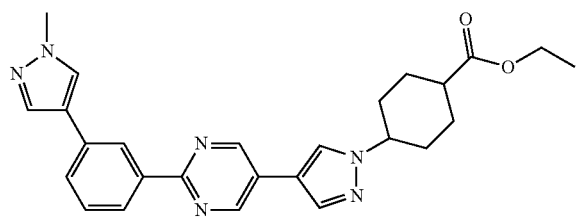 [SMILES: CCOC(=O)C1CCC(n2cc(-c3cnc(-c4cccc(-c5cnn(C)c5)c4)nc3)cn2)CC1]

4-Methanesulfonyloxy-cyclohexanecarboxylic acid ethyl ester (AOKChem Co., Ltd; 689 mg; 2.75 mmol; 1.04 eq.) in DMF (5 mL) was added in one portion to a suspension of 2-[3-(1-methyl-1H-pyrazol-4-yl)phenyl]-5-(1H-pyrazol-4-yl)pyrimidine (example 3, 104 mg; 0.34 mmol; 1.0 eq.) and cesium carbonate (2.35 g; 7.21 mmol; 2.7 eq.) in DMF (10 mL). The reaction mixture was heated in MW at 120° C. for 35 min. It was then poured into water and filtered. The resulting solid was triturated with ACN to give the title compound as a yellow solid (264 mg, 17%). 1H NMR (300 MHz, DMSO-d6) δ 9.16 (s, 2H), 8.57-8.46 (m, 2H), 8.26 (s, 1H), 8.24-8.18 (m, 1H), 8.13 (s, 1H), 7.92 (s, 1H), 7.77-7.66 (m, 1H), 7.51 (t, J=7.8 Hz, 1H), 4.32-3.99 (m, 3H), 3.89 (s, 3H), 2.48-2.34 (m, 1H), 2.23-1.48 (m, 8H), 1.27-1.14 (m, 3H). MS (ESI+): 457.3.

Step 2: Formation of 4-(4-{2-[3-(1-Methyl-1H-pyrazol-4-yl)-phenyl]-pyrimidin-5-yl}-pyrazol-1-yl)-cyclohexanecarboxylic acid

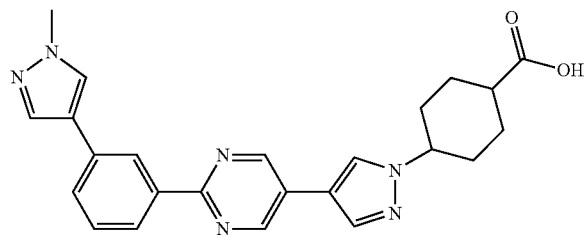 [SMILES: Cn1cc(-c2cccc(-c3ncc(-c4cnn(C5CCC(C(=O)O)CC5)c4)cn3)c2)cn1]

A solution of 4-(4-{2-[3-(1-Methyl-1H-pyrazol-4-yl)-phenyl]-pyrimidin-5-yl}-pyrazol-1-yl)-cyclohexanecarboxylic acid ethyl ester (50 mg; 0.11 mmol; 1.0 eq.) and NaOH (5.00 mL of a 1N solution; 5.0 mmol; 46 eq.) in iPrOH (20 mL) was stirred at RT for 16 h. It was then poured into a 1 N solution of HCl and extracted with EtOAc (twice). Combined organic phases were washed with brine, dried over magnesium sulfate, filtered and concentrated to give a cis-trans mixture of the title compound as a yellow solid (30 mg, 59%). 1H NMR (300 MHz, DMSO-d6) δ 9.17 (s, 2H), 8.57-8.47 (m, 2H), 8.27 (s, 1H), 8.24-8.17 (m, 1H), 8.13 (s, 1H), 7.92 (s, 1H), 7.78-7.66 (m, 1H), 7.51 (t, J=7.8 Hz, 1H), 4.31-4.15 (m, 1H), 3.89 (s, 3H), 2.66-1.45 (m, 9H). HPLC (Condition A): Rt 3.23 min (purity 93.0%). HPLC (Chiralpak IA, EtOH:TFA:THF 90:0.1:10): Rt 7.23; 10.97 min (purity 30.2: 66.6%); MS (ESI+): 429.2.

Example 63

2-[3-(1-Methyl-1H-pyrazol-4-yl)-phenyl]-5-(1H-pyrazol-4-yl)-pyrimidine

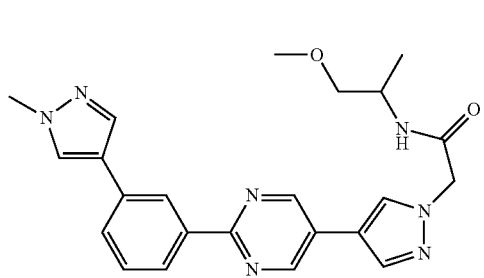 [SMILES: COCC(C)NC(=O)Cn1cc(-c2cnc(-c3cccc(-c4cnn(C)c4)c3)nc2)cn1]

The title compound was obtained following procedure described for example 25, but starting from (4-{2-[3-(1-Methyl-1H-pyrazol-4-yl)-phenyl]-pyrimidin-5-yl}-pyrazol-1-yl)-acetic acid (example 8, 100 mg; 0.28 mmol; 1.0 eq.) and 2-Methoxy-1-methyl-ethylamine (49 mg; 0.55 mmol; 2.0 eq.) as a white solid (13 mg, 11%). 1H NMR (300 MHz, DMSO) δ 9.18 (s, 2H), 8.54 (t, J=1.6 Hz, 1H), 8.42 (s, 1H), 8.27 (s, 1H), 8.25-8.19 (m, 2H), 8.15 (s, 1H), 7.93 (s, 1H), 7.75-7.68 (m, 1H), 7.52 (t, J=7.7 Hz, 1H), 4.86 (s, 2H), 4.03-3.88 (m, 1H), 3.90 (s, 3H), 3.36-3.13 (m, 5H), 1.08 (d, J=6.8 Hz, 3H). MS (ESI+): 432.3.

Example 64

2-[3-(1-Methyl-1H-pyrazol-4-yl)-phenyl]-5-{1-[2-(1-methyl-pyrrolidin-2-yl)-ethyl]-1H-pyrazol-4-yl}-pyrimidine

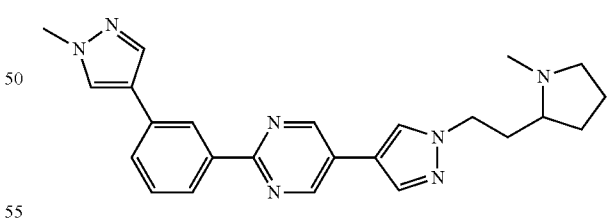

The title compound was obtained following procedure described for example 27, but starting from 2-[3-(1-methyl-1H-pyrazol-4-yl)phenyl]-5-(1H-pyrazol-4-yl)pyrimidine (example 3, 120 mg; 0.40 mmol; 1.0 eq.) and 2-(2-Chloro-ethyl)-1-methyl-pyrrolidine hydrochloride (110 mg; 0.60 mmol; 1.5 eq.) as a white solid (75 mg, 465). 1H NMR (300 MHz, DMSO-d6) δ 9.17 (s, 2H), 8.53 (t, J=1.6 Hz, 1H), 8.51 (s, 1H), 8.27 (s, 1H), 8.25-8.19 (m, 1H), 8.18-8.16 (m, 1H), 7.92 (d, J=0.7 Hz, 1H), 7.75-7.69 (m, 1H), 7.52 (t, J=7.8 Hz, 1H), 4.39-4.11 (m, 2H), 3.90 (s, 3H), 3.29-3.16 (m, 2H), 3.12-3.04 (m, 1H), 2.57 (s, 3H), 2.43-2.26 (m, 1H), 2.16-1.70

(m, 4H), 1.64-1.47 (m, 1H). HPLC (Condition A): Rt 2.51 min (purity 99.3%). MS (ESI+): 414.5.

Example 65

2-[3-(1-Methyl-1H-pyrazol-4-yl)-phenyl]-5-(1-pyrrolidin-3-ylmethyl-1H-pyrazol-4-yl)-pyrimidine hydrochloride Step 1: Formation of 3-(4-{2-[3-(1-Methyl-1H-pyrazol-4-yl)-phenyl]-pyrimidin-5-yl}-pyrazol-1-ylmethyl)-pyrrolidine-1-carboxylic acid tert-butyl ester

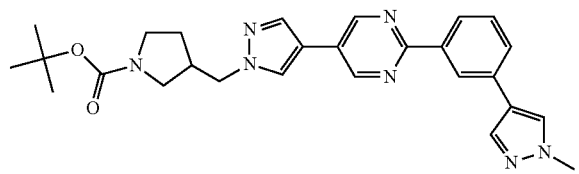 [SMILES: Cn1cc(-c2cccc(-c3ncc(-c4cnn(CC5CCN(C(=O)OC(C)(C)C)C5)c4)cn3)c2)cn1]

A solution of 3-Methanesulfonyloxymethyl-pyrrolidine-1-carboxylic acid tert-butyl ester (prepared as described in WO2010100144; 200 mg; 0.64 mmol; 1.0 eq.), cesium carbonate (420 mg; 1.29 mmol; 2.0 eq.) and 2-[3-(1-methyl-1H-pyrazol-4-yl)phenyl]-5-(1H-pyrazol-4-yl)pyrimidine (example 3, 195 mg; 0.64 mmol; 1.0 eq.) was heated at 100° C. O/N. The reaction mixture was then diluted with water and extracted with EtOAc (three times). Combined organic phases were washed with brine (three times), dried over magnesium sulfate, filtered and concentrated. Purification by autopreparative LC/MS afforded the title compound as a white foam (179 mg, 57%). MS (ESI+): 486.5.

Step 2: Formation of 2-[3-(1-Methyl-1H-pyrazol-4-yl)-phenyl]-5-(1-pyrrolidin-3-ylmethyl-1H-pyrazol-4-yl)-pyrimidine hydrochloride

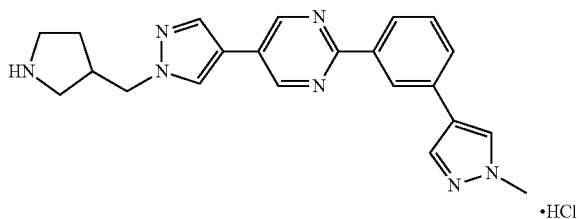 [SMILES: Cn1cc(-c2cccc(-c3ncc(-c4cnn(CC5CCNC5)c4)cn3)c2)cn1 ; Cl]

The title compound was obtained following procedure described for example 13, step 2, but starting from 3-(4-{2-[3-(1-Methyl-1H-pyrazol-4-yl)-phenyl]-pyrimidin-5-yl}-pyrazol-1-ylmethyl)-pyrrolidine-1-carboxylic acid tert-butyl ester (170 mg; 0.35 mmol; 1.0 eq.) as a yellow powder (145 mg, 98%). 1H NMR (300 MHz, DMSO-d6) δ 9.49-9.22 (m, 2H), 9.18 (s, 2H), 8.53 (d, J=3.3 Hz, 2H), 8.27 (s, 1H), 8.25-8.16 (m, 2H), 7.93 (s, 1H), 7.75-7.68 (m, 1H), 7.52 (t, J=7.7 Hz, 1H), 4.30 (d, J=7.2 Hz, 2H), 3.90 (s, 3H), 3.34-3.07 (m, 3H), 3.07-2.90 (m, 1H), 2.88-2.72 (m, 1H), 2.12-1.93 (m, 1H), 1.79-1.61 (m, 1H). HPLC (Condition A): Rt 2.55 min (purity 97.7%). MS (ESI+): 386.2.

Example 66

5-(1-Azetidin-3-ylmethyl-1H-pyrazol-4-yl)-2-[3-(1-methyl-1H-pyrazol-4-yl)-phenyl]-pyrimidine hydrochloride Step 1: Formation of 3-(4-{2-[3-(1-Methyl-1H-pyrazol-4-yl)-phenyl]-pyrimidin-5-yl}-pyrazol-1-ylmethyl)-azetidine-1-carboxylic acid tert-butyl ester

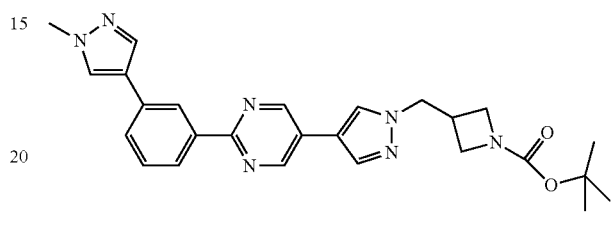

A solution of 3-Methanesulfonyloxymethyl-azetidine-1-carboxylic acid tert-butyl ester (Matrix scientific, 200 mg; 0.68 mmol; 1.0 eq.), cesium carbonate (442 mg; 1.36 mmol; 2.0 eq.) and 2-[3-(1-methyl-1H-pyrazol-4-yl)phenyl]-5-(1H-pyrazol-4-yl)pyrimidine (example 3, 205 mg; 0.68 mmol; 1.0 eq.) in dry DMA (3 mL) was heated at 100° C. O/N. The reaction mixture was then diluted with water and extracted with EtOAc (three times). Combined organic phases were washed with brine (three times), dried over magnesium sulfate, filtered and concentrated. The crude was dissolved in DMSO and precipitated by addition of acetonitrile. It was filtered, rinced with acetonitrile and dried under vacuum to give the title compound as a yellow powder (423 mg, quantitative). MS (ESI+): 472.3.

Step 2: Formation of 5-(1-Azetidin-3-ylmethyl-1H-pyrazol-4-yl)-2-[3-(1-methyl-1H-pyrazol-4-yl)-phenyl]-pyrimidine hydrochloride

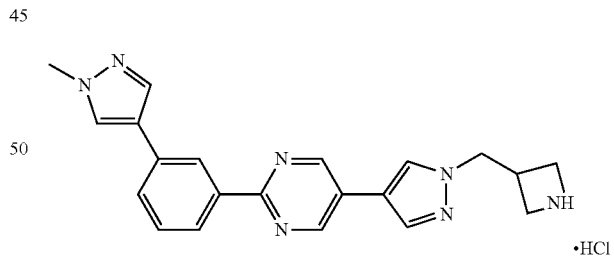

The title compound was obtained following procedure described for example 13, step 2, but starting from 3-(4-{2-[3-(1-Methyl-1H-pyrazol-4-yl)-phenyl]-pyrimidin-5-yl}-pyrazol-1-ylmethyl)-azetidine-1-carboxylic acid tert-butyl ester (240 mg; 0.51 mmol; 1.0 eq.) as a yellow foam (55 mg, 26%). 1H NMR (300 MHz, DMSO) δ 9.18 (s, 2H), 9.14-8.86 (m, 2H), 8.53 (t, J=1.7 Hz, 1H), 8.48 (s, 1H), 8.26 (s, 1H), 8.25-8.18 (m, 2H), 7.92 (d, J=0.8 Hz, 1H), 7.75-7.68 (m, 1H), 7.52 (t, J=7.8 Hz, 1H), 4.48 (d, J=7.1 Hz, 2H), 4.11-3.95 (m, 2H), 3.95-3.78 (m, 5H), 3.36-3.20 (m, 1H)..HPLC (Condition A): Rt 2.49 min (purity 99.4%). MS (ESI+): 372.3.

Example 67

5-[1-(2,2-Difluoro-ethyl)-1H-pyrazol-4-yl]-2-[3-(1-methyl-1H-pyrazol-4-yl)-phenyl]-pyrimidine

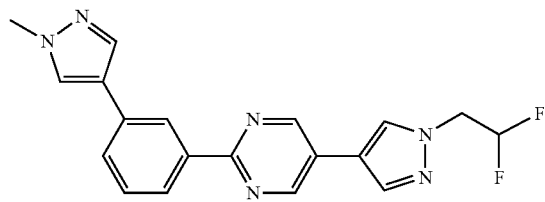 [SMILES: Cn1cc(-c2cccc(-c3ncc(-c4cnn(CC(F)F)c4)cn3)c2)cn1]

The title compound was obtained following procedure described for example 66, step 1, but starting from 2-[3-(1-methyl-1H-pyrazol-4-yl)phenyl]-5-(1H-pyrazol-4-yl)pyrimidine (255 mg; 0.84 mmol; 1.0 eq.) and methanesulfonic acid 2,2-difluoro-ethyl ester (prepared as described in Journal of Organic Chemistry, 74(12), 4547-4553; 2009, 150 mg, 0.84 mmol, 1.0 eq.) as a white solid (140 mg, 45%). NMR (300 MHz, DMSO-d6) δ 9.19 (s, 2H), 8.57-8.47 (m, 2H), 8.30-8.20 (m, 3H), 7.93 (d, J=0.8 Hz, 1H), 7.76-7.69 (m, 1H), 7.52 (t, J=7.7 Hz, 1H), 6.44 (tt, J=54.8, 3.6 Hz, 1H), 4.73 (td, J=15.3, 3.6 Hz, 2H), 3.90 (s, 3H). HPLC (Condition A): Rt 3.46 min (purity 96.4%).

Example 68

1-Morpholin-4-yl-2-{4-[2-(3-pyridin-4-yl-phenyl)-pyrimidin-5-yl]-pyrazol-1-yl}-ethanone

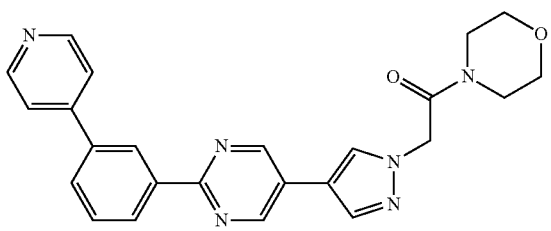 [SMILES: O=C(Cn1cc(-c2cnc(-c3cccc(-c4ccncc4)c3)nc2)cn1)N1CCOCC1]

The title compound was obtained following procedure described for intermediate 5, step 1, but starting from 2-{4-[2-(3-Iodo-phenyl)-pyrimidin-5-yl]-pyrazol-1-yl}-1-morpholin-4-yl-ethanone (intermediate 17, 200 mg; 0.42 mmol; 1.0 eq.) and 4-Pyridineboronic acid (77 mg; 0.63 mmol; 1.5 eq.) as a beige solid (25 mg, 135). 1H NMR (300 MHz, DMSO-d6) d 9.24 (s, 2H), 8.99 (d, J=6.8 Hz, 2H), 8.63 (dt, J=8.0 Hz, 1.5 Hz, 1H), 8.45 (d, J=6.8 Hz, 2H), 8.41 (s, 1H), 8.22-8.15 (m, 3H), 7.81 (t, J=8.0 Hz, 1H), 5.26 (s, 2H), 3.65-3.45 (m, 8H). HPLC (Condition A): Rt 2.03 min (purity 98.7%). MS (ESI+): 427.4.

Example 69

2-[3-(1-Methyl-1H-pyrazol-4-yl)-phenyl]-5-{1-[2-(tetrahydro-pyran-4-yl)-ethyl]-1H-pyrazol-4-yl}-pyrimidine

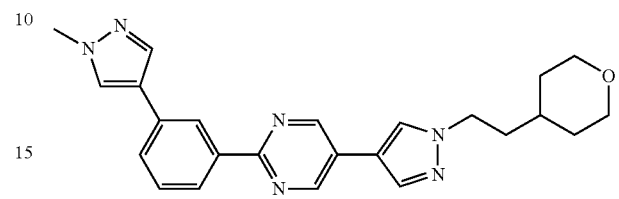

The title compound was obtained following procedure described for example 66, step 1, but starting from 2-[3-(1-methyl-1H-pyrazol-4-yl)phenyl]-5-(1H-pyrazol-4-yl)pyrimidine (example 3, 100 mg; 0.33 mmol; 1.0 eq.) and 4-(2-Bromo-ethyl)-tetrahydropyran (96 mg; 0.50 mmol; 1.5 eq.) as a white foam (57 mg, 42%). $^1$H NMR (300 MHz, DMSO) δ 9.16 (s, 2H), 8.51 (dd, J=22.9, 5.9 Hz, 2H), 8.36-8.05 (m, 3H), 8.00-7.83 (m, 1H), 7.81-7.41 (m, 2H), 11.13-11.08 (m, 0H), 4.34-4.04 (m, 2H), 3.90 (s, 3H), 3.86-3.70 (m, 1H), 3.24 (t, J=11.4 Hz, 2H), 1.93-0.80 (m, 8H).HPLC (Condition A): Rt 3.58 min (purity 99.7%). MS (ESI+): 415.4.

Example 70

2-[3-(1-Methyl-1H-pyrazol-4-yl)-phenyl]-5-(1-(S)-1-pyrrolidin-2-ylmethyl-1H-pyrazol-4-yl)-pyrimidine hydrochloride Step 1: Formation of (S)-2-(4-{2-[3-(1-Methyl-1H-pyrazol-4-yl)-phenyl]-pyrimidin-5-yl}-pyrazol-1-ylmethyl)-pyrrolidine-1-carboxylic acid tert-butyl ester

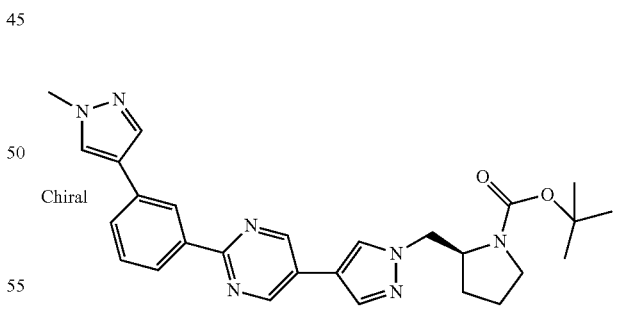

The title compound was obtained following procedure described for example 66, step 1, but starting from (S)-2-Methanesulfonyloxymethyl-pyrrolidine-1-carboxylic acid tert-butyl ester (prepared as described in Organic & Biomolecular Chemistry, 8(16), 3742-3750; 2010, 125 mg; 0.40 mmol; 1.0 eq.) and 2-[3-(1-methyl-1H-pyrazol-4-yl)phenyl]-5-(1H-pyrazol-4-yl)pyrimidine (example 3, 146 mg; 0.48 mmol; 1.2 eq.) as a white solid (90 mg, 46%). MS (ESI+): 486.3.

Step 2: Formation of 2-[3-(1-Methyl-1H-pyrazol-4-yl)-phenyl]-5-(1-(S)-1-pyrrolidin-2-ylmethyl-1H-pyrazol-4-yl)-pyrimidine hydrochloride

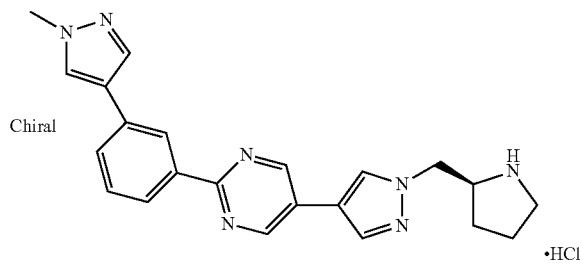 [SMILES: Cn1cc(-c2cccc(-c3ncc(-c4cnn(C[C@@H]5CCCN5)c4)cn3)c2)cn1 ; Cl]
·HCl

The title compound was obtained following procedure described for example 13, step 2, but starting from (S)-2-(4-{2-[3-(1-Methyl-1H-pyrazol-4-yl)-phenyl]-pyrimidin-5-yl}-pyrazol-1-ylmethyl)-pyrrolidine-1-carboxylic acid tert-butyl ester (127 mg; 0.26 mmol; 1.0 eq.) as a yellow powder (92 mg, 83%). 1H NMR (300 MHz, DMSO-d6) δ 9.56-9.25 (m, 2H), 9.20 (s, 2H), 8.60 (s, 1H), 8.54 (t, J=1.7 Hz, 1H), 8.27 (d, J=2.7 Hz, 2H), 8.22 (dt, J=7.7, 1.4 Hz, 1H), 7.93 (s, 1H), 7.81-7.67 (m, 1H), 7.52 (t, J=7.7 Hz, 1H), 4.64-4.49 (m, 2H), 4.04-3.93 (m, 1H), 3.90 (s, 3H), 3.34-3.09 (m, 2H), 2.17-1.61 (m, 4H). HPLC (Condition A): Rt 2.53 min (purity 99.6%). MS (ESI+): 386.4.

Example 71

2-[3-(1-Methyl-1H-pyrazol-4-yl)-phenyl]-5-(1-(R)-1-pyrrolidin-2-ylmethyl-1H-pyrazol-4-yl)-pyrimidine hydrochloride Step 1: Formation of (R)-2-(4-{2-[3-(1-Methyl-1H-pyrazol-4-yl)-phenyl]-pyrimidin-5-yl}-pyrazol-1-ylmethyl)-pyrrolidine-1-carboxylic acid tert-butyl ester

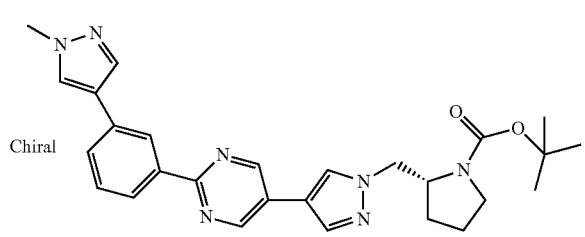 [SMILES: Cn1cc(-c2cccc(-c3ncc(-c4cnn(C[C@H]5CCCN5C(=O)OC(C)(C)C)c4)cn3)c2)cn1]

The title compound was obtained following procedure described for example 66, step 1, but starting from (R)-2-Methanesulfonyloxymethyl-pyrrolidine-1-carboxylic acid tert-butyl ester (prepared as described in Tetrahedron: Asymmetry, 8(13), 2209-2213; 1997, 125 mg; 0.40 mmol; 1.0 eq.) and 2-[3-(1-methyl-1H-pyrazol-4-yl)phenyl]-5-(1H-pyrazol-4-yl)pyrimidine (example 3, 122 mg; 0.40 mmol; 1.0 eq.) as a white foam (121 mg, 62%). MS (ESI+): MS (ESI+): 486.3.

Step 2: Formation of 2-[3-(1-Methyl-1H-pyrazol-4-yl)-phenyl]-5-(1-(R)-1-pyrrolidin-2-ylmethyl-1H-pyrazol-4-yl)-pyrimidine hydrochloride

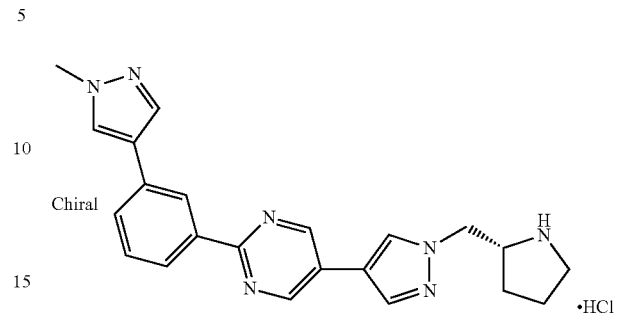
·HCl

The title compound was obtained following procedure described for example 13, step 2, but starting from (R)-2-(4-{2-[3-(1-Methyl-1H-pyrazol-4-yl)-phenyl]-pyrimidin-5-yl}-pyrazol-1-ylmethyl)-pyrrolidine-1-carboxylic acid tert-butyl ester (121.00 mg; 0.25 mmol; 1.0 eq.) as a yellow powder (87 mg, 78%). ¹H NMR (300 MHz, DMSO) δ 9.56-9.25 (m, 2H), 9.20 (s, 2H), 8.60 (s, 1H), 8.54 (t, J=1.7 Hz, 1H), 8.27 (d, J=2.7 Hz, 2H), 8.23 (dt, J=7.7, 1.4 Hz, 1H), 7.93 (s, 1H), 7.81-7.67 (m, 1H), 7.52 (t, J=7.7 Hz, 1H), 4.64-4.49 (m, 2H), 4.04-3.93 (m, 1H), 3.90 (s, 3H), 3.34-3.09 (m, 2H), 2.17-1.61 (m, 4H). HPLC (Condition A): Rt 2.55 min (purity 99.1%). MS (ESI+): 386.4.

Example 72

2-[3-(1-Methyl-1H-[1,2,3]triazol-4-yl)-phenyl]-5-(1-piperidin-4-yl-1H-pyrazol-4-yl)-pyrimidine hydrochloride Step 1: Formation of 4-(4-{2-[3-(1-trimethylsilanyl-ethyl-1H-[1,2,3]triazol-4-yl)-phenyl]-pyrimidin-5-yl}-pyrazol-1-yl)-piperidine-1-carboxylic acid tert-butyl ester

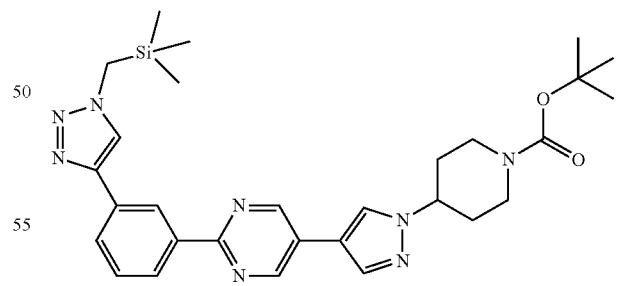

A solution of copper sulfate pentahydrate (2.2 mg; 0.01 mmol; 0.04 eq.) in water (0.2 mL) was added to a mixture of 4-{4-[2-(3-Trimethylsilanylethynyl-phenyl)-pyrimidin-5-yl]-pyrazol-1-yl}-piperidine-1-carboxylic acid tert-butyl ester (intermediate 19, 110 mg; 0.22 mmol; 1.0 eq.), azidomethyl-trimethyl-silane (36 μl; 0.24 mmol; 1.1 eq.) and D-(−)-isoascorbic acid sodium salt (9 mg; 0.04 mmol; 0.2 eq.) in Dioxane-1,4 (3 mL). The vial was sealed and stirred overnight at 8000. The reaction mixture was then diluted with water and extracted with EtOAc (three times). Combined organic phases were washed with brine, dried over magnesium sulfate, filtered and concentrated. Purification by flash chromatography on silica afforded the title compound as a beige solid (60 mg, 49%). 1H NMR (300 MHz, DMSO-d6) δ 9.18 (s, 2H), 8.88 (t, J=1.6 Hz, 1H), 8.57 (s, 1H), 8.54 (s, 1H), 8.34 (dt, J=8.0 Hz, 1.6 Hz, 1H), 8.16 (s, 1H), 7.96 (dt, J=8.0 Hz, 1.6 Hz, 1H), 7.60 (t, J=8.0 Hz, 1H), 4.48-4.38 (m, 1H), 4.11-4.03 (m, 4H), 2.94 (m, 2H), 2.09-2.05 (m, 2H), 1.88-1.74 (m, 2H), 1.43 (s, 9H), 0.13 (s, 9H). MS (ESI+): 559.5.

Step 2: Formation of 2-[3-(1-Methyl-1H-[1,2,3]triazol-4-yl)-phenyl]-5-(1-piperidin-4-yl-1H-pyrazol-4-yl)-pyrimidine hydrochloride

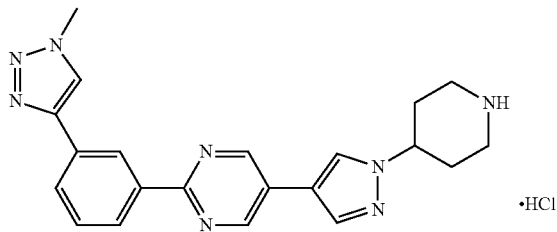 [SMILES: Cn1cc(-c2cccc(-c3ncc(-c4cnn(C5CCNCC5)c4)cn3)c2)nn1 ; Cl]

Tetrabutylammonium fluoride (56 mg; 0.21 mmol; 2.0 eq.) was added to a solution of 4-(4-{2-[3-(1-Trimethylsilanylmethyl-1H-[1,2,3]triazol-4-yl)-phenyl]-pyrimidin-5-yl}-pyrazol-1-yl)-piperidine-1-carboxylic acid tert-butyl ester (60 mg; 0.11 mmol; 1.0 eq.) in THF (1 mL) and the reaction mixture was stirred at RT for 2 h. It was then diluted with a saturated solution of NaHCO₃ and extracted with EtOAc (three times). Combined organic phases were washed with brine, dried over magnesium sulfate, filtered and concentrated. The crude obtained was dissolved in DCM (1 mL) and MeOH (MeOH) and HCl/dioxane (0.4 mL of a 4N solution, 1.6 mmol, 15 eq.) was added. The reaction mixture was stirred at RT for 2 h, concentrated under reduced pressure and purified by autopreparative LC/Ms to give the title compound as a beige solid (15 mg, 33%). 1H NMR (300 MHz, DMSO-d6) δ 9.22 (s, 2H), 9.11 (brs, 1H), 8.94-8.81 (m, 2H), 8.67 (s, 1H), 8.54 (s, 1H), 8.35 (dt, J=7.9 Hz, 1.5 Hz, 1H), 8.22 (s, 1H), 7.96 (dt, J=7.9 Hz, 1.5 Hz, 1H), 7.61 (t, J=7.9 Hz, 1H), 4.61-4.52 (m, 1H), 4.12 (s, 3H), 3.43-3.36 (m, 2H), 3.16-3.06 (m, 2H), 2.28-2.11 (m, 4H). HPLC (Condition A): Rt 2.08 min (purity 98.5%). MS (ESI+): 387.3.

Example 73

1-(3-Hydroxy-azetidin-1-yl)-2-(4-{2-[3-(1-methyl-1H-pyrazol-4-yl)-phenyl]-pyrimidin-5-yl}-pyrazol-1-yl)-ethanone

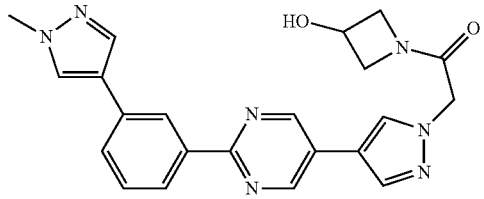 [SMILES: Cn1cc(-c2cccc(-c3ncc(-c4cnn(CC(=O)N5CC(O)C5)c4)cn3)c2)cn1]

The title compound was obtained following procedure described for example 25 but starting from (4-{2-[3-(1-Methyl-1H-pyrazol-4-yl)-phenyl]-pyrimidin-5-yl}-pyrazol-1-yl)-acetic acid (example 8, 80 mg; 0.22 mmol; 1.0 eq.) and azetidin-3-ol hydrochloride (36 mg; 0.33 mmol; 1.5 eq.) as a white solid (5 mg, 5%). 1H NMR (300 MHz, DMSO-d6) δ 9.18 (s, 2H), 8.54 (t, J=1.6 Hz, 1H), 8.40 (s, 1H), 8.27 (s, 1H), 8.25-8.18 (m, 1H), 8.16 (s, 1H), 7.93 (d, J=0.7 Hz, 1H), 7.77-7.67 (m, 1H), 7.52 (t, J=7.8 Hz, 1H), 4.95 (s, 2H), 4.58-4.46 (m, 1H), 4.42-4.29 (m, 1H), 4.17-4.05 (m, 1H), 3.99-3.83 (m, 4H), 3.73-3.59 (m, 1H). HPLC (Condition A): Rt 2.37 min (purity 92.9%). MS (ESI+): 416.2, (ESI−): 414.3, mp=177-181° C.

Example 74

1-(3-Hydroxy-pyrrolidin-1-yl)-2-(4-{2-[3-(1-methyl-1H-pyrazol-4-yl)-phenyl]-pyrimidin-5-yl}-pyrazol-1-yl)-ethanone

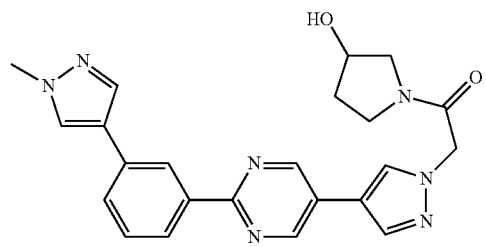 [SMILES: Cn1cc(-c2cccc(-c3ncc(-c4cnn(CC(=O)N5CCC(O)C5)c4)cn3)c2)cn1]

The title compound was obtained following procedure described for example 25 but starting from (4-{2-[3-(1-Methyl-1H-pyrazol-4-yl)-phenyl]-pyrimidin-5-yl}-pyrazol-1-yl)-acetic acid (example 8, 80 mg; 0.22 mmol; 1.0 eq.) and Pyrrolidin-3-ol (29 mg; 0.33 mmol; 1.5 eq.) as A yellow solid (25 mg, 26%). 1H NMR (300 MHz, DMSO-d6) δ 9.19 (s, 2H), 8.54 (s, 1H), 8.39 (s, 1H), 8.31-8.19 (m, 2H), 8.15 (s, 1H), 7.93 (s, 1H), 7.72 (d, J=7.7 Hz, 1H), 7.52 (t, J=7.7 Hz, 1H), 5.25-5.01 (m, 3H), 4.33 (d, J=29.2 Hz, 1H), 3.90 (s, 3H), 3.72-3.25 (m, 4H), 2.09-1.65 (m, 2H). HPLC (Condition A): Rt 2.39 min (purity 99.8%). MS (ESI+): 430.3 (ESI−): 428.1, mp=237-238° C.

Example 75

1-[2-(2-Hydroxy-ethyl)-morpholin-4-yl]-2-(4-{2-[3-(1-methyl-1H-pyrazol-4-yl)-phenyl]-pyrimidin-5-yl}-pyrazol-1-yl)-ethanone

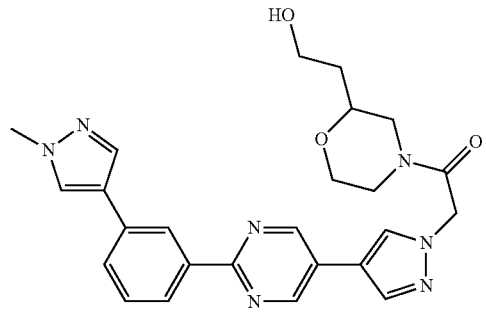 [SMILES: Cn1cc(-c2cccc(-c3ncc(-c4cnn(CC(=O)N5CCOC(CCO)C5)c4)cn3)c2)cn1]

The title compound was obtained following procedure described for example 25 but starting from (4-{2-[3-(1-Methyl-1H-pyrazol-4-yl)-phenyl]-pyrimidin-5-yl}-pyrazol-1-yl)-acetic acid (example 8, 80 mg; 0.22 mmol; 1.0 eq.) and 2-Morpholin-2-yl-ethanol (44 mg; 0.33 mmol; 1.5 eq.) as a yellow solid (17 mg, 16%). 1H NMR (300 MHz, DMSO-d6) δ 9.18 (s, 2H), 8.54 (t, J=1.6 Hz, 1H), 8.38 (s, 1H), 8.31-8.12 (m, 3H), 7.93 (d, J=0.7 Hz, 1H), 7.78-7.66 (m, 1H), 7.52 (t, J=7.8 Hz, 1H), 5.43-5.28 (m, 1H), 5.25-5.10 (m, 1H), 4.25-4.06 (m, 1H), 3.94-3.74 (m, 4H), 3.62-3.31 (m, 6H), 3.27-3.12 (m, 1H), 3.01-2.68 (m, 1H), 1.68-1.42 (m, 2H). HPLC (Condition A): Rt 2.48 min (purity 100%). MS (ESI+): 474.3.

Example 95

Cis-5-{1-[1-(3-Fluoro-tetrahydro-pyran-4-yl)-piperidin-4-yl]-1H-pyrazol-4-yl}-2-[3-(1-methyl-1H-pyrazol-4-yl)-phenyl]-pyrimidine

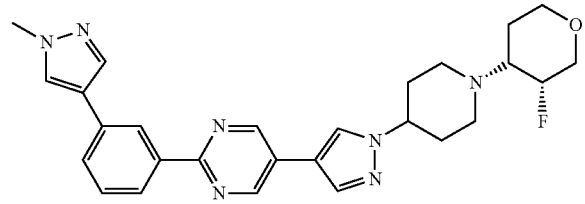

The title compound was obtained following procedure described for example 27 but starting from 2-[3-(1-Methyl-1H-pyrazol-4-yl)-phenyl]-5-(1-piperidin-4-yl-1H-pyrazol-4-yl)-pyrimidine (example 1, 165 mg; 0.26 mmol; 1.0 eq.) and 3-Fluoro-tetrahydro-pyran-4-one (Activate scientific; 60.7 mg; 0.51 mmol; 2.0 eq.). The crude was purified by autopreparative LC/MS to afford the pure cis isomer as a white solid (55 mg, 44%). 1H NMR (300 MHz, DMSO) δ 9.16 (s, 2H), 8.62-8.49 (m, 2H), 8.26 (s, 1H), 8.21 (dt, J=7.8, 1.5 Hz, 1H), 8.13 (s, 1H), 7.92 (s, 1H), 7.71 (dt, J=7.8, 1.5 Hz, 1H), 7.51 (t, J=7.8 Hz, 1H), 4.98 (brd, J=48 Hz, 1H), 4.30-4.12 (m, 1H), 4.00-3.82 (m, 5H), 3.54-3.34 (m, 2H), 3.20-3.03 (m, 2H), 2.79-2.53 (m, 1H), 2.47-2.35 (m, 2H), 2.15-1.79 (m, 5H), 1.66-1.56 (m, 1H). HPLC (Condition A): Rt 2.60 min (purity 100%). MS (ESI+): 488.4.

Example 121

4-(4-{2-[3-(1-Methyl-1H-pyrazol-4-yl)-phenyl]-pyrimidin-5-yl}-pyrazol-1-yl)-cyclohexanecarboxylic acid dimethylamide

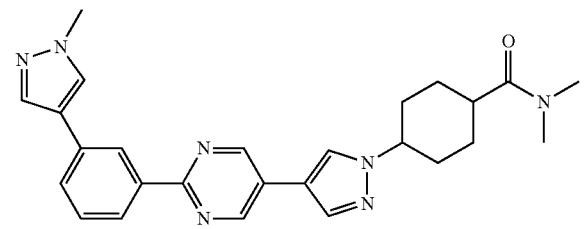 [SMILES: CN(C)C(=O)C1CCC(n2cc(-c3cnc(-c4cccc(-c5cnn(C)c5)c4)nc3)cn2)CC1]

Trimethylaluminium (1.50 mL; 3.0 mmol; 5.4 eq.) was added dropwise over 1 min to a solution of dimethylamine (2.50 mL; 5.0 mmol; 9.1 eq.) in DCE (50 mL) at 0° C. After 10 min, 4-(4-{2-[3-(1-Methyl-1H-pyrazol-4-yl)-phenyl]-pyrimidin-5-yl}-pyrazol-1-yl)-cyclohexanecarboxylic acid ethyl ester (prepared as described in example 62, step; 300 mg; 0.55 mmol; 1.0 eq.) in DCE (50 mL) was added dropwise over 5 min. The reaction solution was stirred for 16 h then a further portion of trimethylaluminium (10 mL; 20 mmol; 36 eq.) was added and the reaction solution refluxed for 4 h. The reaction mixture was then poured into ice-cold MeOH and concentrated under reduced pressure. The residue was redissolved in DCM, washed with 1 N HCl solution, Rochelle's salt solution and brine. Organic phase was finally dried over magnesium sulfate, filtered and concentrated to give the title compounds as a 3:1 mixture of cis and trans 4-(4-{2-[3-(1-Methyl-1H-pyrazol-4-yl)-phenyl]-pyrimidin-5-yl}-pyrazol-1-yl)-cyclohexanecarboxylic acid dimethylamide (165 mg; 60%) in the form of a beige solid. HPLC (Chiralpak IC, EtOH:THF 90:10): Rt 6.61; 10.38 min (purity 76, 24%); MS (ESI+): 456.4.

Example 134

Trans-4-(4-{2-[3-(1-Methyl-1H-pyrazol-4-yl)-phenyl]-pyrimidin-5-yl}-pyrazol-1-yl)-cyclohexanecarboxylic acid dimethylamide

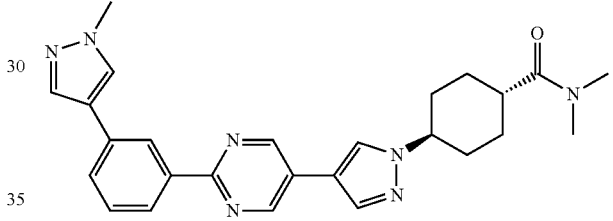

4-(4-{2-[3-(1-Methyl-1H-pyrazol-4-yl)-phenyl]-pyrimidin-5-yl}-pyrazol-1-yl)-cyclohexanecarboxylic acid dimethylamide (example 121; 165 mg; 0.33 mmol) was suspended in DMF and filtered to give the title compound as a white solid (50 mg; 20%). 1H NMR (300 MHz, DMSO) δ 9.16 (s, 2H), 8.53 (t, J=1.6 Hz, 1H), 8.49 (s, 1H), 8.26 (s, 1H), 8.24-8.18 (m, 1H), 8.13 (s, 1H), 7.92 (d, J=0.7 Hz, 1H), 7.74-7.67 (m, 1H), 7.51 (t, J=7.8 Hz, 1H), 4.32-4.16 (m, 1H), 3.89 (s, 3H), 3.05 (s, 3H), 2.83 (s, 3H), 2.77-2.63 (m, 1H), 2.20-2.06 (m, 2H), 1.97-1.77 (m, 4H), 1.67-1.48 (m, 2H). HPLC (Chiralpak IC, EtOH:THF 90:10): Rt 6.91 min (purity 98.4%); MS (ESI+): 456.4.

Example 135

Cis-4-(4-{2-[3-(1-Methyl-1H-pyrazol-4-yl)-phenyl]-pyrimidin-5-yl}-pyrazol-1-yl)-cyclohexanecarboxylic acid dimethylamide

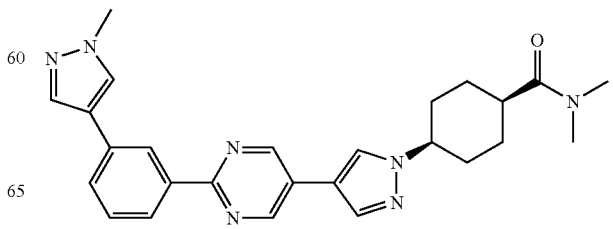

The DMF mother liquor obtained in example 134 was concentrated and the reside purified by Chiral-HPLC (Chiralpack IC; EtOH:THF 90:10) to give the title compound as a white solid (9 mg; 3%). 1H NMR (300 MHz, DMSO) δ 9.20 (s, 2H), 8.60-8.48 (m, 2H), 8.27 (s, 1H), 8.24-8.18 (m, 1H), 8.15 (s, 1H), 7.92 (d, J=0.6 Hz, 1H), 7.78-7.65 (m, 1H), 7.51 (t, J=7.8 Hz, 1H), 4.38-4.26 (m, 1H), 3.89 (s, 3H), 3.03 (s, 3H), 2.89-2.83 (m, 1H), 2.80 (s, 3H), 2.47-2.32 (m, 2H), 2.00-1.85 (m, 2H), 1.79-1.54 (m, 4H). HPLC (Chiralpak IC, EtOH:THF 90:10): Rt 10.84 min (purity 99.9%); MS (ESI+): 456.4.

Example 182

Trans-4-(4-{2-[3-(1-Methyl-1H-pyrazol-4-yl)-phenyl]-pyrimidin-5-yl}-pyrazol-1-yl)-cyclohexanol

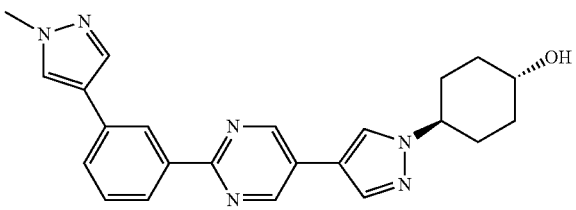 [SMILES: Cn1cc(-c2cccc(-c3ncc(-c4cnn([C@H]5CC[C@H](O)CC5)c4)cn3)c2)cn1]

5-Bromo-2-[3-(1-methyl-1H-pyrazol-4-yl)-phenyl]-pyrimidine (intermediate 2; 700 mg; 2.22 mmol; 1.0 eq.), 4,4,5,5,4',4',5',5'-Octamethyl-[2,2']bi[[1,3,2]dioxaborolanyl](620 mg; 2.44 mmol; 1.1 eq.), Potassium acetate (327 mg; 3.33 mmol; 1.5 eq.) and trans-Dichlorobis(tricyclohexylphosphine)palladium(II), 99% (16.4 mg; 0.02 mmol; 0.01 eq.) were flushed with nitrogen for 10 min before the addition of Dioxane-1,4 (15 mL). The reaction mixture was then heated at reflux under nitrogen for 4 h. The temperature was reduced to 70° C. before the addition of trans-4-(4-Iodo-pyrazol-1-yl)-cyclohexanol (intermediate 22; 714 mg; 2.44 mmol; 1.10 eq.), potassium carbonate (921 mg; 6.66 mmol; 3.0 eq.), trans-Dichlorobis(tricyclohexylphosphine)palladium(II), 99% (16.4 mg; 0.02 mmol; 0.01 eq.) and water (5 mL). The new reaction mixture was heated again at 100° C. for 30 min. It was allowed to cool to RT and diluted with EtOAc. Organic phase was washed with brine, dried over sodium sulfate, filtered and concentrated. Purification by flash chromatography on silica (THF: EtOAc, 50:50) followed by a recrystallisation in THF afforded the tittle compound as an off-white powder (550 mg, 62%). 1H NMR (300 MHz, DMSO) δ 9.14 (s, 2H), 6.51 (m, 1H), 8.48 (s, 1H), 8.25 (s, 1H), 8.20 (m, 1H), 8.11 (s, 1H), 7.91 (s, 1H), 7.69 (m, 1H), 7.50 (t, J=8.1 Hz, 1H), 4.70 (d, J=4.2 Hz, 1H), 4.18 (m, 1H), 3.88 (s, 3H), 3.50 (m, 1H), 1.73-2.08 (m, 6H), 1.36 (m, 2H). HPLC (Condition A): Rt 3.21 min (purity 98.6%). MS (ESI+): 459.4.

Example 250 cis-8-(4-{2-[3-(1-Methyl-1H-pyrazol-4-yl)-phenyl]-pyrimidin-5-yl}-pyrazol-1-yl)-1-aza-spiro[4.5]decan-2-one (first isomer)

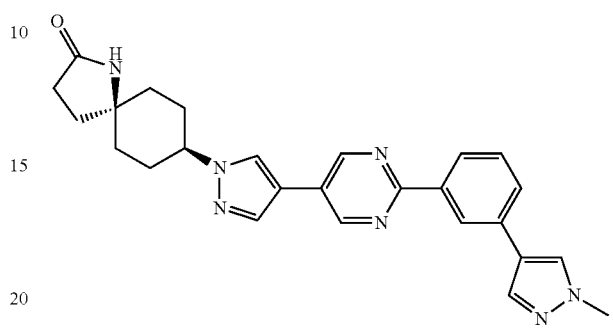

The title compound was obtained following procedure described for example 182 but starting from 5-Bromo-2-[3-(1-methyl-1H-pyrazol-4-yl)-phenyl]-pyrimidine (intermediate 2; 160 mg; 0.51 mmol; 1.0 eq.) and cis-8-(4-Bromo-pyrazol-1-yl)-1-aza-spiro[4.5]decan-2-one (intermediate 23; 166 mg; 0.56 mmol; 1.1 eq.). The crude was purified by autopreparative LC/MS to afford the title compound as a white solid (45 mg, 20%). 1H NMR (300 MHz, DMSO) δ 9.16 (s, 2H), 8.53 (m, 2H), 8.26 (s, 1H), 8.23 (m, 1H), 8.13 (s, 1H), 7.92 (s, 1H), 7.71 (m, 1H), 7.50 (m, 1H), 4.20 (m, 1H), 3.89 (s, 3H), 2.22 (m, 2H), 1.95 (m, 6H), 1.70 (m, 4H). Rt 3.19 min (purity 87.2%). MS (ESI+): 454.5.

Example 251

Trans-8-(4-{2-[3-(1-Methyl-1H-pyrazol-4-yl)-phenyl]-pyrimidin-5-yl}-pyrazol-1-yl)-1-aza-spiro[4.5]decan-2-one (second isomer)

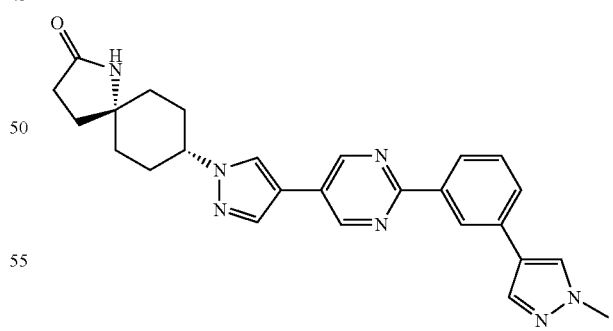

The title compound was obtained following procedure described for example 182 but starting from 5-Bromo-2-[3-(1-methyl-1H-pyrazol-4-yl)-phenyl]-pyrimidine (intermediate 2; 200 mg; 0.63 mmol; 1.0 eq.) and trans-8-(4-Bromo-pyrazol-1-yl)-1-aza-spiro[4.5]decan-2-one (intermediate 24; 208 mg; 0.7 mmol; 1.1 eq.). The crude was purified by autopreparative LC/MS to afford the title compound as a white solid (25 mg, 9%). 1H NMR (300 MHz, DMSO) δ 9.16 (s, 2H), 8.53 (m, 2H), 8.26 (s, 1H), 8.23 (m, 1H), 8.13 (s, 1H), 7.92 (s, 1H), 7.71 (m, 1H), 7.50 (m, 1H), 4.20 (m, 1H), 3.89 (s, 3H), 2.22 (m, 2H), 1.95 (m, 6H), 1.70 (m, 4H). HPLC (Condition A): Rt 3.34 min (purity 100%). MS (ESI+): 454.5.

Example 254

4-[4-(4-{2-[3-(1-Methyl-1H-pyrazol-4-yl)-phenyl]-pyrimidin-5-yl}-pyrazol-1-yl)-cyclohexyl]-morpholin-3-one

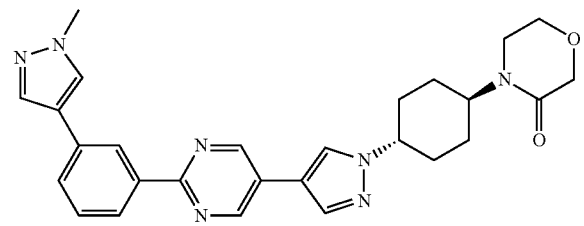 [SMILES: Cn1cc(-c2cccc(-c3ncc(-c4cnn([C@H]5CC[C@H](N6CCOCC6=O)CC5)c4)cn3)c2)cn1]

The title compound was obtained following procedure described for example 182 but starting from 5-Bromo-2-[3-(1-methyl-1H-pyrazol-4-yl)-phenyl]-pyrimidine (intermediate 2; 230 mg; 0.73 mmol; 1.0 eq.) and trans-4-[4-(4-Iodo-pyrazol-1-yl)-cyclohexyl]-morpholin-3-one (intermediate 26; 274 mg; 0.73 mmol; 1.0 eq.). The crude was purified by recrystallisation in methylisobutylketone. The title compound was obtained as a beige solid (16 mg, 5%). 1H NMR (300 MHz, DMSO) δ 9.16 (s, 2H), 8.54 (s, 2H), 8.40-8.06 (m, 3H), 7.93 (s, 1H), 7.71 (d, J=7.9 Hz, 1H), 7.52 (t, J=7.9 Hz, 1H), 4.31 (d, J=39.6 Hz, 2H), 4.05 (s, 2H), 3.95-3.71 (m, 5H), 2.20 (d, J=11.5 Hz, 2H), 2.03-1.49 (m, 6H), 1.23 (s, 1H), 0.84 (t, J=7.3 Hz, 1H). HPLC (Condition A): Rt 3.31 min (purity 99.2%). MS (ESI+): 484.4.

Example 255

3-[4-(4-{2-[3-(1-Methyl-1H-pyrazol-4-yl)-phenyl]-pyrimidin-5-yl}-pyrazol-1-yl)-cyclohexyl]-oxazolidin-2-one

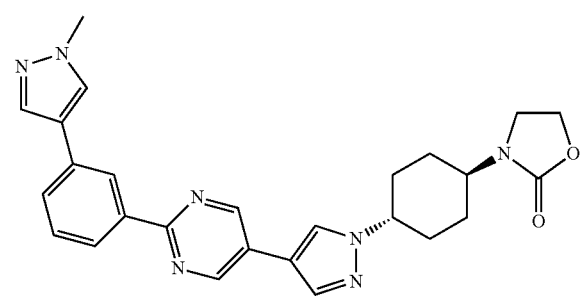 [SMILES: Cn1cc(-c2cccc(-c3ncc(-c4cnn([C@H]5CC[C@H](N6CCOC6=O)CC5)c4)cn3)c2)cn1]

The title compound was obtained following procedure described for example 182 but starting from 5-Bromo-2-[3-(1-methyl-1H-pyrazol-4-yl)-phenyl]-pyrimidine (intermediate 2; 200 mg; 0.63 mmol; 1.0 eq.) and trans-3-[4-(4-Iodo-pyrazol-1-yl)-cyclohexyl]-oxazolidin-2-one (intermediate 27; 231 mg; 0.63 mmol; 1.0 eq.). The crude was triturated in acetonitrile and the suspension filtered and dried under vacuum to afford the title compound as a brown solid (151 mg, 51%). 1H NMR (300 MHz, DMSO) δ 9.21 (s, 2H), 8.58 (d, J=3.6 Hz, 2H), 8.38-8.10 (m, 3H), 7.98 (s, 1H), 7.86-7.44 (m, 2H), 4.32 (dd, J=14.8, 6.5 Hz, 3H), 3.95 (s, 3H), 3.78-3.46 (m, 4H), 2.23 (s, 2H), 2.08-1.57 (m, 7H). HPLC (Condition A): Rt 3.39 min (purity 97.9%). MS (ESI+): 470.4.

Example 258

Cis-1-Hydroxymethyl-4-(4-{2-[3-(1-methyl-1H-pyrazol-4-yl)-phenyl]-pyrimidin-5-yl}-pyrazol-1-yl)-cyclohexanol

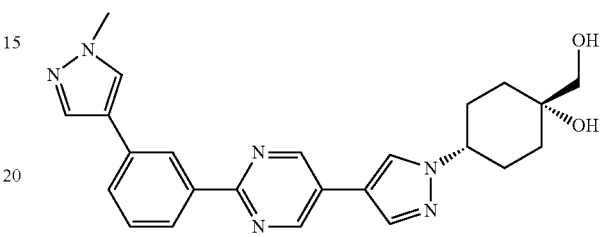

The title compound was obtained following procedure described for example 182 but starting from 4-Iodo-1-(1-oxa-spiro[2.5]oct-6-yl)-1H-pyrazole (intermediate 28; 816 mg; 2.68 mmol; 1.0 eq.) and 5-Bromo-2-[3-(1-methyl-1H-pyrazol-4-yl)-phenyl]-pyrimidine (Intermediate 2; 845 mg; 2.68 mmol; 1.0 eq.) as a yellow solid (6 mg). 1H NMR (300 MHz, DMSO) δ 9.18 (s, 2H), 8.55-8.50 (m, 2H), 8.27 (s, 1H), 8.24-8.19 (m, 1H), 8.12 (s, 1H), 7.92 (s, 1H), 7.74-7.68 (m, 1H), 7.51 (t, J=7.8 Hz, 1H), 4.62 (t, J=5.8 Hz, 1H), 4.20-4.07 (m, 2H), 3.89 (s, 3H), 3.22 (d, J=5.8 Hz, 2H), 2.21-2.05 (m, 2H), 1.93-1.82 (m, 2H), 1.58 (d, J=6.3 Hz, 4H). HPLC (Condition A): Rt 2.92 min (purity 92.3%). MS (ESI+): 431.4.

Example 259

5-[1-(3,3-Difluoro-piperidin-4-yl)-1H-pyrazol-4-yl]-2-[3-(1-methyl-1H-pyrazol-4-yl)-phenyl]-pyrimidine

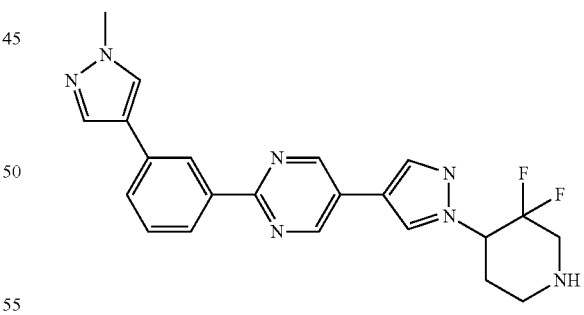

To a solution of 4-(4-Bromo-pyrazol-1-yl)-3,3-difluoro-piperidine (intermediate 29; 150 mg; 0.50 mmol; 1.0 eq.) in Dioxane-1,4 (12 mL) and Water (3.0 mL) was added Potassium carbonate (141 mg; 0.99 mmol; 2.0 eq.) and 2-[3-(1-Methyl-1H-pyrazol-4-yl)-phenyl]-5-(4,4,5,5-tetramethyl-[1,3,2]dioxaborolan-2-yl)-pyrimidine (intermediate 30; 221 mg; 0.60 mmol; 1.2 eq.). The reaction mixture was degasified for 15 min and then 1,1'-Bis(diphenylphosphino)ferrocene] dichloropalladium(II), complex with dichloromethane (20.88 mg; 0.02 mmol; 0.05 eq.) was added. The reaction mixture was then heated at 100° C. for 90 min. It was concentrated under reduced pressure, diluted with Water (15 mL) and extracted with ethylacetate (2×25 mL). Combined organic layers were washed with brine, dried over sodium sulfate, filtered and concentrated. Purification by flash chromatography on silica (DCM: MeOH, 9:1) afforded the title compound as a brown solid (24 mg; 11%). 1H NMR (400 MHz, DMSO-d6) δ 9.21 (s, 2H), 8.53-8.52 (m, 2H), 8.26 (s, 1H), 8.23-8.20 (m, 2H), 7.91 (s, 1H), 7.71 (d, J=8.1 Hz, 1H), 7.51 (t, J=7.8 Hz, 1H), 4.96-4.86 (m, 1H), 3.89 (s, 3H), 3.22-3.15 (m, 1H), 3.08-3.05 (m, 1H), 2.98-2.87 (m, 1H), 2.72-2.67 (m, 1H), 2.66-2.59 (m, 1H), 2.36-2.29 (m, 1H), 2.08-2.05 (m, 1H). HPLC (Condition A): Rt 3.00 min (purity 96.8%). MS (ESI+): 422.2.

Example 260 trans-2-Methyl-8-(4-{2-[3-(1-methyl-1H-pyrazol-4-yl)-phenyl]-pyrimidin-5-yl}-pyrazol-1-yl)-2-aza-spiro[4.5]decan-3-one

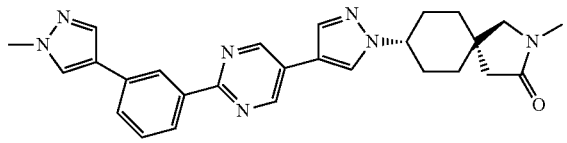

The title compound was obtained following procedure described for example 164 but starting from trans-8-(4-Bromo-pyrazol-1-yl)-2-methyl-2-aza-spiro[4.5]decan-3-one (Intermediate 33; 250 mg; 0.67 mmol; 1.00 eq.) and 2-[3-(1-Methyl-1H-pyrazol-4-yl)-phenyl]-5-(4,4,5,5-tetramethyl-[1,3,2]dioxaborolan-2-yl)-pyrimidine (intermediate 30; 298 mg; 0.80 mmol; 1.2 eq.) as a brown solid (158 mf, 49%). 1H NMR (400 MHz, DMSO) δ 9.15 (s, 2H), 8.54-8.52 (m, 2H), 8.26 (s, 1H), 8.21 (d, J=7.9 Hz, 1H), 8.12 (s, 1H), 7.91 (s, 1H), 7.70 (d, J=7.7 Hz, 1H), 7.50 (t, J=7.8 Hz, 1H), 4.25-4.19 (m, 1H), 3.88 (s, 3H), 3.13 (s, 2H), 2.72 (s, 3H), 2.27 (s, 2H), 2.03-1.99 (m, 2H), 1.91-1.83 (m, 2H), 1.76-1.72 (m, 2H), 1.61-1.55 (m, 2H). HPLC (Condition A): Rt 3.64 min (purity 96.6%). MS (ESI+): 468.3.

Example 262 cis-2-Methyl-8-(4-{2-[3-(1-methyl-1H-pyrazol-4-yl)-phenyl]-pyrimidin-5-yl}-pyrazol-1-yl)-2-aza-spiro[4.5]decan-3-one

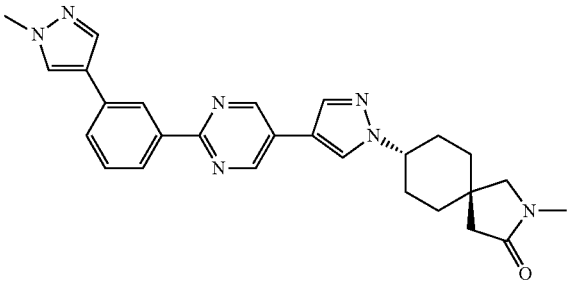

The title compound was obtained following procedure described for example 164 but starting from cis-8-(4-Bromo-pyrazol-1-yl)-2-methyl-2-aza-spiro[4.5]decan-3-one (Intermediate 32; 250 mg; 0.56 mmol; 1.0 eq.) and 2-[3-(1-Methyl-1H-pyrazol-4-yl)-phenyl]-5-(4,4,5,5-tetramethyl-[1,3,2]dioxaborolan-2-yl)-pyrimidine (intermediate 15; 250 mg; 0.67 mmol; 1.2 eq.) as a brown solid (34 mg, 12%). 1H NMR (400 MHz, DMSO) δ 9.15 (s, 2H), 8.53-8.51 (m, 2H), 8.25 (s, 1H), 8.21 (d, J=8.0 Hz, 1H), 8.13 (s, 1H), 7.91 (s, 1H), 7.70 (d, J=7.9 Hz, 1H), 7.50 (t, J=7.8 Hz, 1H), 4.25-4.20 (m, 1H), 3.88 (s, 3H), 3.29 (s, 2H), 2.74 (s, 3H), 2.13 (s, 2H), 2.01-1.98 (m, 2H), 1.93-1.84 (m, 2H), 1.79-1.76 (m, 2H), 1.59-1.52 (m, 2H). HPLC (Condition A): Rt 3.62 min (purity 94.2%). MS (ESI+): 468.3.

Example 265 cis-3-Fluoro-piperidin-4-yl)-1H-pyrazol-4-yl]-2-[3-(1-methyl-1H-pyrazol-4-yl)-phenyl]-pyrimidine

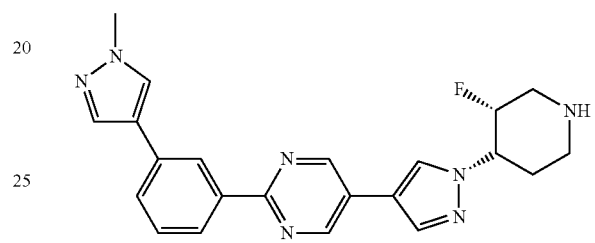

The title compound was obtained following procedure described for example 164 but starting from 4-(4-Bromo-pyrazol-1-yl)-3-fluoro-piperidine (Intermediate 37; 200 mg; 0.80 mmol; 1.0 eq.) and 2-[3-(1-Methyl-1H-pyrazol-4-yl)-phenyl]-5-(4,4,5,5-tetramethyl-[1,3,2]dioxaborolan-2-yl)-pyrimidine (intermediate 15; 296 mg; 0.80 mmol; 1.0 eq.). After Purification of the crude by flash chromatography on silica (DCM:MeOH; 9:1) only the cis isomer was isolated as a brown solid (41 mg, 12%). 1H NMR (400 MHz, DMSO-d6) δ 9.20 (s, 2H), 8.52-8.50 (m, 2H), 8.25-8.19 (m, 3H), 7.91 (s, 1H), 7.70 (d, J=7.8 Hz, 1H), 7.51 (t, J=7.7 Hz, 1H), 4.92 (d, J=52 Hz, 1H), 4.62-4.51 (m, 1H), 3.89 (s, 3H), 3.24-3.10 (m, 2H), 2.85 (dd, J=14, 40 Hz, 1H), 2.67 (m, 1H), 2.45 (m, 1H), 2.23 (m, 1H), 1.95 (m, 1H). HPLC (Condition A): Rt 2.85 min (purity 97.6%). MS (ESI+): 404.3.

Example 280

(3aS,7aS)-7a-Hydroxymethyl-5-((R)-4-{2-[3-(1-methyl-1H-pyrazol-4-yl)-phenyl]-pyrimidin-5-yl}-pyrazol-1-yl)-hexahydro-isobenzofuran-3a-ol (configuration attributed arbitrarily)

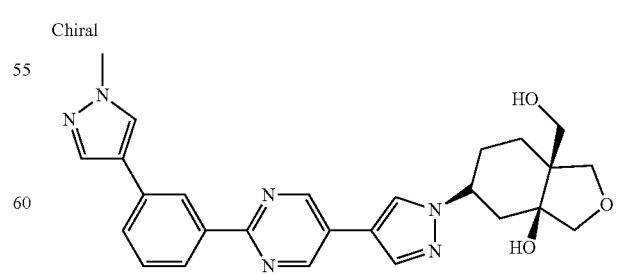

The title compound was obtained following procedure described for example 164 but starting from cis-5-(4-bromopyrazol-1-yl)-cis-7a-(hydroxymethyl)-1,3,4,5,6,7-hexahydroisobenzofuran-3a-ol (intermediate 35; 187 mg;

0.58 mmol; 1.0 eq.) and 2-[3-(1-Methyl-1H-pyrazol-4-yl)-phenyl]-5-(4,4,5,5-tetramethyl-[1,3,2]dioxaborolan-2-yl)-pyrimidine (intermediate 15; 269 mg; 0.69 mmol; 1.2 eq.), as an off-white solid (30 mg; 11%). 1H NMR (400 MHz, DMSO-d6) δ 9.16 (s, 2H), 8.57 (s, 1H), 8.52 (s, 1H), 8.25 (s, 1H), 8.21 (d, J=7.88 Hz, 1H), 8.13 (s, 1H), 7.91 (s, 1H), 7.70 (d, J=7.72 Hz, 1H), 7.49 (t, J=7.72 Hz, 1H), 5.20 (s, 1H), 4.68 (t, J=5.24 Hz, 1H), 4.49-4.43 (m, 1H), 3.89-3.83 (m, 4H), 3.77 (d, J=8.72 Hz, 1H), 3.67 (d, J=7.80 Hz, 1H), 3.54-3.44 (m, 3H), 2.15 (t, J=12.72 Hz, 1H), 2.14-2.03 (m, 1H), 1.96-1.91 (m, 1H), 1.88-1.78 (m, 2H), 1.70-1.68 (m, 1H). HPLC (Condition A): Rt 3.20 min (purity 99.3%). MS (ESI+): 473.2. m.p.: 190.10-201.70° C.

Example 281

(3aR,5R,7aR)-7a-Hydroxymethyl-5-(4-{2-[3-(1-methyl-1H-pyrazol-4-yl)-phenyl]-pyrimidin-5-yl}-pyrazol-1-yl)-hexahydro-isobenzofuran-3a-ol (configuration attributed arbitrarily)

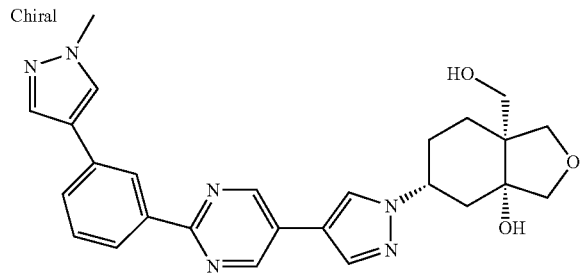 [SMILES: Cn1cc(-c2cccc(-c3ncc(-c4cnn([C@@H]5CC[C@@]6(CO)COC[C@@]6(O)C5)c4)cn3)c2)cn1]

The title compound was obtained following procedure described for example 164 but starting from cis-5-(4-bromopyrazol-1-yl)-cis-7a-(hydroxymethyl)-1,3,4,5,6,7-hexahydroisobenzofuran-3a-ol (intermediate 36; 180 mg; 0.56 mmol; 1.0 eq.) and 2-[3-(1-Methyl-1H-pyrazol-4-yl)-phenyl]-5-(4,4,5,5-tetramethyl-[1,3,2]dioxaborolan-2-yl)-pyrimidine (intermediate 15; 259 mg; 0.67 mmol; 1.2 eq.), as an pale yellow solid (80 mg; 29%). 1H NMR (400 MHz, DMSO-d6) δ 9.16 (s, 2H), 8.57 (s, 1H), 8.52 (s, 1H), 8.26 (s, 1H), 8.21 (d, J=7.8 Hz, 1H), 8.13 (s, 1H), 7.92 (s, 1H), 7.70 (d, J=7.6 Hz, 1H), 7.50 (t, J=7.7 Hz, 1H), 5.21 (s, 1H), 4.68 (d, J=5.2 Hz, 1H), 4.45 (t, J=12.0 Hz, 1H), 3.89-3.84 (m, 3H), 3.77 (d, J=8.8 Hz, 1H), 3.67 (d, J=7.9 Hz, 1H), 3.66-3.51 (m, 1H), 3.52-3.49 (m, 2H), 3.46-3.44 (m, 1H), 2.16 (t, J=12.8 Hz, 1H), 2.07-1.97 (m, 2H), 1.92-1.89 (m, 1H), 1.86-1.78 (m, 1H), 1.67-1.61 (m, 1H). HPLC (Condition A): Rt 3.21 min (purity 92.4%). MS (ESI+): 473.2. m.p.: 191.40-199.70° C.

Example 285

Cis-1-Methyl-8-(4-{2-[3-(1-methyl-1H-pyrazol-4-yl)-phenyl]-pyrimidin-5-yl}-pyrazol-1-yl)-1-aza-spiro[4.5]decan-2-one

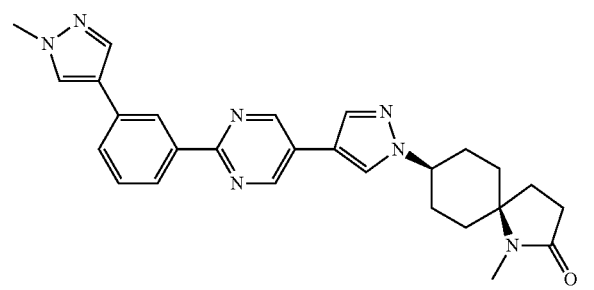 [SMILES: Cn1cc(-c2cccc(-c3ncc(-c4cnn([C@H]5CC[C@]6(CCC(=O)N6C)CC5)c4)cn3)c2)cn1]

The title compound was obtained following procedure described for example 164 but starting from 8-(4-Bromo-pyrazol-1-yl)-1-methyl-1-aza-spiro[4.5]decan-2-one (intermediate 38; 130.0 mg; 0.41 mmol; 1.0 eq.)) and 2-[3-(1-Methyl-1H-pyrazol-4-yl)-phenyl]-5-(4,4,5,5-tetramethyl-[1,3,2]dioxaborolan-2-yl)-pyrimidine (intermediate 15; 171 mg; 0.45 mmol; 1.1 eq.) as Brown Solid (35 mg, 17%). 1H NMR (400 MHz, DMSO-d6) δ 9.16 (s, 2H), 8.53 (d, J=5.0 Hz, 2H), 8.25 (s, 1H), 8.21 (d, J=7.8 Hz, 1H), 8.13 (s, 1H), 7.91 (s, 1H), 7.70 (d, J=7.6 Hz, 1H), 7.51 (t, J=7.8 Hz, 1H), 4.80-4.40 (m, 1H), 3.88 (s, 3H), 2.66 (s, 3H), 2.32-2.25 (m, 2H), 2.09-2.02 (m, 2H), 1.99-1.91 (m, 6H), 1.53-1.51 (m, 2H). HPLC (max plot) 95.4%; (254 nm) 94.2%; Rt (min) 3.59; MS: (ESI+) 468.0.

Example 286 trans-8-(4-{2-[3-(1-Methyl-1H-pyrazol-4-yl)-phenyl]-pyrimidin-5-yl}-pyrazol-1-yl)-2-aza-spiro[4.5]decan-3-one

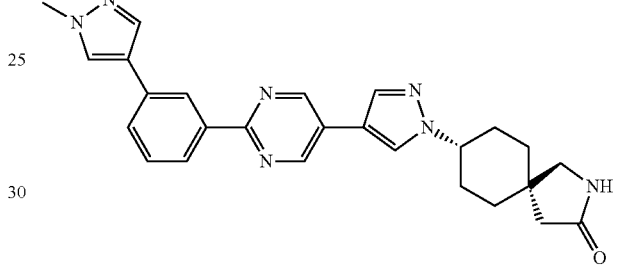

The title compound was obtained following procedure described for example 164 but starting from trans-8-(4-bromo-1H-pyrazol-1-yl)-2-azaspiro[4.5]decan-3-one (intermediate 30) and trans-2-[3-(1-Methyl-1H-pyrazol-4-yl)-phenyl]-5-(4,4,5,5-tetramethyl-[1,3,2]dioxaborolan-2-yl)-pyrimidine (intermediate 15) as a off white Solid; 1H NMR (400 MHz, DMSO-d6) δ 9.15 (s, 2H), 8.53 (s, 1H), 8.52-8.51 (m, 1H), 8.25 (s, 1H), 8.21 (d, J=7.9 Hz, 1H), 8.12 (s, 1H), 7.91 (s, 1H), 7.70 (d, J=7.8 Hz, 1H), 7.55 (bs, 1H), 7.50 (t, J=7.8 Hz, 1H), 4.24-4.19 (m, 1H), 3.88 (s, 3H), 3.18 (s, 2H), 2.03-1.98 (m, 4H), 1.90-1.78 (m, 4H), 1.58-1.52 (m, 2H). HPLC (max plot) 98.6%; (254 nm) 98.9%; Rt (min) 3.42; MS: (ESI+) 454.20. m.p.: 255.0-258.7° C.

Example 287 cis-8-(4-(2-(3-(1-methyl-1H-pyrazol-4-yl)phenyl)pyrimidin-5-yl)-1H-pyrazol-1-yl)-2-azaspiro[4.5]decan-3-one

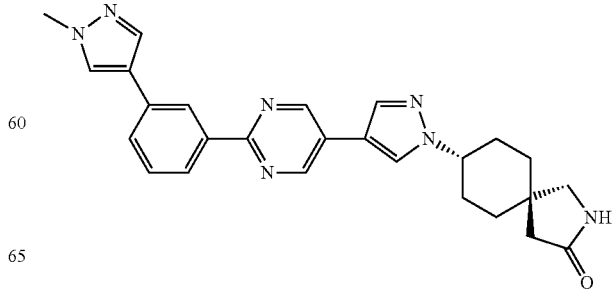

The title compound was obtained following procedure described for example 164 but starting from cis-8-(4-bromo-1H-pyrazol-1-yl)-2-azaspiro[4.5]decan-3-one (Intermediate 31) and 2-[3-(1-Methyl-1H-pyrazol-4-yl)-phenyl]-5-(4,4,5,5-tetramethyl-[1,3,2]dioxaborolan-2-yl)-pyrimidine (intermediate 15) as an off white Solid; 1H NMR (400 MHz, DMSO-d6) δ 9.15 (s, 2H), 8.55 (s, 1H), 8.53-8.52 (m, 1H), 8.26 (s, 1H), 8.21 (d, J=7.8 Hz, 1H), 8.12 (s, 1H), 7.91 (s, 1H), 7.70 (d, J=7.8 Hz, 1H), 7.56 (bs, 1H), 7.50 (t, J=7.8 Hz, 1H), 4.25-4.18 (m, 1H), 3.88 (s, 3H), 3.02 (s, 2H), 2.18 (s, 2H), 2.03-1.99 (m, 2H), 1.91-1.85 (m, 2H), 1.81-1.76 (m, 2H), 1.59-1.51 (m, 2H). HPLC (max plot) 98.8%; (254 nm) 99.0%; Rt (min) 3.44; MS: (ESI+) 454.20. m.p.: 262.00-265.80° C. Other examples have been synthesized following similar procedures as described above or following procedures well known from those skilled in the art.

Example 291

Enzymatic Assays

IRAK1 Enzymatic Assay

IRAK1 is a human purified recombinant enzyme (His-TEV-IRAK1 (194-712))

In this assay, IRAK-1 hydrolyses ATP and autophosphorylates.

Measurement of IRAK-1 inhibition is performed in streptavidin coated 384 well FlashPlate (PerkinElmer #SMP410A).

His-TEV-IRAK-1 (15 ng/well), ATP (1 µM, [33P]ATP 0.25 µCi/well) and compounds in DMSO (range of concentrations from 20 µM to 1 nM) or controls (2% DMSO) are incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Triton-X-100 0.01%. Kinase reaction is stopped by addition of EDTA. Supernatant is discarded, plates are washed three times with 150 mM NaCl and radioactivity is then measured in a Microbeta Trilux reader.

IRAK4 Enzymatic Assay

IRAK4 is a human purified recombinant enzyme (His-TEV-IRAK1 (194-712))

IRAK4 hydrolyses ATP, autophosphorylates and phosphorylates a Serine/Threonine generic peptidic substrate (STK: 61ST1BLC from CisBio International based in Bagnols/Cèze FR).

Measurement of IRAK-4 inhibition is performed in streptavidin coated 384 well FlashPlate (PerkinElmer #SMP410A). His-TEV-IRAK4 (20 ng/well), ATP (2 µM, [$^{33}$P]ATP 0.25 µCi/well), STK1-biotin peptide (300 nM) and compounds in DMSO (range of concentrations from 20 µM to 1nM) or controls (2% DMSO) are incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Tween-20 0.01%, MnCl2 5 mM.

Kinase reaction is stopped by addition of EDTA. Supernatant is discarded, plates are washed three times with 150 mM NaCl and radioactivity is then measured in a Microbeta Trilux reader.

Results are given in the following table:

| Ex | | IRAK4 IC50 (nM) |
|---|---|---|
| 1 | 2-[3-(1-Methyl-1H-pyrazol-4-yl)-phenyl]-5-(1-piperidin-4-yl-1H-pyrazol-4-yl)-pyrimidine hydrochloride | ** |
| 2 | 5-(1-(piperidin-4-yl)-1H-pyrazol-4-yl)-2-(3-(pyridin-3-yl)phenyl)pyrimidine_hydrochloride | ** |
| 3 | 2-[3-(1-methyl-1H-pyrazol-4-yl)phenyl]-5-(1H-pyrazol-4-yl)pyrimidine | ** |
| 4 | 2,2,2-Trifluoro-1-[4-(4-{2-[3-(1-methyl-1H-pyrazol-4-yl)-phenyl]-pyrimidin-5-yl}-pyrazol-1-yl)-piperidin-1-yl]-ethanone | ** |
| 5 | -[4-(4-{2-[3-(1-Methyl-1H-pyrazol-4-yl)-phenyl]-pyrimidin-5-yl}-pyrazol-1-yl)-piperidin-1-yl]-ethanone | *** |
| 6 | 5-[1-(1-Methyl-piperidin-4-yl)-1H-pyrazol-4-yl]-2-[3-(1-methyl-1H-pyrazol-4-yl)-phenyl]-pyrimidine | ** |
| 7 | 2-(3-Furan-3-yl-phenyl)-5-(1-piperidin-4-yl-1H-pyrazol-4-yl)-pyrimidine Hydrochloride | ** |
| 8 | 4-{2-[3-(1-Methyl-1H-pyrazol-4-yl)-phenyl]-pyrimidin-5-yl}-pyrazol-1-yl)-acetic acid | * |
| 9 | 2-(4-{2-[3-(1-Methyl-1H-pyrazol-4-yl)-phenyl]-pyrimidin-5-yl}-pyrazol-1-yl)-1-pyrrolidin-1-yl-ethanone | ** |
| 10 | 4-[2-(4-{2-[3-(1-Methyl-1H-pyrazol-4-yl)-phenyl]-pyrimidin-5-yl}-pyrazol-1-yl)-ethyl]-morpholine | ** |
| 11 | Dimethyl-[2-(4-{2-[3-(1-methyl-1H-pyrazol-4-yl)-phenyl]-pyrimidin-5-yl}-pyrazol-1-yl)-ethyl]-amine | * |
| 12 | 2-[3-(1-Methyl-1H-pyrazol-4-yl)-phenyl]-5-[1-(tetrahydro-furan-3-yl)-1H-pyrazol-4-yl]-pyrimidine | ** |
| 13 | 2-(3-Isoxazol-4-yl-phenyl)-5-(1-piperidin-4-yl-1H-pyrazol-4-yl)-pyrimidine hydrochloride | ** |
| 14 | 2-[3-(1,3-Dimethyl-1H-pyrazol-4-yl)-phenyl]-5-(1-piperidin-4-yl-1H-pyrazol-4-yl)-pyrimidine hydrochloride | * |
| 15 | 2-[3-(1,5-Dimethyl-1H-pyrazol-4-yl)-phenyl]-5-(1-piperidin-4-yl-1H-pyrazol-4-yl)-pyrimidine hydrochloride | ** |
| 16 | 2-{3-[1-(2-Fluoro-1-fluoromethyl-ethyl)-1H-pyrazol-4-yl]-phenyl}-5-(1-piperidin-4-yl-1H-pyrazol-4-yl)-pyrimidine hydrochloride | ** |
| 17 | 2-(4-{3-[5-(1-Piperidin-4-yl-1H-pyrazol-4-yl)-pyrimidin-2-yl]-phenyl}-pyrazol-1-yl)-1-pyrrolidin-1-yl-ethanone hydrochloride | * |
| 18 | 5-(1-Piperidin-4-yl-1H-pyrazol-4-yl)-2-[3-(1H-pyrazol-4-yl)-phenyl]-pyrimidine hydrochloride | *** |
| 19 | 5-(1-Piperidin-4-yl-1H-pyrazol-4-yl)-2-[3-(1-propyl-1H-pyrazol-4-yl)-phenyl]-pyrimidine hydrochloride | ** |

| Ex | | IRAK4 IC50 (nM) |
|---|---|---|
| 20 | 2-[3-(1-Isopropyl-1H-pyrazol-4-yl)-phenyl]-5-(1-piperidin-4-yl-1H-pyrazol-4-yl)-pyrimidine hydrochloride | ** |
| 21 | 2-[3-(1-Benzyl-1H-pyrazol-4-yl)-phenyl]-5-(1-piperidin-4-yl-1H-pyrazol-4-yl)-pyrimidine hydrochloride | ** |
| 22 | 2-[3-(1-Methyl-1H-pyrazol-4-yl)-phenyl]-5-(1-pyridin-3-ylmethyl-1H-pyrazol-4-yl)-pyrimidine | ** |
| 23 | 2-(4-{2-[3-(1-Methyl-1H-pyrazol-4-yl)-phenyl]-pyrimidin-5-yl}-pyrazol-1-yl)-ethanol | ** |
| 24 | 2-[3-Fluoro-5-(1-methyl-1H-pyrazol-4-yl)-phenyl]-5-(1-piperidin-4-yl-1H-pyrazol-4-yl)-pyrimidine hydrochloride | ** |
| 25 | 2-(4-{2-[3-(1-Methyl-1H-pyrazol-4-yl)-phenyl]-pyrimidin-5-yl}-pyrazol-1-yl)-1-piperidin-1-yl-ethanone | * |
| 26 | 5-(1-Azetidin-3-yl-1H-pyrazol-4-yl)-2-[3-(1-methyl-1H-pyrazol-4-yl)-phenyl]-pyrimidine hydrochloride | * |
| 27 | 5-[1-(3-Methoxy-propyl)-1H-pyrazol-4-yl]-2-[3-(1-methyl-1H-pyrazol-4-yl)-phenyl]-pyrimidine | ** |
| 28 | 2-[3-(1-Methyl-1H-pyrazol-4-yl)-phenyl]-5-[1-(1-oxetan-3-yl-piperidin-4-yl)-1H-pyrazol-4-yl]-pyrimidine | ** |
| 29 | 2-[3-(1-Methyl-1H-pyrazol-4-yl)-phenyl]-5-(1-piperidin-4-ylmethyl-1H-pyrazol-4-yl)-pyrimidine hydrochloride | * |
| 30 | trans-5-[1-(3-Fluoro-piperidin-4-yl)-1H-pyrazol-4-yl]-2-[3-(1-methyl-1H-pyrazol-4-yl)-phenyl]-pyrimidine hydrochloride | ** |
| 31 | 1,1,1-Trifluoro-3-[4-(4-{2-[3-(1-methyl-1H-pyrazol-4-yl)-phenyl]-pyrimidin-5-yl}-pyrazol-1-yl)-piperidin-1-yl]-propan-2-ol | ** |
| 32 | 5-(1-Methyl-1H-pyrazol-4-yl)-2-[3-(1-methyl-1H-pyrazol-4-yl)-phenyl]-pyrimidine | ** |
| 33 | 5-(1-Piperidin-4-yl-1H-pyrazol-4-yl)-2-(3-pyridin-4-yl-phenyl)-pyrimidine hydrochloride | ** |
| 34 | 3-(1-Methyl-1H-pyrazol-4-yl)-5-[5-(1-piperidin-4-yl-1H-pyrazol-4-yl)-pyrimidin-2-yl]-phenol Formate | ** |
| 35 | 1-Methoxy-3-(4-{2-[3-(1-methyl-1H-pyrazol-4-yl)-phenyl]-pyrimidin-5-yl}-pyrazol-1-yl)-propan-2-ol | * |
| 36 | 1-Methoxy-3-(4-{2-[3-(1-methyl-1H-pyrazol-4-yl)-phenyl]-pyrimidin-5-yl}-pyrazol-1-yl)-propan-2-ol | ** |
| 37 | 2-(4-{2-[3-(3-Methyl-3H-imidazol-4-yl)-phenyl]-pyrimidin-5-yl}-pyrazol-1-yl)-1-pyrrolidin-1-yl-ethanone | * |
| 38 | N,N-Dimethyl-2-(4-{2-[3-(1-methyl-1H-pyrazol-4-yl)-phenyl]-pyrimidin-5-yl}-pyrazol-1-yl)-acetamide | ** |
| 39 | 2-[3-(1-Methyl-1H-pyrazol-4-yl)-phenyl]-5-{1-[1-(tetrahydro-pyran-4-yl)-piperidin-4-yl]-1H-pyrazol-4-yl}-pyrimidine | *** |
| 40 | 1-(3-Methoxy-azetidin-1-yl)-2-(4-{2-[3-(1-methyl-1H-pyrazol-4-yl)-phenyl]-pyrimidin-5-yl}-pyrazol-1-yl)-ethanone | ** |
| 41 | 2-(4-{2-[3-(1-Methyl-1H-yrazol-4-yl)-phenyl]-pyrimidin-5-yl}-pyrazol-1-ylmethyl)-morpholine hydrochloride | ** |
| 42 | 2-[4-(2-{3-[1-(3-Amino-propyl)-1H-pyrazol-4-yl]-phenyl}-pyrimidin-5-yl)-pyrazol-1-yl]-1-pyrrolidin-1-yl-ethanone hydrochloride | * |
| 43 | 2-{4-[2-(3-Pyridin-4-yl-phenyl)-pyrimidin-5-yl]-pyrazol-1-yl}-1-pyrrolidin-1-yl-ethanone | * |
| 44 | 1-(4-{2-[3-(1-Methyl-1H-pyrazol-4-yl)-phenyl]-pyrimidin-5-yl}-pyrazol-1-yl)-propan-2-one | ** |
| 45 | 2-[3-(1-Methyl-1H-pyrazol-4-yl)-phenyl]-5-[1-(tetrahydro-furan-3-ylmethyl)-1H-pyrazol-4-yl]-pyrimidine | ** |
| 46 | 2-[3-(1-Methyl-1H-pyrazol-4-yl)-phenyl]-5-(1-oxazol-2-ylmethyl-1H-pyrazol-4-yl)-pyrimidine | * |
| 47 | 2-[3-(1-Methyl-1H-pyrazol-4-yl)-phenyl]-5-[1-(2-pyridin-2-yl-ethyl)-1H-pyrazol-4-yl]-pyrimidine | ** |
| 48 | 2-[2-Fluoro-3-(1-methyl-1H-pyrazol-4-yl)-phenyl]-5-(1-piperidin-4-yl-1H-pyrazol-4-yl)-pyrimidine Formate | * |
| 49 | 2-(4-{2-[3-(1-Methyl-1H-pyrazol-4-yl)-phenyl]-pyrimidin-5-yl}-pyrazol-1-yl)-acetamide | * |
| 50 | 2-[4-(2-{3-[1-(2-Amino-ethyl)-1H-pyrazol-4-yl]-phenyl}-pyrimidin-5-yl)-pyrazol-1-yl]-1-pyrrolidin-1-yl-ethanone hydrochloride | * |
| 51 | 1-(4-Methyl-piperazin-1-yl)-2-(4-{2-[3-(1-methyl-1H-pyrazol-4-yl)-phenyl]-pyrimidin-5-yl}-pyrazol-1-yl)-ethanone hydrochloride | ** |
| 52 | 1-(3-Hydroxy-piperidin-1-l)-2-(4-{2-[3-(1-methyl-1H-pyrazol-4-yl)-phenyl]-pyrimidin-5-yl}-pyrazol-1-yl)-ethanone | ** |
| 53 | 2-[3-(1-Methyl-1H-pyrazol-4-yl)-phenyl]-5-[1-(2-pyridin-4-yl-ethyl)-1H-pyrazol-4-yl]-pyrimidine | *** |
| 54 | 2-(4-{2-[3-(1-Methyl-1H-pyrazol-4-yl)-phenyl]-pyrimidin-5-yl}-pyrazol-1-yl)-N-(tetrahydro-pyran-4-yl)-acetamide | ** |
| 55 | 2-(4-{2-[3-(1-Methyl-1H-pyrazol-4-yl)-phenyl]-pyrimidin-5-yl}-pyrazol-1-yl)-1-(2-oxa-6-aza-spiro[3.3]hept-6-yl)-ethanone | ** |

| Ex | | IRAK4 IC50 (nM) |
|---|---|---|
| 56 | 2-(4-{2-[3-(2-Methyl-thiazol-5-yl)-phenyl]-pyrimidin-5-yl}-pyrazol-1-yl)-1-pyrrolidin-1-yl-ethanone | ** |
| 57 | 2-[3-(1-Methyl-1H-pyrazol-4-yl)-phenyl]-5-[1-(2-piperidin-1-yl-ethyl)-1H-pyrazol-4-yl]-pyrimidne | ** |
| 58 | 2-[3-(1-Methyl-1H-pyrazol-4-yl)-phenyl]-5-[1-(2-pyrrolidin-1-yl-ethyl)-1H-pyrazol-4-yl]-pyrimidine | ** |
| 59 | 2-[4-(2-{3-[1-(2-Hydroxy-ethyl)-1H-pyrazol-4-yl]-phenyl}-pyrimidin-5-yl)-pyrazol-1-yl]-1-pyrrolidin-1-yl-ethanone | * |
| 60 | N-(1-Hydroxymethyl-propyl)-2-(4-{2-[3-(1-methyl-1H-pyrazol-4-yl)-phenyl]-pyrimidin-5-yl}-pyrazol-1-yl)-acetamide | * |
| 61 | (3-exo)-8-Methyl-3-(4-{2-[3-(1-methyl-1H-pyrazol-4-yl)-phenyl]-pyrimidin-5-yl}-pyrazol-1-yl)-8-aza-bicyclo[3.2.1]octane | *** |
| 62 | 4-(4-{2-[3-(1-Methyl-1H-pyrazol-4-yl)-phenyl]-pyrimidin-5-yl}-pyrazol-1-yl)-cyclohexanecarboxylic acid | ** |
| 63 | 2-[3-(1-Methyl-1H-pyrazol-4-yl)-phenyl]-5-(1H-pyrazol-4-yl)-pyrimidine | ** |
| 64 | 2-[3-(1-Methyl-1H-pyrazol-4-yl)-phenyl]-5-{1-[2-(1-methyl-pyrrolidin-2-yl)-ethyl]-1H-pyrazol-4-yl}-pyrimidine | ** |
| 65 | 2-[3-(1-Methyl-1H-pyrazol-4-yl)-phenyl]-5-(1-pyrrolidin-3-ylmethyl-1H-pyrazol-4-yl)-pyrimidine hydrochloride | ** |
| 66 | 5-(1-Azetidin-3-ylmethyl-1H-pyrazol-4-yl)-2-[3-(1-methyl-1H-pyrazol-4-yl)-phenyl]-pyrimidine hydrochloride | ** |
| 67 | 5-[1-(2,2-Difluoro-ethyl)-1H-pyrazol-4-yl]-2-[3-(1-methyl-1H-pyrazol-4-yl)-phenyl]-pyrimidine | ** |
| 68 | 1-Morpholin-4-yl-2-{4-[2-(3-pyridin-4-yl-phenyl)-pyrimidin-5-yl]-pyrazol-1-yl}-ethanone | * |
| 69 | 2-[3-(1-Methyl-1H-pyrazol-4-yl)-phenyl]-5-{1-[2-(tetrahydro-pyran-4-yl)-ethyl]-1H-pyrazol-4-yl}-pyrimidine | ** |
| 70 | 2-[3-(1-Methyl-1H-pyrazol-4-yl)-phenyl]-5-(1-(S)-1-pyrrolidin-2-ylmethyl-1H-pyrazol-4-yl)-pyrimidine hydrochloride | * |
| 71 | 2-[3-(1-Methyl-1H-pyrazol-4-yl)-phenyl]-5-(1-(R)-1-pyrrolidin-2-ylmethyl-1H-pyrazol-4-yl)-pyrimidine hydrochloride | * |
| 72 | 2-[3-(1-Methyl-1H-[1,2,3]triazol-4-yl)-phenyl]-5-(1-piperidin-4-yl-1H-pyrazol-4-yl)-pyrimidine hydrochloride | * |
| 73 | 1-(3-Hydroxy-azetidin-1-yl)-2-(4-{2-[3-(1-methyl-1H-pyrazol-4-yl)-phenyl]-pyrimidin-5-yl}-pyrazol-1-yl)-ethanone | ** |
| 74 | 1-(3-Hydroxy-pyrrolidin-1-yl)-2-(4-{2-[3-(1-methyl-1H-pyrazol-4-yl)-phenyl]-pyrimidin-5-yl}-pyrazol-1-yl)-ethanone | ** |
| 75 | 1-[2-(2-Hydroxy-ethyl)-morpholin-4-yl]-2-(4-{2-[3-(1-methyl-1H-pyrazol-4-yl)-phenyl]-pyrimidin-5-yl}-pyrazol-1-yl)-ethanone | ** |
| 76 | 5-[1-(1-Methanesulfonyl-piperidin-4-yl)-1H-pyrazol-4-yl]-2-[3-(1-methyl-1H-pyrazol-4-yl)-phenyl]-pyrimidine | ** |
| 77 | 1-Azetidin-1-yl-2-(4-{2-[3-(1-methyl-1H-pyrazol-4-yl)-phenyl]-pyrimidin-5-yl}-pyrazol-1-yl)-ethanone | ** |
| 78 | 1-Morpholin-4-yl-2-{4-[2-(3-oxazol-5-yl-phenyl)-pyrimidin-5-yl]-pyrazol-1-yl}-ethanone | ** |
| 79 | 1-Morpholin-4-yl-2-(4-{2-[3-(1H-[1,2,3]triazol-4-yl)-phenyl]-pyrimidin-5-yl}-pyrazol-1-yl)-ethanone | * |
| 80 | 1-(2-Methyl-morpholin-4-yl)-2-(4-{2-[3-(1-methyl-1H-pyrazol-4-yl)-phenyl]-pyrimidin-5-yl}-pyrazol-1-yl)-ethanone | ** |
| 81 | 1-((S)-2-Hydroxymethyl-pyrrolidin-1-yl)-2-(4-{2-[3-(1-methyl-1H-pyrazol-4-yl)-phenyl]-pyrimidin-5-yl}-pyrazol-1-yl)-ethanone | ** |
| 82 | N-(2-Hydroxy-1,1-dimethyl-ethyl)-2-(4-{2-[3-(1-methyl-1H-pyrazol-4-yl)-phenyl]-pyrimidin-5-yl}-pyrazol-1-yl)-acetamide | * |
| 83 | 3-(4-{2-[3-(1-Methyl-1H-pyrazol-4-yl)-phenyl]-pyrimidin-5-yl}-pyrazol-1-yl)-1-morpholin-4-yl-propan-1-one | * |
| 84 | 3-(4-{2-[3-(1-Methyl-1H-pyrazol-4-yl)-phenyl]-pyrimidin-5-yl}-pyrazol-1-yl)-1-pyrrolidin-1-yl-propan-1-one | * |
| 85 | N,N-Dimethyl-3-(4-{2-[3-(1-methyl-1H-pyrazol-4-yl)-phenyl]-pyrimidin-5-yl}-pyrazol-1-yl)-propionamide | ** |
| 86 | 2-(4-{2-[3-(1-Methyl-1H-pyrazol-4-yl)-phenyl]-pyrimidin-5-yl}-pyrazol-1-yl)-1-(2-oxa-7-aza-spiro[3.5]non-7-yl)-ethanone | ** |
| 87 | 1-[2-(2-Methoxy-ethyl)-morpholin-4-yl]-2-(4-{2-[3-(1-methyl-1H-pyrazol-4-yl)-phenyl]-pyrimidin-5-yl}-pyrazol-1-yl)-ethanone | ** |
| 88 | 1-(3-Methoxymethyl-piperidin-1-yl)-2-(4-{2-[3-(1-methyl-1H-pyrazol-4-yl)-phenyl]-pyrimidin-5-yl}-pyrazol-1-yl)-ethanone | ** |
| 89 | 2-[3-(1-Methyl-1H-pyrazol-4-yl)-phenyl]-5-{1-[2-(2-methyl-pyridin-3-yl)-ethyl]-1H-pyrazol-4-yl}-pyrimidine | ** |
| 90 | 1-(3-Methoxy-pyrrolidin-1-yl)-2-(4-{2-[3-(1-methyl-1H-pyrazol-4-yl)-phenyl]-pyrimidin-5-yl}-pyrazol-1-yl)-ethanone | ** |

| Ex | | IRAK4 IC50 (nM) |
|---|---|---|
| 91 | N-Methyl-2-(4-{2-[3-(1-methyl-1H-pyrazol-4-yl)-phenyl]-pyrimidin-5-yl}-pyrazol-1-yl)-N-(tetrahydro-pyran-4-yl)-acetamide | ** |
| 92 | 2-(4-{2-[3-(1-Methyl-1H-pyrazol-4-yl)-phenyl]-pyrimidin-5-yl}-pyrazol-1-yl)-1-(1S,4S)-2-oxa-5-aza-bicyclo[2.2.1]hept-5-yl-ethanone | ** |
| 93 | 2-(4-{2-[3-(1-Methyl-1H-pyrazol-4-yl)-phenyl]-pyrimidin-5-yl}-pyrazol-1-yl)-1-[1,4]oxazepan-4-yl-ethanone | ** |
| 94 | 2-(4-{2-[3-(1-Methyl-1H-pyrazol-4-yl)-phenyl]-pyrimidin-5-yl}-pyrazol-1-yl)-1-(8-oxa-3-aza-bicyclo[3.2.1]oct-3-yl)-ethanone | ** |
| 95 | Cis-5-{1-[1-(3-Fluoro-tetrahydro-pyran-4-yl)-piperidin-4-yl]-1H-pyrazol-4-yl}-2-[3-(1-methyl-1H-pyrazol-4-yl)-phenyl]-pyrimidine | ** |
| 96 | 5-{1-[2-(3,4-Dimethoxy-phenyl)-ethyl]-1H-pyrazol-4-yl}-2-[3-(1-methyl-1H-pyrazol-4-yl)-phenyl]-pyrimidine | ** |
| 97 | 2-[3-(1-Methyl-1H-pyrazol-4-yl)-phenyl]-5-[1-(tetrahydro-pyran-4-yl)-1H-pyrazol-4-yl]-pyrimidine | ** |
| 98 | 5-[1-(2-Methoxy-ethyl)-1H-pyrazol-4-yl]-2-[3-(1-methyl-1H-pyrazol-4-yl)-phenyl]-pyrimidine | ** |
| 99 | N,N-Dimethyl-2-(4-{2-[3-(1-methyl-1H-pyrazol-4-yl)-phenyl]-pyrimidin-5-yl}-pyrazol-1-yl)-propionamide | * |
| 100 | 1-(3-Methoxy-azetidin-1-yl)-3-(4-{2-[3-(1-methyl-1H-pyrazol-4-yl)-phenyl]-pyrimidin-5-yl}-pyrazol-1-yl)-propan-1-one | * |
| 101 | 3-(4-{2-[3-(1-Methyl-1H-pyrazol-4-yl)-phenyl]-pyrimidin-5-yl}-pyrazol-1-yl)-1-(2-oxa-6-aza-spiro[3.3]hept-6-yl)-propan-1-one | * |
| 102 | 1-(4-Methyl-piperazin-1-yl)-3-(4-{2-[3-(1-methyl-1H-pyrazol-4-yl)-phenyl]-pyrimidin-5-yl}-pyrazol-1-yl)-propan-1-one | * |
| 103 | 2-(4-{2-[3-(1-Methyl-1H-pyrazol-4-yl)-phenyl]-pyrimidin-5-yl}-pyrazol-1-yl)-1-morpholin-4-yl-propan-1-one | * |
| 104 | [4-(4-{2-[3-(1-Methyl-1H-pyrazol-4-yl)-phenyl]-pyrimidin-5-yl}-pyrazol-1-yl)-piperidin-1-yl]-(tetrahydro-furan-3-yl)-methanone | ** |
| 105 | 2-Methoxy-1-[4-(4-{2-[3-(1-methyl-1H-pyrazol-4-yl)-phenyl]-pyrimidin-5-yl}-pyrazol-1-yl)-piperidin-1-yl]-ethanone | ** |
| 106 | 2-Hydroxy-1-[4-(4-{2-[3-(1-methyl-1H-pyrazol-4-yl)-phenyl]-pyrimidin-5-yl}-pyrazol-1-yl)-piperidin-1-yl]-ethanone | ** |
| 107 | [4-(4-{2-[3-(1-Methyl-1H-pyrazol-4-yl)-phenyl]-pyrimidin-5-yl}-pyrazol-1-yl)-piperidin-1-yl]-(tetrahydro-pyran-4-yl)-methanone | ** |
| 108 | [4-(4-{2-[3-(1-Methyl-1H-pyrazol-4-yl)-phenyl]-pyrimidin-5-yl}-pyrazol-1-yl)-piperidin-1-yl]-(tetrahydro-pyran-2-yl)-methanone | ** |
| 109 | 3-Methoxy-1-[4-(4-{2-[3-(1-methyl-1H-pyrazol-4-yl)-phenyl]-pyrimidin-5-yl}-pyrazol-1-yl)-piperidin-1-yl]-propan-1-one | ** |
| 110 | (1R,5S)-3-(4-{2-[3-(1-Methyl-1H-pyrazol-4-yl)-phenyl]-pyrimidin-5-yl}-pyrazol-1-yl)-8-aza-bicyclo[3.2.1]octane | ** |
| 111 | 2-Ethoxy-1-[4-(4-{2-[3-(1-methyl-1H-pyrazol-4-yl)-phenyl]-pyrimidin-5-yl}-pyrazol-1-yl)-piperidin-1-yl]-ethanone | ** |
| 112 | 5-{1-[1-(3-Ethoxy-2,2-dimethyl-cyclobutyl)-piperidin-4-yl]-1H-pyrazol-4-yl}-2-[3-(1-methyl-1H-pyrazol-4-yl)-phenyl]-pyrimidine | ** |
| 113 | 1-Methyl-4-[4-(4-{2-[3-(1-methyl-1H-pyrazol-4-yl)-phenyl]-pyrimidin-5-yl}-pyrazol-1-yl)-piperidine-1-carbonyl]-pyrrolidin-2-one | ** |
| 114 | 3,3,3-Trifluoro-1-[4-(4-{2-[3-(1-methyl-1H-pyrazol-4-yl)-phenyl]-pyrimidin-5-yl}-pyrazol-1-yl)-piperidin-1-yl]-propan-1-one | ** |
| 115 | 3,3,3-Trifluoro-2-hydroxy-1-[4-(4-{2-[3-(1-methyl-1H-pyrazol-4-yl)-phenyl]-pyrimidin-5-yl}-pyrazol-1-yl)-piperidin-1-yl]-propan-1-one | ** |
| 116 | 2-[3-(1-Methyl-1H-pyrazol-4-yl)-phenyl]-5-((R)-1-pyrrolidin-3-yl-1H-pyrazol-4-yl)-pyrimidine | ** |
| 117 | 3-[4-(4-{2-[3-(1-Methyl-1H-pyrazol-4-yl)-phenyl]-pyrimidin-5-yl}-pyrazol-1-yl)-piperidine-1-carbonyl]-cyclobutanone | ** |
| 118 | 1,1,1-Trifluoro-3-[(1R,5S)-3-(4-{2-[3-(1-methyl-1H-pyrazol-4-yl)-phenyl]-pyrimidin-5-yl}-pyrazol-1-yl)-8-aza-bicyclo[3.2.1]oct-8-yl]-propan-2-ol | ** |
| 119 | 1-[(1R,5S)-3-(4-{2-[3-(1-Methyl-1H-pyrazol-4-yl)-phenyl]-pyrimidin-5-yl}-pyrazol-1-yl)-8-aza-bicyclo[3.2.1]oct-8-yl]-ethanone | ** |
| 120 | (3-Hydroxy-cyclobutyl)-[4-(4-{2-[3-(1-methyl-1H-pyrazol-4-yl)-phenyl]-pyrimidin-5-yl}-pyrazol-1-yl)-piperidin-1-yl]-methanone | ** |
| 121 | 4-(4-{2-[3-(1-Methyl-1H-pyrazol-4-yl)-phenyl]-pyrimidin-5-yl}-pyrazol-1-yl)-cyclohexanecarboxylic acid dimethylamide | *** |

| Ex | | IRAK4 IC50 (nM) |
|---|---|---|
| 122 | 5-{1-[1-((S)-3-Methoxy-tetrahydro-pyran-4-yl)-piperidin-4-yl]-1H-pyrazol-4-yl}-2-[3-(1-methyl-1H-pyrazol-4-yl)-phenyl]-pyrimidine | ** |
| 123 | [4-(4-{2-[3-(1-Methyl-1H-pyrazol-4-yl)-phenyl]-pyrimidin-5-yl}-pyrazol-1-yl)-piperidin-1-yl]-((S)-1-methyl-pyrrolidin-2-yl)-methanone | ** |
| 124 | (S)-2-Amino-3-methyl-1-[4-(4-{2-[3-(1-methyl-1H-pyrazol-4-yl)-phenyl]-pyrimidin-5-yl}-pyrazol-1-yl)-piperidin-1-yl]-butan-1-one | ** |
| 125 | 2-[3-(1-Methyl-1H-pyrazol-4-yl)-phenyl]-5-((S)-1-pyrrolidin-3-yl-1H-pyrazol-4-yl)-pyrimidine | ** |
| 126 | 1-[(S)-3-(4-{2-[3-(1-Methyl-1H-pyrazol-4-yl)-phenyl]-pyrimidin-5-yl}-pyrazol-1-yl)-pyrrolidin-1-yl]-ethanone | ** |
| 127 | 1-(3-Hydroxy-8-aza-bicyclo[3.2.1]oct-8-yl)-2-(4-{2-[3-(1-methyl-1H-pyrazol-4-yl)-phenyl]-pyrimidin-5-yl}-pyrazol-1-yl)-ethanone | ** |
| 128 | 1-(3-Hydroxy-8-aza-bicyclo[3.2.1]oct-8-yl)-2-(4-{2-[3-(1-methyl-1H-pyrazol-4-yl)-phenyl]-pyrimidin-5-yl}-pyrazol-1-yl)-ethanone | ** |
| 129 | 3-(4-{2-[3-(1-Methyl-1H-pyrazol-4-yl)-phenyl]-pyrimidin-5-yl}-pyrazol-1-yl)-dihydro-furan-2-one | ** |
| 130 | 1-[(R)-3-(4-{2-[3-(1-Methyl-1H-pyrazol-4-yl)-phenyl]-pyrimidin-5-yl}-pyrazol-1-yl)-pyrrolidin-1-yl]-ethanone | * |
| 131 | 2-[3-(1-Methyl-1H-pyrazol-4-yl)-phenyl]-5-{1-[2-(tetrahydro-furan-3-yl)-ethyl]-1H-pyrazol-4-yl}-pyrimidine | ** |
| 132 | 3-[2-(4-{2-[3-(1-Methyl-1H-pyrazol-4-yl)-phenyl]-pyrimidin-5-yl}-pyrazol-1-yl)-ethyl]dihydro-furan-2-one | ** |
| 133 | 9-Isopropyl-3-(4-{2-[3-(1-methyl-1H-pyrazol-4-yl)-phenyl]-pyrimidin-5-yl}-pyrazol-1-yl)-9-aza-bicyclo[3.3.1]nonane | ** |
| 134 | Trans-4-(4-{2-[3-(1-Methyl-1H-pyrazol-4-yl)-phenyl]-pyrimidin-5-yl}-pyrazol-1-yl)-cyclohexanecarboxylic acid dimethylamide | *** |
| 135 | Cis-4-(4-{2-[3-(1-Methyl-1H-pyrazol-4-yl)-phenyl]-pyrimidin-5-yl}-pyrazol-1-yl)-cyclohexanecarboxylic acid dimethylamide | ** |
| 136 | 4-(3-{5-[1-(Tetrahydro-pyran-4-yl)-1H-pyrazol-4-yl]-pyrimidin-2-yl}-phenyl)-pyridin-2-ylamine | ** |
| 137 | 4-{2-[3-(1-Methyl-1H-pyrazol-4-yl)-phenyl]-pyrimidin-5-yl}-1-(tetrahydro-pyran-4-yl)-1H-pyrazole-3-carboxylic acid amide | * |
| 138 | 3-Methyl-5-(3-{5-[1-(tetrahydro-pyran-4-yl)-1H-pyrazol-4-yl]-pyrimidin-2-yl}-phenyl)-pyridazine | ** |
| 139 | 2-[3-(2-Methyl-pyridin-4-yl)-phenyl]-5-[1-(tetrahydro-pyran-4-yl)-1H-pyrazol-4-yl]-pyrimidine | ** |
| 140 | 4-{2-[3-(1-Methyl-1H-pyrazol-4-yl)-phenyl]-pyrimidin-5-yl}-1-(tetrahydro-pyran-4-yl)-1H-pyrazole-3-carboxylic acid | * |
| 141 | 2-[3-(1-Methyl-1H-pyrazol-4-yl)-phenyl]-5-(1-oxetan-3-yl-1H-pyrazol-4-yl)-pyrimidine | ** |
| 142 | Exo-9-Methyl-3-(4-{2-[3-(1-methyl-1H-pyrazol-4-yl)-phenyl]-pyrimidin-5-yl}-pyrazol-1-yl)-9-aza-bicyclo[3.3.1]nonane | ** |
| 143 | Trans-4-(4-{2-[3-(1-Methyl-1H-pyrazol-4-yl)-phenyl]-pyrimidin-5-yl}-pyrazol-1-yl)-cyclohexanecarboxylic acid methylamide | *** |
| 144 | 1-Methyl-4-{2-[3-(1-methyl-1H-pyrazol-4-yl)-phenyl]-pyrimidin-5-yl}-1H-pyrazole-3-carboxylic acid methylamide | * |
| 145 | N-Methyl-2-(4-{2-[3-(1-methyl-1H-pyrazol-4-yl)-phenyl]-pyrimidin-5-yl}-pyrazol-1-yl)-N-oxetan-3-yl-acetamide | ** |
| 146 | 1-(3-Methoxymethyl-morpholin-4-yl)-2-(4-{2-[3-(1-methyl-1H-pyrazol-4-yl)-phenyl]-pyrimidin-5-yl}-pyrazol-1-yl)-ethanone | ** |
| 147 | 1-(3-Methyl-morpholin-4-yl)-2-(4-{2-[3-(1-methyl-1H-pyrazol-4-yl)-phenyl]-pyrimidin-5-yl}-pyrazol-1-yl)-ethanone | ** |
| 148 | 1-((1R,4R)-5-Methyl-2,5-diaza-bicyclo[2.2.1]hept-2-yl)-2-(4-{2-[3-(1-methyl-1H-pyrazol-4-yl)-phenyl]-pyrimidin-5-yl}-pyrazol-1-yl)-ethanone | * |
| 149 | N,N-Dimethyl-2-(4-{2-[3-(1-methyl-1H-pyrazol-4-yl)-phenyl]-pyrimidin-5-yl}-pyrazol-1-yl)-isobutyramide | ** |
| 150 | 2-Methyl-2-(4-{2-[3-(1-methyl-1H-pyrazol-4-yl)-phenyl]-pyrimidin-5-yl}-pyrazol-1-yl)-1-morpholin-4-yl-propan-1-one | * |
| 151 | [4-(3-{5-[1-(Tetrahydro-pyran-4-yl)-1H-pyrazol-4-yl]-pyrimidin-2-yl}-phenyl)-pyridin-2-yl]-methanol | ** |
| 152 | Trans-4-(4-{2-[3-(1-Methyl-1H-pyrazol-4-yl)-phenyl]-pyrimidin-5-yl}-pyrazol-1-yl)-cyclohexanecarboxylic acid (2-methoxy-ethyl)-methyl-amide | *** |
| 153 | (3-Hydroxy-azetidin-1-yl)-[4-{2-[3-(1-methyl-1H-pyrazol-4-yl)-phenyl]-pyrimidin-5-yl}-1-(tetrahydro-pyran-4-yl)-1H-pyrazol-3-yl]-methanone | * |

-continued

| Ex | | IRAK4 IC50 (nM) |
|---|---|---|
| 154 | 4-{2-[3-(1-Methyl-1H-pyrazol-4-yl)-phenyl]-pyrimidin-5-yl}-1-(tetrahydro-pyran-4-yl)-1H-pyrazole-3-carboxylic acid (2-hydroxy-ethyl)-amide | * |
| 155 | (1-Methyl-4-{2-[3-(1-methyl-1H-pyrazol-4-yl)-phenyl]-pyrimidin-5-yl}-1H-pyrazol-3-yl)-methanol | * |
| 156 | 4-(4-{2-[3-(1-Methyl-1H-pyrazol-4-yl)-phenyl]-pyrimidin-5-yl}-pyrazol-1-yl)-cyclohexylamine | ** |
| 157 | 3-(4-{2-[3-(1-Methyl-1H-pyrazol-4-yl)-phenyl]-pyrimidin-5-yl}-pyrazol-1-yl)-cyclobutanecarboxylic acid methylamide | ** |
| 158 | 3-(4-{2-[3-(1-Methyl-1H-pyrazol-4-yl)-phenyl]-pyrimidin-5-yl}-pyrazol-1-yl)-cyclobutanecarboxylic acid dimethylamide | ** |
| 159 | Trans-4-(4-{2-[3-(1-Methyl-1H-pyrazol-4-yl)-phenyl]-pyrimidin-5-yl}-pyrazol-1-yl)-cyclohexanecarboxylic acid (2-methoxy-ethyl)-amide | *** |
| 160 | Trans-(4-Methyl-piperazin-1-yl)-[4-(4-{2-[3-(1-methyl-1H-pyrazol-4-yl)-phenyl]-pyrimidin-5-yl}-pyrazol-1-yl)-cyclohexyl]-methanone | *** |
| 161 | Cis-N-[4-(4-{2-[3-(1-Methyl-1H-pyrazol-4-yl)-phenyl]-pyrimidin-5-yl}-pyrazol-1-yl)-cyclohexyl]-acetamide | *** |
| 162 | Trans-[4-(4-{2-[3-(1-Methyl-1H-pyrazol-4-yl)-phenyl]-pyrimidin-5-yl}-pyrazol-1-yl)-cyclohexyl]-morpholin-4-yl-methanone | *** |
| 163 | Trans-4-(4-{2-[3-(1-Methyl-1H-pyrazol-4-yl)-phenyl]-pyrimidin-5-yl}-pyrazol-1-yl)-cyclohexanecarboxylic acid ((R)-1-hydroxymethyl-2-methyl-propyl)-amide | ** |
| 164 | Trans-4-(4-{2-[3-(1-Methyl-1H-pyrazol-4-yl)-phenyl]-pyrimidin-5-yl}-pyrazol-1-yl)-cyclohexanecarboxylic acid ((R)-1-hydroxymethyl-2-methyl-propyl)-amide | ** |
| 165 | [4-{2-[3-(1-Methyl-1H-pyrazol-4-yl)-phenyl]-pyrimidin-5-yl}-1-(tetrahydro-pyran-4-yl)-1H-pyrazol-3-yl]-methanol | nd |
| 166 | Cis-3-Methoxy-N-[4-(4-{2-[3-(1-methyl-1H-pyrazol-4-yl)-phenyl]-pyrimidin-5-yl}-pyrazol-1-yl)-cyclohexyl]-propionamide | ** |
| 167 | 5-{1-[1-((3S,4S)-3-Fluoro-tetrahydro-pyran-4-yl)-piperidin-4-yl]-1H-pyrazol-4-yl}-2-[3-(1-methyl-1H-pyrazol-4-yl)-phenyl]-pyrimidine | ** |
| 168 | ((R)-3-Methoxy-pyrrolidin-1-yl)-trans-[4-(4-{2-[3-(1-methyl-1H-pyrazol-4-yl)-phenyl]-pyrimidin-5-yl}-pyrazol-1-yl)-cyclohexyl]-methanone | *** |
| 169 | 4-Hydroxy-N-methyl-2-(4-{2-[3-(1-methyl-1H-pyrazol-4-yl)-phenyl]-pyrimidin-5-yl}-pyrazol-1-yl)-butyramide | * |
| 170 | Trans-4-(4-{2-[3-(1-Methyl-1H-pyrazol-4-yl)-phenyl]-pyrimidin-5-yl}-pyrazol-1-yl)-cyclohexanecarboxylic acid cyclopropylamide | *** |
| 171 | 4-(4-{2-[3-(1-Methyl-1H-pyrazol-4-yl)-phenyl]-pyrimidin-5-yl}-pyrazol-1-yl)-cyclohexanecarboxylic acid (2-dimethylamino-ethyl)-amide | *** |
| 172 | 4-(4-{2-[3-(1-Methyl-1H-pyrazol-4-yl)-phenyl]-pyrimidin-5-yl}-pyrazol-1-yl)-azepane | *** |
| 173 | Trans-4-(4-{2-[3-(1-Methyl-1H-pyrazol-4-yl)-phenyl]-pyrimidin-5-yl}-pyrazol-1-yl)-cyclohexanecarboxylic acid isobutyl-amide | *** |
| 174 | 4-(4-{2-[3-(1-Methyl-1H-pyrazol-4-yl)-phenyl]-pyrimidin-5-yl}-pyrazol-1-yl)-cyclohexanecarboxylic acid isopropylamide | ** |
| 175 | 5-{1-[1-(2-Fluoro-phenyl)-piperidin-4-yl]-1H-pyrazol-4-yl}-2-[3-(1-methyl-1H-pyrazol-4-yl)-phenyl]-pyrimidine | ** |
| 176 | 5-[1-(1,1-Dioxo-hexahydro-1l6-thiopyran-4-yl)-1H-pyrazol-4-yl]-2-[3-(1-methyl-1H-pyrazol-4-yl)-phenyl]-pyrimidine | ** |
| 177 | 5-[1-(1,1-Dioxo-hexahydro-1l6-thiopyran-3-yl)-1H-pyrazol-4-yl]-2-[3-(1-methyl-1H-pyrazol-4-yl)-phenyl]-pyrimidin | *** |
| 178 | 4-(4-{2-[3-(1-Methyl-1H-pyrazol-4-yl)-phenyl]-pyrimidin-5-yl}-pyrazol-1-yl)-cyclohexanecarboxylic acid (2-methoxy-1-methyl-ethyl)-amide | *** |
| 179 | 7-(4-{2-[3-(1-Methyl-1H-pyrazol-4-yl)-phenyl]-pyrimidin-5-yl}-pyrazol-1-yl)-3-oxa-9-aza-bicyclo[3.3.1]nonane | *** |
| 180 | cis-3-(4-{2-[3-(1-Methyl-1H-pyrazol-4-yl)-phenyl]-pyrimidin-5-yl}-pyrazol-1-yl)-cyclohexanecarboxylic acid methylamide | ** |
| 181 | trans-3-(4-{2-[3-(1-Methyl-1H-pyrazol-4-yl)-phenyl]-pyrimidin-5-yl}-pyrazol-1-yl)-cyclohexanecarboxylic acid methylamide | ** |
| 182 | Trans-4-(4-{2-[3-(1-Methyl-1H-pyrazol-4-yl)-phenyl]-pyrimidin-5-yl}-pyrazol-1-yl)-cyclohexanol | *** |
| 183 | 2-[3-(1-Methyl-1H-pyrazol-4-yl)-phenyl]-5-((R)-1-piperidin-3-yl-1H-pyrazol-4-yl)-pyrimidine | ** |

| Ex | | IRAK4 IC50 (nM) |
|---|---|---|
| 184 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-ethyl)-amide | *** |
| 185 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-ethyl)-methyl-amide | *** |
| 186 | ((R)-3-Hydroxy-pyrrolidin-1-yl)-[4-(4-{2-[3-(1-methyl-1H-pyrazol-4-yl)-phenyl]-pyrimidin-5-yl}-pyrazol-1-yl)-cyclohexyl]-methanone | *** |
| 187 | trans-4-(4-{2-[3-(6-Methyl-pyridazin-4-yl)-phenyl]-pyrimidin-5-yl}-pyrazol-1-yl)-cyclohexanecarboxylic acid dimethylamide | *** |
| 188 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-1-methyl-ethyl)-amide | ** |
| 189 | 4-(4-{2-[3-(1-Methyl-1H-pyrazol-4-yl)-phenyl]-pyrimidin-5-yl}-pyrazol-1-yl)-cyclohexanone | ** |
| 190 | Trans-4-(4-{2-[3-(1-Methyl-1H-pyrazol-4-yl)-phenyl]-pyrimidin-5-yl}-pyrazol-1-yl)-cyclohexanecarboxylic acid (3-hydroxy-propyl)-amide | *** |
| 191 | Trans-((S)-3-Methoxy-pyrrolidin-1-yl)-[4-(4-{2-[3-(1-methyl-1H-pyrazol-4-yl)-phenyl]-pyrimidin-5-yl}-pyrazol-1-yl)-cyclohexyl]-methanone | *** |
| 192 | Trans-4-(4-{2-[3-(1-Methyl-1H-pyrazol-4-yl)-phenyl]-pyrimidin-5-yl}-pyrazol-1-yl)-cyclohexanecarboxylic acid tert-butylamide | *** |
| 193 | exo-1-[7-(4-{2-[3-(1-Methyl-1H-pyrazol-4-yl)-phenyl]-pyrimidin-5-yl}-pyrazol-1-yl)-3-oxa-9-aza-bicyclo[3.3.1]non-9-yl]-ethanone | ** |
| 194 | cis-cis-9-(4-{2-[3-(1-Methyl-1H-pyrazol-4-yl)-phenyl]-pyrimidin-5-yl}-pyrazol-1-yl)-3-oxa-bicyclo[3.3.1]nonane-7-carboxylic acid dimethylamide | * |
| 195 | 3-(4-{2-[3-(1-Methyl-1H-pyrazol-4-yl)-phenyl]-pyrimidin-5-yl}-pyrazol-1-yl)-cyclohexanone | ** |
| 196 | Cis-4-(4-{2-[3-(1-Methyl-1H-pyrazol-4-yl)-phenyl]-pyrimidin-5-yl}-pyrazol-1-yl)-cyclohexanol | ** |
| 197 | Trans-4-(4-{2-[3-(1-Methyl-1H-pyrazol-4-yl)-phenyl]-pyrimidin-5-yl}-pyrazol-1-yl)-cyclohexanecarboxylic acid ethylamide | *** |
| 198 | Trans-4-(4-{2-[3-(1-Methyl-1H-pyrazol-4-yl)-phenyl]-pyrimidin-5-yl}-pyrazol-1-yl)-cyclohexanecarboxylic acid ((S)-2-hydroxy-1-methyl-ethyl)-amide | *** |
| 199 | Trans-4-(4-{2-[3-(1-Methyl-1H-pyrazol-4-yl)-phenyl]-pyrimidin-5-yl}-pyrazol-1-yl)-cyclohexanecarboxylic acid ((R)-2-hydroxy-1-methyl-ethyl)-amide | *** |
| 200 | Trans-4-(4-{2-[3-(1-Methyl-1H-pyrazol-4-yl)-phenyl]-pyrimidin-5-yl}-pyrazol-1-yl)-cyclohexanecarboxylic acid isopropyl-methyl-amide | *** |
| 201 | 1-[(3R,4R)-3-Hydroxy-4-(4-{2-[3-(1-methyl-1H-pyrazol-4-yl)-phenyl]-pyrimidin-5-yl}-pyrazol-1-yl)-piperidin-1-yl]ethanone (stereochemistry attributed arbitrarely) | ** |
| 202 | 1-[(3S,4S)-3-Hydroxy-4-(4-{2-[3-(1-methyl-1H-pyrazol-4-yl)-phenyl]-pyrimidin-5-yl}-pyrazol-1-yl)-piperidin-1-yl]ethanone (stereochemistry attributed arbitrarely) | ** |
| 203 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-butyl)-amide | *** |
| 204 | 4-(4-{2-[3-(1-Methyl-1H-pyrazol-4-yl)-phenyl]-pyrimidin-5-yl}-pyrazol-1-yl)-cyclohexanecarboxylic acid ethyl-methyl-amide | *** |
| 205 | trans-((S)-3-Hydroxy-pyrrolidin-1-yl)-[4-(4-{2-[3-(1-methyl-1H-pyrazol-4-yl)-phenyl]-pyrimidin-5-yl}-pyrazol-1-yl)-cyclohexyl]-methanone | *** |
| 206 | Trans-4-(4-{2-[3-(1-Methyl-1H-pyrazol-4-yl)-phenyl]-pyrimidin-5-yl}-pyrazol-1-yl)-cyclohexanecarboxylic acid amide | *** |
| 207 | 2-[3-(1-Methyl-1H-pyrazol-4-yl)-phenyl]-5-[1-(tetrahydro-thiopyran-3-yl)-1H-pyrazol-4-yl]-pyrimidine | *** |
| 208 | Trans-4-[4-(4-{2-[3-(1-Methyl-1H-pyrazol-4-yl)-phenyl]-pyrimidin-5-yl}-pyrazol-1-yl)-cyclohexyl]-morpholine | *** |
| 209 | cis-4-[4-(4-{2-[3-(1-Methyl-1H-pyrazol-4-yl)-phenyl]-pyrimidin-5-yl}-pyrazol-1-yl)-cyclohexyl]-morpholine | * |
| 210 | N-[2-(4-{2-[3-(1-Methyl-1H-pyrazol-4-yl)-phenyl]-pyrimidin-5-yl}-pyrazol-1-yl)-ethyl]-methanesulfonamide | * |
| 211 | 2-(4-{2-[3-(1-Methyl-1H-pyrazol-4-yl)-phenyl]-pyrimidin-5-yl}-pyrazol-1-yl)-cyclopentanol | ** |

| Ex | | IRAK4 IC50 (nM) |
|---|---|---|
| 212 | 3-(4-{2-[3-(1-Methyl-1H-pyrazol-4-yl)-phenyl]-pyrimidin-5-yl}-pyrazol-1-yl)-propane-1,2-diol | ** |
| 213 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-1,1-dimethyl-ethyl)-amide | *** |
| 214 | 3-Isopropoxy-2-(4-{2-[3-(1-methyl-1H-pyrazol-4-yl)-phenyl]-pyrimidin-5-yl}-pyrazol-1-yl)-propan-1-ol | * |
| 215 | 2-(4-{2-[3-(1-Methyl-1H-pyrazol-4-yl)-phenyl]-pyrimidin-5-yl}-pyrazol-1-yl)-1-pyridin-2-yl-ethanol | ** |
| 216 | 2-[3-(1-Methyl-1H-pyrazol-4-yl)-phenyl]-5-[1-(tetrahydro-thiophen-3-yl)-1H-pyrazol-4-yl]-pyrimidine | ** |
| 217 | trans-5-{1-[4-(2-Methoxy-ethoxy)-cyclohexyl]-1H-pyrazol-4-yl}-2-[3-(1-methyl-1H-pyrazol-4-yl)-phenyl]-pyrimidine | *** |
| 218 | cis-5-{1-[4-(2-Methoxy-ethoxy)-cyclohexyl]-1H-pyrazol-4-yl}-2-[3-(1-methyl-1H-pyrazol-4-yl)-phenyl]-pyrimidine | ** |
| 219 | 5-[1-(1,1-Dioxo-tetrahydro-1lambda6-thiophen-3-yl)-1H-pyrazol-4-yl]-2-[3-(1-methyl-1H-pyrazol-4-yl)-phenyl]-pyrimidine | ** |
| 220 | trans-5-[1-(4-Cyclopropylmethoxy-cyclohexyl)-1H-pyrazol-4-yl]-2-[3-(1-methyl-1H-pyrazol-4-yl)-phenyl]-pyrimidine | *** |
| 221 | 2-[3-(1-Methyl-1H-pyrazol-4-yl)-phenyl]-5-[1-(tetrahydro-pyran-3-yl)-1H-pyrazol-4-yl]-pyrimidine | ** |
| 222 | 6-(4-{2-[3-(1-Methyl-1H-pyrazol-4-yl)-phenyl]-pyrimidin-5-yl}-pyrazol-1-yl)-spiro[3.3]heptane-2-carboxylic acid dimethylamide | ** |
| 223 | 1-[4-(4-{2-[3-(1-Methyl-1H-pyrazol-4-yl)-phenyl]-pyrimidin-5-yl}-pyrazol-1-yl)-azepan-1-yl]-ethanone | ** |
| 224 | trans-2-Methyl-1-[4-(4-{2-[3-(1-methyl-1H-pyrazol-4-yl)-phenyl]-pyrimidin-5-yl}-pyrazol-1-yl)-cyclohexyloxy]-propan-2-ol | *** |
| 225 | 1-[(3S,4S)-3-Hydroxy-4-(4-{2-[3-(1-methyl-1H-pyrazol-4-yl)-phenyl]-pyrimidin-5-yl}-pyrazol-1-yl)-piperidin-1-yl]-ethanone | ** |
| 226 | 1-[(3R,4R)-3-Hydroxy-4-(4-{2-[3-(1-methyl-1H-pyrazol-4-yl)-phenyl]-pyrimidin-5-yl}-pyrazol-1-yl)-piperidin-1-yl]-ethanone (Stereochemistry attributed arbitrarely) | ** |
| 227 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-2-methyl-propyl)-amide | *** |
| 228 | trans-4-(4-{2-[3-(1-Methyl-1H-pyrazol-4-yl)-phenyl]-pyrimidin-5-yl}-pyrazol-1-yl)-cyclohexanecarboxylic acid (3-hydroxy-butyl)-amide | *** |
| 229 | Trans-4-(4-{2-[3-(2-Methyl-pyridin-4-yl)-phenyl]-pyrimidin-5-yl}-pyrazol-1-yl)-cyclohexanecarboxylic acid dimethylamide | ** |
| 230 | trans-4-(4-{2-[3-(1-Methyl-1H-pyrazol-4-yl)-phenyl]-pyrimidin-5-yl}-pyrazol-1-yl)-cyclohexanecarboxylic acid cyanomethyl-amide | *** |
| 231 | (1S,4R)-4-[4-[2-[3-(1-methylpyrazol-4-yl)phenyl]pyrimidin-5-yl]pyrazol-1-yl]cyclopent-2-en-1-ol | ** |
| 232 | Trans-dimethyl-[4-(4-{2-[3-(1-methyl-1H-pyrazol-4-yl)-phenyl]-pyrimidin-5-yl}-pyrazol-1-yl)-cyclohexylmethyl]-amine | *** |
| 233 | Trans-4-{4-[2-(3-Pyridazin-4-yl-phenyl)-pyrimidin-5-yl]-pyrazol-1-yl}-cyclohexanecarboxylic acid dimethylamide | ** |
| 234 | Trans-4-(4-{2-[3-(6-Chloro-pyridazin-3-yl)-phenyl]-pyrimidin-5-yl}-pyrazol-1-yl)-cyclohexanecarboxylic acid dimethylamide | * |
| 235 | 2-[3-(1-Methyl-1H-pyrazol-4-yl)-phenyl]-5-[1-(Trans-1-oxo-tetrahydro-thiopyran-3-yl)-1H-pyrazol-4-yl]-pyrimidine (racemate; isomery attributed arbitrarely) | ** |
| 236 | 2-[3-(1-Methyl-1H-pyrazol-4-yl)-phenyl]-5-[1-(Cis-1-oxo-tetrahydro-thiopyran-3-yl)-1H-pyrazol-4-yl]-pyrimidine (racemate; isomery attributed arbitrarely) | *** |
| 237 | Trans-4-(4-{2-[3-(6-Methyl-pyridazin-3-yl)-phenyl]-pyrimidin-5-yl}-pyrazol-1-yl)-cyclohexanecarboxylic acid dimethylamide | * |
| 238 | Trans-[4-(4-{2-[3-(1-Methyl-1H-pyrazol-4-yl)-phenyl]-pyrimidin-5-yl}-pyrazol-1-yl)-cyclohexyl]-methanol | *** |
| 239 | Trans-4-(4-{2-[3-(6-Amino-pyridazin-3-yl)-phenyl]-pyrimidin-5-yl}-pyrazol-1-yl)-cyclohexanecarboxylic acid dimethylamide | ** |
| 240 | 5-(3-{5-[1-((S)-1,1-Dioxo-hexahydro-1l6-thiopyran-3-yl)-1H-pyrazol-4-yl]-pyrimidin-2-yl}-phenyl)-3-methyl-pyridazine (stereochemistry attributed arbitrarely) | ** |
| 241 | 5-(3-{5-[1-((R)-1,1-Dioxo-hexahydro-1l6-thiopyran-3-yl)-1H-pyrazol-4-yl]-pyrimidin-2-yl}-phenyl)-3-methyl-pyridazine (stereochemistry attributed arbitrarely) | ** |

-continued

| Ex | | IRAK4 IC50 (nM) |
|---|---|---|
| 242 | Trans-4-(4-{2-[3-(1-Methyl-1H-pyrazol-4-yl)-phenyl]-pyrimidin-5-yl}-pyrazol-1-yl)-cyclohexanecarboxylic acid (2,3-dihydroxy-propyl)-amide | *** |
| 243 | 5-[1-((2R,4R)-2-Methyl-piperidin-4-yl)-1H-pyrazol-4-yl]-2-[3-(1-methyl-1H-pyrazol-4-yl)-phenyl]-pyrimidine formic acid | ** |
| 244 | ((3S,4S)-3,4-Dihydroxy-pyrrolidin-1-yl)-[4-(4-{2-[3-(1-methyl-1H-pyrazol-4-yl)-phenyl]-pyrimidin-5-yl}-pyrazol-1-yl)-cyclohexyl]-methanone | *** |
| 245 | (Trans-3-Hydroxy-4-methoxy-pyrrolidin-1-yl)-[4-Trans-(4-{2-[3-(1-methyl-1H-pyrazol-4-yl)-phenyl]-pyrimidin-5-yl}-pyrazol-1-yl)-cyclohexyl]-methanone | *** |
| 246 | 5-[1-((2S,4S)-2-Methyl-piperidin-4-yl)-1H-pyrazol-4-yl]-2-[3-(1-methyl-1H-pyrazol-4-yl)-phenyl]-pyrimidine | *** |
| 247 | trans-4-(4-{2-[3-(6-Methyl-pyridazin-4-yl)-phenyl]-pyrimidin-5-yl}-pyrazol-1-yl)-cyclohexanol | ** |
| 248 | 1-[(2S,4S)-2-Methyl-4-(4-{2-[3-(1-methyl-1H-pyrazol-4-yl)-phenyl]-pyrimidin-5-yl}-pyrazol-1-yl)-piperidin-1-yl]-ethanone | *** |
| 249 | 1-[(2R,4R)-2-Methyl-4-(4-{2-[3-(1-methyl-1H-pyrazol-4-yl)-phenyl]-pyrimidin-5-yl}-pyrazol-1-yl)-piperidin-1-yl]-ethanone | ** |
| 250 | cis-8-(4-{2-[3-(1-Methyl-1H-pyrazol-4-yl)-phenyl]-pyrimidin-5-yl}-pyrazol-1-yl)-1-aza-spiro[4.5]decan-2-one (first isomer) | *** |
| 251 | Cis-8-(4-{2-[3-(1-Methyl-1H-pyrazol-4-yl)-phenyl]-pyrimidin-5-yl}-pyrazol-1-yl)-1-aza-spiro[4.5]decan-2-one (second isomer) | ** |
| 252 | Cis-5-[1-(4-Methoxy-cyclohexyl)-1H-pyrazol-4-yl]-2-[3-(1-methyl-1H-pyrazol-4-yl)-phenyl]-pyrimidine | *** |
| 253 | trans-5-[1-(4-Methoxy-cyclohexyl)-1H-pyrazol-4-yl]-2-[3-(1-methyl-1H-pyrazol-4-yl)-phenyl]-pyrimidine | *** |
| 254 | 4-[4-(4-{2-[3-(1-Methyl-1H-pyrazol-4-yl)-phenyl]-pyrimidin-5-yl}-pyrazol-1-yl)-cyclohexyl]-morpholin-3-one | *** |
| 255 | :3-[4-(4-{2-[3-(1-Methyl-1H-pyrazol-4-yl)-phenyl]-pyrimidin-5-yl}-pyrazol-1-yl)-cyclohexyl]-oxazolidin-2-one | ** |
| 256 | Trans-[4-(4-{2-[3-(6-Methyl-pyridazin-4-yl)-phenyl]-pyrimidin-5-yl}-pyrazol-1-yl)-cyclohexyl]-methanol | *** |
| 257 | 3-[cis-3-(4-{2-[3-(1-Methyl-1H-pyrazol-4-yl)-phenyl]-pyrimidin-5-yl}-pyrazol-1-yl)-cyclohexyl]-oxazolidin-2-one | *** |
| 258 | Cis-1-Hydroxymethyl-4-(4-{2-[3-(1-methyl-1H-pyrazol-4-yl)-phenyl]-pyrimidin-5-yl}-pyrazol-1-yl)-cyclohexanol | *** |
| 259 | 5-[1-(3,3-Difluoro-piperidin-4-yl)-1H-pyrazol-4-yl]-2-[3-(1-methyl-1H-pyrazol-4-yl)-phenyl]-pyrimidine | ** |
| 260 | trans-2-Methyl-8-(4-{2-[3-(1-methyl-1H-pyrazol-4-yl)-phenyl]-pyrimidin-5-yl}-pyrazol-1-yl)-2-aza-spiro[4.5]decan-3-one | *** |
| 261 | ((S)-2-Hydroxymethyl-morpholin-4-yl)-[4-((S)-4-{2-[3-(1-methyl-1H-pyrazol-4-yl)-phenyl]-pyrimidin-5-yl}-pyrazol-1-yl)-cyclohexyl]-methanone | *** |
| 262 | cis-2-Methyl-8-(4-{2-[3-(1-methyl-1H-pyrazol-4-yl)-phenyl]-pyrimidin-5-yl}-pyrazol-1-yl)-2-aza-spiro[4.5]decan-3-one | *** |
| 263 | Cis-1-[3-Fluoro-4-(4-{2-[3-(1-methyl-1H-pyrazol-4-yl)-phenyl]-pyrimidin-5-yl}-pyrazol-1-yl)-piperidin-1-yl]-ethanone | *** |
| 264 | 5-[1-(1,9-Dioxa-spiro[5.5]undec-4-yl)-1H-pyrazol-4-yl]-2-[3-(1-methyl-1H-pyrazol-4-yl)-phenyl]-pyrimidine | ** |
| 265 | cis-3-Fluoro-piperidin-4-yl)-1H-pyrazol-4-yl]-2-[3-(1-methyl-1H-pyrazol-4-yl)-phenyl]-pyrimidine | ** |
| 266 | ((R)-2-Hydroxymethyl-morpholin-4-yl)-[4-((S)-4-{2-[3-(1-methyl-1H-pyrazol-4-yl)-phenyl]-pyrimidin-5-yl}-pyrazol-1-yl)-cyclohexyl]-methanone | *** |
| 267 | 5-[1-(1,9-Dioxa-spiro[5.5]undec-4-yl)-1H-pyrazol-4-yl]-2-[3-(1-methyl-1H-pyrazol-4-yl)-phenyl]-pyrimidine | *** |
| 268 | 5-[(R)-1-(1-Methanesulfonyl-piperidin-3-yl)-1H-pyrazol-4-yl]-2-[3-(1-methyl-1H-pyrazol-4-yl)-phenyl]-pyrimidine | *** |
| 269 | 1-[3-((R)-4-{2-[3-(1-Methyl-1H-pyrazol-4-yl)-phenyl]-pyrimidin-5-yl}-pyrazol-1-yl)-piperidin-1-yl]-ethanone | *** |
| 270 | 2-[3-(1-Methyl-1H-pyrazol-4-yl)-phenyl]-5-{1-[1-(tetrahydro-pyran-3-yl)-piperidin-4-yl]-1H-pyrazol-4-yl}-pyrimidine | *** |
| 271 | 4-[4-(4-{2-[3-(1-Methyl-1H-pyrazol-4-yl)-phenyl]-pyrimidin-5-yl}-pyrazol-1-yl)-tetrahydro-pyran-3-ylmethyl]-morpholine | * |
| 272 | 5-[(R)-1-(1-Methanesulfonyl-piperidin-3-yl)-1H-pyrazol-4-yl]-2-[3-(1-methyl-1H-pyrazol-4-yl)-phenyl]-pyrimidine | *** |
| 273 | trans,cis-9-(4-{2-[3-(1-Methyl-1H-pyrazol-4-yl)-phenyl]-pyrimidin-5-yl}-pyrazol-1-yl)-3-oxa-bicyclo[3.3.1]nonane-7-carboxylic acid dimethylamide | ** |
| 274 | 1-[3-((R)-4-{2-[3-(1-Methyl-1H-pyrazol-4-yl)-phenyl]-pyrimidin-5-yl}-pyrazol-1-yl)-piperidin-1-yl]-ethanone | *** |

| Ex | | IRAK4 IC50 (nM) |
|---|---|---|
| 275 | 2-[3-(1-Methyl-1H-pyrazol-4-yl)-phenyl]-5-{1-[1-(3-methyl-tetrahydro-pyran-4-yl)-piperidin-4-yl]-1H-pyrazol-4-yl}-pyrimidine | *** |
| 276 | [9-(4-{2-[3-(1-Methyl-1H-pyrazol-4-yl)-phenyl]-pyrimidin-5-yl}-pyrazol-1-yl)-3-oxa-bicyclo[3.3.1]non-7-yl]-methanol | ** |
| 277 | Trans-2-[4-(-4-{2-[3-(1-Methyl-1H-pyrazol-4-yl)-phenyl]-pyrimidin-5-yl}-pyrazol-1-yl)-cyclohexyloxy]-ethanol | *** |
| 278 | (5-Methyl-2,5-diaza-bicyclo[2.2.1]hept-2-yl)-trans-[4-(-4-{2-[3-(1-methyl-1H-pyrazol-4-yl)-phenyl]-pyrimidin-5-yl}-pyrazol-1-yl)-cyclohexyl]-methanone hydrobromide | *** |
| 279 | 5-[1-(Cis-3-Methanesulfonyl-cyclohexyl)-1H-pyrazol-4-yl]-2-[3-(1-methyl-1H-pyrazol-4-yl)-phenyl]-pyrimidine (isomery attributed arbitrarely) | *** |
| 280 | (3aS,7aS)-7a-Hydroxymethyl-5-((R)-4-{2-[3-(1-methyl-1H-pyrazol-4-yl)-phenyl]-pyrimidin-5-yl}-pyrazol-1-yl)-hexahydro-isobenzofuran-3a-ol (configuration attributed arbitrarily) | *** |
| 281 | (3aR,5R,7aR)-7a-Hydroxymethyl-5-(4-{2-[3-(1-methyl-1H-pyrazol-4-yl)-phenyl]-pyrimidin-5-yl}-pyrazol-1-yl)-hexahydro-isobenzofuran-3a-ol (configuration attributed arbitrarily) | ** |
| 282 | 5-[1-(trans-3-Methanesulfonyl-cyclohexyl)-1H-pyrazol-4-yl]-2-[3-(1-methyl-1H-pyrazol-4-yl)-phenyl]-pyrimidine (isomery attributed arbitrarely) | ** |
| 283 | 2-[3-(1-Methyl-1H-pyrazol-4-yl)-phenyl]-5-((S)-1-piperidin-3-yl-1H-pyrazol-4-yl)-pyrimidine | *** |
| 284 | 1-[3,3-Difluoro-4-(4-{2-[3-(1-methyl-1H-pyrazol-4-yl)-phenyl]-pyrimidin-5-yl}-pyrazol-1-yl)-piperidin-1-yl]-ethanone | *** |
| 285 | 1-Methyl-8-(4-{2-[3-(1-methyl-1H-pyrazol-4-yl)-phenyl]-pyrimidin-5-yl}-pyrazol-1-yl)-1-aza-spiro[4.5]decan-2-one | *** |
| 286 | trans-8-(4-{2-[3-(1-Methyl-1H-pyrazol-4-yl)-phenyl]-pyrimidin-5-yl}-pyrazol-1-yl)-2-aza-spiro[4.5]decan-3-one | *** |
| 287 | cis-8-(4-(2-(3-(1-methyl-1H-pyrazol-4-yl)phenyl)pyrimidin-5-yl)-1H-pyrazol-1-yl)-2-azaspiro[4.5]decan-3-one | *** |
| 288 | imino(methyl)(3-(4-(2-(3-(1-methyl-1H-pyrazol-4-yl)phenyl)pyrimidin-5-yl)-1H-pyrazol-1-yl)cyclohexyl)-λ6-sulfanone | *** |
| 289 | 2-trans-[4-(4-{2-[3-(1-Methyl-1H-pyrazol-4-yl)-phenyl]-pyrimidin-5-yl}-pyrazol-1-yl)-cyclohexylamino]-ethano | *** |
| 290 | Trans-3-(4-{2-[3-(1-Methyl-1H-pyrazol-4-yl)-phenyl]-pyrimidin-5-yl}-pyrazol-1-yl)-cyclohexanol | ** |
| 291 | 4-(3-Methyl-4-{2-[3-(1-methyl-1H-pyrazol-4-yl)-phenyl]-pyrimidin-5-yl}-pyrazol-1-yl)-cyclohexanol | ** |
| 292 | 4-(4-{2-[2-Fluoro-5-(1-methyl-1H-pyrazol-4-yl)-phenyl]-pyrimidin-5-yl}-pyrazol-1-yl)-cyclohexanol | ** |

*: $1\ \mu M < IC_{50} < 5\ \mu M$
**: $0.1\ \mu M < IC_{50} < 1\ \mu M$
***: $IC_{50} < 0.1\ \mu M$ n.d: not determined

Example 293

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:
1. A compound of Formula (I)

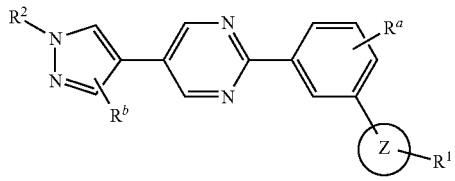

wherein
R¹ denotes absent, A, or Q-Het,

Z is
wherein
X denotes O, S or N,
Y denotes C or N,
T denotes C or N, or
Z denotes a pyridine or a pyridazine group,
$R^a$ is absent, $OR^3$, $CF_3$, Hal, or $NO_2$,
$R^b$ is absent, A, or COHet,
$R^2$ denotes H, Het, Q-Het, Cyc, A or OA, each Het is independently a 4-9 membered monocyclic ring or a fused, spiro or bridged bicyclic ring, which is saturated, unsaturated, or aromatic, which contains 1 to 3 heteroatoms independently selected from N, O, and S, and a group CO, SO or $SO_2$, and wherein 1 or 2 H atoms may be replaced by A, OA, COA, CN, Hal, $NO_2$, $OR^3$, SOA and/or $SO_2A$,
Cyc denotes a 4-8 saturated carbocyclic ring optionally containing a group SO, $SO_2$, or CO, and optionally substituted once or twice by a group selected from $CO(NR^3)_2$, COHet, $OR^3$, $Het^1$, A, $CH_2Het^1$, $NH_2$, NHCOA, $OCH_2Cyc^1$, $SO_2A$ and -SA(=NH)(=O),
each Q is independent a linear or branched alkylene, having 1 to 6 carbon atoms wherein 1-5 H atoms may be replaced by a group independently selected from $OR^3$, Hal, and $N(R^3)_2$, and wherein 1 or 2 $CH_2$ groups may be replaced by a group independently selected from CO, SO, $SO_2$ and $NR^3$, or Q denotes a 4-8-membered bivalent heterocyclic ring, which is saturated, unsaturated or aromatic and which contains 1 to 3 heteroatoms independently selected from N, O and S,
each A is independently a linear or branched alkyl having 1 to 10 carbon atoms wherein 1 to 7 H atoms may be replaced by a group independently selected from —$OR^3$, Hal, $NHSO_2A$, $SO_2A$, SOA, and $N(R^3)_2$, and wherein 1, 2 or 3 non-adjacent —$CH_2$—groups may be replaced by a group independently selected from —CO—, $NR^3$ and —O—,
each Hal is independently F, Cl, Br or I,
each $R^3$ is independently H or $C_1$-$C_6$-alkyl wherein 1 H atom may be replaced by a group selected from OH, O—$C_1$-$C_6$-alkyl, and Hal,
each $Het^1$ is independently a five- or six membered saturated monocyclic heterocycle which contains 1-3 N—and/or O-atoms, which optionally is monosubstituted by A, $Cyc^1$ denotes cycloalkyl with 3-7 atoms, and pharmaceutically acceptable, solvates, tautomers, salts, hydrates and stereoisomers thereof, including mixtures thereof in all ratios.

2. The compound of claim 1 wherein Z denotes one of the following groups:

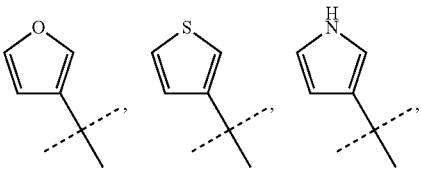

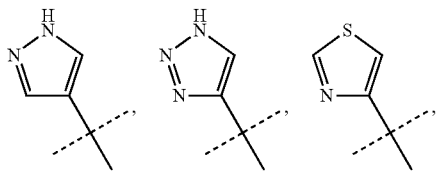

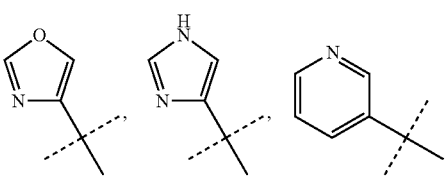

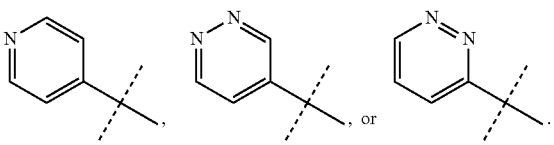

3. The compound of claim 1 wherein the group Z—R¹ denotes one of the following groups:

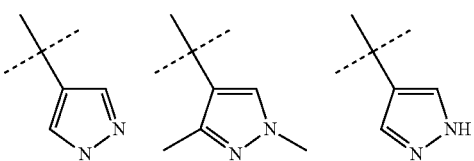

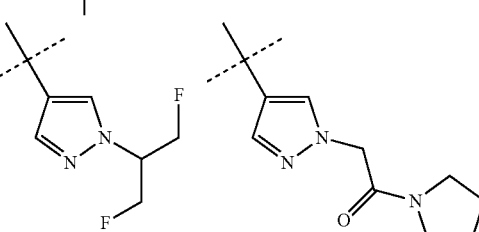

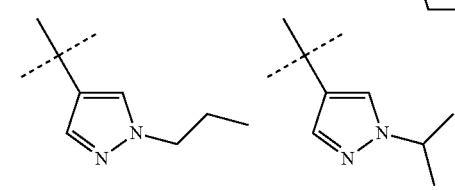

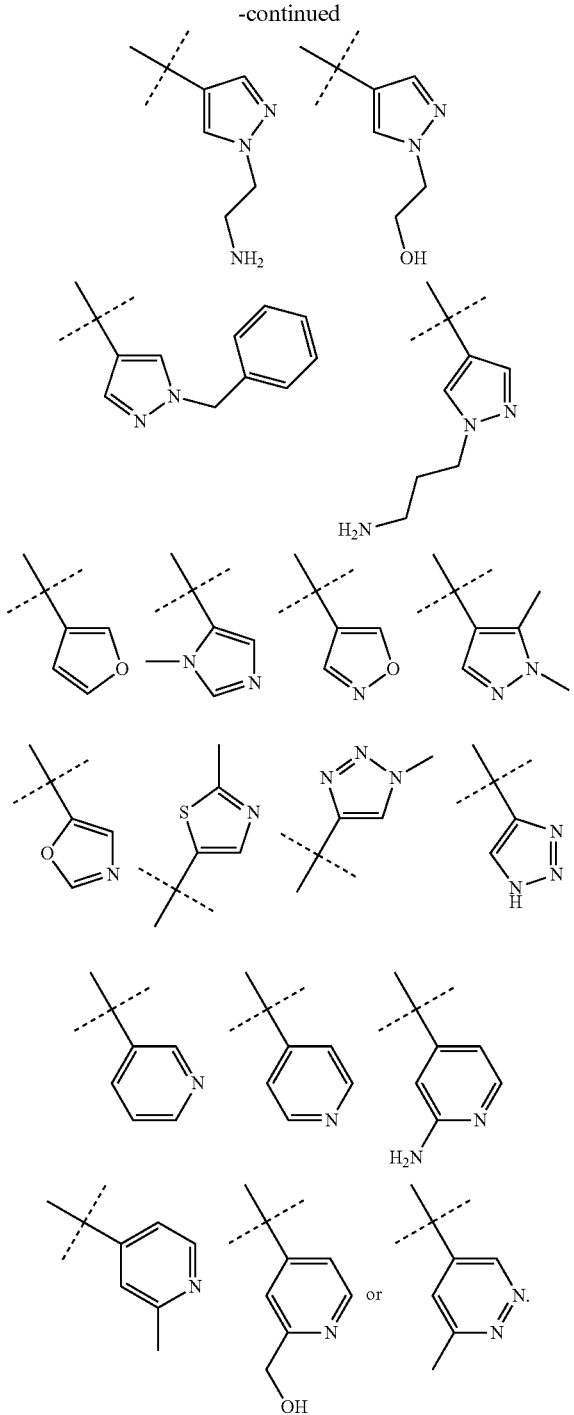
4. The compound of claim 1 wherein R² denotes one of the following groups:
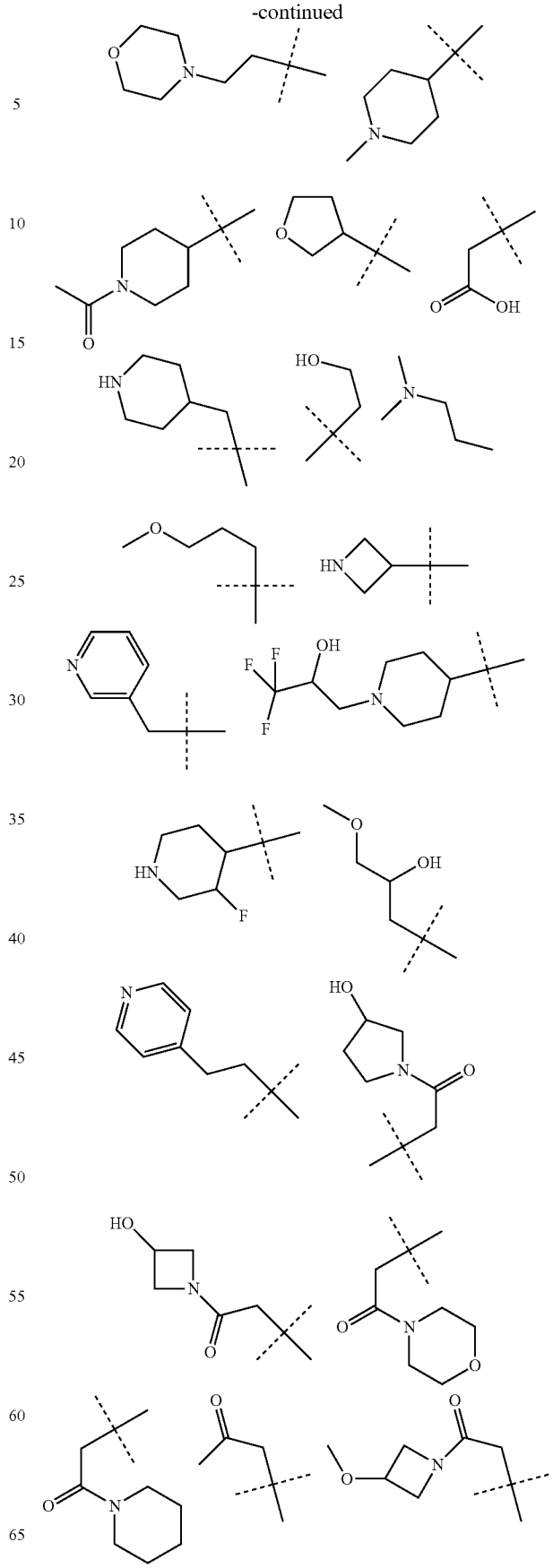

255
-continued
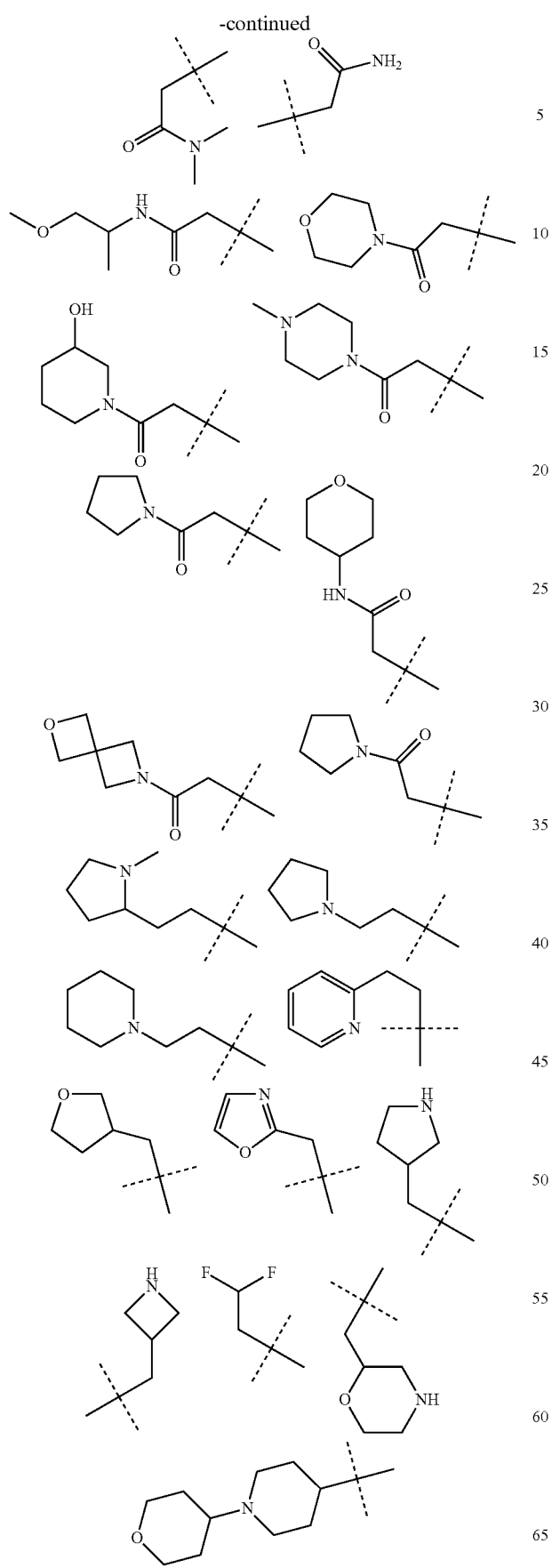
256
-continued
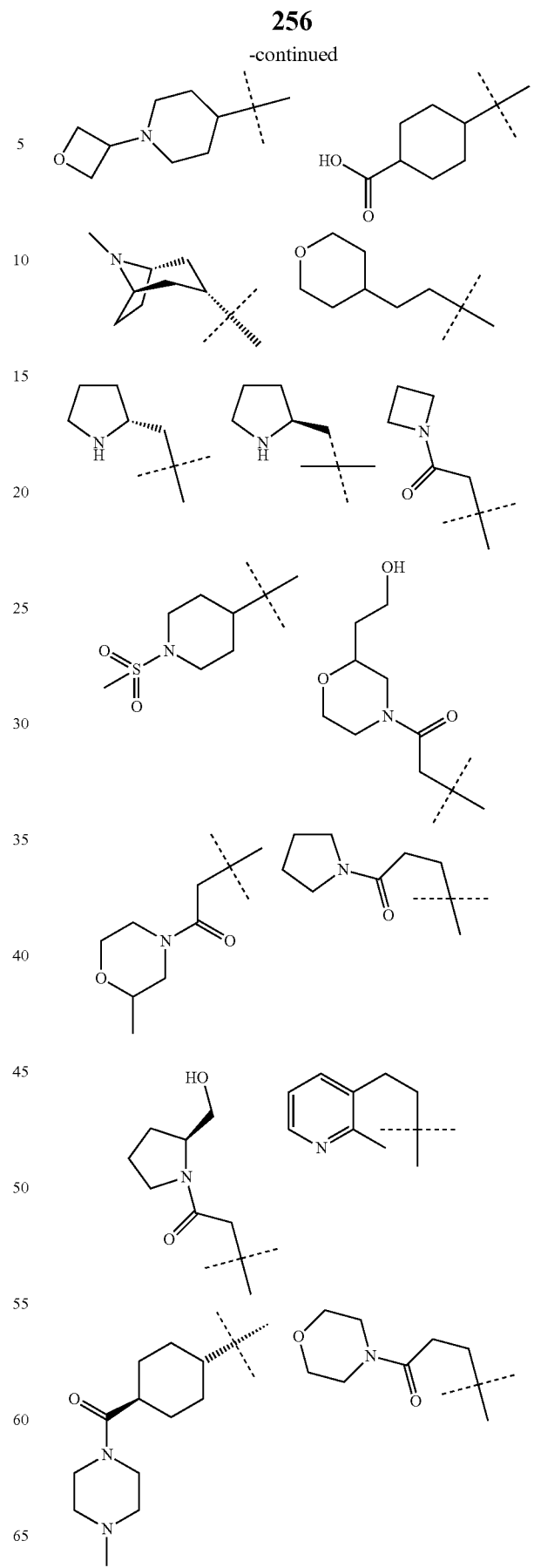

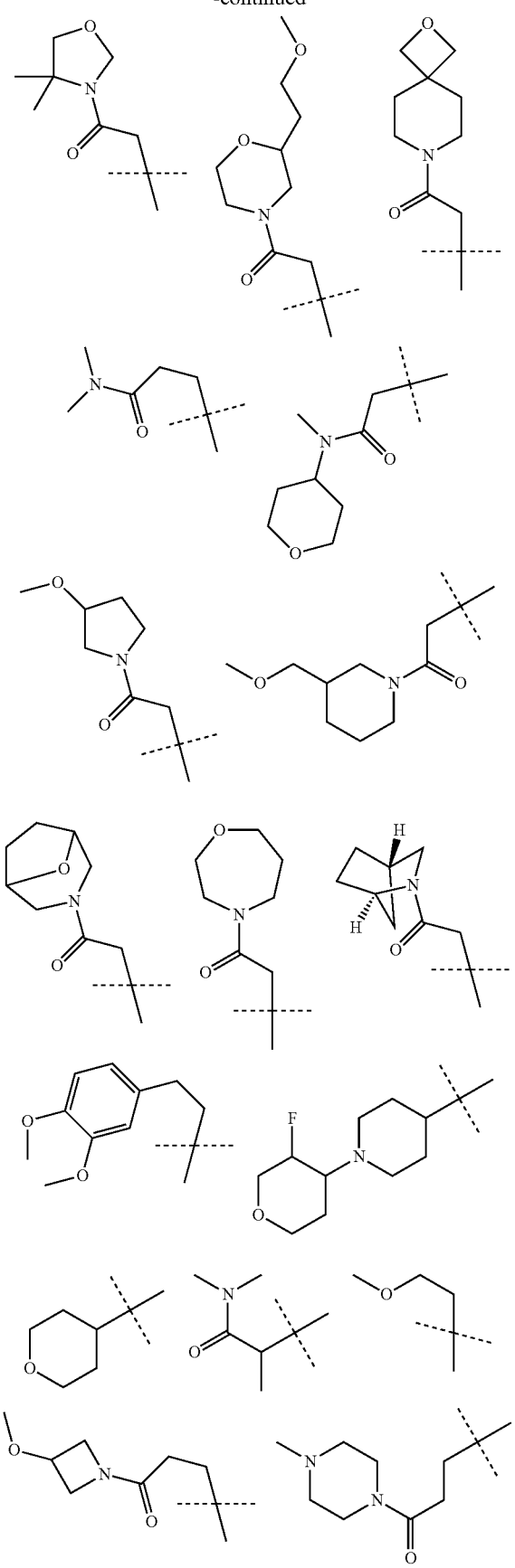
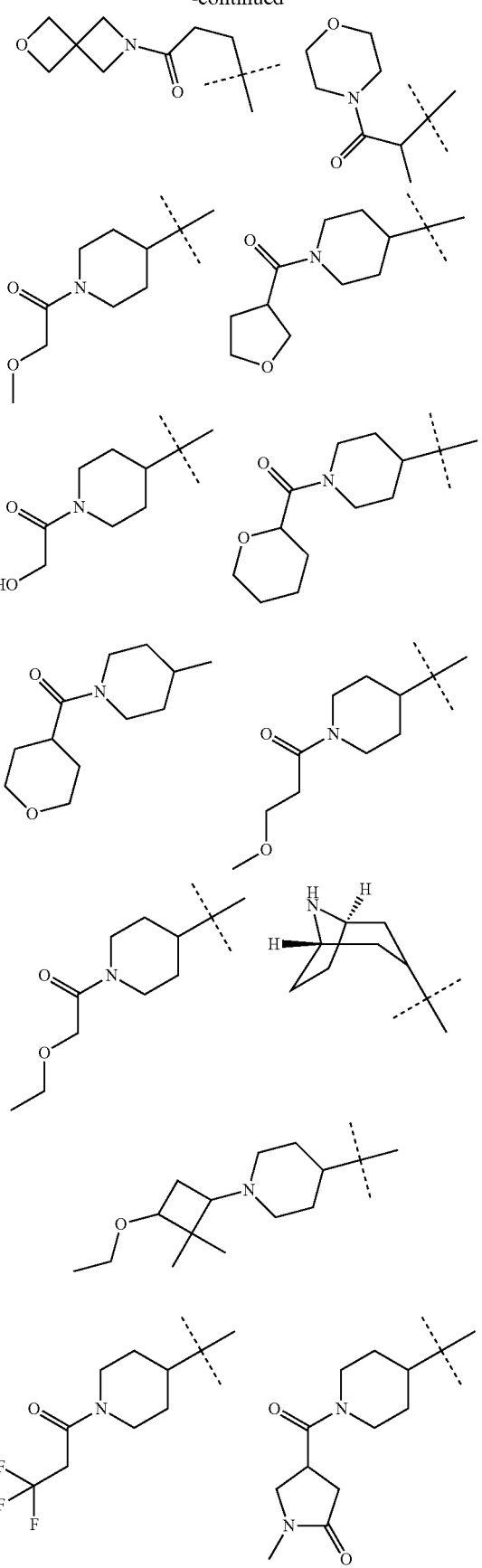

259
-continued
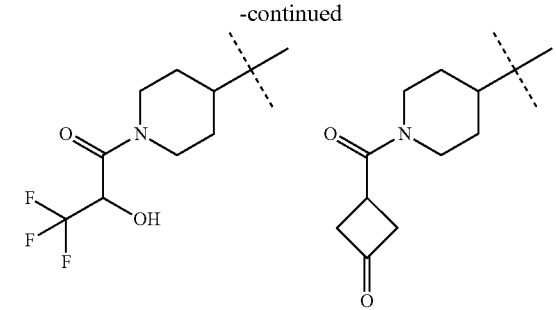
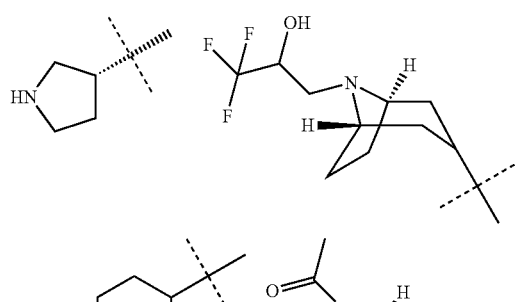
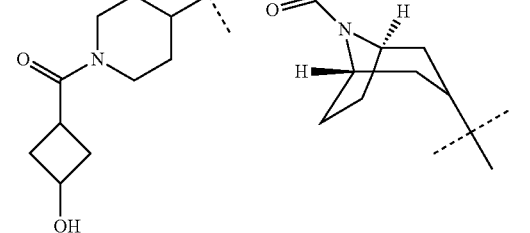
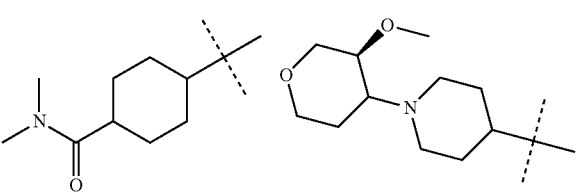
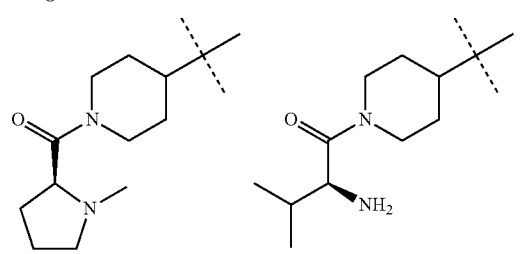
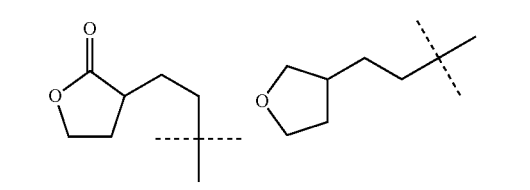
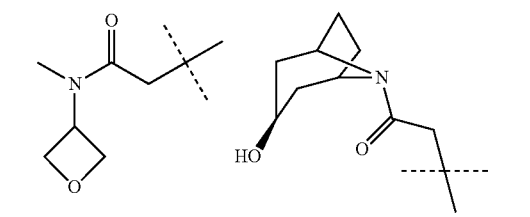
260
-continued
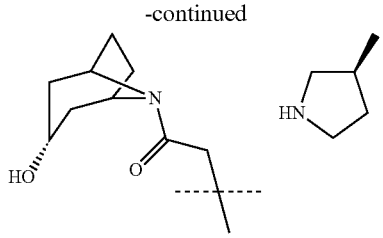
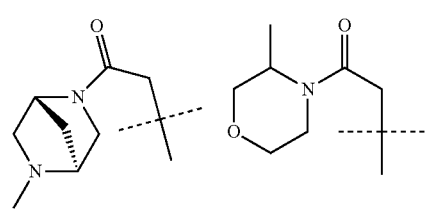
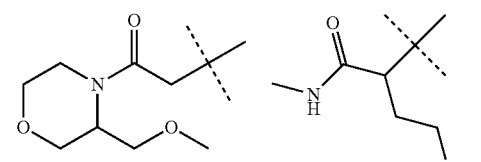
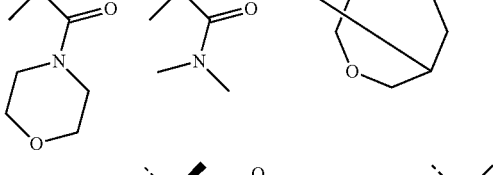
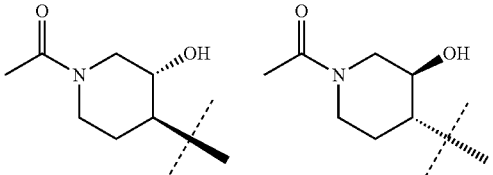
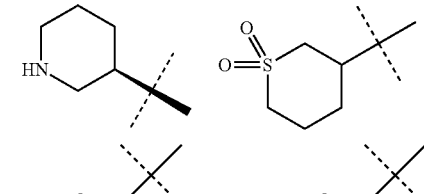
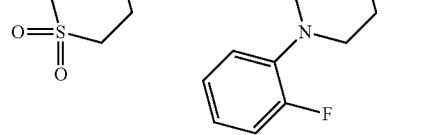

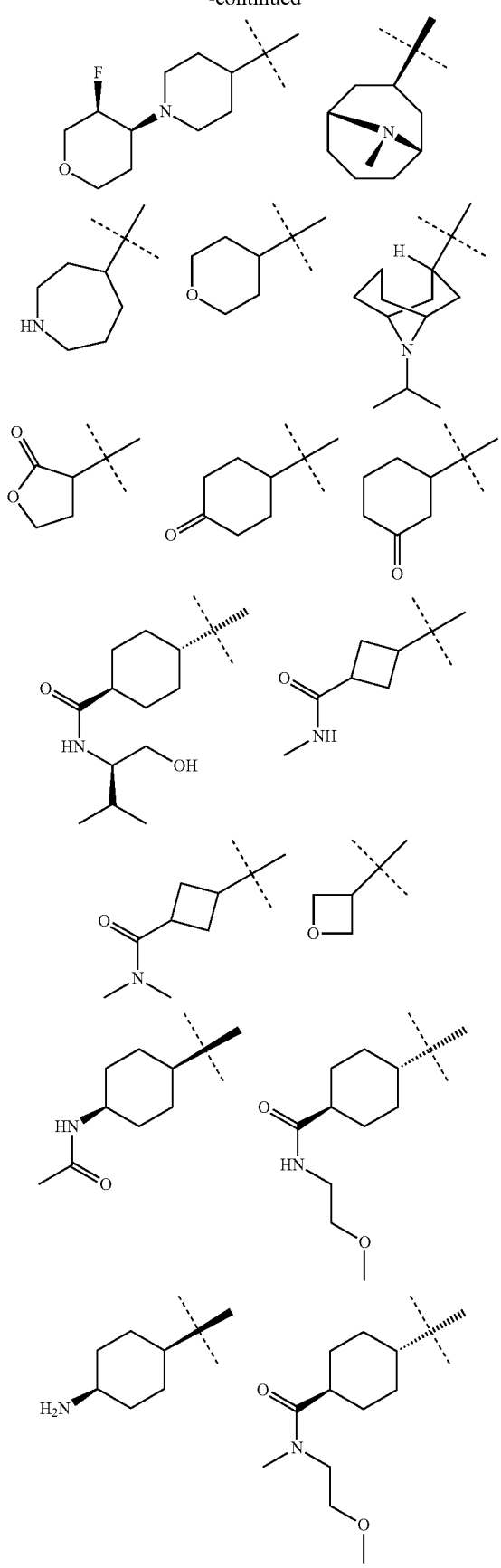
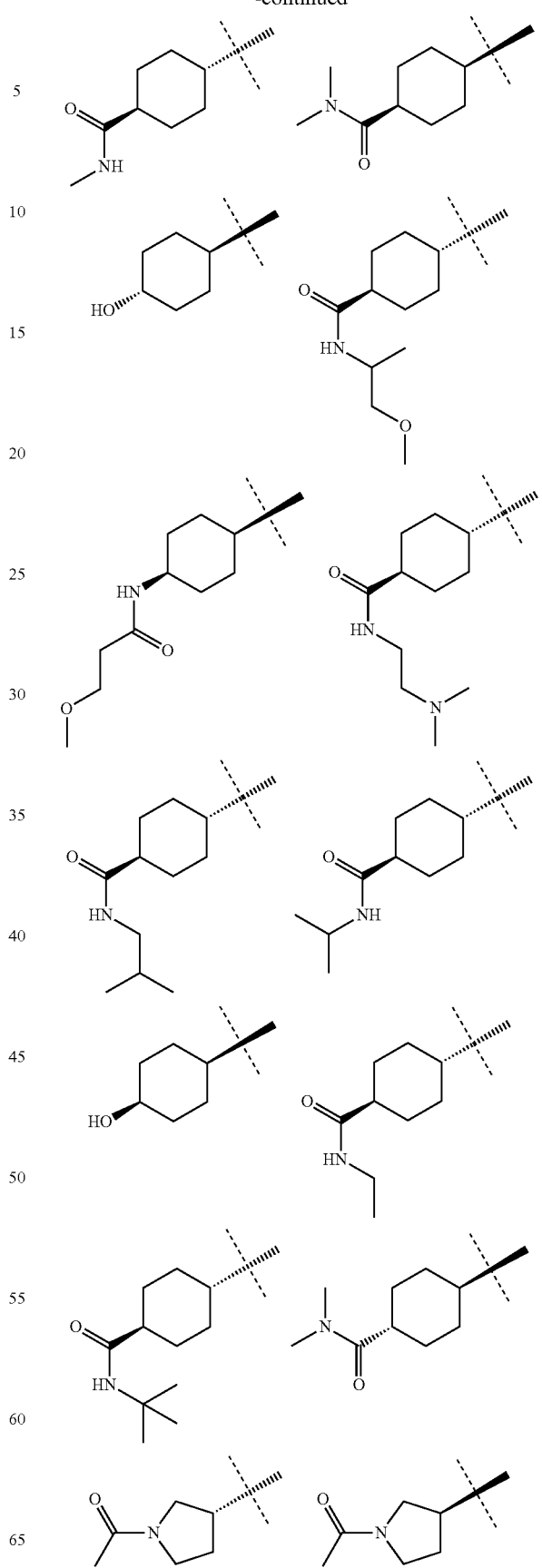

263
-continued
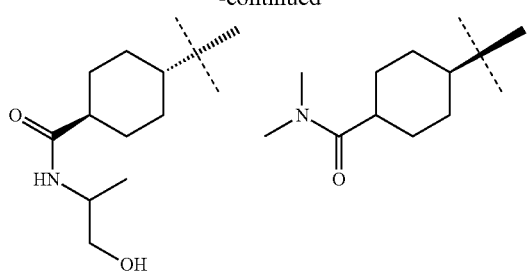
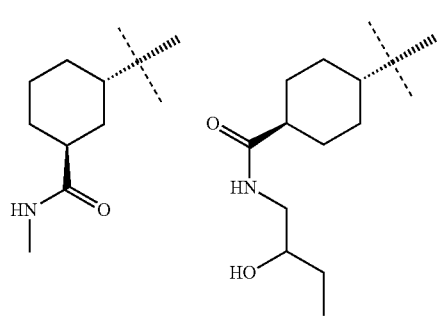
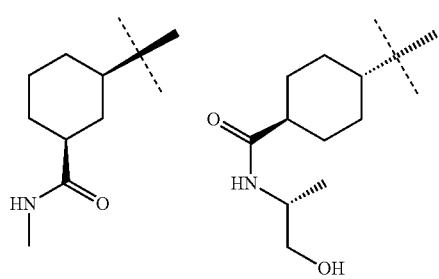
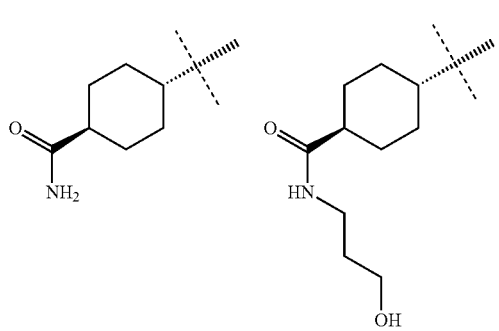
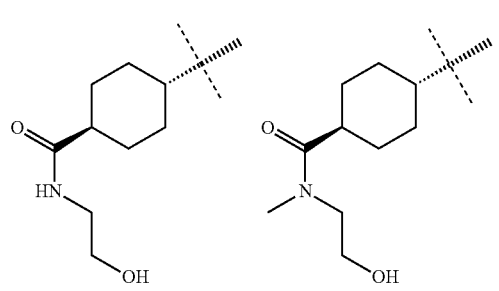
264
-continued
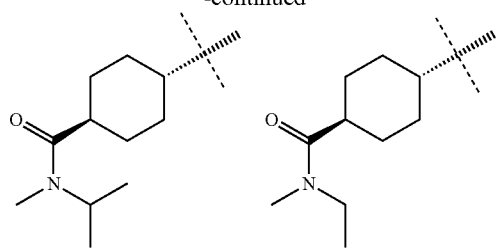
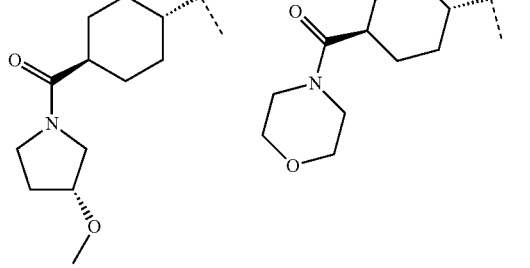
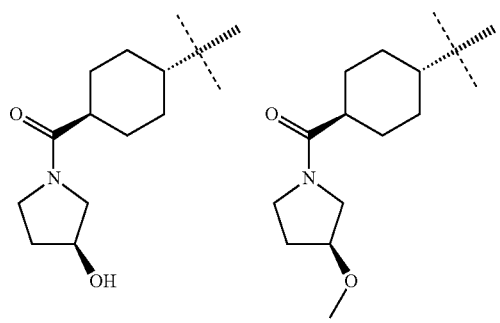
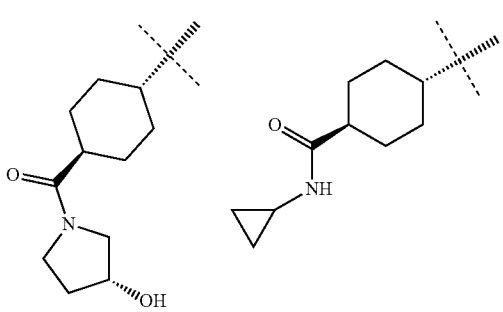
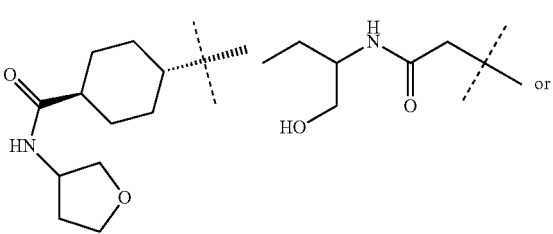

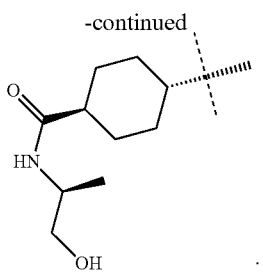

5. The compound of claim 1 wherein $R^b$ is selected from one of the following groups:

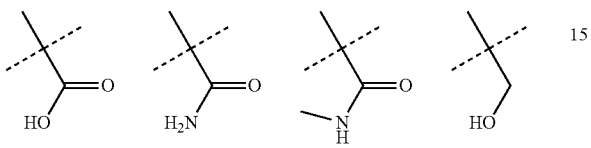

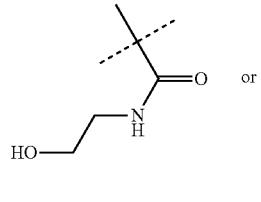

6. The compound of claim 1, selected from the following group;

| Ex | |
|---|---|
| 1 | 2-[3-(1-Methyl-1H-pyrazol-4-yl)-phenyl]-5-(1-piperidin-4-yl-1H-pyrazol-4-yl)-pyrimidine hydrochloride |
| 2 | 5-(1-(piperidin-4-yl)-1H-pyrazol-4-yl)-2-(3-(pyridin-3-yl)phenyl)pyrimidine_hydrochloride |
| 3 | 2-[3-(1-methyl-1H-pyrazol-4-yl)phenyl]-5-(1H-pyrazol-4-yl)pyrimidine |
| 4 | 2,2,2-Trifluoro-1-[4-(4-{2-[3-(1-methyl-1H-pyrazol-4-yl)-phenyl]-pyrimidin-5-yl}-pyrazol-1-yl)-piperidin-1-yl]-ethanone |
| 5 | -[4-(4-{2-[3-(1-Methyl-1H-pyrazol-4-yl)-phenyl]-pyrimidin-5-yl}-pyrazol-1-yl)-piperidin-1-yl]-ethanone |
| 6 | 5-[1-(1-Methyl-piperidin-4-yl)-1H-pyrazol-4-yl]-2-[3-(1-methyl-1H-pyrazol-4-yl)-phenyl]-pyrimidine |
| 7 | 2-(3-Furan-3-yl-phenyl)-5-(1-piperidin-4-yl-1H-pyrazol-4-yl)-pyrimidine Hydrochloride |
| 8 | 4-{2-[3-(1-Methyl-1H-pyrazol-4-yl)-phenyl]-pyrimidin-5-yl}-pyrazol-1-yl)-acetic acid |
| 9 | 2-(4-{2-[3-(1-Methyl-1H-pyrazol-4-yl)-phenyl]-pyrimidin-5-yl}-pyrazol-1-yl)-1-pyrrolidin-1-yl-ethanone |
| 10 | 4-[2-(4-{2-[3-(1-Methyl-1H-pyrazol-4-yl)-phenyl]-pyrimidin-5-yl}-pyrazol-1-yl)-ethyl]-morpholine |
| 11 | Dimethyl-[2-(4-{2-[3-(1-methyl-1H-pyrazol-4-yl)-phenyl]-pyrimidin-5-yl}-pyrazol-1-yl)-ethyl]-amine |
| 12 | 2-[3-(1-Methyl-1H-pyrazol-4-yl)-phenyl]-5-[1-(tetrahydro-furan-3-yl)-1H-pyrazol-4-yl]-pyrimidine |
| 13 | 2-(3-Isoxazol-4-yl-phenyl)-5-(1-piperidin-4-yl-1H-pyrazol-4-yl)-pyrimidine hydrochloride |
| 14 | 2-[3-(1,3-Dimethyl-1H-pyrazol-4-yl)-phenyl]-5-(1-piperidin-4-yl-1H-pyrazol-4-yl)-pyrimidine hydrochloride |
| 15 | 2-[3-(1,5-Dimethyl-1H-pyrazol-4-yl)-phenyl]-5-(1-piperidin-4-yl-1H-pyrazol-4-yl)-pyrimidine hydrochloride |
| 16 | 2-{3-[1-(2-Fluoro-1-fluoromethyl-ethyl)-1H-pyrazol-4-yl]-phenyl}-5-(1-piperidin-4-yl-1H-pyrazol-4-yl)-pyrimidine hydrochloride |
| 17 | 2-(4-{3-[5-(1-Piperidin-4-yl-1H-pyrazol-4-yl)-pyrimidin-2-yl]-phenyl}-pyrazol-1-yl)-1-pyrrolidin-1-yl-ethanone hydrochloride |
| 18 | 5-(1-Piperidin-4-yl-1H-pyrazol-4-yl)-2-[3-(1H-pyrazol-4-yl)-phenyl]-pyrimidine hydrochloride |
| 19 | 5-(1-Piperidin-4-yl-1H-pyrazol-4-yl)-2-[3-(1-propyl-1H-pyrazol-4-yl)-phenyl]-pyrimidine hydrochloride |
| 20 | 2-[3-(1-Isopropyl-1H-pyrazol-4-yl)-phenyl]-5-(1-piperidin-4-yl-1H-pyrazol-4-yl)-pyrimidine hydrochloride |
| 21 | 2-[3-(1-Benzyl-1H-pyrazol-4-yl)-phenyl]-5-(1-piperidin-4-yl-1H-pyrazol-4-yl)-pyrimidine hydrochloride |
| 22 | 2-[3-(1-Methyl-1H-pyrazol-4-yl)-phenyl]-5-(1-pyridin-3-ylmethyl-1H-pyrazol-4-yl)-pyrimidine |
| 23 | 2-(4-{2-[3-(1-Methyl-1H-pyrazol-4-yl)-phenyl]-pyrimidin-5-yl}-pyrazol-1-yl)-ethanol |
| 24 | 2-[3-Fluoro-5-(1-methyl-1H-pyrazol-4-yl)-phenyl]-5-(1-piperidin-4-yl-1H-pyrazol-4-yl)-pyrimidine hydrochloride |
| 25 | 2-(4-{2-[3-(1-Methyl-1H-pyrazol-4-yl)-phenyl]-pyrimidin-5-yl}-pyrazol-1-yl)-1-piperidin-1-yl-ethanone |
| 26 | 5-(1-Azetidin-3-yl-1H-pyrazol-4-yl)-2-[3-(1-methyl-1H-pyrazol-4-yl)-phenyl]-pyrimidine hydrochloride |
| 27 | 5-[1-(3-Methoxy-propyl)-1H-pyrazol-4-yl]-2-[3-(1-methyl-1H-pyrazol-4-yl)-phenyl]-pyrimidine |

-continued

| Ex | |
|---|---|
| 28 | 2-[3-(1-Methyl-1H-pyrazol-4-yl)-phenyl]-5-[1-(1-oxetan-3-yl-piperidin-4-yl)-1H-pyrazol-4-yl]-pyrimidine |
| 29 | 2-[3-(1-Methyl-1H-pyrazol-4-yl)-phenyl]-5-(1-piperidin-4-ylmethyl-1H-pyrazol-4-yl)-pyrimidine hydrochloride |
| 30 | trans-5-[1-(3-Fluoro-piperidin-4-yl)-1H-pyrazol-4-yl]-2-[3-(1-methyl-1H-pyrazol-4-yl)-phenyl]-pyrimidine hydrochloride |
| 31 | 1,1,1-Trifluoro-3-[4-(4-{2-[3-(1-methyl-1H-pyrazol-4-yl)-phenyl]-pyrimidin-5-yl}-pyrazol-1-yl)-piperidin-1-yl]-propan-2-ol |
| 32 | 5-(1-Methyl-1H-pyrazol-4-yl)-2-[3-(1-methyl-1H-pyrazol-4-yl)-phenyl]-pyrimidine |
| 33 | 5-(1-Piperidin-4-yl-1H-pyrazol-4-yl)-2-(3-pyridin-4-yl-phenyl)-pyrimidine hydrochloride |
| 34 | 3-(1-Methyl-1H-pyrazol-4-yl)-5-[5-(1-piperidin-4-yl-1H-pyrazol-4-yl)-pyrimidin-2-yl]-phenol Formate |
| 35 | 1-Methoxy-3-(4-{2-[3-(1-methyl-1H-pyrazol-4-yl)-phenyl]-pyrimidin-5-yl}-pyrazol-1-yl)-propan-2-ol |
| 36 | 1-Methoxy-3-(4-{2-[3-(1-methyl-1H-pyrazol-4-yl)-phenyl]-pyrimidin-5-yl}-pyrazol-1-yl)-propan-2-ol |
| 37 | 2-(4-{2-[3-(3-Methyl-3H-imidazol-4-yl)-phenyl]-pyrimidin-5-yl}-pyrazol-1-yl)-1-pyrrolidin-1-yl-ethanone |
| 38 | N,N-Dimethyl-2-(4-{2-[3-(1-methyl-1H-pyrazol-4-yl)-phenyl]-pyrimidin-5-yl}-pyrazol-1-yl)-acetamide |
| 39 | 2-[3-(1-Methyl-1H-pyrazol-4-yl)-phenyl]-5-{1-[1-(tetrahydro-pyran-4-yl)-piperidin-4-yl]-1H-pyrazol-4-yl}-pyrimidine |
| 40 | 1-(3-Methoxy-azetidin-1-yl)-2-(4-{2-[3-(1-methyl-1H-pyrazol-4-yl)-phenyl]-pyrimidin-5-yl}-pyrazol-1-yl)-ethanone |
| 41 | 2-(4-{2-[3-(1-Methyl-1H-yrazol-4-yl)-phenyl]-pyrimidin-5-yl}-pyrazol-1-ylmethyl)-morpholine hydrochloride |
| 42 | 2-[4-(2-{3-[1-(3-Amino-propyl)-1H-pyrazol-4-yl]-phenyl}-pyrimidin-5-yl)-pyrazol-1-yl]-1-pyrrolidin-1-yl-ethanone hydrochloride |
| 43 | 2-{4-[2-(3-Pyridin-4-yl-phenyl)-pyrimidin-5-yl]-pyrazol-1-yl}-1-pyrrolidin-1-yl-ethanone |
| 44 | 1-(4-{2-[3-(1-Methyl-1H-pyrazol-4-yl)-phenyl]-pyrimidin-5-yl}-pyrazol-1-yl)-propan-2-one |
| 45 | 2-[3-(1-Methyl-1H-pyrazol-4-yl)-phenyl]-5-[1-(tetrahydro-furan-3-ylmethyl)-1H-pyrazol-4-yl]-pyrimidine |
| 46 | 2-[3-(1-Methyl-1H-pyrazol-4-yl)-phenyl]-5-(1-oxazol-2-ylmethyl-1H-pyrazol-4-yl)-pyrimidine |
| 47 | 2-[3-(1-Methyl-1H-pyrazol-4-yl)-phenyl]-5-[1-(2-pyridin-2-yl-ethyl)-1H-pyrazol-4-yl]-pyrimidine |
| 48 | 2-[2-Fluoro-3-(1-methyl-1H-pyrazol-4-yl)-phenyl]-5-(1-piperidin-4-yl-1H-pyrazol-4-yl)-pyrimidine Formate |
| 49 | 2-(4-{2-[3-(1-Methyl-1H-pyrazol-4-yl)-phenyl]-pyrimidin-5-yl}-pyrazol-1-yl)-acetamide |
| 50 | 2-[4-(2-{3-[1-(2-Amino-ethyl)-1H-pyrazol-4-yl]-phenyl}-pyrimidin-5-yl)-pyrazol-1-yl]-1-pyrrolidin-1-yl-ethanone hydrochloride |
| 51 | 1-(4-Methyl-piperazin-1-yl)-2-(4-{2-[3-(1-methyl-1H-pyrazol-4-yl)-phenyl]-pyrimidin-5-yl}-pyrazol-1-yl)-ethanone hydrochloride |
| 52 | 1-(3-Hydroxy-piperidin-1-l)-2-(4-{2-[3-(1-methyl-1H-pyrazol-4-yl)-phenyl]-pyrimidin-5-yl}-pyrazol-1-yl)-ethanone |
| 53 | 2-[3-(1-Methyl-1H-pyrazol-4-yl)-phenyl]-5-[1-(2-pyridin-4-yl-ethyl)-1H-pyrazol-4-yl]-pyrimidine |
| 54 | 2-(4-{2-[3-(1-Methyl-1H-pyrazol-4-yl)-phenyl]-pyrimidin-5-yl}-pyrazol-1-yl)-N-(tetrahydro-pyran-4-yl)-acetamide |
| 55 | 2-(4-{2-[3-(1-Methyl-1H-pyrazol-4-yl)-phenyl]-pyrimidin-5-yl}-pyrazol-1-yl)-1-(2-oxa-6-aza-spiro[3.3]hept-6-yl)-ethanone |
| 56 | 2-(4-{2-[3-(2-Methyl-thiazol-5-yl)-phenyl]-pyrimidin-5-yl}-pyrazol-1-yl)-1-pyrrolidin-1-yl-ethanone |
| 57 | 2-[3-(1-Methyl-1H-pyrazol-4-yl)-phenyl]-5-[1-(2-piperidin-1-yl-ethyl)-1H-pyrazol-4-yl]-pyrimidne |
| 58 | 2-[3-(1-Methyl-1H-pyrazol-4-yl)-phenyl]-5-[1-(2-pyrrolidin-1-yl-ethyl)-1H-pyrazol-4-yl]-pyrimidine |
| 59 | 2-[4-(2-{3-[1-(2-Hydroxy-ethyl)-1H-pyrazol-4-yl]-phenyl}-pyrimidin-5-yl)-pyrazol-1-yl]-1-pyrrolidin-1-yl-ethanone |
| 60 | N-(1-Hydroxymethyl-propyl)-2-(4-{2-[3-(1-methyl-1H-pyrazol-4-yl)-phenyl]-pyrimidin-5-yl}-pyrazol-1-yl)-acetamide |
| 61 | (3-exo)-8-Methyl-3-(4-{2-[3-(1-methyl-1H-pyrazol-4-yl)-phenyl]-pyrimidin-5-yl}-pyrazol-1-yl)-8-aza-bicyclo[3.2.1]octane |
| 62 | 4-(4-{2-[3-(1-Methyl-1H-pyrazol-4-yl)-phenyl]-pyrimidin-5-yl}-pyrazol-1-yl)-cyclohexanecarboxylic acid |
| 63 | 2-[3-(1-Methyl-1H-pyrazol-4-yl)-phenyl]-5-(1H-pyrazol-4-yl)-pyrimidine |
| 64 | 2-[3-(1-Methyl-1H-pyrazol-4-yl)-phenyl]-5-{1-[2-(1-methyl-pyrrolidin-2-yl)-ethyl]-1H-pyrazol-4-yl}-pyrimidine |
| 65 | 2-[3-(1-Methyl-1H-pyrazol-4-yl)-phenyl]-5-(1-pyrrolidin-3-ylmethyl-1H-pyrazol-4-yl)-pyrimidine hydrochloride |

| Ex | |
|---|---|
| 66 | 5-(1-Azetidin-3-ylmethyl-1H-pyrazol-4-yl)-2-[3-(1-methyl-1H-pyrazol-4-yl)-phenyl]-pyrimidine hydrochloride |
| 67 | 5-[1-(2,2-Difluoro-ethyl)-1H-pyrazol-4-yl]-2-[3-(1-methyl-1H-pyrazol-4-yl)-phenyl]-pyrimidine |
| 68 | 1-Morpholin-4-yl-2-{4-[2-(3-pyridin-4-yl-phenyl)-pyrimidin-5-yl]-pyrazol-1-yl}-ethanone |
| 69 | 2-[3-(1-Methyl-1H-pyrazol-4-yl)-phenyl]-5-{1-[2-(tetrahydro-pyran-4-yl)-ethyl]-1H-pyrazol-4-yl}-pyrimidine |
| 70 | 2-[3-(1-Methyl-1H-pyrazol-4-yl)-phenyl]-5-(1-(S)-1-pyrrolidin-2-ylmethyl-1H-pyrazol-4-yl)-pyrimidine hydrochloride |
| 71 | 2-[3-(1-Methyl-1H-pyrazol-4-yl)-phenyl]-5-(1-(R)-1-pyrrolidin-2-ylmethyl-1H-pyrazol-4-yl)-pyrimidine hydrochloride |
| 72 | 2-[3-(1-Methyl-1H-[1,2,3]triazol-4-yl)-phenyl]-5-(1-piperidin-4-yl-1H-pyrazol-4-yl)-pyrimidine hydrochloride |
| 73 | 1-(3-Hydroxy-azetidin-1-yl)-2-(4-{2-[3-(1-methyl-1H-pyrazol-4-yl)-phenyl]-pyrimidin-5-yl}-pyrazol-1-yl)-ethanone |
| 74 | 1-(3-Hydroxy-pyrrolidin-1-yl)-2-(4-{2-[3-(1-methyl-1H-pyrazol-4-yl)-phenyl]-pyrimidin-5-yl}-pyrazol-1-yl)-ethanone |
| 75 | 1-[2-(2-Hydroxy-ethyl)-morpholin-4-yl]-2-(4-{2-[3-(1-methyl-1H-pyrazol-4-yl)-phenyl]-pyrimidin-5-yl}-pyrazol-1-yl)-ethanone |
| 76 | 5-[1-(1-Methanesulfonyl-piperidin-4-yl)-1H-pyrazol-4-yl]-2-[3-(1-methyl-1H-pyrazol-4-yl)-phenyl]-pyrimidine |
| 77 | 1-Azetidin-1-yl-2-(4-{2-[3-(1-methyl-1H-pyrazol-4-yl)-phenyl]-pyrimidin-5-yl}-pyrazol-1-yl)-ethanone |
| 78 | 1-Morpholin-4-yl-2-{4-[2-(3-oxazol-5-yl-phenyl)-pyrimidin-5-yl]-pyrazol-1-yl}-ethanone |
| 79 | 1-Morpholin-4-yl-2-(4-{2-[3-(1H-[1,2,3]triazol-4-yl)-phenyl]-pyrimidin-5-yl}-pyrazol-1-yl)-ethanone |
| 80 | 1-(2-Methyl-morpholin-4-yl)-2-(4-{2-[3-(1-methyl-1H-pyrazol-4-yl)-phenyl]-pyrimidin-5-yl}-pyrazol-1-yl)-ethanone |
| 81 | 1-((S)-2-Hydroxymethyl-pyrrolidin-1-yl)-2-(4-{2-[3-(1-methyl-1H-pyrazol-4-yl)-phenyl]-pyrimidin-5-yl}-pyrazol-1-yl)-ethanone |
| 82 | 1-(4,4-dimethyloxazolidin-3-yl)-2-[4-[2-[3-(1-methylpyrazol-4-yl)phenyl]pyrimidin-5-yl]pyrazol-1-yl]ethanone |
| 82a | N-(2-Hydroxy-1,1-dimethyl-ethyl)-2-(4-{2-[3-(1-methyl-1H-pyrazol-4-yl)-phenyl]-pyrimidin-5-yl}-pyrazol-1-yl)-acetamide |
| 83 | 3-(4-{2-[3-(1-Methyl-1H-pyrazol-4-yl)-phenyl]-pyrimidin-5-yl}-pyrazol-1-yl)-1-morpholin-4-yl-propan-1-one |
| 84 | 3-(4-{2-[3-(1-Methyl-1H-pyrazol-4-yl)-phenyl]-pyrimidin-5-yl}-pyrazol-1-yl)-1-pyrrolidin-1-yl-propan-1-one |
| 85 | N,N-Dimethyl-3-(4-{2-[3-(1-methyl-1H-pyrazol-4-yl)-phenyl]-pyrimidin-5-yl}-pyrazol-1-yl)-propionamide |
| 86 | 2-(4-{2-[3-(1-Methyl-1H-pyrazol-4-yl)-phenyl]-pyrimidin-5-yl}-pyrazol-1-yl)-1-(2-oxa-7-aza-spiro[3.5]non-7-yl)-ethanone |
| 87 | 1-[2-(2-Methoxy-ethyl)-morpholin-4-yl]-2-(4-{2-[3-(1-methyl-1H-pyrazol-4-yl)-phenyl]-pyrimidin-5-yl}-pyrazol-1-yl)-ethanone |
| 88 | 1-(3-Methoxymethyl-piperidin-1-yl)-2-(4-{2-[3-(1-methyl-1H-pyrazol-4-yl)-phenyl]-pyrimidin-5-yl}-pyrazol-1-yl)-ethanone |
| 89 | 2-[3-(1-Methyl-1H-pyrazol-4-yl)-phenyl]-5-{1-[2-(2-methyl-pyridin-3-yl)-ethyl]-1H-pyrazol-4-yl}-pyrimidine |
| 90 | 1-(3-Methoxy-pyrrolidin-1-yl)-2-(4-{2-[3-(1-methyl-1H-pyrazol-4-yl)-phenyl]-pyrimidin-5-yl}-pyrazol-1-yl)-ethanone |
| 91 | N-Methyl-2-(4-{2-[3-(1-methyl-1H-pyrazol-4-yl)-phenyl]-pyrimidin-5-yl}-pyrazol-1-yl)-N-(tetrahydro-pyran-4-yl)-acetamide |
| 92 | 2-(4-{2-[3-(1-Methyl-1H-pyrazol-4-yl)-phenyl]-pyrimidin-5-yl}-pyrazol-1-yl)-1-(1S,4S)-2-oxa-5-aza-bicyclo[2.2.1]hept-5-yl-ethanone |
| 93 | 2-(4-{2-[3-(1-Methyl-1H-pyrazol-4-yl)-phenyl]-pyrimidin-5-yl}-pyrazol-1-yl)-1-[1,4]oxazepan-4-yl-ethanone |
| 94 | 2-(4-{2-[3-(1-Methyl-1H-pyrazol-4-yl)-phenyl]-pyrimidin-5-yl}-pyrazol-1-yl)-1-(8-oxa-3-aza-bicyclo[3.2.1]oct-3-yl)-ethanone |
| 95 | Cis-5-{1-[1-(3-Fluoro-tetrahydro-pyran-4-yl)-piperidin-4-yl]-1H-pyrazol-4-yl}-2-[3-(1-methyl-1H-pyrazol-4-yl)-phenyl]-pyrimidine |
| 96 | 5-{1-[2-(3,4-Dimethoxy-phenyl)-ethyl]-1H-pyrazol-4-yl}-2-[3-(1-methyl-1H-pyrazol-4-yl)-phenyl]-pyrimidine |
| 97 | 2-[3-(1-Methyl-1H-pyrazol-4-yl)-phenyl]-5-[1-(tetrahydro-pyran-4-yl)-1H-pyrazol-4-yl]-pyrimidine |
| 98 | 5-[1-(2-Methoxy-ethyl)-1H-pyrazol-4-yl]-2-[3-(1-methyl-1H-pyrazol-4-yl)-phenyl]-pyrimidine |
| 99 | N,N-Dimethyl-2-(4-{2-[3-(1-methyl-1H-pyrazol-4-yl)-phenyl]-pyrimidin-5-yl}-pyrazol-1-yl)-propionamide |
| 100 | 1-(3-Methoxy-azetidin-1-yl)-3-(4-{2-[3-(1-methyl-1H-pyrazol-4-yl)-phenyl]-pyrimidin-5-yl}-pyrazol-1-yl)-propan-1-one |
| 101 | 3-(4-{2-[3-(1-Methyl-1H-pyrazol-4-yl)-phenyl]-pyrimidin-5-yl}-pyrazol-1-yl)-1-(2-oxa-6-aza-spiro[3.3]hept-6-yl)-propan-1-one |
| 102 | 1-(4-Methyl-piperazin-1-yl)-3-(4-{2-[3-(1-methyl-1H-pyrazol-4-yl)-phenyl]-pyrimidin-5-yl}-pyrazol-1-yl)-propan-1-one |

| Ex | |
|---|---|
| 103 | 2-(4-{2-[3-(1-Methyl-1H-pyrazol-4-yl)-phenyl]-pyrimidin-5-yl}-pyrazol-1-yl)-1-morpholin-4-yl-propan-1-one |
| 104 | [4-(4-{2-[3-(1-Methyl-1H-pyrazol-4-yl)-phenyl]-pyrimidin-5-yl}-pyrazol-1-yl)-piperidin-1-yl]-(tetrahydro-furan-3-yl)-methanone |
| 105 | 2-Methoxy-1-[4-(4-{2-[3-(1-methyl-1H-pyrazol-4-yl)-phenyl]-pyrimidin-5-yl}-pyrazol-1-yl)-piperidin-1-yl]-ethanone |
| 106 | 2-Hydroxy-1-[4-(4-{2-[3-(1-methyl-1H-pyrazol-4-yl)-phenyl]-pyrimidin-5-yl}-pyrazol-1-yl)-piperidin-1-yl]-ethanone |
| 107 | [4-(4-{2-[3-(1-Methyl-1H-pyrazol-4-yl)-phenyl]-pyrimidin-5-yl}-pyrazol-1-yl)-piperidin-1-yl]-(tetrahydro-pyran-4-yl)-methanone |
| 108 | [4-(4-{2-[3-(1-Methyl-1H-pyrazol-4-yl)-phenyl]-pyrimidin-5-yl}-pyrazol-1-yl)-piperidin-1-yl]-(tetrahydro-pyran-2-yl)-methanone |
| 109 | 3-Methoxy-1-[4-(4-{2-[3-(1-methyl-1H-pyrazol-4-yl)-phenyl]-pyrimidin-5-yl}-pyrazol-1-yl)-piperidin-1-yl]-propan-1-one |
| 110 | (1R,5S)-3-(4-{2-[3-(1-Methyl-1H-pyrazol-4-yl)-phenyl]-pyrimidin-5-yl}-pyrazol-1-yl)-8-aza-bicyclo[3.2.1]octane |
| 111 | 2-Ethoxy-1-[4-(4-{2-[3-(1-methyl-1H-pyrazol-4-yl)-phenyl]-pyrimidin-5-yl}-pyrazol-1-yl)-piperidin-1-yl]-ethanone |
| 112 | 5-{1-[1-(3-Ethoxy-2,2-dimethyl-cyclobutyl)-piperidin-4-yl]-1H-pyrazol-4-yl}-2-[3-(1-methyl-1H-pyrazol-4-yl)-phenyl]-pyrimidine |
| 113 | 1-Methyl-4-[4-(4-{2-[3-(1-methyl-1H-pyrazol-4-yl)-phenyl]-pyrimidin-5-yl}-pyrazol-1-yl)-piperidine-1-carbonyl]-pyrrolidin-2-one |
| 114 | 3,3,3-Trifluoro-1-[4-(4-{2-[3-(1-methyl-1H-pyrazol-4-yl)-phenyl]-pyrimidin-5-yl}-pyrazol-1-yl)-piperidin-1-yl]-propan-1-one |
| 115 | 3,3,3-Trifluoro-2-hydroxy-1-[4-(4-{2-[3-(1-methyl-1H-pyrazol-4-yl)-phenyl]-pyrimidin-5-yl}-pyrazol-1-yl)-piperidin-1-yl]-propan-1-one |
| 116 | 2-[3-(1-Methyl-1H-pyrazol-4-yl)-phenyl]-5-((R)-1-pyrrolidin-3-yl-1H-pyrazol-4-yl)-pyrimidine |
| 117 | 3-[4-(4-{2-[3-(1-Methyl-1H-pyrazol-4-yl)-phenyl]-pyrimidin-5-yl}-pyrazol-1-yl)-piperidine-1-carbonyl]-cyclobutanone |
| 118 | 1,1,1-Trifluoro-3-[(1R,5S)-3-(4-{2-[3-(1-methyl-1H-pyrazol-4-yl)-phenyl]-pyrimidin-5-yl}-pyrazol-1-yl)-8-aza-bicyclo[3.2.1]oct-8-yl]-propan-2-ol |
| 119 | 1-[(1R,5S)-3-(4-{2-[3-(1-Methyl-1H-pyrazol-4-yl)-phenyl]-pyrimidin-5-yl}-pyrazol-1-yl)-8-aza-bicyclo[3.2.1]oct-8-yl]-ethanone |
| 120 | (3-Hydroxy-cyclobutyl)-[4-(4-{2-[3-(1-methyl-1H-pyrazol-4-yl)-phenyl]-pyrimidin-5-yl}-pyrazol-1-yl)-piperidin-1-yl]-methanone |
| 121 | 4-(4-{2-[3-(1-Methyl-1H-pyrazol-4-yl)-phenyl]-pyrimidin-5-yl}-pyrazol-1-yl)-cyclohexanecarboxylic acid dimethylamide |
| 122 | 5-{1-[1-((S)-3-Methoxy-tetrahydro-pyran-4-yl)-piperidin-4-yl]-1H-pyrazol-4-yl}-2-[3-(1-methyl-1H-pyrazol-4-yl)-phenyl]-pyrimidine |
| 123 | [4-(4-{2-[3-(1-Methyl-1H-pyrazol-4-yl)-phenyl]-pyrimidin-5-yl}-pyrazol-1-yl)-piperidin-1-yl]-((S)-1-methyl-pyrrolidin-2-yl)-methanone |
| 124 | (S)-2-Amino-3-methyl-1-[4-(4-{2-[3-(1-methyl-1H-pyrazol-4-yl)-phenyl]-pyrimidin-5-yl}-pyrazol-1-yl)-piperidin-1-yl]-butan-1-one |
| 125 | 2-[3-(1-Methyl-1H-pyrazol-4-yl)-phenyl]-5-((S)-1-pyrrolidin-3-yl-1H-pyrazol-4-yl)-pyrimidine |
| 126 | 1-[(S)-3-(4-{2-[3-(1-Methyl-1H-pyrazol-4-yl)-phenyl]-pyrimidin-5-yl}-pyrazol-1-yl)-pyrrolidin-1-yl]ethanone |
| 127 | 1-(3-Hydroxy-8-aza-bicyclo[3.2.1]oct-8-yl)-2-(4-{2-[3-(1-methyl-1H-pyrazol-4-yl)-phenyl]-pyrimidin-5-yl}-pyrazol-1-yl)-ethanone |
| 128 | 1-(3-Hydroxy-8-aza-bicyclo[3.2.1]oct-8-yl)-2-(4-{2-[3-(1-methyl-1H-pyrazol-4-yl)-phenyl]-pyrimidin-5-yl}-pyrazol-1-yl)-ethanone |
| 129 | 3-(4-{2-[3-(1-Methyl-1H-pyrazol-4-yl)-phenyl]-pyrimidin-5-yl}-pyrazol-1-yl)-dihydro-furan-2-one |
| 130 | 1-[(R)-3-(4-{2-[3-(1-Methyl-1H-pyrazol-4-yl)-phenyl]-pyrimidin-5-yl}-pyrazol-1-yl)-pyrrolidin-1-yl]ethanone |
| 131 | 2-[3-(1-Methyl-1H-pyrazol-4-yl)-phenyl]-5-{1-[2-(tetrahydro-furan-3-yl)-ethyl]-1H-pyrazol-4-yl}-pyrimidine |
| 132 | 3-[2-(4-{2-[3-(1-Methyl-1H-pyrazol-4-yl)-phenyl]-pyrimidin-5-yl}-pyrazol-1-yl)-ethyl]dihydro-furan-2-one |
| 133 | 9-Isopropyl-3-(4-{2-[3-(1-methyl-1H-pyrazol-4-yl)-phenyl]-pyrimidin-5-yl}-pyrazol-1-yl)-9-aza-bicyclo[3.3.1]nonane |
| 134 | Trans-4-(4-{2-[3-(1-Methyl-1H-pyrazol-4-yl)-phenyl]-pyrimidin-5-yl}-pyrazol-1-yl)-cyclohexanecarboxylic acid dimethylamide |
| 135 | Cis-4-(4-{2-[3-(1-Methyl-1H-pyrazol-4-yl)-phenyl]-pyrimidin-5-yl}-pyrazol-1-yl)-cyclohexanecarboxylic acid dimethylamide |
| 136 | 4-(3-{5-[1-(Tetrahydro-pyran-4-yl)-1H-pyrazol-4-yl]-pyrimidin-2-yl}-phenyl)-pyridin-2-ylamine |
| 137 | 4-{2-[3-(1-Methyl-1H-pyrazol-4-yl)-phenyl]-pyrimidin-5-yl}-1-(tetrahydro-pyran-4-yl)-1H-pyrazole-3-carboxylic acid amide |
| 138 | 3-Methyl-5-(3-{5-[1-(tetrahydro-pyran-4-yl)-1H-pyrazol-4-yl]-pyrimidin-2-yl}-phenyl)-pyridazine |
| 139 | 2-[3-(2-Methyl-pyridin-4-yl)-phenyl]-5-[1-(tetrahydro-pyran-4-yl)-1H-pyrazol-4-yl]-pyrimidine |
| 140 | 4-{2-[3-(1-Methyl-1H-pyrazol-4-yl)-phenyl]-pyrimidin-5-yl}-1-(tetrahydro-pyran-4-yl)-1H-pyrazole-3-carboxylic acid |

| Ex | |
|---|---|
| 141 | 2-[3-(1-Methyl-1H-pyrazol-4-yl)-phenyl]-5-(1-oxetan-3-yl-1H-pyrazol-4-yl)-pyrimidine |
| 142 | Exo-9-Methyl-3-(4-{2-[3-(1-methyl-1H-pyrazol-4-yl)-phenyl]-pyrimidin-5-yl}-pyrazol-1-yl)-9-aza-bicyclo[3.3.1]nonane |
| 143 | Trans-4-(4-{2-[3-(1-Methyl-1H-pyrazol-4-yl)-phenyl]-pyrimidin-5-yl}-pyrazol-1-yl)-cyclohexanecarboxylic acid methylamide |
| 144 | 1-Methyl-4-{2-[3-(1-methyl-1H-pyrazol-4-yl)-phenyl]-pyrimidin-5-yl}-1H-pyrazole-3-carboxylic acid methylamide |
| 145 | N-Methyl-2-(4-{2-[3-(1-methyl-1H-pyrazol-4-yl)-phenyl]-pyrimidin-5-yl}-pyrazol-1-yl)-N-oxetan-3-yl-acetamide |
| 146 | 1-(3-Methoxymethyl-morpholin-4-yl)-2-(4-{2-[3-(1-methyl-1H-pyrazol-4-yl)-phenyl]-pyrimidin-5-yl}-pyrazol-1-yl)-ethanone |
| 147 | 1-(3-Methyl-morpholin-4-yl)-2-(4-{2-[3-(1-methyl-1H-pyrazol-4-yl)-phenyl]-pyrimidin-5-yl}-pyrazol-1-yl)-ethanone |
| 148 | 1-(((1R,4R)-5-Methyl-2,5-diaza-bicyclo[2.2.1]hept-2-yl)-2-(4-{2-[3-(1-methyl-1H-pyrazol-4-yl)-phenyl]-pyrimidin-5-yl}-pyrazol-1-yl)-ethanone |
| 149 | N,N-Dimethyl-2-(4-{2-[3-(1-methyl-1H-pyrazol-4-yl)-phenyl]-pyrimidin-5-yl}-pyrazol-1-yl)-isobutyramide |
| 150 | 2-Methyl-2-(4-{2-[3-(1-methyl-1H-pyrazol-4-yl)-phenyl]-pyrimidin-5-yl}-pyrazol-1-yl)-1-morpholin-4-yl-propan-1-one |
| 151 | [4-(3-{5-[1-(Tetrahydro-pyran-4-yl)-1H-pyrazol-4-yl]-pyrimidin-2-yl}-phenyl)-pyridin-2-yl]-methanol |
| 152 | Trans-4-(4-{2-[3-(1-Methyl-1H-pyrazol-4-yl)-phenyl]-pyrimidin-5-yl}-pyrazol-1-yl)-cyclohexanecarboxylic acid (2-methoxy-ethyl)-methyl-amide |
| 153 | (3-Hydroxy-azetidin-1-yl)-[4-{2-[3-(1-methyl-1H-pyrazol-4-yl)-phenyl]-pyrimidin-5-yl}-1-(tetrahydro-pyran-4-yl)-1H-pyrazol-3-yl]-methanone |
| 154 | 4-{2-[3-(1-Methyl-1H-pyrazol-4-yl)-phenyl]-pyrimidin-5-yl}-1-(tetrahydro-pyran-4-yl)-1H-pyrazole-3-carboxylic acid (2-hydroxy-ethyl)-amide |
| 155 | (1-Methyl-4-{2-[3-(1-methyl-1H-pyrazol-4-yl)-phenyl]-pyrimidin-5-yl}-1H-pyrazol-3-yl)-methanol |
| 156 | 4-(4-{2-[3-(1-Methyl-1H-pyrazol-4-yl)-phenyl]-pyrimidin-5-yl}-pyrazol-1-yl)-cyclohexylamine |
| 157 | 3-(4-{2-[3-(1-Methyl-1H-pyrazol-4-yl)-phenyl]-pyrimidin-5-yl}-pyrazol-1-yl)-cyclobutanecarboxylic acid methylamide |
| 158 | 3-(4-{2-[3-(1-Methyl-1H-pyrazol-4-yl)-phenyl]-pyrimidin-5-yl}-pyrazol-1-yl)-cyclobutanecarboxylic acid dimethylamide |
| 159 | Trans-4-(4-{2-[3-(1-Methyl-1H-pyrazol-4-yl)-phenyl]-pyrimidin-5-yl}-pyrazol-1-yl)-cyclohexanecarboxylic acid (2-methoxy-ethyl)-amide |
| 160 | Trans-(4-Methyl-piperazin-1-yl)-[4-(4-{2-[3-(1-methyl-1H-pyrazol-4-yl)-phenyl]-pyrimidin-5-yl}-pyrazol-1-yl)-cyclohexyl]-methanone |
| 161 | Cis-N-[4-(4-{2-[3-(1-Methyl-1H-pyrazol-4-yl)-phenyl]-pyrimidin-5-yl}-pyrazol-1-yl)-cyclohexyl]-acetamide |
| 162 | Trans-[4-(4-{2-[3-(1-Methyl-1H-pyrazol-4-yl)-phenyl]-pyrimidin-5-yl}-pyrazol-1-yl)-cyclohexyl]-morpholin-4-yl-methanone |
| 163 | Trans-4-(4-{2-[3-(1-Methyl-1H-pyrazol-4-yl)-phenyl]-pyrimidin-5-yl}-pyrazol-1-yl)-cyclohexanecarboxylic acid ((R)-1-hydroxymethyl-2-methyl-propyl)-amide |
| 164 | Trans-4-(4-{2-[3-(1-Methyl-1H-pyrazol-4-yl)-phenyl]-pyrimidin-5-yl}-pyrazol-1-yl)-cyclohexanecarboxylic acid((R)-1-hydroxymethyl-2-methyl-propyl)-amide |
| 165 | [4-{2-[3-(1-Methyl-1H-pyrazol-4-yl)-phenyl]-pyrimidin-5-yl}-1-(tetrahydro-pyran-4-yl)-1H-pyrazol-3-yl]-methanol |
| 166 | Cis-3-Methoxy-N-[4-(4-{2-[3-(1-methyl-1H-pyrazol-4-yl)-phenyl]-pyrimidin-5-yl}-pyrazol-1-yl)-cyclohexyl]-propionamide |
| 167 | 5-{1-[1-((3S,4S)-3-Fluoro-tetrahydro-pyran-4-yl)-piperidin-4-yl]-1H-pyrazol-4-yl}-2-[3-(1-methyl-1H-pyrazol-4-yl)-phenyl]-pyrimidine |
| 168 | ((R)-3-Methoxy-pyrrolidin-1-yl)-trans-[4-(4-{2-[3-(1-methyl-1H-pyrazol-4-yl)-phenyl]-pyrimidin-5-yl}-pyrazol-1-yl)-cyclohexyl]-methanone |
| 169 | 4-Hydroxy-N-methyl-2-(4-{2-[3-(1-methyl-1H-pyrazol-4-yl)-phenyl]-pyrimidin-5-yl}-pyrazol-1-yl)-butyramide |
| 170 | Trans-4-(4-{2-[3-(1-Methyl-1H-pyrazol-4-yl)-phenyl]-pyrimidin-5-yl}-pyrazol-1-yl)-cyclohexanecarboxylic acid cyclopropylamide |
| 171 | 4-(4-{2-[3-(1-Methyl-1H-pyrazol-4-yl)-phenyl]-pyrimidin-5-yl}-pyrazol-1-yl)-cyclohexanecarboxylic acid (2-dimethylamino-ethyl)-amide |
| 172 | 4-(4-{2-[3-(1-Methyl-1H-pyrazol-4-yl)-phenyl]-pyrimidin-5-yl}-pyrazol-1-yl)-azepane |
| 173 | Trans-4-(4-{2-[3-(1-Methyl-1H-pyrazol-4-yl)-phenyl]-pyrimidin-5-yl}-pyrazol-1-yl)-cyclohexanecarboxylic acid isobutyl-amide |
| 174 | 4-(4-{2-[3-(1-Methyl-1H-pyrazol-4-yl)-phenyl]-pyrimidin-5-yl}-pyrazol-1-yl)-cyclohexanecarboxylic acid isopropylamide |
| 175 | 5-{1-[1-(2-Fluoro-phenyl)-piperidin-4-yl]-1H-pyrazol-4-yl}-2-[3-(1-methyl-1H-pyrazol-4-yl)-phenyl]-pyrimidine |

| Ex | |
|---|---|
| 176 | 5-[1-(1,1-Dioxo-hexahydro-1l6-thiopyran-4-yl)-1H-pyrazol-4-yl]-2-[3-(1-methyl-1H-pyrazol-4-yl)-phenyl]-pyrimidine |
| 177 | 5-[1-(1,1-Dioxo-hexahydro-1l6-thiopyran-3-yl)-1H-pyrazol-4-yl]-2-[3-(1-methyl-1H-pyrazol-4-yl)-phenyl]-pyrimidin |
| 178 | 4-(4-{2-[3-(1-Methyl-1H-pyrazol-4-yl)-phenyl]-pyrimidin-5-yl}-pyrazol-1-yl)-cyclohexanecarboxylic acid (2-methoxy-1-methyl-ethyl)-amide |
| 179 | 7-(4-{2-[3-(1-Methyl-1H-pyrazol-4-yl)-phenyl]-pyrimidin-5-yl}-pyrazol-1-yl)-3-oxa-9-aza-bicyclo[3.3.1]nonane |
| 180 | cis-3-(4-{2-[3-(1-Methyl-1H-pyrazol-4-yl)-phenyl]-pyrimidin-5-yl}-pyrazol-1-yl)-cyclohexanecarboxylic acid methylamide |
| 181 | trans-3-(4-{2-[3-(1-Methyl-1H-pyrazol-4-yl)-phenyl]-pyrimidin-5-yl}-pyrazol-1-yl)-cyclohexanecarboxylic acid methylamide |
| 182 | Trans-4-(4-{2-[3-(1-Methyl-1H-pyrazol-4-yl)-phenyl]-pyrimidin-5-yl}-pyrazol-1-yl)-cyclohexanol |
| 183 | 2-[3-(1-Methyl-1H-pyrazol-4-yl)-phenyl]-5-((R)-1-piperidin-3-yl-1H-pyrazol-4-yl)-pyrimidine |
| 184 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-ethyl)-amide |
| 185 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-ethyl)-methyl-amide |
| 186 | ((R)-3-Hydroxy-pyrrolidin-1-yl)-[4-(4-{2-[3-(1-methyl-1H-pyrazol-4-yl)-phenyl]-pyrimidin-5-yl}-pyrazol-1-yl)-cyclohexyl]-methanone |
| 187 | trans-4-(4-{2-[3-(6-Methyl-pyridazin-4-yl)-phenyl]-pyrimidin-5-yl}-pyrazol-1-yl)-cyclohexanecarboxylic acid dimethylamide |
| 188 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-1-methyl-ethyl)-amide |
| 189 | 4-(4-{2-[3-(1-Methyl-1H-pyrazol-4-yl)-phenyl]-pyrimidin-5-yl}-pyrazol-1-yl)-cyclohexanone |
| 190 | Trans-4-(4-{2-[3-(1-Methyl-1H-pyrazol-4-yl)-phenyl]-pyrimidin-5-yl}-pyrazol-1-yl)-cyclohexanecarboxylic acid (3-hydroxy-propyl)-amide |
| 191 | Trans-((S)-3-Methoxy-pyrrolidin-1-yl)-[4-(4-{2-[3-(1-methyl-1H-pyrazol-4-yl)-phenyl]-pyrimidin-5-yl}-pyrazol-1-yl)-cyclohexyl]-methanone |
| 192 | Trans-4-(4-{2-[3-(1-Methyl-1H-pyrazol-4-yl)-phenyl]-pyrimidin-5-yl}-pyrazol-1-yl)-cyclohexanecarboxylic acid tert-butylamide |
| 193 | exo-1-[7-(4-{2-[3-(1-Methyl-1H-pyrazol-4-yl)-phenyl]-pyrimidin-5-yl}-pyrazol-1-yl)-3-oxa-9-aza-bicyclo[3.3.1]non-9-yl]-ethanone |
| 194 | cis-cis-9-(4-{2-[3-(1-Methyl-1H-pyrazol-4-yl)-phenyl]-pyrimidin-5-yl}-pyrazol-1-yl)-3-oxa-bicyclo[3.3.1]nonane-7-carboxylic acid dimethylamide |
| 195 | 3-(4-{2-[3-(1-Methyl-1H-pyrazol-4-yl)-phenyl]-pyrimidin-5-yl}-pyrazol-1-yl)-cyclohexanone |
| 196 | Cis-4-(4-{2-[3-(1-Methyl-1H-pyrazol-4-yl)-phenyl]-pyrimidin-5-yl}-pyrazol-1-yl)-cyclohexanol |
| 197 | Trans-4-(4-{2-[3-(1-Methyl-1H-pyrazol-4-yl)-phenyl]-pyrimidin-5-yl}-pyrazol-1-yl)-cyclohexanecarboxylic acid ethylamide |
| 198 | Trans-4-(4-{2-[3-(1-Methyl-1H-pyrazol-4-yl)-phenyl]-pyrimidin-5-yl}-pyrazol-1-yl)-cyclohexanecarboxylic acid ((S)-2-hydroxy-1-methyl-ethyl)-amide |
| 199 | Trans-4-(4-{2-[3-(1-Methyl-1H-pyrazol-4-yl)-phenyl]-pyrimidin-5-yl}-pyrazol-1-yl)-cyclohexanecarboxylic acid ((R)-2-hydroxy-1-methyl-ethyl)-amide |
| 200 | Trans-4-(4-{2-[3-(1-Methyl-1H-pyrazol-4-yl)-phenyl]-pyrimidin-5-yl}-pyrazol-1-yl)-cyclohexanecarboxylic acid isopropyl-methyl-amide |
| 201 | 1-[(3R,4R)-3-Hydroxy-4-(4-{2-[3-(1-methyl-1H-pyrazol-4-yl)-phenyl]-pyrimidin-5-yl}-pyrazol-1-yl)-piperidin-1-yl]-ethanone (stereochemistry attributed arbitrarely) |
| 202 | 1-[(3S,4S)-3-Hydroxy-4-(4-{2-[3-(1-methyl-1H-pyrazol-4-yl)-phenyl]-pyrimidin-5-yl}-pyrazol-1-yl)-piperidin-1-yl]-ethanone (stereochemistry attributed arbitrarely) |
| 203 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-butyl)-amide |
| 204 | 4-(4-{2-[3-(1-Methyl-1H-pyrazol-4-yl)-phenyl]-pyrimidin-5-yl}-pyrazol-1-yl)-cyclohexanecarboxylic acid ethyl-methyl-amide |
| 205 | trans-((S)-3-Hydroxy-pyrrolidin-1-yl)-[4-(4-{2-[3-(1-methyl-1H-pyrazol-4-yl)-phenyl]-pyrimidin-5-yl}-pyrazol-1-yl)-cyclohexyl]-methanone |
| 206 | Trans-4-(4-{2-[3-(1-Methyl-1H-pyrazol-4-yl)-phenyl]-pyrimidin-5-yl}-pyrazol-1-yl)-cyclohexanecarboxylic acid amide |
| 207 | 2-[3-(1-Methyl-1H-pyrazol-4-yl)-phenyl]-5-[1-(tetrahydro-thiopyran-3-yl)-1H-pyrazol-4-yl]-pyrimidine |
| 208 | Trans-4-[4-(4-{2-[3-(1-Methyl-1H-pyrazol-4-yl)-phenyl]-pyrimidin-5-yl}-pyrazol-1-yl)-cyclohexyl]-morpholine |
| 209 | cis-4-[4-(4-{2-[3-(1-Methyl-1H-pyrazol-4-yl)-phenyl]-pyrimidin-5-yl}-pyrazol-1-yl)-cyclohexyl]-morpholine |

| Ex | |
|---|---|
| 210 | N-[2-(4-{2-[3-(1-Methyl-1H-pyrazol-4-yl)-phenyl]-pyrimidin-5-yl}-pyrazol-1-yl)-ethyl]-methanesulfonamide |
| 211 | 2-(4-{2-[3-(1-Methyl-1H-pyrazol-4-yl)-phenyl]-pyrimidin-5-yl}-pyrazol-1-yl)-cyclopentanol |
| 212 | 3-(4-{2-[3-(1-Methyl-1H-pyrazol-4-yl)-phenyl]-pyrimidin-5-yl}-pyrazol-1-yl)-propane-1,2-diol |
| 213 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-1,1-dimethyl-ethyl)-amide |
| 214 | 3-Isopropoxy-2-(4-{2-[3-(1-methyl-1H-pyrazol-4-yl)-phenyl]-pyrimidin-5-yl}-pyrazol-1-yl)-propan-1-ol |
| 215 | 2-(4-{2-[3-(1-Methyl-1H-pyrazol-4-yl)-phenyl]-pyrimidin-5-yl}-pyrazol-1-yl)-1-pyridin-2-yl-ethanol |
| 216 | 2-[3-(1-Methyl-1H-pyrazol-4-yl)-phenyl]-5-[1-(tetrahydro-thiophen-3-yl)-1H-pyrazol-4-yl]-pyrimidine |
| 217 | trans-5-{1-[4-(2-Methoxy-ethoxy)-cyclohexyl]-1H-pyrazol-4-yl}-2-[3-(1-methyl-1H-pyrazol-4-yl)-phenyl]-pyrimidine |
| 218 | cis-5-{1-[4-(2-Methoxy-ethoxy)-cyclohexyl]-1H-pyrazol-4-yl}-2-[3-(1-methyl-1H-pyrazol-4-yl)-phenyl]-pyrimidine |
| 219 | 5-[1-(1,1-Dioxo-tetrahydro-1lambda6-thiophen-3-yl)-1H-pyrazol-4-yl]-2-[3-(1-methyl-1H-pyrazol-4-yl)-phenyl]-pyrimidine |
| 220 | trans-5-[1-(4-Cyclopropylmethoxy-cyclohexyl)-1H-pyrazol-4-yl]-2-[3-(1-methyl-1H-pyrazol-4-yl)-phenyl]-pyrimidine |
| 221 | 2-[3-(1-Methyl-1H-pyrazol-4-yl)-phenyl]-5-[1-(tetrahydro-pyran-3-yl)-1H-pyrazol-4-yl]-pyrimidine |
| 222 | 6-(4-{2-[3-(1-Methyl-1H-pyrazol-4-yl)-phenyl]-pyrimidin-5-yl}-pyrazol-1-yl)-spiro[3.3]heptane-2-carboxylic acid dimethylamide |
| 223 | 1-[4-(4-{2-[3-(1-Methyl-1H-pyrazol-4-yl)-phenyl]-pyrimidin-5-yl}-pyrazol-1-yl)-azepan-1-yl]-ethanone |
| 224 | trans-2-Methyl-1-[4-(4-{2-[3-(1-methyl-1H-pyrazol-4-yl)-phenyl]-pyrimidin-5-yl}-pyrazol-1-yl)-cyclohexyloxy]-propan-2-ol |
| 225 | 1-[(3S,4S)-3-Hydroxy-4-(4-{2-[3-(1-methyl-1H-pyrazol-4-yl)-phenyl]-pyrimidin-5-yl}-pyrazol-1-yl)-piperidin-1-yl]-ethanone |
| 226 | 1-[(3R,4R)-3-Hydroxy-4-(4-{2-[3-(1-methyl-1H-pyrazol-4-yl)-phenyl]-pyrimidin-5-yl}-pyrazol-1-yl)-piperidin-1-yl]-ethanone (Stereochemistry attributed arbitrarely) |
| 227 | trans-4-(4-{2-[3-(1-Methyl-1H-pyrazol-4-yl)-phenyl]-pyrimidin-5-yl}-pyrazol-1-yl)-cyclohexanecarboxylic acid (2-hydroxy-2-methyl-propyl)-amide |
| 228 | trans-4-(4-{2-[3-(1-Methyl-1H-pyrazol-4-yl)-phenyl]-pyrimidin-5-yl}-pyrazol-1-yl)-cyclohexanecarboxylic acid (3-hydroxy-butyl)-amide |
| 229 | Trans-4-(4-{2-[3-(2-Methyl-pyridin-4-yl)-phenyl]-pyrimidin-5-yl}-pyrazol-1-yl)-cyclohexanecarboxylic acid dimethylamide |
| 230 | trans-4-(4-{2-[3-(1-Methyl-1H-pyrazol-4-yl)-phenyl]-pyrimidin-5-yl}-pyrazol-1-yl)-cyclohexanecarboxylic acid cyanomethyl-amide |
| 231 | (1S,4R)-4-[4-[2-[3-(1-methylpyrazol-4-yl)phenyl]pyrimidin-5-yl]pyrazol-1-yl]cyclopent-2-en-1-ol |
| 232 | Trans-dimethyl-[4-(4-{2-[3-(1-methyl-1H-pyrazol-4-yl)-phenyl]-pyrimidin-5-yl}-pyrazol-1-yl)-cyclohexylmethyl]-amine |
| 233 | Trans-4-{4-[2-(3-Pyridazin-4-yl-phenyl)-pyrimidin-5-yl]-pyrazol-1-yl}-cyclohexanecarboxylic acid dimethylamide |
| 234 | Trans-4-(4-{2-[3-(6-Chloro-pyridazin-3-yl)-phenyl]-pyrimidin-5-yl}-pyrazol-1-yl)-cyclohexanecarboxylic acid dimethylamide |
| 235 | 2-[3-(1-Methyl-1H-pyrazol-4-yl)-phenyl]-5-[1-(Trans-1-oxo-tetrahydro-thiopyran-3-yl)-1H-pyrazol-4-yl]-pyrimidine (racemate; isomery attributed arbitrarely) |
| 236 | 2-[3-(1-Methyl-1H-pyrazol-4-yl)-phenyl]-5-[1-(Cis-1-oxo-tetrahydro-thiopyran-3-yl)-1H-pyrazol-4-yl]-pyrimidine (racemate; isomery attributed arbitrarely) |
| 237 | Trans-4-(4-{2-[3-(6-Methyl-pyridazin-3-yl)-phenyl]-pyrimidin-5-yl}-pyrazol-1-yl)-cyclohexanecarboxylic acid dimethylamide |
| 238 | Trans-[4-(4-{2-[3-(1-Methyl-1H-pyrazol-4-yl)-phenyl]-pyrimidin-5-yl}-pyrazol-1-yl)-cyclohexyl]-methanol |
| 239 | Trans-4-(4-{2-[3-(6-Amino-pyridazin-3-yl)-phenyl]-pyrimidin-5-yl}-pyrazol-1-yl)-cyclohexanecarboxylic acid dimethylamide |
| 240 | 5-(3-{5-[1-((S)-1,1-Dioxo-hexahydro-1l6-thiopyran-3-yl)-1H-pyrazol-4-yl]-pyrimidin-2-yl}-phenyl)-3-methyl-pyridazine (stereochemistry attributed arbitrarely) |
| 241 | 5-(3-{5-[1-((R)-1,1-Dioxo-hexahydro-1l6-thiopyran-3-yl)-1H-pyrazol-4-yl]-pyrimidin-2-yl}-phenyl)-3-methyl-pyridazine (stereochemistry attributed arbitrarely) |
| 242 | Trans-4-(4-{2-[3-(1-Methyl-1H-pyrazol-4-yl)-phenyl]-pyrimidin-5-yl}-pyrazol-1-yl)-cyclohexanecarboxylic acid (2,3-dihydroxy-propyl)-amide |
| 243 | 5-[1-((2R,4R)-2-Methyl-piperidin-4-yl)-1H-pyrazol-4-yl]-2-[3-(1-methyl-1H-pyrazol-4-yl)-phenyl]-pyrimidine formic acid |

| Ex | |
|---|---|
| 244 | ((3S,4S)-3,4-Dihydroxy-pyrrolidin-1-yl)-[4-(4-{2-[3-(1-methyl-1H-pyrazol-4-yl)-phenyl]-pyrimidin-5-yl}-pyrazol-1-yl)-cyclohexyl]-methanone |
| 245 | (Trans-3-Hydroxy-4-methoxy-pyrrolidin-1-yl)-[4-Trans-(4-{2-[3-(1-methyl-1H-pyrazol-4-yl)-phenyl]-pyrimidin-5-yl}-pyrazol-1-yl)-cyclohexyl]-methanone |
| 246 | 5-[1-((2S,4S)-2-Methyl-piperidin-4-yl)-1H-pyrazol-4-yl]-2-[3-(1-methyl-1H-pyrazol-4-yl)-phenyl]-pyrimidine |
| 247 | trans-4-(4-{2-[3-(6-Methyl-pyridazin-4-yl)-phenyl]-pyrimidin-5-yl}-pyrazol-1-yl)-cyclohexanol |
| 248 | 1-[(2S,4S)-2-Methyl-4-(4-{2-[3-(1-methyl-1H-pyrazol-4-yl)-phenyl]-pyrimidin-5-yl}-pyrazol-1-yl)-piperidin-1-yl]-ethanone |
| 249 | 1-[(2R,4R)-2-Methyl-4-(4-{2-[3-(1-methyl-1H-pyrazol-4-yl)-phenyl]-pyrimidin-5-yl}-pyrazol-1-yl)-piperidin-1-yl]-ethanone |
| 250 | cis-8-(4-{2-[3-(1-Methyl-1H-pyrazol-4-yl)-phenyl]-pyrimidin-5-yl}-pyrazol-1-yl)-1-aza-spiro[4.5]decan-2-one (first isomer) |
| 251 | Cis-8-(4-{2-[3-(1-Methyl-1H-pyrazol-4-yl)-phenyl]-pyrimidin-5-yl}-pyrazol-1-yl)-1-aza-spiro[4.5]decan-2-one (second isomer) |
| 252 | Cis-5-[1-(4-Methoxy-cyclohexyl)-1H-pyrazol-4-yl]-2-[3-(1-methyl-1H-pyrazol-4-yl)-phenyl]-pyrimidine |
| 253 | trans-5-[1-(4-Methoxy-cyclohexyl)-1H-pyrazol-4-yl]-2-[3-(1-methyl-1H-pyrazol-4-yl)-phenyl]-pyrimidine |
| 254 | 4-[4-(4-{2-[3-(1-Methyl-1H-pyrazol-4-yl)-phenyl]-pyrimidin-5-yl}-pyrazol-1-yl)-cyclohexyl]-morpholin-3-one |
| 255 | :3-[4-(4-{2-[3-(1-Methyl-1H-pyrazol-4-yl)-phenyl]-pyrimidin-5-yl}-pyrazol-1-yl)-cyclohexyl]-oxazolidin-2-one |
| 256 | Trans-[4-(4-{2-[3-(6-Methyl-pyridazin-4-yl)-phenyl]-pyrimidin-5-yl}-pyrazol-1-yl)-cyclohexyl]-methanol |
| 257 | 3-[cis-3-(4-{2-[3-(1-Methyl-1H-pyrazol-4-yl)-phenyl]-pyrimidin-5-yl}-pyrazol-1-yl)-cyclohexyl]-oxazolidin-2-one |
| 258 | Cis-1-Hydroxymethyl-4-(4-{2-[3-(1-methyl-1H-pyrazol-4-yl)-phenyl]-pyrimidin-5-yl}-pyrazol-1-yl)-cyclohexanol |
| 259 | 5-[1-(3,3-Difluoro-piperidin-4-yl)-1H-pyrazol-4-yl]-2-[3-(1-methyl-1H-pyrazol-4-yl)-phenyl]-pyrimidine |
| 260 | trans-2-Methyl-8-(4-{2-[3-(1-methyl-1H-pyrazol-4-yl)-phenyl]-pyrimidin-5-yl}-pyrazol-1-yl)-2-aza-spiro[4.5]decan-3-one |
| 261 | ((S)-2-Hydroxymethyl-morpholin-4-yl)-[4-((S)-4-{2-[3-(1-methyl-1H-pyrazol-4-yl)-phenyl]-pyrimidin-5-yl}-pyrazol-1-yl)-cyclohexyl]-methanone |
| 262 | cis-2-Methyl-8-(4-{2-[3-(1-methyl-1H-pyrazol-4-yl)-phenyl]-pyrimidin-5-yl}-pyrazol-1-yl)-2-aza-spiro[4.5]decan-3-one |
| 263 | Cis-1-[3-Fluoro-4-(4-{2-[3-(1-methyl-1H-pyrazol-4-yl)-phenyl]-pyrimidin-5-yl}-pyrazol-1-yl)-piperidin-1-yl]-ethanone |
| 264 | 5-[1-(1,9-Dioxa-spiro[5.5]undec-4-yl)-1H-pyrazol-4-yl]-2-[3-(1-methyl-1H-pyrazol-4-yl)-phenyl]-pyrimidine |
| 265 | cis-3-Fluoro-piperidin-4-yl)-1H-pyrazol-4-yl]-2-[3-(1-methyl-1H-pyrazol-4-yl)-phenyl]-pyrimidine |
| 266 | ((R)-2-Hydroxymethyl-morpholin-4-yl)-[4-((S)-4-{2-[3-(1-methyl-1H-pyrazol-4-yl)-phenyl]-pyrimidin-5-yl}-pyrazol-1-yl)-cyclohexyl]-methanone |
| 267 | 5-[1-(1,9-Dioxa-spiro[5.5]undec-4-yl)-1H-pyrazol-4-yl]-2-[3-(1-methyl-1H-pyrazol-4-yl)-phenyl]-pyrimidine |
| 268 | 5-[(R)-1-(1-Methanesulfonyl-piperidin-3-yl)-1H-pyrazol-4-yl]-2-[3-(1-methyl-1H-pyrazol-4-yl)-phenyl]-pyrimidine |
| 269 | 1-[3-((R)-4-{2-[3-(1-Methyl-1H-pyrazol-4-yl)-phenyl]-pyrimidin-5-yl}-pyrazol-1-yl)-piperidin-1-yl]-ethanone |
| 270 | 2-[3-(1-Methyl-1H-pyrazol-4-yl)-phenyl]-5-{1-[1-(tetrahydro-pyran-3-yl)-piperidin-4-yl]-1H-pyrazol-4-yl}-pyrimidine |
| 271 | 4-[4-(4-{2-[3-(1-Methyl-1H-pyrazol-4-yl)-phenyl]-pyrimidin-5-yl}-pyrazol-1-yl)-tetrahydro-pyran-3-ylmethyl]-morpholine |
| 272 | 5-[(R)-1-(1-Methanesulfonyl-piperidin-3-yl)-1H-pyrazol-4-yl]-2-[3-(1-methyl-1H-pyrazol-4-yl)-phenyl]-pyrimidine |
| 273 | trans,cis-9-(4-{2-[3-(1-Methyl-1H-pyrazol-4-yl)-phenyl]-pyrimidin-5-yl}-pyrazol-1-yl)-3-oxa-bicyclo[3.3.1]nonane-7-carboxylic acid dimethylamide |
| 274 | 1-[3-((R)-4-{2-[3-(1-Methyl-1H-pyrazol-4-yl)-phenyl]-pyrimidin-5-yl}-pyrazol-1-yl)-piperidin-1-yl]-ethanone |
| 275 | 2-[3-(1-Methyl-1H-pyrazol-4-yl)-phenyl]-5-{1-[1-(3-methyl-tetrahydro-pyran-4-yl)-piperidin-4-yl]-1H-pyrazol-4-yl}-pyrimidine |
| 276 | [9-(4-{2-[3-(1-Methyl-1H-pyrazol-4-yl)-phenyl]-pyrimidin-5-yl}-pyrazol-1-yl)-3-oxa-bicyclo[3.3.1]non-7-yl]-methanol |
| 277 | Trans-2-[4-(-4-{2-[3-(1-Methyl-1H-pyrazol-4-yl)-phenyl]-pyrimidin-5-yl}-pyrazol-1-yl)-cyclohexyloxy]-ethanol |
| 278 | (5-Methyl-2,5-diaza-bicyclo[2.2.1]hept-2-yl)-trans-[4-(-4-{2-[3-(1-methyl-1H-pyrazol-4-yl)-phenyl]-pyrimidin-5-yl}-pyrazol-1-yl)-cyclohexyl]-methanone hydrobromide |

| Ex | |
|---|---|
| 279 | 5-[1-(Cis-3-Methanesulfonyl-cyclohexyl)-1H-pyrazol-4-yl]-2-[3-(1-methyl-1H-pyrazol-4-yl)-phenyl]-pyrimidine (isomery attributed arbitrarely) |
| 280 | (3aS,7aS)-7a-Hydroxymethyl-5-((R)-4-{2-[3-(1-methyl-1H-pyrazol-4-yl)-phenyl]-pyrimidin-5-yl}-pyrazol-1-yl)-hexahydro-isobenzofuran-3a-ol (configuration attributed arbitrarily) |
| 281 | (3aR,5R,7aR)-7a-Hydroxymethyl-5-(4-{2-[3-(1-methyl-1H-pyrazol-4-yl)-phenyl]-pyrimidin-5-yl}-pyrazol-1-yl)-hexahydro-isobenzofuran-3a-ol (configuration attributed arbitrarily) |
| 282 | 5-[1-(trans-3-Methanesulfonyl-cyclohexyl)-1H-pyrazol-4-yl]-2-[3-(1-methyl-1H-pyrazol-4-yl)-phenyl]-pyrimidine (isomery attributed arbitrarely) |
| 283 | 2-[3-(1-Methyl-1H-pyrazol-4-yl)-phenyl]-5-((S)-1-piperidin-3-yl-1H-pyrazol-4-yl)-pyrimidine |
| 284 | 1-[3,3-Difluoro-4-(4-{2-[3-(1-methyl-1H-pyrazol-4-yl)-phenyl]-pyrimidin-5-yl}-pyrazol-1-yl)-piperidin-1-yl]-ethanone |
| 285 | 1-Methyl-8-(4-{2-[3-(1-methyl-1H-pyrazol-4-yl)-phenyl]-pyrimidin-5-yl}-pyrazol-1-yl)-1-aza-spiro[4.5]decan-2-one |
| 286 | trans-8-(4-{2-[3-(1-Methyl-1H-pyrazol-4-yl)-phenyl]-pyrimidin-5-yl}-pyrazol-1-yl)-2-aza-spiro[4.5]decan-3-one |
| 287 | cis-8-(4-(2-(3-(1-methyl-1H-pyrazol-4-yl)phenyl)pyrimidin-5-yl)-1H-pyrazol-1-yl)-2-azaspiro[4.5]decan-3-one |
| 288 | imino(methyl)(3-(4-(2-(3-(1-methyl-1H-pyrazol-4-yl)phenyl)pyrimidin-5-yl)-1H-pyrazol-1-yl)cyclohexyl)-λ6-sulfanone |
| 289 | 2-trans-[4-(4-{2-[3-(1-Methyl-1H-pyrazol-4-yl)-phenyl]-pyrimidin-5-yl}-pyrazol-1-yl)-cyclohexylamino]-ethano |
| 290 | Trans-3-(4-{2-[3-(1-Methyl-1H-pyrazol-4-yl)-phenyl]-pyrimidin-5-yl}-pyrazol-1-yl)-cyclohexanol |
| 291 | 4-(3-Methyl-4-{2-[3-(1-methyl-1H-pyrazol-4-yl)-phenyl]-pyrimidin-5-yl}-pyrazol-1-yl)-cyclohexanol or |
| 292 | 4-(4-{2-[2-Fluoro-5-(1-methyl-1H-pyrazol-4-yl)-phenyl]-pyrimidin-5-yl}-pyrazol-1-yl)-cyclohexanol. |

7. A method for the treatment of multiple sclerosis, rheumatoid arthritis, lupus nephritis, or systemic lupus erythematosus, comprising administering to a subject a therapeutically effective amount of a compound of claim 1.

8. A pharmaceutical composition comprising at least one compound of claim 1 and an excipient or an adjuvant.

9. The pharmaceutical composition according to claim 8 which further comprising at least one further medicament used in the treatment of inflammatory diseases or immune disorders or immunomodulating agent.

10. A process for producing compounds of Formula (I) according to claim 1, comprising the step of reacting a compound of Formula (II)

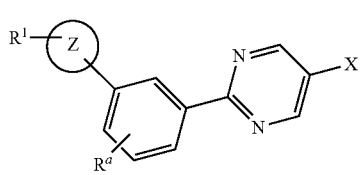

(II)

Wherein X denotes Hal or a triflate group and wherein $R^1$, $R^a$ and Z are as defined in claim 1, With a compound of Formula (III)

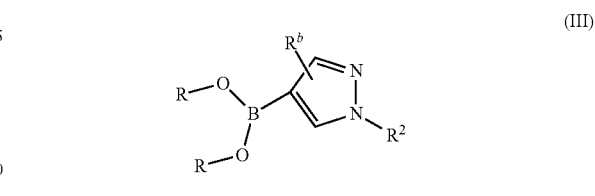

(III)

Wherein R is H or a $C_1$-$C_6$-alkyl group, and wherein $R^b$ and $R^2$ are as defined in claim 1.

11. The compound of claim 1, wherein Z is pyridazine, pyrazole, or 4-pyridine.

12. The compound of claim 1, wherein $R^1$ is a linear or branched $C_1$-$C_6$alkyl group.

13. The compound of claim 1, wherein $R^2$ is a piperidine or Cyc.

14. The compound of claim 1, wherein $R^b$ is H.

15. The compound of claim 1, wherein $R^b$ is COHet or a linear or branched $C_1$-$C_6$-alkyl group wherein 1 H atoms are optionally substituted by a group selected from $NR^3$ and $OR^3$, and wherein 1 $CH_2$ group is optionally substituted by CO.

* * * * *